US009539293B2

(12) United States Patent
Kelly

(10) Patent No.: US 9,539,293 B2
(45) Date of Patent: Jan. 10, 2017

(54) PORCINE LACTIC ACID BACTERIAL STRAINS

(75) Inventor: Denise Kelly, Aberdeen (GB)

(73) Assignee: 4D Pharma Research Limited (GB)

( * ) Notice: Subject to any disclaimer, the term of this patent is extended or adjusted under 35 U.S.C. 154(b) by 0 days.

(21) Appl. No.: 14/232,475

(22) PCT Filed: Jul. 13, 2012

(86) PCT No.: PCT/GB2012/051686
§ 371 (c)(1),
(2), (4) Date: Oct. 17, 2014

(87) PCT Pub. No.: WO2013/008039
PCT Pub. Date: Jan. 17, 2013

(65) Prior Publication Data
US 2015/0050254 A1    Feb. 19, 2015

(30) Foreign Application Priority Data

Jul. 14, 2011 (GB) .................................. 1112091.2

(51) Int. Cl.
| | | |
|---|---|---|
| A61K 35/74 | (2015.01) | |
| A61K 35/747 | (2015.01) | |
| C12R 1/225 | (2006.01) | |
| C12R 1/23 | (2006.01) | |
| C12R 1/25 | (2006.01) | |
| C12N 1/20 | (2006.01) | |

(52) U.S. Cl.
CPC ............. *A61K 35/747* (2013.01); *A23K 10/18* (2016.05); *A23L 33/135* (2016.08); *C12N 1/20* (2013.01); *C12R 1/225* (2013.01); *C12R 1/23* (2013.01); *C12R 1/25* (2013.01); *A23V 2002/00* (2013.01)

(58) Field of Classification Search
None
See application file for complete search history.

(56) References Cited

U.S. PATENT DOCUMENTS

2012/0020943 A1    1/2012 Lin

FOREIGN PATENT DOCUMENTS

| WO | WO 01/58275 | 8/2001 |
|---|---|---|
| WO | 02070670 A1 | 9/2002 |
| WO | 02094296 A1 | 11/2002 |
| WO | 2005007834 A1 | 1/2005 |
| WO | 2008134450 A2 | 6/2008 |

OTHER PUBLICATIONS

Martin R. et al. Isolation of Lactobacilli From Sow Milk and Evaluation of Their Probiotic Potential. J of Dairy Research 76(4)418-425, Nov. 2009.*

International Search Report for International Application No. PCT/GB2012/051686 dated Dec. 20, 2012. 6 pages.
Candela et al. 'Interaction of probiotic Lactobacillus and Bifidobacterium strains with human intestinal epithelial cells: Adhesion properties, competition against enteropathogens and modulation of IL-8 production'. International Journal of Food Microbiology. 2008, vol. 125, No. 3, pp. 286-292.
Nemeth et al. 'Inhibition of *Salmonella*-induced IL-8 synthesis and expression of Hsp70 in enterocyte-like Caco-2 cells after exposure to non-starter lactobacilli'. International Journal of Food Microbiology. 2006, vol. 112, No. 3, pp. 266-274.
Mulder et al. 'Environmentally-acquired bacteria influence microbial diversity and natural innate immune responses at gut surfaces'. Bmc Biology. 2009, vol. 7, No. 1, pp. 79.
Leser et al. 'Culture-independent analysis of gut bacteria: the pig gastrointestinal tract microbiota revisited'. Applied and Environmental Microbiology. 2002, vol. 68, No. 2, pp. 673-690.
Petsuriyawong et al. 'Screening of probiotic lactic acid bacteria from piglet feces'. Nature Science. 2011, vol. 45, pp. 245-253.
Casey et al. 'Isolation and characterization of anti-*Salmonella* lactic acid bacteria from the porcine gastrointestinal tract'. Letters in Applied Microbiology. 2004, vol. 39, No. 5, pp. 431-438.
International Preliminary Report on Patentability for International Application No. PCT/GB2012/051686 dated Jan. 23, 2014.
Blandino, G., Fazio, D., Di Marco, R. Probiotics: Overview of microbiological and immunological characteristics (2008). *Expert Review of Anti-Infective Therapy*, 6 (4), pp. 497-508.
Cintas LM, Casaus MP, Herranz C, Nes IF, Hernandez PE. Review: bacteriocins of lactic acid bacteria (2001). Food Sci Technol 7(4):281-305.
Clarridge III, J.E. Impact of 16S rRNA gene sequence analysis for identification of bacteria on clinical microbiology and infectious diseases (2004). Clinical Microbiology Reviews, 17 (4), pp. 840-862.
Cotter, P.O., Hill, C., Ross, R.P. Food microbiology: Bacteriocins: Developing innate immunity for food (2005). Nature Reviews Microbiology, 3 (10), pp. 777-788.
DeAngelis, M., Siragusa, S., Berloco, M., Caputo, L., Settanni, L., Alfonsi, G., Amerio, M., Grandi, A., Ragni, A., Gobbetti, M. Selection of potential probiotic lactobacilli from pig feces to be used as additives in pelleted feeding (2006). Research in Microbiology, 157 (8), pp. 792-801.
Elmadfa, I., Klein, P., Meyer, A.L. Immune-stimulating effects of lactic acid bacteria in vivo and in vitro (2010). *Proceedings of the Nutrition Society*, 69 (3), pp. 416-420.
Gopal, P.K., Sullivan, P.A., Smart, J.B. Utilization of galacto-oligosaccharides as selective substrates for growth by lactic acid bacteria including Bifidobacterium lactis DR10 and Lactobacillus rhamnosus DR20 (2001). International Dairy Journal, 11 (1-2), pp. 19-25.
Gousia, P., Economou, V., Sakkas, H., Leveidiotou, S., Papadopoulou, C. Antimicrobial resistance of major foodborne pathogens from major meat products (2011). *Foodborne Pathogens and Disease*, 8 (1), pp. 27-38.

(Continued)

*Primary Examiner* — Ralph Gitomer
(74) *Attorney, Agent, or Firm* — Wilson Sonsini Goodrich & Rosati

(57) ABSTRACT

Described herein are porcine lactic acid bacterial strain compositions and processes of obtaining porcine lactic acid bacterial strains. Further aspects of the invention relate to food additives, supplements and probiotic compositions comprising said bacterial strains, and therapeutic uses of said bacterial strain compositions.

14 Claims, 25 Drawing Sheets

(56) References Cited

OTHER PUBLICATIONS

Jackson MS, Bird AR, McOrist AL. Comparison of two selective media for the detection and enumeration of Lactobacilli in human faeces (2002). *J Microbial Methods*. 51 (3), pp. 313-21.

Korhonen, J.M., Sclivagnotis, Y., Von Wright, A. Characterization of dominant cultivable lactobacilli and their antibiotic resistance profiles from faecal samples of weaning piglets (2007). *Journal of Applied Microbiology*, 103 (6), pp. 2496-2503.

Lähteinen, T., Malinen, E., Koort, J.M.K., Mertaniemi-Hannus, U., Hankimo, T., Karikoski, N., Pakkanen, S., Laine, H., Sillanpaa, H., Soderholm, H., Palva, A. Probiotic properties of Lactobacillus isolates originating from porcine intestine and feces (2010) *Anaerobe*, 16 (3), pp. 293-300.

Liu, Y., Fatheree, N. Y., Mangalat, N., Rhoads, J.M. Human-derived probiotic Lactobacillus reuteri strains differentially reduce intestinal inflammation (2010). *American Journal of Physiology-Gastrointestinal and Liver Physiology*, 299 (5), pp. G1087-G1096.

Ljungh, A., Wadstrom, T. Lactic acid bacteria as probiotics (2006). *Current Issues in Intestinal Microbiology*, 7 (2), pp. 73-90.

Martin, R, Delgado, S, Maldonado, A, Jimenez, E, Olivares, M, Fernandez, L, Sobrino, OJ, Rodriguez, JM. Isolation of lactobacilli from sow milk and evaluation of their probiotic potential (2009). Journal of Dairy Research, 76 (4), pp. 418-425.

Mulder IE, Schmidt B, Stokes CR, Lewis M, Bailey M, Aminov R1, Prosser J1, Gill BP, Pluske JR, Mayer CD, Musk CC, Kelly D. Environmentally-acquired bacteria influence microbial diversity and natural innate immune responses at gut surfaces (2009). BMC Biol. 7:79.

Naughton PJ; Grant G. (2005) Modelling of salmonellosis In: Microbial Ecology of the Growing Animal Holzapfel WH, Naughton PJ. (Eds). London, Elsevier. pp. 235-257.

Neeser, J.R., Granath, D., Rouvet, M., Servin, A., Teneberg, S., Karlsson, K.A. Lactobacillus johnsonii La1 shares carbohydrate-binding specificities with several enteropathogenic bacteria (2000). Glycobiology, 10 (11), pp. 1193-1199.

Nicolau, D.P. Current challenges in the management of the infected patient (2011). *Current Opinion in Infectious Diseases*, 24 (Suppl1), pp. S1-S10.

Ohashi, Y., Ushida, K. Health-beneficial effects of probiotics: Its mode of action (2009). Animal Science Journal, 80 (4), pp. 361-371.

Reddy, K.B.P.K., Awasthi, S.P., Madhu, AN., Prapulla, S.G. Role of cryoprotectants on the viability and functional properties of probiotic lactic acid bacteria during freeze drying (2009). *Food Biotechnology*, 23 (3), pp. 243-265.

Tatusova et al., BLAST 2 Sequences, a new tool for comparing protein and nucleotide sequences, FEMS Microbiology Letters 174 (1999) 247-250.

Tatusova et al., Erratum to BLAST 2 Sequences, a new tool for comparing protein and nucleotide sequences, FEMS Microbiology Letters 177 (1999) 187-188.

Altschul et al., Basic Local Alignment Search Tool, J. Mol. Biol. (1990) 215, 403-410.

Salminen et al., Probiotics: how should they be defined?, Trends in Food Science & Technology 10 (1999) 107-110.

Ausubel et al 1999 Short Protocols in Molecular Biology, 4th Ed—Chapter 18.

Robertson, J.M.C., McKenzie, N. H., Duncan, M., Allen-Vercoe, E., Woodward, M.J., Flint, H.J., Grant, G. Lack of flagella disadvantages Salmonella enterica serovar Enteritidis during the early stages of infection in the rat (2003). Journal of Medical Microbiology, 52 (1), pp. 91-99.

Schreiber, O., Petersson, J., Phillipson, M., Perry, M., Roos, S., Holm, L. Lactobacillus reuteri prevents colitis by reducing P-selectin-associated leukocyte- and plateletendothelial cell interactions (2009). American Journal of Physiology-Gastrointestinal and Liver Physiology, 296 (3), pp. G534-G542.

Smith, C.L., Geier, M.S., Yazbeck, R., Torres, D.M., Butler, R.N., Howarth, G.S. Lactobacillus fermentum BR11 and fructo-oligosaccharide partially reduce jejunal inflammation in a model of intestinal mucositis in rats (2008). Nutrition and Cancer, 60 (6), pp. 757-767.

Strasser, S., Neureiter, M., Geppl, M., Braun, R., Danner, H. Influence of lyophilization, fluidized bed drying, addition of protectants, and storage on the viability of lactic acid bacteria (2009). *Journal of Applied Microbiology*, 107 (1), pp. 167-177.

Tomas, M.S.J., Bru, E., Martos, G., Nader-Macias, M.E. Stability of freeze-dried vaginal Lactobacillus strains in the presence of different lyoprotectors (2009). *Canadian Journal of Microbiology*, 55 (5), pp. 544-552.

Tzortzis, G., Baillon, M.L.A, Gibson, G.R., Rastall, R.A. Modulation of anti-pathogenic activity in canine-derived Lactobacillus species by carbohydrate growth substrate (2004). Journal of Applied Microbiology, 96 (3), pp. 552-559.

Williams, N. T. Probiotics (2010). *American Journal of Health-System Pharmacy*, 67 (6), pp. 449-458.

Yao, W., Zhu Wei-yun, W.-Y., Smidt, H., Verstegen, M.W.A. Cultivation-Independent Analysis of the Development of the Lactobacillus spp. Community in the Intestinal Tract of Newborn Piglets (2011) Agricultural Sciences in China, 10 (3), pp. 438-447.

Yun, J.H., Lee, K.B., Sung, Y.K., Kim, E.B., Lee, H.-G., Choi, Y.J. Isolation and characterization of potential probiotic lactobacilli from pig feces (2009). Journal of Basic Microbiology, 49 (2), pp. 220-226.

\* cited by examiner

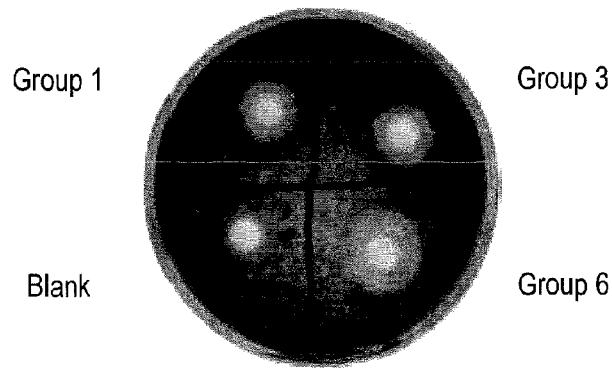

XLD agar containing S. enteritidis S1400 [$10^6$ cfu/ml].
Approximately 5 mm wells cut in agar
An aliquot (60μl) of conditionel media or MRS broth added to the wells.
Plates incubated aerobically for 16 hours at 37°C.
Image captured and area of inhibition measured.

Group 1      <20000 units of inhibition
Group 2      20000-40000 units of inhibition
Group 3      40000-60000 units of inhibition
Group 4      60000-80000 units of inhibition
Group 5      80000-100000 units of inhibition
Group 6      >>100000 units of inhibition

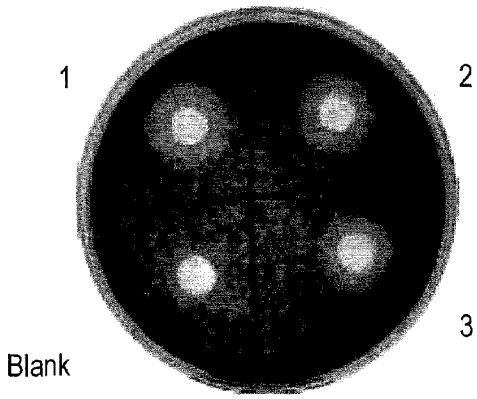

| Bacterial Sample | Inner circle Diameter | Outer circle Diameter | Inhibition Area |
|---|---|---|---|
| 1 | 174 | 366 | 81430 |
| 2 | 174 | 354 | 74644 |
| 3 | 174 | 336 | 64889 |

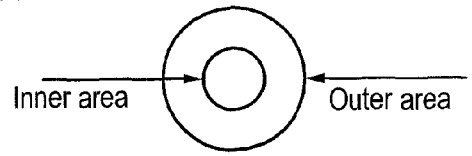

Inhibition area = $[(\pi R^2) - (\pi r^2)]$

FIG. 1

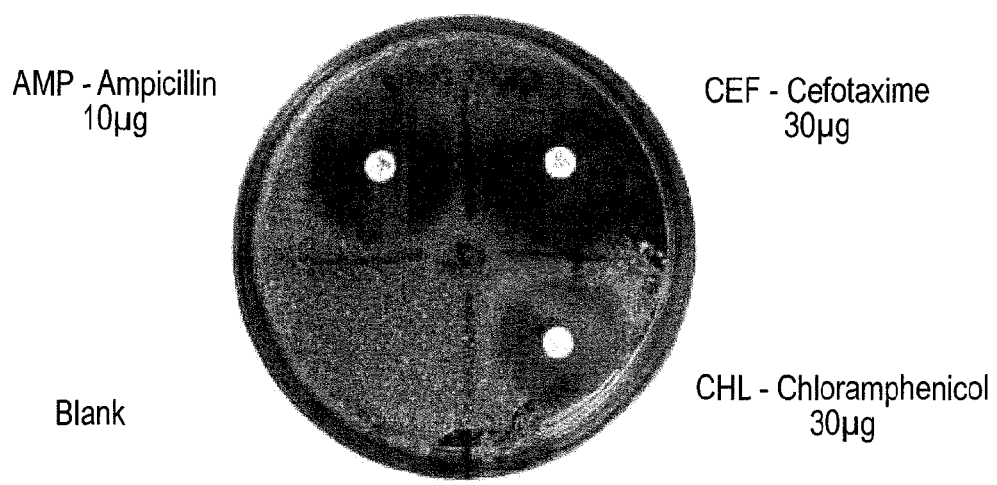
AMP - Ampicillin 10μg
CEF - Cefotaxime 30μg
Blank
CHL - Chloramphenicol 30μg
Inhibition area = $\pi R^2$
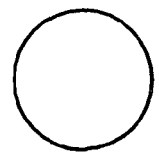
Ampicillin
Cefotaxime
Chloramphenicol
Erythromycin
Tetracycline
Vancomycin
Gentamicin
Kanamycin
Metronizadole
Nalidixic acid
FIG. 5

Bacterium evaluated: Lactobacillus plantarum

| Day | | Control | Salmonella | L. mucosae | L. mucosae + salmonella |
|---|---|---|---|---|---|
| -7 | AM | MRS broth | MRS broth | L. mucosae | L. mucosae |
| -4 | AM | MRS broth | MRS broth | L. mucosae | L. mucosae |
| -2 | AM | MRS broth | MRS broth | L. mucosae | L. mucosae |
| | | ↓ | ↓ | ↓ | ↓ |
| 0 | AM | MRS broth | MRS broth | L. mucosae | L. mucosae |
| | PM | LB media | SE S1400 | LB media | SE S140 |
| | | ↓ | ↓ | ↓ | ↓ |
| 1 | AM | MRS broth | MRS broth | L. mucosae | L. mucosae |
| 2 | AM | MRS broth | MRS broth | L. mucosae | L. mucosae |
| 3 | AM | MRS broth | MRS broth | L. mucosae | L. mucosae |
| 4 | AM | MRS broth | MRS broth | L. mucosae | L. mucosae |
| 5 | AM | MRS broth | MRS broth | L. mucosae | L. mucosae |
| 6 | AM | MRS broth | MRS broth | L. mucosae | L. mucosae |
| 7 | AM | MRS broth | MRS broth | L. mucosae | L. mucosae |
| 8 | AM | MRS broth | MRS broth | L. mucosae | L. mucosae |
| 9 | AM | MRS broth | MRS broth | L. mucosae | L. mucosae |
| 10 | | Euthanase | Euthanase | Euthanase | Euthanase |

SE S1400, S enteritidis S1400. LB media, Luria Bertani broth

FIG. 10

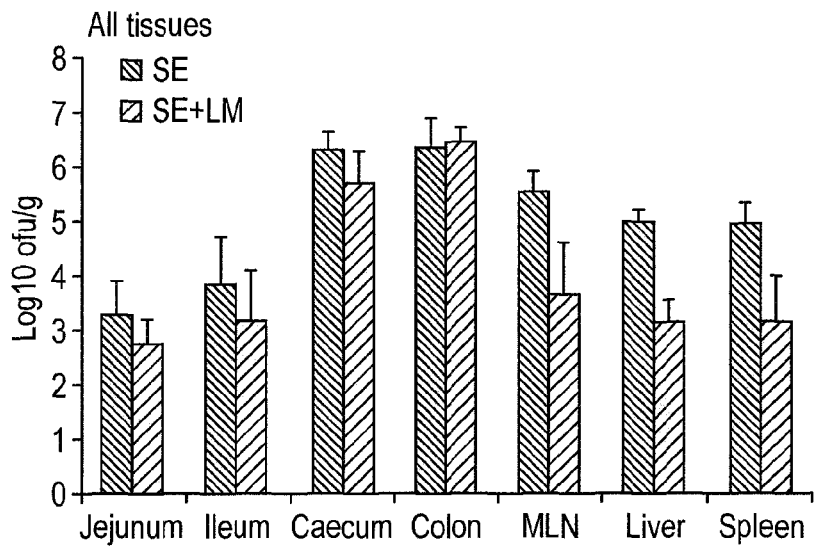
FIG. 11a
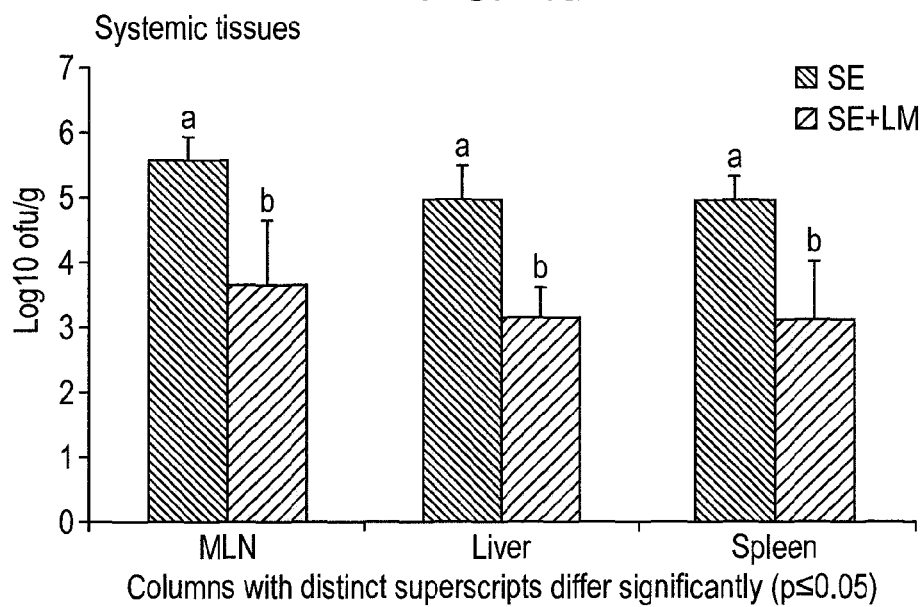
Columns with distinct superscripts differ significantly (p≤0.05)
FIG. 11b
Statistical analysis
S. enteritidis vs S. enteritidis + L. mucosae
| | |
|---|---|
| Jejunum | p>0.05 |
| Ileum | p>0.05 |
| Caecum | p>0.05 |
| Colon | p>0.05 |
| MLN | p<0.01 |
| Liver | p<0.01 |
| Spleen | p<0.01 |
FIG. 11c Columns with distinct superscripts differ significantly (p≤0.05)

| Day | | Salmonella | L. mucosae + salmonella |
|---|---|---|---|
| -7 | AM | MRS broth | L. mucosae |
| -4 | AM | MRS broth | L. mucosae |
| -2 | AM | MRS broth | L. mucosae |
| | | ↓ | ↓ |
| 0 | AM | MRS broth | L. mucosae |
| | PM | SE S1400 | SE S1400 |
| | | ↓ | ↓ |
| 1 | AM | MRS broth | L. mucosae |
| 2 | AM | MRS broth | L. mucosae |
| 3 | AM | MRS broth | L. mucosae |
| 4 | AM | MRS broth | L. mucosae |
| 5 | AM | MRS broth | L. mucosae |
| 6 | | Euthanase | Euthanase |

SE S1400, S enteritidis S1400. LB media, Luria Bertani broth

FIG. 13

All tissues
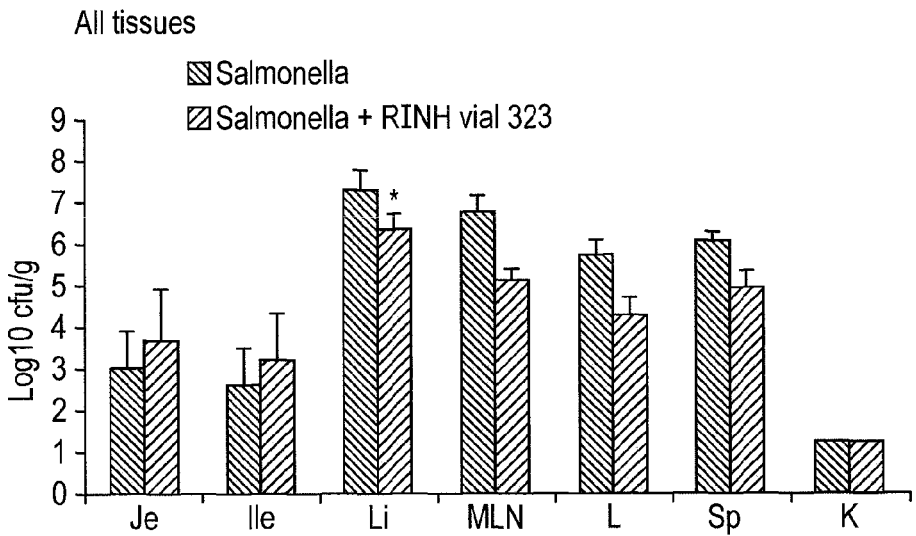
FIG. 14a
Systemic tissues
Columns with distinct superscripts differ significantly (p≤0.05)
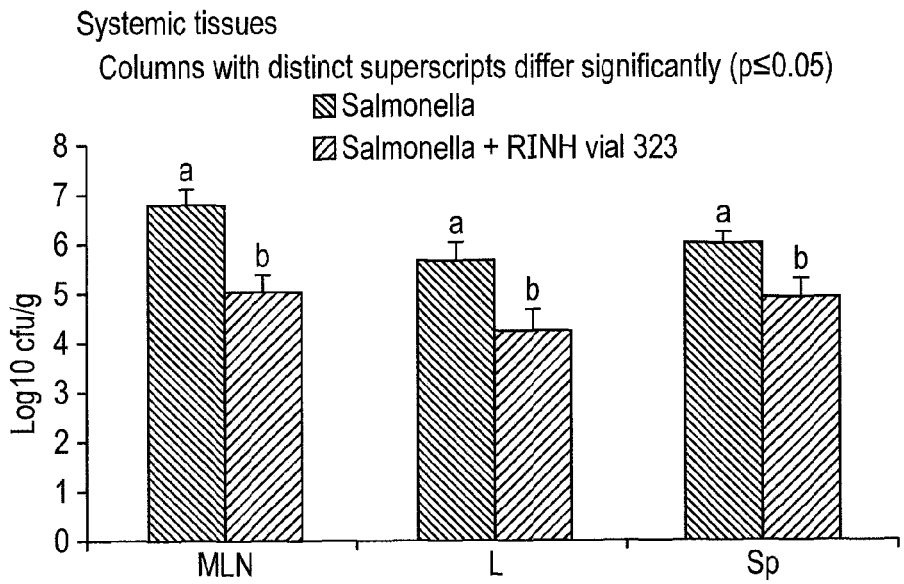
FIG. 14b
Statistical analysis
S. enteritidis vs S. enteritidis + 323
| | |
|---|---|
| Jejunum | p>0.05 |
| Ileum | p>0.05 |
| Large intestine | p<0.05 |
| MLN | p<0.05 |
| Liver | p<0.05 |
| Spleen | p<0.05 |
FIG. 14c

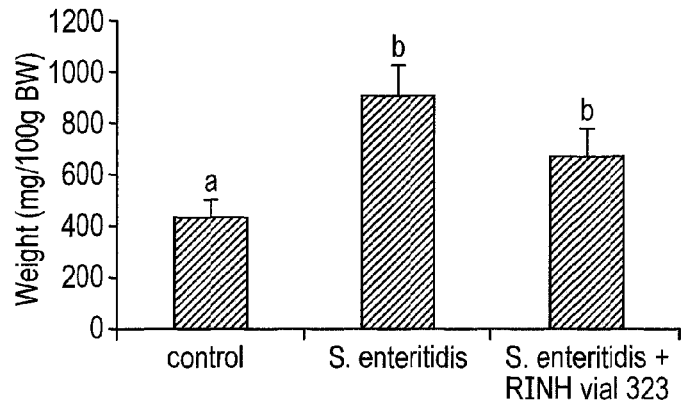

Columns with distinct superscripts differ significantly (p≤0.05)

FIG. 15

| LAB Challenge Day | | Control | Salmonella | Group 6<br>L. reuteri 31<br>Salmonella | Group 6<br>L. reuteri 32<br>Salmonella | Group 3<br>L. mucosae<br>Salmonella | Group 1<br>L. reuteri 46<br>Salmonella | Group 1;<br>L. reuteri 47<br>Salmonella |
|---|---|---|---|---|---|---|---|---|
| -6 | AM | MRS broth | MRS broth | LR 31 | LR 32 | L. mucosae | LR 46 | LR 47 |
| -4 | AM | MRS broth | MRS broth | LR 31 | LR 32 | L. mucosae | LR 46 | LR 47 |
| -2 | AM | MRS broth | MRS broth | LR 31 | LR 32 | L. mucosae | LR 46 | LR 47 |
| | | ↓ | ↓ | ↓ | ↓ | ↓ | ↓ | ↓ |
| 0 | AM | MRS broth | MRS broth | LR 31 | LR 32 | L. mucosae | LR 46 | LR 47 |
| | PM | LB media | SE S1400 | SE S1400 | SE S1400 | SE S1400 | SE S1400 | SE S1400 |
| | | ↓ | ↓ | ↓ | ↓ | ↓ | ↓ | ↓ |
| 1 | AM | MRS broth | MRS broth | LR 31 | LR 32 | L. mucosae | LR 46 | LR 47 |
| 2 | AM | MRS broth | MRS broth | LR 31 | LR 32 | L. mucosae | LR 46 | LR 47 |
| 3 | AM | MRS broth | MRS broth | LR 31 | LR 32 | L. mucosae | LR 46 | LR 47 |
| 4 | AM | MRS broth | MRS broth | LR 31 | LR 32 | L. mucosae | LR 46 | LR 47 |
| 5 | AM | MRS broth | MRS broth | LR 31 | LR 32 | L. mucosae | LR 46 | LR 47 |
| 6 | AM | MRS broth | MRS broth | LR 31 | LR 32 | L. mucosae | LR 46 | LR 47 |
| 7 | AM | MRS broth | MRS broth | LR 31 | LR 32 | L. mucosae | LR 46 | LR 47 |
| 8 | AM | MRS broth | MRS broth | LR 31 | LR 32 | L. mucosae | LR 46 | LR 47 |
| 9 | AM | MRS broth | MRS broth | LR 31 | LR 32 | L. mucosae | LR 46 | LR 47 |
| 10 | | Euthanase | Euthanase | Euthanase | Euthanase | Euthanase | Euthanase | Euthanase |

LR 31, Pig L. reuteri vial 3. LR 32, Pig L. reuteri vial 32. LR 46, Pig L reuteri vial 46. LR 47, Pig L. reuteri vial 47. SE S1400, S. enteritidis S1400. LB media, Luria Bertani broth

FIG. 16

(a) Caecum
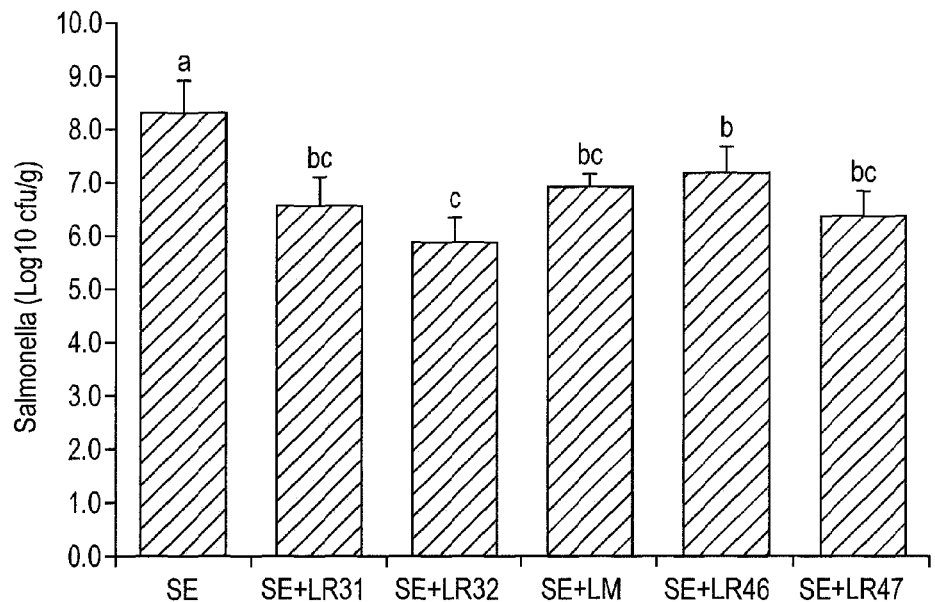
(b) Colon
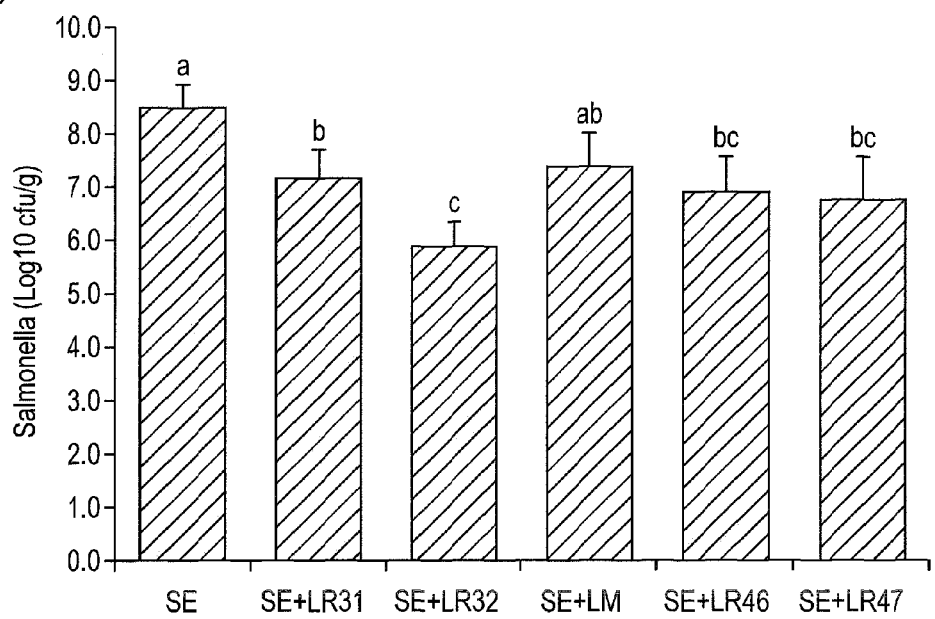
Columns with distinct superscripts differ significantly (p≤0.05)
FIG. 18

```
                        SEQUENCE LISTING

<160> NUMBER OF SEQ ID NOS: 92

<210> SEQ ID NO 1
<211> LENGTH: 698
<212> TYPE: DNA
<213> ORGANISM: Lactobacillus sp.
<220> FEATURE:
<221> NAME/KEY: modified_base
<222> LOCATION: (600)..(600)
<223> OTHER INFORMATION: a, c, t, g, unknown or other
<220> FEATURE:
<221> NAME/KEY: modified_base
<222> LOCATION: (627)..(627)
<223> OTHER INFORMATION: a, c, t, g, unknown or other
<220> FEATURE:
<221> NAME/KEY: modified_base
<222> LOCATION: (695)..(695)
<223> OTHER INFORMATION: a, c, t, g, unknown or other

<400> SEQUENCE: 1
ggtggagcat gtggtttaat tcgaagctac gcgaagaacc ttaccaggtc ttgacatctt      60
gcgctaacct tagagataag gcgttccctt cggggacgca atgacaggtg gtgcatggtc     120
gtcgtcagct cgtgtcgtga gatgttgggt taagtcccgc aacgagcgca acccttgtta    180
ctagttgcca gcattaagtt gggcactcta gtgagactgc cggtgacaaa ccggaggaag    240
gtggggacga cgtcagatca tcatgcccct tatgacctgg gctacacacg tgctacaatg    300
gacggtacaa cgagtcgcaa gctcgcgaga gtaagctaat ctcttaaagc cgttctcagt    360
tcggactgta ggctgcaact cgcctacacg aagtcggaat cgctagtaat cgcggatcag    420
catgccgcgg tgaatacgtt cccgggcctt gtacacaccg cccgtcacac catgggagtt    480
tgtaacgccc aaagtcggtg gcctaaccat tatggaggga gccgcctaag tgcgggacag    540
atgactgggg tgaagtcgta acaaggtagc ctgtattttc ttgcggttgt tccccccccn   600
ggcgggactg ccttactcct ttcaccnccc gcgccctgg aggggccgg aaccccctc      660 ccaaccccc taacccacct ccttcctttt aaccngct                             698

<210> SEQ ID NO 2
<211> LENGTH: 766
<212> TYPE: DNA
<213> ORGANISM: Lactobacillus sp.
<220> FEATURE:
<221> NAME/KEY: modified_base
<222> LOCATION: (531)..(531)
<223> OTHER INFORMATION: a, c, t, g, unknown or other
<220> FEATURE:
<221> NAME/KEY: modified_base
<222> LOCATION: (538)..(538)
<223> OTHER INFORMATION: a, c, t, g, unknown or other
<220> FEATURE:
<221> NAME/KEY: modified_base
<222> LOCATION: (567)..(567)
<223> OTHER INFORMATION: a, c, t, g, unknown or other
<220> FEATURE:
<221> NAME/KEY: modified_base
<222> LOCATION: (751)..(751)
<223> OTHER INFORMATION: a, c, t, g, unknown or other

<400> SEQUENCE: 2
gactttctag gttggatacc gtcactgcgt gaacagttac tctcacgcac gttcttctcc      60
```

```
aacaacagag ctttacgagc cgaaacccct cttcactcac gcggtgttgc tccatcaggc    120
ttgcgcccat tgtggaagat tccctactgc tgcctcccgt aggagtatgg accgtgtctc    180
agttccattg tggccgatca gtctctcaac tcggctatgc atcatcgcct tggtaagccg    240
ttaccttacc aactagctaa tgcaccgcag gtccatccca gagtgatagc aaagccatc     300 tttcaaacaa agccatgtg ctttttgttg ttatgcggta ttagcatctg tttccaaatg     360
ttatcccccg ctccggggca ggttacctac gtgttactca cccgtccgcc actcactggt    420
gatccatcgt caatcaggtg caagcaccat caatcagttg ggccagtgcg tacgacttgc    480
atgtattagg cacaccgccg gcgttcatcc tgagccatga tcaaactcta ngcgtcantt    540
ttacggtctc ggctcgtttc tctgttntct gacatcaacg tgcgttacat ttgcggttta    600
cgcattgatt gtactccctc cacataggtg gcggcatacc cttcgtgctc ctctactcat    660
ctcgttcatt acaactcgct tgttaccttc ccggtgggg ttctctacct ccttcgtttt     720
ctctcacctc attctctctc ccatcctctc ntctttcctc ttgctc                   766

<210> SEQ ID NO 3
<211> LENGTH: 674
<212> TYPE: DNA
<213> ORGANISM: Lactobacillus sp.

<400> SEQUENCE: 3
ggtggagcat gtggtttaat tcgaagctac gcgaagaacc ttaccaggtc ttgacatact     60
atgcaaatct aagagattag acgttccctt cggggacatg gatacaggtg gtgcatggtt   120
gtcgtcagct cgtgtcgtga gatgttgggt taagtcccgc aacgagcgca acccttatta   180
tcagttgcca gcattaagtt gggcactctg gtgagactgc cggtgacaaa ccggaggaag   240
gtggggatga cgtcaaatca tcatgcccct tgatgacctg gctacacac gtgctacaat    300 ggatggtaca acgagttgcg aactcgcgag agtaagctaa tctcttaaag ccattctcag   360
ttacggatgt gtaggctgca actcgcctata catgaagtcg gaatcgctag taatcgcgga   420
tacagcatgc cgcggtgaat actgttcccg ggcctatgtg acacaccgcc cgtcacacca   480
tgagcagttt gtaatcaccc acacagtcgg tggggtaacc tttataggaa ccagccgcct   540
acagtgcggg accgatgatt atgggtgcac tcgtatcact gtaacttaaa cccttgcggc   600
cgtactcccc aggcggaatg cttaatacgt tacctgcaac cctgaagggc ggaatccctc   660
caacgattat caat                                                     674

<210> SEQ ID NO 4
<211> LENGTH: 697
<212> TYPE: DNA
<213> ORGANISM: Lactobacillus sp.
<220> FEATURE:
<221> NAME/KEY: modified_base
<222> LOCATION: (534)..(534)
<223> OTHER INFORMATION: a, c, t, g, unknown or other
<220> FEATURE:
<221> NAME/KEY: modified_base
<222> LOCATION: (653)..(653)
<223> OTHER INFORMATION: a, c, t, g, unknown or other

<400> SEQUENCE: 4
gtggctttct ggttaaatac cgtcaatacc tgaacagtta ctctcagata tgttcttctt     60
taacaacaga gttttacgag ccgaaaccct tcttcactca cgcggcgttg ctccatcaga   120
ctttcgtcca ttgtggaaga ttccctactg ctgcctcccg taggagtttg gccgtgtct    180 cagtcccaat gtggccgatt accctctcag gtcggctacg tatcattgcc atggtgagcc    240
```

-continued

```
gttaccccac catctagcta atacgccgcg ggaccatcca aaagtgatag ccgaagccat    300 cttctcaagct cggaccatgc ggtccaagtt gttatgcggt attagcatct gtttccaggt    360
gttatccccc gcttctgggc aggtttccca cgtgttactc accagttcgc cactcactca    420
aatgtaaatc atgatgcaag caccaatcaa taccaaagtt cgttcgactt gcatgtatta    480
ggcacgccgc cagcgttcgt cgctgagcca tgatcaaact actaaaggcc cccnatgcct    540
cccacccgct tgttgccgg ggcccccgt tcccataccc cttttggacg ttttccagcc    600
ccttggcggg ccctgtacct cccccaggg cggggaatgc cttaattgcg ttnaccttgc    660
accccctgaa ggggcggaat ccctccaacg attacct    697
```

<210> SEQ ID NO 5
<211> LENGTH: 653
<212> TYPE: DNA
<213> ORGANISM: Lactobacillus sp.

<400> SEQUENCE: 5

```
ggtggagcat gtggtttaat tcgaagcaac gcgaagaacc ttaccaggtc ttgacatcca     60
gtcgcataac ctaagagatt aggtgttccc ttcggggacg ctgagacagg tggtgcatgg    120
ctgtcgtcag ctcgtgtcgt gagatgttgg gttaagtccc gcaacgagcg caacccttgt    180
cattagttgc catcattaag ttgggcactc taatgagact gccggtgaca aaccggagga    240
aggtggggat gacgtcaaga tcatcatgcc ccttatgacc tgggctacac acgtgctaca    300
atggacggta caacgagata gcgaacctgc gaagagctaa gcggatctct aaagccgtt    360 ctcagttcgg actgtaggct gcaactcgcc tacacgaagc ttggaatcgc tagtaatcgc    420
ggatcagcac tgccgcggtg aatacgttcc cgggccttgt acacaccgcc cgtcacacca    480
tgagagtctg taactcccaa agtcggtggg ataaccttct atagcgagtg agtccgttcg    540
atgggtaggg acaagatgaa tgagcggtga aaggtcgtta aaccaagggt agcaagtaag    600
gatccctttg ggggttttat ctccacgggg ggggtgtttc ttttctgtct tta    653
```

<210> SEQ ID NO 6
<211> LENGTH: 717
<212> TYPE: DNA
<213> ORGANISM: Lactobacillus sp.
<220> FEATURE:
<221> NAME/KEY: modified_base
<222> LOCATION: (452)..(452)
<223> OTHER INFORMATION: a, c, t, g, unknown or other
<220> FEATURE:
<221> NAME/KEY: modified_base
<222> LOCATION: (466)..(466)
<223> OTHER INFORMATION: a, c, t, g, unknown or other
<220> FEATURE:
<221> NAME/KEY: modified_base
<222> LOCATION: (482)..(482)
<223> OTHER INFORMATION: a, c, t, g, unknown or other
<220> FEATURE:
<221> NAME/KEY: modified_base
<222> LOCATION: (543)..(543)
<223> OTHER INFORMATION: a, c, t, g, unknown or other
<220> FEATURE:
<221> NAME/KEY: modified_base
<222> LOCATION: (557)..(557)
<223> OTHER INFORMATION: a, c, t, g, unknown or other
<220> FEATURE:
<221> NAME/KEY: modified_base
<222> LOCATION: (584)..(584)
<223> OTHER INFORMATION: a, c, t, g, unknown or other
<220> FEATURE:
<221> NAME/KEY: modified_base
<222> LOCATION: (586)..(586)

<223> OTHER INFORMATION: a, c, t, g, unknown or other
<220> FEATURE:
<221> NAME/KEY: modified_base
<222> LOCATION: (613)..(613)
<223> OTHER INFORMATION: a, c, t, g, unknown or other

<400> SEQUENCE: 6

| | | | | | |
|---|---|---|---|---|---|
| actttctaga | gttagatgat | accgttcaac | atgacagatg | gccacgttta | cttactctca | 60 |
| ctgactactg | ttctttcatc | tcacacaaca | gagctttacg | agccgaaacc | cttcttcact | 120 |
| cacgcggcgt | tgctccatca | gagctttgcg | tcccattgtg | gaagattccc | tactgctgcc | 180 |
| tcccgtagga | gtatgggccg | tgtctcagtc | ccattgtggc | cgatcagtct | ctcaactcgg | 240 |
| ctatgcatca | tcgccttggt | aagccgttac | cttaccaact | agctaatgca | ccgcaggtcc | 300 |
| atccaagagt | gatagccgaa | ccatctttca | caactctaaa | catgcttgta | gtgttgttat | 360 |
| tccggtatta | acattctgtt | tccaggttgt | tattcccagc | tgctctcggg | gcagggttta | 420 |
| ccccaacgtt | ggtttacctt | caccccggt | tncggcccgg | cttcgncctt | gggttagtac | 480 |
| tnacgattct | gctattatat | acgatgggct | agacgaccag | cctaacacaa | tttcaatttc | 540 |
| gtnaagtgtc | gagaggncct | acggtcgtcc | cgttaacgtg | tagncatttt | ggcttatttg | 600 |
| ttaagttgtc | cancgggcca | ccgaccccca | gggcccggtt | ggtccgggtt | tcccccattg | 660 |
| caacgtcgcc | aaagtgcgga | aatttcgaaa | ataccccttaa | ccaatgaaaa | aaacata | 717 |

<210> SEQ ID NO 7
<211> LENGTH: 620
<212> TYPE: DNA
<213> ORGANISM: Lactobacillus sp.
<220> FEATURE:
<221> NAME/KEY: modified_base
<222> LOCATION: (601)..(601)
<223> OTHER INFORMATION: a, c, t, g, unknown or other
<220> FEATURE:
<221> NAME/KEY: modified_base
<222> LOCATION: (603)..(603)
<223> OTHER INFORMATION: a, c, t, g, unknown or other
<220> FEATURE:
<221> NAME/KEY: modified_base
<222> LOCATION: (605)..(606)
<223> OTHER INFORMATION: a, c, t, g, unknown or other
<220> FEATURE:
<221> NAME/KEY: modified_base
<222> LOCATION: (609)..(617)
<223> OTHER INFORMATION: a, c, t, g, unknown or other

<400> SEQUENCE: 7

| | | | | | |
|---|---|---|---|---|---|
| ggtggagcat | gtggtttaat | tcgaagctac | gcgaagaacc | ttaccaggtc | ttgacatact | 60 |
| atgcaaatct | aagagattag | acgttccctt | cggggacatg | gatacaggtg | gtgcatggtt | 120 |
| gtcgtcagct | cgtgtcgtga | gatgttgggg | ttaagtcccg | caacgagcgc | aaccccttatt | 180 |
| atcagttgcc | agcattaagt | tgggcactct | ggtgagactg | ccggtgacaa | accggaggaa | 240 |
| ggtggggatg | acgtcaaatc | atcatgcccc | ttatgacctg | ggctacacac | gtgctacaat | 300 |
| ggatggtaca | acgagttgcg | aactcgcgag | agtaagctaa | tctcttaaag | ccattctcag | 360 |
| ttcggattgt | aggctgcaac | tcgcctacat | gaagtcggaa | tcgctagtaa | tcgcggatca | 420 |
| gcatgccgcg | gtgaatacgt | tcccgggcct | tgtacacacc | gcccgtcaca | ccatgagagt | 480 |
| ttgtaacacc | caaagtcggt | gggggtaacc | ttttaggaa | accagcccgc | cctaaagggt | 540 |
| ggggaacaag | aatgaattag | ggggttgaaa | agttccgtta | aaccaaaagg | ggttagcccc | 600 |
| ngntnngann | nnnnnnngac | | | | | 620 |

<210> SEQ ID NO 8
<211> LENGTH: 526
<212> TYPE: DNA
<213> ORGANISM: Lactobacillus sp.
<220> FEATURE:
<221> NAME/KEY: modified_base
<222> LOCATION: (524)..(524)
<223> OTHER INFORMATION: a, c, t, g, unknown or other

<400> SEQUENCE: 8

```
gctttctggt taaataccgt caatacctga acagttactc tcagatatgt gtcttcttta      60
acaacagagt tttacgagcc gaaacccttc ttcactcacg cggcgttgct ccatcagact     120
ttcgtccatt gtggaagatt ccctactgct gcctcccgta ggagtttggg ccgtgtctca     180
gtcccaatgt ggccgattac cctctcaggt cggctacgta tcattgccat ggtgagccgt     240
tacccccacc atctagctaa tacgccgcgg gaccatccaa aagtgatagc cgaagccatc     300
tttcaagctc ggaccatgcg gtccaagttg ttatgcggta ttagcatctg tttccagggt     360
gttattcccc cgcttcgtgg cagggtttc ccacgtgtta ctcaccagtt cgccactcac     420
tcaaatgtaa atcatgatgc aagcaccaat caataccaga gttcgttcga cttgcatgta     480
ttaggcacgc cgccagcgtt cgtcctgagc catgatcaaa ctcnga                    526
```

<210> SEQ ID NO 9
<211> LENGTH: 533
<212> TYPE: DNA
<213> ORGANISM: Lactobacillus sp.

<400> SEQUENCE: 9

```
gtgactttct aagtaattac cgtcaaataa atggccagtt actacctcta tctttcttca      60
ctaccaacag agctttacga gccgaaaccc ttcttcactc acgcggcgtt gctccatcag     120
actttcgtcc attgtggaag attccctact gctgcctccc gtaggagttt gggccgtgtc     180
tcagtcccaa tgtggccgat cagtctctca actcggctat gcatcattgc cttggtaagc     240
cgttacctta ccaactagct aatgcaccgc aggtccatcc aagagtgata gcagaaccat     300
ctttcaaact ctagacatgc gtctagtgtt gttatccggt attagcatct gtttccaggt     360
gttatcccag tctcttgggc aggttaccca cgtgttactc acccgtccgc cgctcgcttg     420
tatctagttt catttagtgc aagcaccaaa atcatctagg caagctcgct cgacttgcat     480
gtattaggca cgccgccagc gttcgtcctg agccaggatc gaactctaac taa            533
```

<210> SEQ ID NO 10
<211> LENGTH: 668
<212> TYPE: DNA
<213> ORGANISM: Lactobacillus reuteri

<400> SEQUENCE: 10

```
tgcctaatac atgcaagtcg tacgcactgg cccaactgat tgatggtgct tgcacctgat      60
tgacgatgga tcaccagtga gtggcggacg ggtgagtaac acgtaggtaa cctgccccgg     120
agcgggggat aacatttgga aacagatgct aataccgcat aacaacaaaa gccacatggc     180
ttttgtttga agatggcctt tggctatcac tctgggatgg acctgcggtg cattagctag     240
ttggtaaggt aacggcttac caaggcgatg atgcatagcc gagttgagag actgatcggc     300
cacaatggaa ctgagacacg gtccatactc ctacgggagg cagcagtagg gaatcttcca     360
caatgggcgc aagcctgatg gagcaacacc gcgtgagtga agaagggttt cggctcgtaa     420
agctctgttg ttggagaaga acgtgcgtga gagtaactgt tcacgcagtg acggtatcca     480
```

| | |
|---|---|
| accagaaagt cacggctaac tacgtgccag cagccgcggt aatacgtagg tggcaagcgt | 540 |
| tatccggatt tattgggcgt aaagcgagcg caggcggttg cttaggtctg atgtgaaagc | 600 |
| cttcggctta accgaagaag tgcatcggaa accgggcgac ttgagtgcag aagaggacag | 660 |
| tggaactc | 668 |

<210> SEQ ID NO 11
<211> LENGTH: 671
<212> TYPE: DNA
<213> ORGANISM: Lactobacillus reuteri

<400> SEQUENCE: 11

| | |
|---|---|
| tcggatttat tgggcgtaaa gcgagcgcag gcggttgctt aggtctgatg tgaaagcctt | 60 |
| cggcttaacc gaagaagtgc atcggaaacc gggcgacttg agtgcagaag aggacagtgg | 120 |
| aactccatgt gtagcggtgg aatgcgtaga tatatggaag aaccagtg gcgaaggcgg | 180 |
| ctgtctggtc tgcaactgac gctgaggctc gaaagcatgg gtagcgaaca ggattagata | 240 |
| ccctggtagt ccatgccgta aacgatgagt gctaggtgtt ggagggtttc cgcccttcag | 300 |
| tgccggagct aacgcattaa gcactccgcc tggggagtac daccgcaagg ttgaaactca | 360 |
| aaggaattga cgggggcccg cacaagcggt ggagcatgtg gtttaattcg aagctacgcg | 420 |
| aagaaccttta ccaggtcttg acatcttgcg ctaaccttag ataaggcg ttcccttcgg | 480 |
| ggacgcaatg acaggtggtg catggtcgtc gtcagctcgt gtcgtgagat gttgggttaa | 540 |
| gtcccgcaac gagcgcaacc cttgttacta gttgccagca ttaagttggg cactctagtg | 600 |
| agactgccgg tgacaaaccg gaggaaggtg gggacgacgt cagatcatca tgccccttat | 660 |
| gacctgggct a | 671 |

<210> SEQ ID NO 12
<211> LENGTH: 569
<212> TYPE: DNA
<213> ORGANISM: Lactobacillus reuteri

<400> SEQUENCE: 12

| | |
|---|---|
| gagcatgtgg tttaattcga agctacgcga agaaccttac caggtcttga catcttgcgc | 60 |
| taaccttaga gataaggcgt tcccttcggg gacgcaatga caggtggtgc atggtcgtcg | 120 |
| tcagctcgtg tcgtgagatg ttgggttaag tcccgcaacg agcgcaaccc ttgttactag | 180 |
| ttgccagcat taagttgggc actctagtga gactgccggt gacaaaccgg aggaaggtgg | 240 |
| ggacgacgtc agatcatcat gccccttatg acctgggcta cacacgtgct acaatggacg | 300 |
| gtacaacgag tcgcaagctc gcgagagtaa gctaatctct taaagccgtt ctcagttcgg | 360 |
| actgtaggct gcaactcgcc tacacgaagt cggaatcgct agtaatcgcg gatcagcatg | 420 |
| ccgcggtgaa tacgttcccg ggccttgtac acaccgcccg tcacaccatg ggagtttgta | 480 |
| acgcccaaag tcggtggcct aaccattatg gagggagccg cctaaggcgg acagatgac | 540 |
| tggggtgaag tcgtaacaag gtagccgta | 569 |

<210> SEQ ID NO 13
<211> LENGTH: 724
<212> TYPE: DNA
<213> ORGANISM: Lactobacillus reuteri

<400> SEQUENCE: 13

| | |
|---|---|
| ctccccaggc ggagtgctta atgcgttagc tccggcactg aagggcggaa accctccaac | 60 |
| acctagcact catcgtttac ggcatggact accagggtat ctaatcctgt tcgctaccca | 120 |

```
tgctttcgag cctcagcgtc agttgcagac cagacagccg ccttcgccac tggtgttctt    180
ccatatatct acgcattcca ccgctacaca tggagttcca ctgtcctctt ctgcactcaa    240
gtcgcccggt ttccgatgca cttcttcggt taagccgaag gctttcacat cagacctaag    300
caaccgcctg cgctcgcttt acgcccaata aatccggata acgcttgcca cctacgtatt    360
accgcggctg ctggcacgta gttagccgtg actttctggt tggataccgt cactgcgtga    420
acagttactc tcacgcacgt tcttctccaa caacagagct ttacgagccg aaacccttct    480
tcactcacgc ggtgttgctc catcaggctt gcgcccattg tggaagattc cctactgctg    540
cctcccgtag gagtatggac cgtgtctcag ttccattgtg gccgatcagt ctctcaactc    600
ggctatgcat catcgccttg gtaagccgtt accttaccaa ctagctaatg caccgcaggt    660
ccatcccaga gtgatagcca aagccatctt tcaaacaaaa gccatgtggc ttttgttgtt    720
atgc                                                                724
```

<210> SEQ ID NO 14
<211> LENGTH: 522
<212> TYPE: DNA
<213> ORGANISM: Lactobacillus reuteri

<400> SEQUENCE: 14

```
tttctggttg dataccgtca ctgcgtgaac agttactctc acgcacgttc ttctccaaca     60
acagagcttt acgagccgaa acccttcttc actcacgcgg tgttgctcca tcaggcttgc    120
gcccattgtg gaagattccc tactgctgcc tcccgtagga gtatggaccg tgtctcagtt    180
ccattgtggc cgatcagtct ctcaactcgg ctatgcatca tcgccttggt aagccgttac    240
cttaccaact agctaatgca ccgcaggtcc atcccagagt gatagccaaa gccatctttc    300
aaacaaaagc catgtggctt tgttgttat gcggtattag catctgtttc caaatgttat    360
cccccgctcc ggggcaggtt acctacgtgt tactcacccg tccgccactc actggtgatc    420
catcgtcaat caggtgcaag caccatcaat cagttgggcc agtgcgtacg acttgcatgt    480
attaggcaca ccgccggcgt tcatcctgag ccatgatcaa ac                       522
```

<210> SEQ ID NO 15
<211> LENGTH: 681
<212> TYPE: DNA
<213> ORGANISM: Lactobacillus reuteri

<400> SEQUENCE: 15

```
ccgccttagg cggctccctc cataatggtt aggccaccga ctttgggcgt tacaaactcc     60
catggtgtga cgggcggtgt gtacaaggcc cgggaacgta ttcaccgcgg catgctgatc    120
cgcgattact agcgattccg acttcgtgta ggcgagttgc agcctacagt ccgaactgag    180
aacggcttta agagattagc ttactctcgc gagcttgcga ctcgttgtac cgtccattgt    240
agcacgtgtg tagcccaggt cataaggggc atgatgatct gacgtcgtcc caccttcct    300 ccggtttgtc accggcagtc tcactagagt gcccaactta atgctggcaa ctagtaacaa    360
gggttgcgct cgttgcggga cttaacccaa catctcacga cacgagctga cgacgaccat    420
gcaccacctg tcattgcgtc cccgaaggga acgccttatc tctaaggtta gcgcaagatg    480
tcaagacctg gtaaggttct tcgcgtagct tcgaattaaa ccacatgctc caccgcttgt    540
gcgggccccc gtcaattcct ttgagtttcc accttgcggt cgtactcccc aggcggagtg    600
cttaatgcgt tagctccggc actgaagggc ggaaaccctc caacacctag cactcatcgt    660
```
ttacggcatg gactaccagg g                                            681

<210> SEQ ID NO 16
<211> LENGTH: 682
<212> TYPE: DNA
<213> ORGANISM: Lactobacillus plantarum

<400> SEQUENCE: 16
gtgcctaata catgcaagtc gaacgaactc tggtattgat tggtgcttgc atcatgattt    60
acatttgagt gagtggcgaa ctggtgagta acacgtggga aacctgccca gaagcggggg   120
ataacacctg gaaacagatg ctaataccgc ataacaactt ggaccgcatg gtccgagttt   180
gaaagatggc ttcggctatc acttttggat ggtcccgcgg cgtattagct agatggtgag   240
gtaacggctc accatggcaa tgatacgtag ccgacctgag agggtaatcg gccacattgg   300
gactgagaca cggcccaaac tcctacggga ggcagcagta gggaatcttc cacaatggac   360
gaaagtctga tggagcaacg ccgcgtgagt gaagaagggt ttcggctcgt aaaactctgt   420
tgttaaagaa gaacatatct gagagtaact gttcaggtat tgacgtgatt aaccagaaa    480
gccacggcta actacgtgcc agcagccgcg gtaatacgta ggtggcaagc gttgtccgga   540
tttattgggc gtaaagcgag cgcaggcggt tttttaagtc tgatgtgaaa gccttcggct   600
caaccgaaga agtgcatcgg aaactgggaa gcttgagtgc agaagaggac agtggaactc   660
catgtgtagc ggtgaaatgc gt                                           682

<210> SEQ ID NO 17
<211> LENGTH: 621
<212> TYPE: DNA
<213> ORGANISM: Lactobacillus plantarum

<400> SEQUENCE: 17
cggatttatt gggcgtaaag cgagcgcagg cggttttttta agtctgatgt gaaagccttc    60
ggctcaaccg aagaagtgca tcggaaactg gaaacttga gtgcagaaga ggacagtgga   120
actccatgtg tagcggtgaa atgcgtagat atatggaaga acaccagtgg cgaaggcggc   180
tgtctggtct gtaactgacg ctgaggctcg aaagtatggg tagcaaacag gattagatac   240
cctggtagtc cataccgtaa acgatgaatg ctaagtgttg gagggtttcc gcccttcagt   300
gctgcagcta acgcattaag cattccgcct ggggagtacg gccgcaaggc tgaaactcaa   360
aggaattgac gggggcccgc acaagcggtg gagcatgtgg tttaattcga agctacgcga   420
agaaccttac caggtcttga catactatgc aaatctaaga gattagacgt tcccttcggg   480
gacatggata caggtggtgc atggttgtcg tcagctcgtg tcgtgagatg ttgggttaag   540
tcccgcaacg agcgcaaccc ttattatcag ttgccagcat taagttgggc actctggtga   600
gactgccggt gacaaaccgg a                                            621

<210> SEQ ID NO 18
<211> LENGTH: 572
<212> TYPE: DNA
<213> ORGANISM: Lactobacillus plantarum

<400> SEQUENCE: 18
tggagcatgt ggtttaattc gaagctacgc gaagaacctt accaggtctt gacatactat    60
gcaaatctaa gagattagac gttcccttcg gggacatgga tacaggtggt gcatggttgt   120
cgtcagctcg tgtcgtgaga tgttgggtta agtcccgcaa cgagcgcaac ccttattatc   180
agttgccagc attaagttgg cactctggtg agactgccg gtgacaaacc ggaggaaggt    240

```
gggatgacg tcaaatcatc atgcccctta tgacctgggc tacacacgtg ctacaatgga    300
tggtacaacg agttgcgaac tcgcgagagt aagctaatct cttaaagcca ttctcagttc    360
ggattgtagg ctgcaactcg cctacatgaa gtcggaatcg ctagtaatcg cggatcagca    420
tgccgcggtg aatacgttcc cgggccttgt acacaccgcc cgtcacacca tgagagtttg    480
taacacccaa agtcggtggg gtaacctttt aggaaccagc cgcctaaggt gggacagatg    540
attagggtga agtcgtaaca aggtagcccg ta                                   572
```

```
<210> SEQ ID NO 19
<211> LENGTH: 720
<212> TYPE: DNA
<213> ORGANISM: Lactobacillus plantarum

<400> SEQUENCE: 19
actccccagg cggaatgctt aatgcgttag ctgcagcact gaagggcgga aaccctccaa     60
cacttagcat tcatcgttta cggtatggac taccagggta tctaatcctg tttgctaccc    120
atactttcga gcctcagcgt cagttacaga ccagacagcc gccttcgcca ctggtgttct    180
tccatatatc tacgcatttc accgctacac atggagttcc actgtcctct tctgcactca    240
agtttcccag tttccgatgc acttcttcgg ttgagccgaa ggctttcaca tcagacttaa    300 aaaccgcct cgctcgctt tacgcccaat aaatccggac aacgcttgcc acctacgtat    360
taccgcggct gctggcacgt agttagccgt ggctttctgg ttaaataccg tcaatacctg    420
aacagttact ctcagatatg ttcttcttta caacagagt tttacgagcc gaaacccttc    480
ttcactcacg cggcgttgct ccatcagact ttcgtccatt gtggaagatt ccctactgct    540
gcctcccgta ggagtttggg ccgtgtctca gtcccaatgt ggccgattac cctctcaggt    600
cggctacgta tcattgccat ggtgagccgt taccccacca tctagctaat acgccgcggg    660
accatccaaa agtgatagcc gaagccatct ttcaaactcg gaccatgcgg tccaagttgt    720
```

```
<210> SEQ ID NO 20
<211> LENGTH: 519
<212> TYPE: DNA
<213> ORGANISM: Lactobacillus plantarum

<400> SEQUENCE: 20
gctttctggt taaataccgt caatacctga acagttactc tcagatatgt tcttctttaa     60
caacagagtt ttacgagccg aaaaccttct tcactcacgc ggcgttgctc catcagactt    120
tcgtccattg tggaagattc cctactgctg cctcccgtag gagtttgggc cgtgtctcag    180
tcccaatgtg gccgattacc ctctcaggtc ggctacgtat cattgccatg gtgagccgtt    240
accccaccat ctagctaata cgccgcggga ccatccaaaa gtgatagccg aagccatctt    300
tcaaactcgg accatgcggt ccaagttgtt atgcggtatt agcatctgtt ccaggtgtt    360 atccccgct tctgggcagg tttcccacgt gttactcacc agttcgccac tcactcaaat    420
gtaaatcatg atgcaagcac caatcaatac caaagttcgt tcgacttgca tgtattaggc    480
acgccgccag cgttcgtcct gagccagatc aaactctaa                            519
```

```
<210> SEQ ID NO 21
<211> LENGTH: 687
<212> TYPE: DNA
<213> ORGANISM: Lactobacillus plantarum

<400> SEQUENCE: 21
```

```
ccaccttagg cggctggttc ctaaaaggtt accccaccga ctttgggtgt tacaaactct      60
catggtgtga cgggcggtgt gtacaaggcc cgggaacgta ttcaccgcgg catgctgatc     120
cgcgattact agcgattccg acttcatgta ggcgagttgc agcctacaat ccgaactgag     180
aatggcttta agagattagc ttactctcgc gagttcgcaa ctcgttgtac catccattgt     240
agcacgtgtg tagcccaggt cataagggc atgatgattt gacgtcatcc ccaccttcct     300
ccggtttgtc accggcagtc tcaccagagt gcccaactta atgctggcaa ctgataataa     360
gggttgcgct cgttgcggga cttaacccaa catctcacga cacgagctga cgacaaccat     420
gcaccacctg tatccatgtc cccgaaggga acgtctaatc tcttagattt gcatagtatg     480
tcaagacctg gtaaggttct tcgcgtagct tcgaattaaa ccacatgctc caccgcttgt     540
gcgggccccc gtcaattcct ttgagtttca gccttgcggc cgtactcccc aggcggaatg     600
cttaatgcgt tagctgcagc actgaaggc ggaaaccctc caacacttag cattcatcgt     660
ttacggtatg gactaccagg gtatcta                                         687

<210> SEQ ID NO 22
<211> LENGTH: 656
<212> TYPE: DNA
<213> ORGANISM: Lactobacillus reuteri

<400> SEQUENCE: 22
atgctagtcg tacgcactgg cccaactgat tgatggtgct tgcacctgat tgacgatgga      60
tcaccagtga gtggcggacg ggtgagtaac acgtaggtaa cctgccccgg agcggggat     120 aacatttgga aacagatgct aataccgcat aacaacaaaa gccacatggc ttttgtttga     180
agatggcttt ggctatcac tctgggatgg acctgcggtg cattagctag ttggtaaggt     240
aacggcttac caaggcgatg atgcatagcc gagttgagag actgatcggc cacaatggaa     300
ctgagacacg gtccatactc ctacgggagg cagcagtagg gaatcttcca caatgggcgc     360
aagcctgatg gagcaacacc gcgtgagtga agaagggttt cggctcgtaa agctctgttg     420
ttggagaaga acgtgcgtga gagtaactgt tcacgcagtg acggtatcca accagaaagt     480
cacggctaac tacgtgccag cagccgcggt aatacgtagg tggcaagcgt tatccggatt     540
tattgggcgt aaagcgagcg caggcggttg cttaggtctg atgtgaaagc cttcggctta     600
accgaagaag tgcatcggaa accgggcgac ttgagtgcag aagaggacag tggaac        656

<210> SEQ ID NO 23
<211> LENGTH: 719
<212> TYPE: DNA
<213> ORGANISM: Lactobacillus reuteri

<400> SEQUENCE: 23
tccggattta ttgggcgtaa agcgagcgca ggcggttgct taggtctgat gtgaaagcct      60
tcggcttaac cgaagaagtg catcggaaac cgggcgactt gagtgcagaa gaggacagtg     120
gaactccatg tgtagcggtg gaatgcgtag atatatggaa gaacaccagt ggcgaaggcg     180
gctgtctggt ctgcaactga cgctgaggct cgaaagcatg ggtagcgaac aggattagat     240
accctggtag tccatgccgt aaacgatgag tgctaggtgt tggagggttt ccgcccttca     300
gtgccggagc taacgcatta agcactccgc ctggggagta cgaccgcaag gttgaaactc     360
aaaggaattg acggggcccc gcacaagcgg tggagcatgt ggtttaattc gaagctacgc     420
gaagaacctt accaggtctt gacatcttgc gctaacctta gagataaggc gttcccttcg     480
gggacgcaat gacaggtggt gcatggtcgt cgtcagctcg tgtcgtgaga tgttgggtta     540
```

```
agtcccgcaa cgagcgcaac ccttgttact agttgccagc attaagttgg gcactctagt    600
gagactgccg gtgacaaacc ggaggaaggt ggggacgacg tcagatcatc atgcccctta    660
tgacctgggc tacacacgtg ctacaatgga cggtacaacg agtcgcaagc tcgcgagag    719
```

<210> SEQ ID NO 24
<211> LENGTH: 570
<212> TYPE: DNA
<213> ORGANISM: Lactobacillus reuteri

<400> SEQUENCE: 24

```
ggagcatgtg gtttaattcg aagctacgcg aagaacctta ccaggtcttg acatcttgcg     60
ctaaccttag agataaggcg ttcccttcgg ggacgcaatg acaggtggtg catggtcgtc    120
gtcagctcgt gtcgtgagat gttgggttaa gtcccgcaac gagcgcaacc cttgttacta    180
gttgccagca ttaagttggg cactctagtg agactgccgg tgacaaaccg gaggaaggtg    240
gggacgacgt cagatcatca tgcccttat gacctgggct acacacgtgc tacaatggac    300
ggtacaacga gtcgcaagct cgcgagagta agctaatctc ttaaagccgt tctcagttcg    360
gactgtaggc tgcaactcgc ctacacgaag tcggaatcgc tagtaatcgc ggatcagcat    420
gccgcggtga atacgttccc gggccttgta cacaccgccc gtcacaccat gggagtttgt    480
aacgcccaaa gtcggtggcc taacctttat ggagggagcc gcctaaggcg ggacagatga    540
ctggggtgaa gtcgtaacaa ggtagccgta                                    570
```

<210> SEQ ID NO 25
<211> LENGTH: 713
<212> TYPE: DNA
<213> ORGANISM: Lactobacillus reuteri

<400> SEQUENCE: 25

```
tccccaggcg gagtgcttaa tgcgttagct ccggcactga agggcggaaa ccctccaaca     60
cctagcactc atcgtttacg gcatggacta ccagggtatc taatcctgtt cgctacccat    120
gctttcgagc ctcagcgtca gttgcagacc agacagccgc cttcgccact ggtgttcttc    180
catatatcta cgcattccac cgctacacat ggagttccac tgtcctcttc tgcactcaag    240
tcgcccggtt tccgatgcac ttcttcggtt aagccgaagg ctttcacatc agacctaagc    300
aaccgcctgc gctcgcttta cgcccaataa atccggataa cgcttgccac ctacgtatta    360
ccgcggctgc tggcacgtag ttagccgtga ctttctggtt ggataccgtc actgcgtgaa    420
cagttactct cacgcacgtt cttctccaac aacagagctt tacgagccga acccttctt    480 cactcacgcg gtgttgctcc atcaggcttg cgcccattgt ggaagattcc ctactgctgc    540
ctcccgtagg agtatggacc gtgtctcagt tccattgtgg ccgatcagtc tctcaactcg    600
gctatgcatc atcgccttgg taagccgtta ccttaccaac tagctaatgc accgcaggtc    660
catcccagag tgatagccaa agccatcttt caaacaaaag ccatgtggct ttt           713
```

<210> SEQ ID NO 26
<211> LENGTH: 522
<212> TYPE: DNA
<213> ORGANISM: Lactobacillus reuteri

<400> SEQUENCE: 26

```
tttctggttg gataccgtca ctgcgtgaac agttactctc acgcacgttc ttctccaaca     60
acagagcttt acgagccgaa acccttcttc actcacgcgg tgttgctcca tcaggcttgc    120
```

```
gcccattgtg gaagattccc tactgctgcc tcccgtagga gtatggaccg tgtctcagtt    180
ccattgtggc cgatcagtct ctcaactcgg ctatgcatca tcgccttggt aagccgttac    240
cttaccaact agctaatgca ccgcaggtcc atcccagagt gatagccaaa gccatctttc    300
aaacaaaagc catgtggctt tgttgttat gcggtattag catctgtttc caaatgttat    360
cccccgctcc ggggcaggtt acctacgtgt tactcacccg tccgccactc actggtaatc    420
catcgtcaat caggtgcaag caccatcaat cagttgggcc agtgcgtacg acttgcatgt    480
attaggcaca ccgccggcgt tcatcctgag ccatgatcaa ac                       522
```

<210> SEQ ID NO 27
<211> LENGTH: 661
<212> TYPE: DNA
<213> ORGANISM: Lactobacillus reuteri

<400> SEQUENCE: 27

```
gcggctccct ccataaaggt tagcgccacc gactttgggc gttacaaact cccatggtgt     60
gacgggcggt gtgtacaagg cccgggaacg tattcaccgc ggcatgctga tccgcgatta    120
ctagcgattc cgacttcgtg taggcgagtt gcagcctaca gtccgaactg agaacggctt    180
taagagatta gcttactctc gcgagcttgc gactcgttgt accgtccatt gtagcacgtg    240
tgtagcccag gtcataaggg gcatgatgat ctgacgtcgt ccccaccttc ctccggtttg    300
tcaccggcag tctcactaga gtgcccaact taatgctggc aactagtaac aagggttgcg    360
ctcgttgcgg gacttaaccc aacatctcac gacacgagct gacgacgacc atgcaccacc    420
tgtcattgcg tccccgaagg gaacgcctta tctctaaggt tagcgcaaga tgtcaagacc    480
tggtaaggtt cttcgcgtag cttcgaatta aaccacatgc tccaccgctt gtgcgggccc    540
ccgtcaattc ctttgagttt caaccttgcg gtcgtactcc ccaggcggag tgcttaatgc    600
gttagctccg gcactgaagg gcggaaaccc tccaacacct agcactcatc gtttacggca    660
t                                                                    661
```

<210> SEQ ID NO 28
<211> LENGTH: 716
<212> TYPE: DNA
<213> ORGANISM: Lactobacillus reuteri

<400> SEQUENCE: 28

```
gtgtgcctaa tacatgcaag tcgtacgcac tggcccaact gattgatggt gcttgcacct     60
gattgacgat ggatcaccag tgagtggcgg acgggtgagt aacacgtagg taacctgccc    120
cggagcgggg gataacattt ggaaacagat gctaataccg cataacaaca aaagccacat    180
ggcttttgtt tgaaagatgg ctttggctat cactctggga tggacctgcg gtgcattagc    240
tagttggtaa ggtaacggct taccaaggcg atgatgcata gccgagttga gagactgatc    300
ggccacaatg gaactgagac acggtccata ctcctacggg aggcagcagt agggaatctt    360
ccacaatggg cgcaagcctg atggagcaac accgcgtgag tgaagaaggg tttcggctcg    420
taaagctctg ttgttggaga agaacgtgcg tgagagtaac tgttcacgca gtgacggtat    480
ccaaccagaa agtcacggct aactacgtgc cagcagccgc ggtaatacgt aggtggcaag    540
cgttatccgg atttattggg cgtaaagcga gcgcaggcgg ttgcttaggt ctgatgtgaa    600
agccttcggc ttaaccgaag aagtgcatcg gaaaccgggc gacttgagtg cagaagagga    660
cagtggaact ccatgtgtag cggtggaatg cgtagatata tggaagaaca ccagtg        716
```

<210> SEQ ID NO 29
<211> LENGTH: 683
<212> TYPE: DNA
<213> ORGANISM: Lactobacillus reuteri

<400> SEQUENCE: 29

```
tcggatttat tgggcgtaaa gcgagcgcag gcggttgctt aggtctgatg tgaaagcctt      60
cggcttaacc gaagaagtgc atcggaaacc gggcgacttg agtgcagaag aggacagtgg     120
aactccatgt gtagcggtgg aatgcgtaga tatatggaag acaccagtg gcgaaggcgg     180
ctgtctggtc tgcaactgac gctgaggctc gaaagcatgg gtagcgaaca ggattagata     240
ccctggtagt ccatgccgta acgatgagt gctaggtgtt ggagggtttc cgcccttcag     300
tgccggagct aacgcattaa gcactccgcc tggggagtac gaccgcaagg ttgaaactca     360
aaggaattga cgggggcccg cacaagcggt ggagcatgtg gtttaattcg aagctacgcg     420
aagaacctta ccaggtcttg acatcttgcg ctaaccttag agataaggcg ttcccttcgg     480
ggacgcaatg acaggtggtg catggtcgtc gtcagctcgt gtcgtgagat gttgggttaa     540
gtcccgcaac gagcgcaacc cttgttacta gttgccagca ttaagttggg cactctagtg     600
agactgccgg tgacaaaccg gaggaaggtg gggacgacgt cagatcatca tgccccttat     660
gacctgggct acacacgtgc tac                                              683
```

<210> SEQ ID NO 30
<211> LENGTH: 571
<212> TYPE: DNA
<213> ORGANISM: Lactobacillus reuteri

<400> SEQUENCE: 30

```
tggagcatgt ggtttaattc gaagctacgc gaagaacctt accaggtctt gacatcttgc      60
gctaacctta gagataaggc gttcccttcg ggacgcaat gacaggtggt gcatggtcgt     120
cgtcagctcg tgtcgtgaga tgttgggtta agtcccgcaa cgagcgcaac ccttgttact     180
agttgccagc attaagttgg gcactctagt gagactgccg gtgacaaacc ggaggaaggt     240
ggggacgacg tcagatcatc atgccccttat gacctgggc tacacacgtg ctacaatgga     300
cggtacaacg agtcgcaagc tcgcgagagt aagctaatct cttaaagccg ttctcagttc     360
ggactgtagg ctgcaactcg cctacacgaa gtcggaatcg ctagtaatcg cggatcagca     420
tgccgcggtg aatacgttcc cgggccttgt acacaccgcc cgtcacacca tgggagtttg     480
taacgcccaa agtcggtggc ctaacccttta tggagggagc cgcctaaggc gggacagatg     540
actggggtga agtcgtaaca aggtagccgt a                                    571
```

<210> SEQ ID NO 31
<211> LENGTH: 717
<212> TYPE: DNA
<213> ORGANISM: Lactobacillus reuteri

<400> SEQUENCE: 31

```
tactccccag gcggagtgct taatgcgtta gctccggcac tgaagggcgg aaaccctcca      60
acacctagca ctcatcgttt acggcatgga ctaccagggt atctaatcct gttcgctacc     120
catgctttcg agcctcagcg tcagttgcag accagacagc cgccttcgcc actggtgttc     180
ttccatatat ctacgcattc caccgctaca catggagttc cactgtcctc ttctgcactc     240
aagtcgcccg gtttccgatg cacttcttcg gttaagccga aggctttcac atcagaccta     300
agcaaccgcc tgcgctcgct ttacgcccaa taaatccgga taacgcttgc cacctacgta     360
```

| | |
|---|---|
| ttaccgcggc tgctggcacg tagttagccg tgactttctg gttggatacc gtcactgcgt | 420 |
| gaacagttac tctcacgcac gttcttctcc aacaacagag ctttacgagc cgaaacccctt | 480 |
| cttcactcac gcggtgttgc tccatcaggc ttgcgcccat tgtggaagat tccctactgc | 540 |
| tgcctcccgt aggagtatgg accgtgtctc agttccattg tggccgatca gtctctcaac | 600 |
| tcggctatgc atcatcgcct tggtaagccg ttaccttacc aactagctaa tgcaccgcag | 660 |
| gtccatccca gagtgatagc caaagccatc tttcaaacaa aagccatgtg cttttg | 717 |

<210> SEQ ID NO 32
<211> LENGTH: 522
<212> TYPE: DNA
<213> ORGANISM: Lactobacillus reuteri

<400> SEQUENCE: 32

| | |
|---|---|
| tttctggttg ataccgtca ctgcgtgaac agttactctc acgcacgttc ttctccaaca | 60 |
| acagagcttt acgagccgaa acccttcttc actcacgcgg tgttgctcca tcaggcttgc | 120 |
| gcccattgtg gaagattccc tactgctgcc tcccgtagga gtatggaccg tgtctcagtt | 180 |
| ccattgtggc cgatcagtct ctcaactcgg ctatgcatca tcgccttggt aagccgttac | 240 |
| cttaccaact agctaatgca ccgcaggtcc atcccagagt gatagccaaa gccatctttc | 300 |
| aaacaaaagc catgtggctt tgttgttat gcggtattag catctgtttc caaatgttat | 360 |
| cccccgctcc ggggcaggtt acctacgtgt tactcacccg tccgccactc actggtgatc | 420 |
| catcgtcaat caggtgcaag caccatcaat cagttgggcc agtgcgtacg acttgcatgt | 480 |
| attaggcaca ccgccggcgt ccatcctgag ccatgatcaa ac | 522 |

<210> SEQ ID NO 33
<211> LENGTH: 661
<212> TYPE: DNA
<213> ORGANISM: Lactobacillus reuteri

<400> SEQUENCE: 33

| | |
|---|---|
| ccgccttagg cggctccctc cataaaggtt aggccaccga ctttgggcgt tacaaactcc | 60 |
| catggtgtga cgggcggtgt gtacaaggcc cgggaacgta ttcaccgcgg catgctgatc | 120 |
| cgcgattact agcgattccg acttcgtgta ggcgagttgc agcctacagt ccgaactgag | 180 |
| aacggcttta agagattagc ttactctcgc gagcttgcga ctcgttgtac cgtccattgt | 240 |
| agcacgtgtg tagcccaggt cataagggc atgatgatct gacgtcgtcc ccaccttcct | 300 |
| ccggtttgtc accggcagtc tcactagagt gcccaactta atgctggcaa ctagtaacaa | 360 |
| gggttgcgct cgttgcggga cttaacccaa catctcacga cacgagctga cgacgaccat | 420 |
| gcaccacctg tcattgcgtc cccgaaggga acgccttatc tctaaggtta gcgcaagatg | 480 |
| tcaagacctg gtaaggttct tcgcgtagct tcgaattaaa ccacatgctc caccgcttgt | 540 |
| gcgggccccc gtcaattcct ttgagtttca accttgcggt cgtactcccc aggcggagtg | 600 |
| cttaatgcgt tagctccggc actgaagggc ggaaaccctc caacacctag cactcatcgt | 660 |
| t | 661 |

<210> SEQ ID NO 34
<211> LENGTH: 660
<212> TYPE: DNA
<213> ORGANISM: Lactobacillus plantarum

<400> SEQUENCE: 34

| | |
|---|---|
| gtgcctaata catgcaagtc gaacgaactc tggtattgat tggtgcttgc atcatgattt | 60 |

```
acatttgagt gagtggcgaa ctggtgagta acacgtggga aacctgccca gaagcggggg    120
ataacacctg gaaacagatg ctaataccgc ataacaactt ggaccgcatg gtccgagttt    180
gaaagatggc ttcggctatc acttttggat ggtcccgcgg cgtattagct agatggtgag    240
gtaacggctc accatggcaa tgatacgtag ccgacctgag agggtaatcg ccacattgg     300 gactgagaca cggcccaaac tcctacggga ggcagcagta gggaatcttc cacaatggac    360
gaaagtctga tggagcaacg ccgcgtgagt gaagaagggt ttcggctcgt aaaactctgt    420
tgttaaagaa gaacatatct gagagtaact gttcaggtat tgacggtatt taaccagaaa    480
gccacggcta actacgtgcc agcagccgcg gtaatacgta ggtggcaagc gttgtccgga    540
tttattgggc gtaaagcgag cgcaggcggt tttttaagtc tgatgtgaaa gccttcggct    600
caaccgaaga agtgcatcgg aaactgggaa acttgagtgc agaagaggac agtggaactc    660
```

```
<210> SEQ ID NO 35
<211> LENGTH: 670
<212> TYPE: DNA
<213> ORGANISM: Lactobacillus plantarum

<400> SEQUENCE: 35
```

```
ggatttattg ggcgtaaagc gagcgcaggc ggttttttaa gtctgatgtg aaagccttcg     60
gctcaaccga agaagtgcat cggaaactgg gaaacttgag tgcagaagag gacagtggaa    120
ctccatgtgt agcggtgaaa tgcgtagata tatggaagaa caccagtggc gaaggcggct    180
gtctggtctg taactgacgc tgaggctcga agtatgggt agcaaacagg attagatacc     240
ctggtagtcc ataccgtaaa cgatgaatgc taagtgttgg agggtttccg ccccttcagtg    300 ctgcagctaa cgcattaagc attccgcctg gggagtacgg ccgcaaggct gaaactcaaa    360
ggaattgacg ggggcccgca caagcggtgg agcatgtggt ttaattcgaa gctacgcgaa    420
gaaccttacc aggtcttgac atactatgca aatctaagag attagacgtt cccttcgggg    480
acatggatac aggtggtgca tggttgtcgt cagctcgtgt cgtgagatgt tgggttaagt    540
cccgcaacga gcgcaaccct tattatcagt tgccagcatt aagttgggca ctctggtgag    600
actgccggtg acaaaccgga ggaaggtggg gatgacgtca aatcatcatg cccttatga     660 cctgggctac                                                           670
```

```
<210> SEQ ID NO 36
<211> LENGTH: 573
<212> TYPE: DNA
<213> ORGANISM: Lactobacillus plantarum

<400> SEQUENCE: 36
```

```
gtggagcatg tggtttaatt cgaagctacg cgaagaacct taccaggtct tgacatacta     60
tgcaaatcta agagattaga cgttcccttc ggggacatgg atacaggtgg tgcatggttg    120
tcgtcagctc gtgtcgtgag atgttgggtt aagtcccgca acgagcgcaa cccttattat    180
cagttgccag cattaagttg gcactctggt gagactgccg gtgacaaaac cggaggaagg    240
tggggatgac gtcaaatcat catgcccctt atgacctggg ctacacacgt gctacaatgg    300
atggtacaac gagttgcgaa ctcgcgagag taagctaatc tcttaaagcc attctcagtt    360
cggattgtag gctgcaactc gcctacatga agtcggaatc gctagtaatc gcggatcagc    420
atgccgcggt gaatacgttc ccgggccttg tacacaccgc ccgtcacacc atgagagttt    480
gtaacaccca aagtcggtgg ggtaaccttt taggaaccag ccgcctaagg tgggacagat    540
```
gattagggtg aagtcgtaac aaggtagccc gta        573

<210> SEQ ID NO 37
<211> LENGTH: 743
<212> TYPE: DNA
<213> ORGANISM: Lactobacillus plantarum

<400> SEQUENCE: 37
actccccagg cggaatgctt aatgcgttag ctgcagcact gaagggcgga aaccctccaa        60
cacttagcat tcatcgttta cggtatggac taccagggta tctaatcctg tttgctaccc       120
atactttcga gcctcagcgt cagttacaga ccagacagcc gccttcgcca ctggtgttct       180
tccatatatc tacgcatttc accgctacac atggagttcc actgtcctct tctgcactca       240
agtttcccag tttccgatgc acttcttcgg ttgagccgaa ggctttcaca tcagacttaa       300
aaaaccgcct gcgctcgctt tacgcccaat aaatccggac aacgcttgcc acctacgtat       360
taccgcggct gctggcacgt agttagccgt ggctttctgg ttaaataccg tcaataccctg       420
aacagttact ctcagatatg ttcttcttta acaacagagt tttacgagcc gaaacccttc       480
ttcactcacg cggcgttgct ccatcagact ttcgtccatt gtggaagatt ccctactgct       540
gcctcccgta ggagtttggg ccgtgtctca gtcccaatgt ggccgattac cctctcaggt       600
cggctacgta tcattgccat ggtgagccgt tacctcacca tctagctaat acgccgcggg       660
accatccaaa agtgatagcc gaagccatct ttcaaactcg gaccatgcgg tccaagttgt       720
tatgcggtat tagcatctgt ttc                                               743

<210> SEQ ID NO 38
<211> LENGTH: 513
<212> TYPE: DNA
<213> ORGANISM: Lactobacillus plantarum

<400> SEQUENCE: 38
tttctggtta ataccgtcaa ataccctgaac agttactctc agatatgttc ttctttaaca        60
acagagtttt acgagccgaa acccttcttc actcacgcgg cgttgctcca tcagactttc       120
gtccattgtg gaagattccc tactgctgcc tcccgtagga gtttgggccg tgtctcagtc       180
ccaatgtggc cgattaccct ctcaggtcgg ctacgtatca ttgccatggt gagccgttac       240
ctcaccatct agctaatacg ccgcgggacc atccaaaagt gatagccgaa gccatctttc       300
aaactcggac catgcggtcc aagttgttat gcggtattag catctgtttc caggtgttat       360
ccccgcttc tgggcaggtt cccacgtgt tactcaccag ttcgccactc actcaaatgt       420
aaatcatgat gcaagcacca atcaatacca gagttcgttc gacttgcatg tattaggcac       480
gccgccagcg ttcgtcctga gccatgatca aac                                    513

<210> SEQ ID NO 39
<211> LENGTH: 747
<212> TYPE: DNA
<213> ORGANISM: Lactobacillus plantarum

<400> SEQUENCE: 39
ccaccttagg cggctggttc ctaaaaggtt accccaccga ctttgggtgt tacaaactct        60
catggtgtga cgggcggtgt gtacaaggcc cgggaacgta ttcaccgcgg catgctgatc       120
cgcgattact agcgattccg acttcatgta ggcgagttgc agcctacaat ccgaactgag       180
aatggcttta agagattagc ttactctcgc gagttcgcaa ctcgttgtac catccattgt       240
agcacgtgtg tagcccaggt cataaggggc atgatgattt gacgtcatcc ccaccttcct       300

```
ccggtttgtc accggcagtc tcaccagagt gcccaactta atgctggcaa ctgataataa    360
ggggttgcgct cgttgcggga cttaacccaa catctcacga cacgagctga cgacaaccat    420
gcaccacctg tatccatgtc cccgaaggga acgtctaatc tcttagattt gcatagtatg    480
tcaagacctg gtaaggttct tcgcgtagct tcgaattaaa ccacatgctc caccgcttgt    540
gcgggccccc gtcaattcct ttgagtttca gccttgcggc cgtactcccc aggcggaatg    600
cttaatgcgt tagctgcagc actgaagggc ggaaaccctc caacacttag cattcatcgt    660
ttacggtatg gactaccagg gtatctaatc ctgtttgcta cccatacttt cgagcctcag    720
cgtcagttac agaccagaca gccgcct                                         747

<210> SEQ ID NO 40
<211> LENGTH: 617
<212> TYPE: DNA
<213> ORGANISM: Lactobacillus johnsonii

<400> SEQUENCE: 40
gtgcctaata catgcaagtc gagcgagctt gcctagatga ttttagtgct tgcactaaat     60
gaaactagat acaagcgagc ggcggacggg tgagtaacac gtgggtaacc tgcccaagag    120
actgggataa cacctggaaa cagatgctaa taccggataa caacactaga cgcatgtcta    180
gagtttgaaa gatggttctg ctatcactct tggatggacc tgcggtgcat tagctagttg    240
gtaaggtaac ggcttaccaa ggcaatgatg catagccgag ttgagagact gatcggccac    300
attgggactg agacacggcc caaactccta cgggaggcag cagtagggaa tcttccacaa    360
tggacgaaag tctgatggag caacgccgcg tgagtgaaga agggtttcgg ctcgtaaagc    420
tctgttggta gtgaagaaag atagaggtag taactggcct ttatttgacg gtaattactt    480
agaaagtcac ggctaactac gtgccagcag ccgcggtaat acgtaggtgg caagcgttgt    540
ccggatttat tgggcgtaaa gcgagtgcag gcggttcaat aagtctgatg tgaaagcctt    600
cggctcaacc ggagaat                                                   617

<210> SEQ ID NO 41
<211> LENGTH: 523
<212> TYPE: DNA
<213> ORGANISM: Lactobacillus johnsonii

<400> SEQUENCE: 41
tccggattta ttgggcgtaa agcgagtgca ggcggttcaa taagtctgat gtgaaagcct     60
tcggctcaac cggagaattg catcagaaac tgttgaactt gagtgcagaa gaggagagtg    120
gaactccatg tgtagcggtg gaatgcgtag atatatggaa gaacaccagt ggcgaaggcg    180
gctctctggt ctgcaactga cgctgaggct cgaaagcatg ggtagcgaac aggattagat    240
accctggtag tccatgccgt aaacgatgag tgctaagtgt tgggaggttt ccgcctctca    300
gtgctgcagc taacgcatta agcactccgc ctggggagta cgaccgcaag gttgaaactc    360
aaaggaattg acggggcccc gcacaagcgg tggagcatgt ggtttaattc gaagcaacgc    420
gaagaacctt accaggtctt gacatccagt gcaaacctaa gagattaggt gttcccttcg    480
gggacgctga gacaggtggt gcatggctgt cgtcagctcg tgt                      523

<210> SEQ ID NO 42
<211> LENGTH: 482
<212> TYPE: DNA
<213> ORGANISM: Lactobacillus johnsonii
```

```
<400> SEQUENCE: 42
ggagcatgtg gtttaattcg aagcaacgcg aagaaccttä ccaggtcttg acatccagtg      60
caaacctaag agattaggtg tgtcccttcg gggacgctga acaggtggt gcatggctgt     120 cgtcagctcg tgtcgtgaga tgttgggtta agtcccgcaa cgagcgcaac ccttgtcatt    180
agttgccatc attaagttgg gcactctaat gagactgccg gtgacaaacc ggaggaaggt    240
ggggatgacg tcaagtcatc atgcccctta tgacctgggc tacacacgtg ctacaatgga    300
cggtacaacg agaagcgaac ctgcgaaggc aagcggatct cttaaagccg ttctcagttc    360
ggactgtagg ctgcaactcg cctacacgaa gctggaatcg ctagtaatcg cggatcagca    420
cgccgcggtg aatacgttcc cgggccttgt acacaccgcc cgtcacacca tgagagtctg    480
ta                                                                    482

<210> SEQ ID NO 43
<211> LENGTH: 719
<212> TYPE: DNA
<213> ORGANISM: Lactobacillus johnsonii

<400> SEQUENCE: 43
actccccagg cggagtgctt aatgcgttag ctgcagcact gagaggcgga aacctcccaa     60
cacttagcac tcatcgttta cggcatggac taccagggta tctaatcctg ttcgctaccc    120
atgctttcga gcctcagcgt cagttgcaga ccagagagcc gccttcgcca ctggtgttct    180
tccatatatc tacgcattcc accgctacac atggagttcc actctcctct tctgcactca    240
agttcaacag tttctgatgc aattctccgg ttgagccgaa ggctttcaca tcagacttat    300
tgaaccgcct gcactcgctt tacgcccaat aaatccggac aacgcttgcc acctacgtat    360
taccgcggct gctggcacgt agttagccgt gactttctaa gtaattaccg tcaaataaag    420
gccagttact acctctatct ttcttcacta ccaacagagc tttacgagcc gaaacccttc    480
ttcactcacg cggcgttgct ccatcagact ttcgtccatt gtggaagatt ccctactgct    540
gcctcccgta ggagtttggg ccgtgtctca gtcccaatgt ggccgatcag tctctcaact    600
cggctatgca tcattgcctt ggtaagccgt taccttacca actagctaat gcaccgcagg    660
tccatccaag agtgatagca gaaccatctt tcaaactcta gacatgcgtc tagtgttgt    719

<210> SEQ ID NO 44
<211> LENGTH: 521
<212> TYPE: DNA
<213> ORGANISM: Lactobacillus johnsonii

<400> SEQUENCE: 44
actttctaag taattaccgt caaataaagg ccagttacta cctctatctt tcttcactac     60
caacagagct ttacgagccg aaacccttct tcactcacgc ggcgttgctc catcagactt    120
tcgtccattg tggaagattc cctactgctg cctcccgtag gagtttgggc cgtgtctcag    180
tcccaatgtg gccgatcagt ctctcaactc ggctatgcat cattgccttg gtaagccgtt    240
accttaccaa ctagctaatg caccgcaggt ccatccaaga gtgatagcag aaccatcttt    300
caaactctag acatgcgtct agtgttgtta ccggtatta gcatctgttt ccaggtgtta    360
tcccagtctc ttgggcaggt tacccacgtg ttactcaccc gtccgccgct cgcttgtatc    420
tagtttcatt tagtgcaagc actaaaatca tctaggcaag ctcgctcgac ttgcatgtat    480
taggcacgcc gccagcgttc gtcctgagcc atgatcaaac t                        521
```

```
<210> SEQ ID NO 45
<211> LENGTH: 748
<212> TYPE: DNA
<213> ORGANISM: Lactobacillus johnsonii

<400> SEQUENCE: 45
ctaccttaga cggctgactc ctataaaggt tatcccaccg gctttgggtg ttacagactc    60
tcatggtgtg acgggcggtg tgtacaaggc ccgggaacgt attcaccgcg gcgtgctgat   120
ccgcgattac tagcgattcc agcttcgtgt aggcgagttg cagcctacag tccgaactga   180
gaacggcttt aagagatccg cttgccttcg caggttcgct tctcgttgta ccgtccattg   240
tagcacgtgt gtagcccagg tcataagggg catgatgact tgacgtcatc ccaccttcc   300 tccggtttgt caccggcagt ctcattagag tgcccaactt aatgatggca actaatgaca   360
agggttgcgc tcgttgcggg acttaaccca acatctcacg acacgagctg acgacagcca   420
tgcaccacct gtctcagcgt ccccgaaggg aacacctaat ctcttaggtt tgcactggat   480
gtcaagacct ggtaaggttc ttcgcgttgc ttcgaattaa accacatgct ccaccgcttg   540
tgcgggcccc cgtcaattcc tttgagtttc aaccttgcgg tcgtactccc caggcggagt   600
gcttaatgcg ttagctgcag cactgagagg cggaaacctc ccaacactta gcactcatcg   660
tttacggcat ggactaccag ggtatctaat cctgttcgct acccatgctt tcgagcctca   720
gcgtcagttg cagaccagag agccgcct                                      748

<210> SEQ ID NO 46
<211> LENGTH: 694
<212> TYPE: DNA
<213> ORGANISM: Lactobacillus reuteri

<400> SEQUENCE: 46
gtgtgcctaa tacatgcaag tcgtacgcac tggcccaact gattgatggt gcttgcacct    60
gattgacgat ggatcaccag tgagtggcgg acgggtgagt aacacgtagg taacctgccc   120
cggagcgggg gataacattt ggaaacagat gctaataccg cataacaaca aaagccacat   180
ggcttttgtt tgaaagatgg cttcggctat cactctggga tggacctgcg gtgcattagc   240
tagttggtaa ggtaacggct taccaaggcg atgatgcata gccagttga gagactgatc    300 ggccacaatg gaactgagac acggtccata ctcctacggg aggcagcagt agggaatctt   360
ccacaatggg cgcaagcctg atggagcaac accgcgtgag tgaagaaggg tttcggctcg   420
taaagctctg ttgttggaga gaacgtgcg tgagagtaac tgttcacgca gtgacggtat   480
ccaaccagaa agtcacggct aactacgtgc cagcagccgc ggtaatacgt aggtggcaag   540
cgttatccgg atttattggg cgtaaagcga gcgcaggcgg ttgcttaggt ctgatgtgaa   600
agccttcggc ttaaccgaag aagtgcatcg gaaaccgggc gacttgagtg cagaagagga   660
cagtggaact ccatgtgtag cggtggaatg cgta                               694

<210> SEQ ID NO 47
<211> LENGTH: 409
<212> TYPE: DNA
<213> ORGANISM: Lactobacillus reuteri

<400> SEQUENCE: 47
cggatttatt gggcgtaaag cgagcgcagg cggttgctta ggtctgatgt gaaagccttc    60
ggcttaaccg aagaagtgca tcggaaaccg ggcgacttga gtgcagaaga ggacagtgga   120
actccatgtg tagcggtgga atgcgtagat atatggaaga acaccagtgg cgaaggcggc   180
```

```
tgtctggtct gcaactgacg ctgaggctcg aaagcatggg tagcgaacag gattagatac    240
cctggtagtc catgccgtaa acgatgagtg ctaggtgttg gagggtttcc gcccttcagt    300
gccggagcta acgcattaag cactccgcct ggggagtacg accgcaaggt tgaaactcaa    360
aggaattgac gggggcccgc acaagcggtg gagcatgtgg tttaattcg                409

<210> SEQ ID NO 48
<211> LENGTH: 467
<212> TYPE: DNA
<213> ORGANISM: Lactobacillus reuteri

<400> SEQUENCE: 48
gagcatgtgg tttaattcga agctacgcga agaaccttac caggtcttga catcttgcgc     60
taaccttaga gataaggcgt tcccttcggg gacgcaatga caggtggtgc atggtcgtcg    120
tcagctcgtg tcgtgagatg ttgggttaag tcccgcaacg agcgcaaccc ttgttactag    180
ttgccagcat taagttgggc actctagtga gactgccggt gacaaaccgg aggaaggtgg    240
ggacgacgtc agatcatcat gccccttatg acctgggcta cacacgtgct acaatggacg    300
gtacaacgag tcgcaagctc gcgagagtaa gctaatctct aaagccgttc tcagttcgg     360 actgtaggct gcaactcgcc tacacgaagt cggaatcgct agtaatcgcg gatcagcatg    420
ccgcggtgaa tacgttcccg ggccttgtac acaccgcccg tcacacc                  467

<210> SEQ ID NO 49
<211> LENGTH: 661
<212> TYPE: DNA
<213> ORGANISM: Lactobacillus reuteri

<400> SEQUENCE: 49
actccccagg cggagtgctt aatgcgttag ctccggcact gaagggcgga aaccctccaa     60
cacctagcac tcatcgttta cggcatggac taccagggta tctaatcctg ttcgctaccc    120
atgctttcga gcctcagcgt cagttgcaga ccagacagcc gccttcgcca ctggtgttct    180
tccatatatc tacgcattcc accgctacac atggagttcc actgtcctct ctgcactca     240 agtcgcccgg tttccgatgc acttcttcgg ttaagccgaa ggctttcaca tcagacctaa    300
gcaaccgcct gcgctcgctt tacgcccaat aaatccggat aacgcttgcc acctacgtat    360
taccgcggct gctggcacgt agttagccgt gactttctgg ttggataccg tcactgcgtg    420
aacagttact ctcacgcacg ttcttctcca caacagagc tttacgagcc gaaacccttc     480
ttcactcacg cggtgttgct ccatcaggct tgcgcccatt gtggaagatt ccctactgct    540
gcctcccgta ggagtatgga ccgtgtctca gttccattgt ggccgatcag tctctcaact    600
cggctatgca tcatcgccttt ggtaagccgt taccttacca actagctaat gcaccgcagg    660
t                                                                   661

<210> SEQ ID NO 50
<211> LENGTH: 525
<212> TYPE: DNA
<213> ORGANISM: Lactobacillus reuteri

<400> SEQUENCE: 50
tttctggttg ataccgtca ctgcgtgaac agttactctc acgcacgttc ttctccaaca      60
acagagcttt acgagccgaa acccttcttc actcacgcgg tgttgctcca tcaggcttgc    120
gcccattgtg gaagattccc tactgctgcc tcccgtagga gtatggaccg tgtctcagtt    180
ccattgtggc cgatcagtct ctcaactcgg ctatgcatca tcgccttggt aagccgttac    240
```

```
cttaccaact agctaatgca ccgcaggtcc atcccagagt gatagccaaa gccatctttc    300
aaacaaaagc catgtggctt ttgttgttat gcggtattag catctgtttc caaatgttat    360
cccccgctcc ggggcaggtt acctacgtgt tactcacccg tccgccactc actggtgatc    420
catcgtcaat caggtgcaag caccatcaat cagttgggcc agtgcgtacg acttgcatgt    480
attaggcaca ccgccggcgt tcatcctgag ccatgatcaa actct                    525
```

<210> SEQ ID NO 51
<211> LENGTH: 761
<212> TYPE: DNA
<213> ORGANISM: Lactobacillus reuteri

<400> SEQUENCE: 51

```
tcccgcctta ggcggctccc tccataatgg ttaggccacc gactttgggc gttacaaact     60
cccatggtgt gacgggcggt gtgtacaagg cccgggaacg tattcaccgc ggcatgctga    120
tccgcgatta ctagcgattc cgacttcgtg taggcgagtt gcagcctaca gtccgaactg    180
agaacggctt taagagatta gcttactctc gcgagcttgc gactcgttgt accgtccatt    240
gtagcacgtg tgtagcccag gtcataaggg gcatgatgat ctgacgtcgt ccccaccttc    300
ctccggtttg tcaccggcag tctcactaga gtgcccaact taatgctggc aactagtaac    360
aagggttgcg ctcgttgcgg gacttaaccc aacatctcac gacacgagct gacgacgacc    420
atgcaccacc tgtcattgcg tccccgaagg gaacgcctta tctctaaggt tagcgcaaga    480
tgtcaagacc tggtaaggtt cttcgcgtag cttcgaatta aaccacatgc tccaccgctt    540
gtgcgggccc ccgtcaattc ctttgagttt caaccttgcg gtcgtactcc ccaggcggag    600
tgcttaatgc gttagctccg gcactgaagg gcggaaaccc tccaacacct agcactcatc    660
gtttacggca tggactacca gggtatctaa tcctgttcgc tacccatgct ttcgagcctc    720
agcgtcagtt gcagaccaga cagccgcctt cgccactggt g                        761
```

<210> SEQ ID NO 52
<211> LENGTH: 651
<212> TYPE: DNA
<213> ORGANISM: Lactobacillus reuteri

<400> SEQUENCE: 52

```
gtgtgcctaa tacatgcaag tcgtacgcac tggcccaact gattgatggt gcttgcacct     60
gattgacgat ggatcaccag tgagtggcgg acgggtgagt aacacgtagg taacctgccc    120
cggagcgggg gataacattt ggaaacagat gctaataccg cataacaaca aaagccacat    180
ggcttttgtt tgaaagatgg ctttggctat cactctggga tggacctgcg gtgcattagc    240
tagttggtaa ggtaacggct taccaaggcg atgatgcata gccgagttga gactgatc     300 ggccacaatg gaactgagac acggtccata ctcctacggg aggcagcagt agggaatctt    360
ccacaatggg cgcaagcctg atggagcaac accgcgtgag tgaagaaggg tttcggctcg    420
taaagctctg ttgttggaga agaacgtgcg tgagagtaac tgttcacgca gtgacggtat    480
ccaaccagaa agtcacggct aactacgtgc cagcagccgc ggtaatacgt aggtggcaag    540
cgttatccgg atttattggg cgtaaagcga gcgcaggcgg ttgcttaggt ctgatgtgaa    600
agccttcggc ttaaccgaag aagtgcatcg gaaaccgggc gacttgagtg c             651
```

<210> SEQ ID NO 53
<211> LENGTH: 645
<212> TYPE: DNA

<213> ORGANISM: Lactobacillus reuteri

<400> SEQUENCE: 53

| | | | | | | |
|---|---|---|---|---|---|---|
| ttatccggat | ttattgggcg | taaagcgagc | gcaggcggtt | gcttaggtct | gatgtgaaag | 60 |
| ccttcggctt | aaccgaagaa | gtgcatcgga | aaccgggcaa | cttgagtgca | gaagaggaca | 120 |
| gtggaactcc | atgtgtagcg | gtggaatgcg | tagatatatg | gaagaacacc | agtggcgaag | 180 |
| gcggctgtct | ggtctgcaac | tgacgctgag | gctcgaaagc | atgggtagcg | aacaggatta | 240 |
| gataccctgg | tagtccatgc | cgtaaacgat | gagtgctagg | tgttgagggt | tttccgccct | 300 |
| tcagtgccgg | agctaacgca | ttaagcactc | cgcctgggga | gtacgaccgc | aaggttgaaa | 360 |
| ctcaaaggaa | ttgacggggg | cccgcacaag | cggtggagca | tgtggtttaa | ttcgaagcta | 420 |
| cgcgaagaac | cttaccaggt | cttgacatct | tgcgctaacc | ttagagataa | ggcgtccctt | 480 |
| cggggacgca | atgacaggtg | gtgcatggtc | gtcgtcagct | cgtgtcgtga | gatgttgggt | 540 |
| taagtcccgc | aacgagcgca | acccttgtta | ctagttgcca | gcattaagtt | gggcactcta | 600 |
| gtgagactgc | cggtgacaaa | ccggaggaag | gtggggacga | cgtca | | 645 |

<210> SEQ ID NO 54
<211> LENGTH: 573
<212> TYPE: DNA
<213> ORGANISM: Lactobacillus reuteri

<400> SEQUENCE: 54

| | | | | | | |
|---|---|---|---|---|---|---|
| ggtggagcat | gtggtttaat | tcgaagctac | gcgaagaacc | ttaccaggtc | ttgacatctt | 60 |
| gcgctaacct | tagagataag | gcgttccctt | cggggacgca | atgacaggtg | gtgcatggtc | 120 |
| gtcgtcagct | cgtgtcgtga | gatgttgggt | taagtcccgc | aacgagcgca | acccttgtta | 180 |
| ctagttgcca | gcattaagtt | gggcactcta | gtgagactgc | cggtgacaaa | ccggaggaag | 240 |
| gtggggacga | cgtcagatca | tcatgcccct | tatgacctgg | gctacacacg | tgctacaatg | 300 |
| gacggtacaa | cgagtcgcaa | gctcgcgaga | gtaagctaat | ctcttaaagc | cgttctcagt | 360 |
| tcggactgta | ggctgcaact | cgcctacacg | aagtcggaat | cgctagtaat | cgcggatcag | 420 |
| catgccgcgg | tgaatacgtt | cccgggcctt | gtacacaccg | cccgtcacac | catgggagtt | 480 |
| tgtaacgccc | aaagtcggtg | gcctaaccat | tatggaggga | gccgcctaag | gcgggacaga | 540 |
| tgactggggt | gaagtcgtaa | caaggtagcc | gta | | | 573 |

<210> SEQ ID NO 55
<211> LENGTH: 705
<212> TYPE: DNA
<213> ORGANISM: Lactobacillus reuteri

<400> SEQUENCE: 55

| | | | | | | |
|---|---|---|---|---|---|---|
| tactccccag | gcggagtgct | taatgcgtga | gctccggcac | tgaagggcgg | aaaccctcca | 60 |
| acacctagca | ctcatcgttt | acggcatgga | ctaccagggt | atctaatcct | gttcgctacc | 120 |
| catgctttcg | agcctcagcg | tcagttgcag | accagacagc | cgccttcgcc | actggtgttc | 180 |
| ttccatatat | ctacgcattc | caccgctaca | catggagttc | cactgtcctc | ttctgcactc | 240 |
| aagtcgcccg | gttccgatg | cacttcttcg | gttaagccga | aggctttcac | atcagaccta | 300 |
| agcaaccgcc | tgcgctcgct | ttacgcccaa | taaatccgga | taacgcttgc | cacctacgta | 360 |
| ttaccgcggc | tgctggcacg | tagttagccg | tgactttctg | gttggatacc | gtcactgcgt | 420 |
| gaacagttac | tctcacgcac | gttcttctcc | aacaacagag | ctttacgagc | cgaaaccctt | 480 |
| cttcactcac | gcggtgttgc | tccatcaggc | ttgcgcccat | tgtggaagat | tccctactgc | 540 |

| | |
|---|---|
| tgcctcccgt aggagtatgg accgtgtctc agttccattg tggccgatca gtctctcaac | 600 |
| tcggctatgc atcatcgcct tggtaagccg ttaccttacc aactagctaa tgcaccgcag | 660 |
| gtccatccca gagtgatagc caaagccatc tttcaaacaa aagcc | 705 |

<210> SEQ ID NO 56
<211> LENGTH: 527
<212> TYPE: DNA
<213> ORGANISM: Lactobacillus reuteri

<400> SEQUENCE: 56

| | |
|---|---|
| gtgactttct ggttggatac cgtcactgcg tgaacagtta ctctcacgca cgtgcttctc | 60 |
| caacaacaga gctttacgag ccgaaaccct tcttcactca cgcggtgttg ctccatcagg | 120 |
| cttgcgccca ttgtggaaga ttccctactg ctgcctcccg taggagtatg gaccgtgtct | 180 |
| cagttccatt gtggccgatc agtctctcaa ctcggctatg catcatcgcc ttggtaagcc | 240 |
| gttaccttac caactagcta atgcaccgca ggtccatccc agagtgatag ccaaagccat | 300 |
| ctttcaaaca aaagccatgt ggcttttgtt gttatgcggt attagcatct gtttccaaat | 360 |
| gttatccccc gctccggggc aggttaccta cgtgttactc acccgtccgc cactcactgg | 420 |
| tgatccatcg tcaatcaggt gcaagcacca tcaatcagtt gggccagtgc gtacgacttg | 480 |
| catgtattag gcacaccgcc ggcgttcatc ctgagccatg atcaaac | 527 |

<210> SEQ ID NO 57
<211> LENGTH: 719
<212> TYPE: DNA
<213> ORGANISM: Lactobacillus reuteri

<400> SEQUENCE: 57

| | |
|---|---|
| tcccgcactt aggcggctcc ctccataatg gttaggccac cgactttggg cgttacaaac | 60 |
| tcccatggtg tgacgggcgg tgtgtacaag gcccgggaac gtattcaccg cggcatgctg | 120 |
| atccgcgatt actagcgatt ccgacttcgt gtaggcgagt tgcagcctac agtccgaact | 180 |
| gagaacggct ttaagagatt agcttactct cgcgagcttg cgactcgttg taccgtccat | 240 |
| tgtagcacgt gtgtagccca ggtcataagg ggcatgatga tctgacgtcg tccccacctt | 300 |
| cctccggttt gtcaccggca gtctcactag agtgcccaac ttaatgctgg caactagtaa | 360 |
| caagggttgc gctcgttgcg ggacttaacc caacatctca cgacacgagc tgacgacgac | 420 |
| catgcaccac ctgtcattgc gtccccgaag ggaacgcctt atctctaagg ttagcgcaag | 480 |
| atgtcaagac ctggtaaggt tcttcgcgta gcttcgaatt aaaccacatg ctccaccgct | 540 |
| tgtgcgggcc ccgtcaatt cctttgagtt tcaaccttgc ggtcgtactc cccaggcgga | 600 |
| gtgcttaatg cgttagctcc ggcactgaag ggcggaaacc ctccaacacc tagcactcat | 660 |
| cgtttacggc atggactacc agggtatcta atcctgttcg ctacccatgc tttcgagcc | 719 |

<210> SEQ ID NO 58
<211> LENGTH: 690
<212> TYPE: DNA
<213> ORGANISM: Lactobacillus johnsonii

<400> SEQUENCE: 58

| | |
|---|---|
| gcgtgcctaa tacatgcaag tcgagcgagc ttgcctagat gattttagtg cttgcactaa | 60 |
| atgaaactag atacaagcga gcggcggacg ggtgagtaac acgtgggtaa cctgcccaag | 120 |
| agactgggat aacacctgga aacagatgct aataccggat aacaacacta gacgcatgtc | 180 |

```
tagagtttga aagatggttc tgctatcact cttggatgga cctgcggtgc attagctagt    240
tggtaaggta acggcttacc aaggcaatga tgcatagccg agttgagaga ctgatcggcc    300
acattgggac tgagacacgg cccaaactcc tacgggaggc agcagtaggg aatcttccac    360 aatgacgaa agtctgatgg agcaacgccg cgtgagtgaa gaagggtttc ggctcgtaaa     420
gctctgttgg tagtgaagaa agatagaggt agtaactggc ctttatttga cggtaattac    480
ttagaaagtc acggctaact acgtgccagc agccgcggta atacgtaggt ggcaagcgtt    540
gtccggattt attgggcgta aagcgagtgc aggcggttca ataagtctga tgtgaaagcc    600
ttcggctcaa ccggagaatt gcatcagaaa ctgttgaact tgagtgcaga agaggagagt    660
ggaactccat gtgtagcggt ggaatgcgta                                     690
```

<210> SEQ ID NO 59
<211> LENGTH: 638
<212> TYPE: DNA
<213> ORGANISM: Lactobacillus johnsonii

<400> SEQUENCE: 59

```
tgtccggatt tattgggcgt aaagcgagtg caggcggttc aataagtctg atgtgaaagc     60
cttcggctca accggagaat tgcatcagaa actgttgaac ttgagtgcag aagaggagag    120
tggaactcca tgtgtagcgg tggaatgcgt agatatatgg aagaacacca gtggcgaagg    180
cggctctctg gtctgcaact gacgctgagg ctcgaaagca tgggtagcga acaggattag    240
ataccctggt agtccatgcc gtaaacgatg agtgctaagt gttgggaggt ttccgcctct    300
cagtgctgca gctaacgcat taagcactcc gcctggggag tacgaccgca aggttgaaac    360
tcaaaggaat tgacggggggc cgcacaagc ggtggagcat gtggtttaat tcgaagcaac    420
gcgaagaacc ttaccaggtc ttgacatcca gtgcaaacct aagagattag gtgttccctt    480
cggggacgct gagacaggtg gtgcatggct gtcgtcagct cgtgtcgtga gatgttgggt    540
taagtcccgc aacgagcgca acccttgtca ttagttgcca tcattaagtt gggcactcta    600
atgagactgc cggtgacaaa ccggaggaag gtggggat                            638
```

<210> SEQ ID NO 60
<211> LENGTH: 569
<212> TYPE: DNA
<213> ORGANISM: Lactobacillus johnsonii

<400> SEQUENCE: 60

```
ggtggagcat gtggtttaat tcgaagcaac gcgaagaacc ttaccaggtc ttgacatcca     60
gtgcaaacct aagagattag gtgttccctt cggggacgct gagacaggtg gtgcatggct    120
gtcgtcagct cgtgtcgtga gatgttgggt taagtcccgc aacgagcgca acccttgtca    180
ttagttgcca tcattaagtt gggcactcta atgagactgc cggtgacaaa ccggaggaag    240
gtggggatga cgtcaagtca tcatgcccct tatgacctgg gctacacacg tgctacaatg    300
gacggtacaa cgagaagcga acctgcgaag gcaagcggat ctcttaaagc cgttctcagt    360
tcggactgta ggctgcaact cgcctacacg aagctggaat cgctagtaat cgcggatcag    420
cacgccgcgg tgaatacgtt cccgggcctt gtacacaccg cccgtcacac catgagagtc    480
tgtaacaccc aaagccggtg gataacctt tataggagtc agccgtctaa ggtaggacag    540
atgattaggg tgaagtcgta acaaggtag                                      569
```

<210> SEQ ID NO 61
<211> LENGTH: 716

```
<212> TYPE: DNA
<213> ORGANISM: Lactobacillus johnsonii
<220> FEATURE:
<221> NAME/KEY: modified_base
<222> LOCATION: (684)..(684)
<223> OTHER INFORMATION: a, c, t, g, unknown or other

<400> SEQUENCE: 61
tactccccag gcggagtgct taatgcgtta gctgcagcac tgagaggcgg aaacctccca      60
acacttagca ctcatcgttt acggcatgga ctaccagggt atctaatcct gttcgctacc     120
catgctttcg agcctcagcg tcagttgcag accagagagc cgccttcgcc actggtgttc     180
ttccatatat ctacgcattc caccgctaca catggagttc cactctcctc ttctgcactc     240
aagttcaaca gtttctgatg caattctccg gttgagccga aggctttcac atcagactta     300
ttgaaccgcc tgcactcgct ttacgcccaa taaatccgga caacgcttgc cacctacgta     360
ttaccgcggc tgctggcacg tagttagccg tgactttcta agtaattacc gtcaaataaa     420
ggccagttac tacctctatc tttcttcact accaacagag ctttacgagc cgaaacccrt     480
cttcactcac gcggcgttgc tccatcagac tttcgtccat tgtggaagat ccctactgc      540 tgcctcccgt aggagtttgg gccgtgtctc agtcccaatg tggccgatca gtctctcaac     600
tcggctatgc atcattgcct tggtaagccg ttaccttacc aactagctaa tgcaccgcag     660
gtccatccaa gagtgatagc aganccatct ttcaaactct agacatgcgt ctagtg         716

<210> SEQ ID NO 62
<211> LENGTH: 514
<212> TYPE: DNA
<213> ORGANISM: Lactobacillus johnsonii

<400> SEQUENCE: 62
gtgactttct aagtaattac cgtcaaataa aggccagtta ctacctctat ctttcttcac      60
taccaacaga gctttacgag ccgaaaccct tcttcactca cgcggcgttg ctccatcaga     120
ctttcgtcca ttgtggaaga ttccctactg ctgcctcccg taggagtttg ggccgtgtct     180
cagtcccaat gtggccgatc agtctctcaa ctcggctatg catcattgcc ttggtaagcc     240
gttaccttac caactagcta atgcaccgca ggtccatcca agagtgatag cagaaccatc     300
tttcaaactc tagacatgcg tctagtgttg ttatccggta ttagcatctg tttccaggtg     360
ttatcccagt ctcttgggca ggttaccac gtgttactca cccgtccgcc gctcgcttgt     420
atctagtttc atttagtgca agcactaaaa tcatctaggc aagctcgctc gacttgcatg     480
tattaggcac gccgccagcg ttcgtcctga gcca                                 514

<210> SEQ ID NO 63
<211> LENGTH: 711
<212> TYPE: DNA
<213> ORGANISM: Lactobacillus johnsonii

<400> SEQUENCE: 63
tcctacactt agacggctga ctcctataaa ggttatccca ccggctttgg gtgttacaga      60
ctctcatggt gtgacgggcg gtgtgtacaa ggcccgggaa cgtattcacc gcggcgtgct     120
gatccgcgat tactagcgat tccagcttcg tgtaggcgag ttgcagccta cagtccgaac     180
tgagaacggc tttaagagat ccgcttgcct tcgcaggttc gcttctcgtt gtaccgtcca     240
ttgtagcacg tgtgtagccc aggtcataag gggcatgatg acttgacgtc atccccacct     300
tcctccggtt tgtcaccggc agtctcatta gagtgcccaa cttaatgatg caactaatg      360
```

-continued

```
acaagggttg cgctcgttgc gggacttaac ccaacatctc acgacacgag ctgacgacag    420
ccatgcacca cctgtctcag cgtccccgaa gggaacacct aatctcttag gtttgcactg    480
gatgtcaaga cctggtaagg ttcttcgcgt tgcttcgaat taaaccacat gctccaccgc    540
ttgtgcgggc ccccgtcaat tcctttgagt ttcaaccttg cggtcgtact ccccaggcgg    600
agtgcttaat gcgttagctg cagcactgag aggcggaaac ctcccaacac ttagcactca    660
tcgtttacgg catggactac cagggtatct aatcctgttc gctacccatg c             711

<210> SEQ ID NO 64
<211> LENGTH: 543
<212> TYPE: DNA
<213> ORGANISM: Lactobacillus reuteri

<400> SEQUENCE: 64
gtgtgcctaa tacatgcaag tcgtacgcac tggcccaact gattgatggt gcttgcacct     60
gattgacgat ggatcaccag tgagtggcgg acgggtgagt aacacgtagg taacctgccc    120
cggagcgggg gataacattt ggaaacagat gctaataccg cataacaaca aaagccacat    180
ggcttttgtt tgaaagatgg ctttggctat cactctggga tggacctgcg gtgcattagc    240
tagttggtaa ggtaacggct taccaaggcg atgatgcata gccgagttga gagactgatc    300
ggccacaatg gaactgagac acggtccata ctcctacggg aggcagcagt agggaatctt    360
ccacaatggg cgcaagcctg atggagcaac accgcgtgag tgaagaaggg tttcggctcg    420
taaagctctg ttgttggaga agaacgtgcg tgagagtaac tgttcacgca gtgacggtat    480
ccaaccagaa agtcacggct aactacgtgc cagcagccgc ggtaatacgt aggtggcaag    540
cgt                                                                  543

<210> SEQ ID NO 65
<211> LENGTH: 628
<212> TYPE: DNA
<213> ORGANISM: Lactobacillus reuteri

<400> SEQUENCE: 65
tatccggatt tattgggcgt aaagcgagcg caggcggttg cttaggtctg atgtgaaagc     60
cttcggctta accgaagaag tgcatcggaa accgggcgac ttgagtgcag aagaggacag    120
tggaactcca tgtgtagcgg tggaatgcgt agatatatgg aagaacacca gtggcgaagg    180
cggctgtctg gtctgcaact gacgctgagg ctcgaaagca tgggtagcga acaggattag    240
ataccctggt agtccatgcc gtaaacgatg agtgctaggt gttggagggt ttccgccctt    300
cagtgccgga gctaacgcat taagcactcc gcctggggag tacgaccgca aggttgaaac    360
tcaaaggaat tgacggggc ccgcacaagc ggtggagcat gtggtttaat tcgaagctac    420
gcgaagaacc ttaccaggtc ttgacatctt gcgctaacct tagagataag gcgttccctt    480
cggggacgca atgacaggtg gtgcatggtc gtcgtcagct cgtgtcgtga gatgttgggt    540
taagtcccgc aacgagcgca acccttgtta ctagttgcca gcattaagtt gggcactcta    600
gtgagactgc cggtgacaaa ccggagga                                       628

<210> SEQ ID NO 66
<211> LENGTH: 557
<212> TYPE: DNA
<213> ORGANISM: Lactobacillus reuteri

<400> SEQUENCE: 66
gtggagcatg tggtttaatt cgaagctacg cgaagaacct taccaggtct tgacatcttg     60
```

```
cgctaacctt agagataagg cgttcccttc ggggacgcaa tgacaggtgg tgcatggtcg    120
tcgtcagctc gtgtcgtgag atgttgggtt aagtcccgca acgagcgcaa cccttgttac    180
tagttgccag cattaagttg ggcactctag tgagactgcc ggtgacaaac cggaggaagg    240
tggggacgac gtcagatcat catgcccctt atgacctggg ctacacacgt gctacaatgg    300
acggtacaac gagtcgcaag ctcgcgagag taagctaatc tcttaaagcc gttctcagtt    360
cggactgtag gctgcaactc gcctacacga agtcggaatc gctagtaatc gcggatcagc    420
atgccgcggt gaatacgttc ccgggccttg tacacaccgc ccgtcacacc atgggagttt    480
gtaacgccca aagtcggtgg cctaaccatt atggagggag ccgcctaagg cgggacagat    540
gactggggtg aagtcgt                                                   557

<210> SEQ ID NO 67
<211> LENGTH: 619
<212> TYPE: DNA
<213> ORGANISM: Lactobacillus reuteri

<400> SEQUENCE: 67
tactccccag gcggagtgct taatgcgtta gctccggcac tgaagggcgg aaaccctcca     60
acacctagca ctcatcgttt acggcatgga ctaccagggt atctaatcct gttcgctacc    120
catgctttcg agcctcagcg tcagttgcag accagacagc cgccttcgcc actggtgttc    180
ttccatatat ctacgcattc caccgctaca catggagttc cactgtcctc ttctgcactc    240
aagtcgcccg gtttccgatg cacttcttcg gttaagccga aggctttcac atcagaccta    300
agcaaccgcc tgcgctcgct ttacgcccaa taaatccgga taacgcttgc cacctacgta    360
ttaccgcggc tgctggcacg tagttagccg tgactttctg gttggatacc gtcactgcgt    420
gaacagttac tctcacgcac gttcttctcc aacaacagag ctttacgagc cgaaaccctt    480
cttcactcac gcggtgttgc tccatcaggc ttgcgcccat tgtggaagat tccctactgc    540
tgcctcccgt aggagtatgg accgtgtctc agttccattg tggccgatca gtctctcaac    600
tcggctatgc atcatcgcc                                                 619

<210> SEQ ID NO 68
<211> LENGTH: 509
<212> TYPE: DNA
<213> ORGANISM: Lactobacillus reuteri

<400> SEQUENCE: 68
gtgactttct ggttggatac cgtcactgcg tgaacagtta ctctcacgca cgttcttctc     60
caacaacaga gctttacgag ccgaaaccct tcttcactca cgcggtgttg ctccatcagg    120
cttgcgccca ttgtggaaga ttccctactg ctgcctcccg taggagtatg gaccgtgtct    180
cagttccatt gtggccgatc agtctctcaa ctcggctatg catcatcgcc ttggtaagcc    240
gttaccttac caactagcta atgcaccgca ggtccatccc agagtgatag ccaaagccat    300
ctttcaaaca aaagccatgt ggcttttgtt gttatgcggt attagcatct gtttccaaat    360
gttatccccc gctccggggc aggttaccta cgtgttactc acccgtccgc cactcactgg    420
tgatccatcg tcaatcaggt gcaagcacca tcaatcagtt gggccagtgc gtacgacttg    480
catgtattag gcacaccgcc ggcgttcat                                      509

<210> SEQ ID NO 69
<211> LENGTH: 590
<212> TYPE: DNA
```

<213> ORGANISM: Lactobacillus reuteri

<400> SEQUENCE: 69

| | | | | | |
|---|---|---|---|---|---|
| tcccgcctta | ggcggctccc | tccataatgg | ttaggccacc | gactttgggc | gttacaaact | 60
| cccatggtgt | gacgggcggt | gtgtacaagg | cccgggaacg | tattcaccgc | ggcatgctga | 120
| tccgcgatta | ctagcgattc | cgacttcgtg | taggcgagtt | gcagcctaca | gtccgaactg | 180
| agaacggctt | taagagatta | gcttactctc | gcgagcttgc | gactcgttgt | accgtccatt | 240
| gtagcacgtg | tgtagcccag | gtcataaggg | gcatgatgat | ctgacgtcgt | ccccaccttc | 300
| ctccggtttg | tcaccggcag | tctcactaga | gtgcccaact | taatgctggc | aactagtaac | 360
| aagggttgcg | ctcgttgcgg | gacttaaccc | aacatctcac | gacacgagct | gacgacgacc | 420
| atgcaccacc | tgtcattgcg | tccccgaagg | gaacgcctta | tctctaaggt | tagcgcaaga | 480
| tgtcaagacc | tggtaaggtt | cttcgcgtag | cttcgaatta | aaccacatgc | tccaccgctt | 540
| gtgcgggccc | ccgtcaattc | ctttgagttt | caaccttgcg | gtcgtactcc | | 590

<210> SEQ ID NO 70
<211> LENGTH: 666
<212> TYPE: DNA
<213> ORGANISM: Lactobacillus plantarum

<400> SEQUENCE: 70

| | | | | | |
|---|---|---|---|---|---|
| gtgcctaata | catgcaagtc | gaacgaactc | tggtattgat | tggtgcttgc | atcatgattt | 60
| acatttgagt | gagtggcgaa | ctggtgagta | acacgtggga | aacctgccca | gaagcggggg | 120
| ataacacctg | gaaacagatg | ctaataccgc | ataacaactt | ggaccgcatg | gtccgagttt | 180
| gaaagatggc | ttcggctatc | acttttggat | ggtcccgcgg | cgtattagct | agatggtgag | 240
| gtaacggctc | accatggcaa | tgatacgtag | ccgacctgag | agggtaatcg | gccacattgg | 300
| gactgagaca | cggcccaaac | tcctacggga | ggcagcagta | gggaatcttc | cacaatggac | 360
| gaaagtctga | tggagcaacg | ccgcgtgagt | gaagaagggt | ttcggctcgt | aaaactctgt | 420
| tgttaaagaa | gaacatatct | gagagtaact | gttcaggtat | tgacggtatt | taaccagaaa | 480
| gccacggcta | actacgtgcc | agcagccgcg | gtaatacgta | ggtggcaagc | gttgtccgga | 540
| tttattgggc | gtaaagcgag | cgcaggcggt | tttttaagtc | tgatgtgaaa | gccttcggct | 600
| caaccgaaga | agtgcatcgg | aaactgggaa | acttgagtgc | agaagaggac | agtggaactc | 660
| atgtgt | | | | | | 666

<210> SEQ ID NO 71
<211> LENGTH: 677
<212> TYPE: DNA
<213> ORGANISM: Lactobacillus plantarum

<400> SEQUENCE: 71

| | | | | | |
|---|---|---|---|---|---|
| tccggattta | tgggcgtaa | agcgagcgca | ggcggttttt | taagtctgat | gtgaaagcct | 60
| tcggctcaac | cgaagaagtg | catcggaaac | tgggaaactt | gagtgcagaa | gaggacagtg | 120
| gaactccatg | tgtagcggtg | aaatgcgtag | atatatggaa | gaacaccagt | ggcgaaggcg | 180
| gctgtctggt | ctgtaactga | cgctgaggct | cgaaagtatg | ggtagcaaac | aggattagat | 240
| accctggtag | tccataccgt | aaacgatgaa | tgctaagtgt | tggagggttt | ccgcccttca | 300
| gtgctgcagc | taacgcatta | agcattccgc | ctggggagta | cggccgcaag | gctgaaactc | 360
| aaaggaattg | acggggcccc | gcacaagcgg | tggagcatgt | ggtttaattc | gaagctacgc | 420
| gaagaacctt | accaggtctt | gacatactat | gcaaatctaa | gagattagac | gttcccttcg | 480

```
gggacatgga tacaggtggt gcatggttgt cgtcagctcg tgtcgtgaga tgttgggtta      540
agtcccgcaa cgagcgcaac ccttattatc agttgccagc attaagttgg gcactctggt      600
gagactgccg gtgacaaacc ggaggaaggt ggggatgacg tcaaatcatc atgccccta       660 tgacctgggc tacacac                                                     677

<210> SEQ ID NO 72
<211> LENGTH: 574
<212> TYPE: DNA
<213> ORGANISM: Lactobacillus plantarum

<400> SEQUENCE: 72
ggtggagcat gtggtttaat tcgaagctac gcgaagaacc ttaccaggtc ttgacatact       60
atgcaaatct aagagattag acgttccctt cggggacatg gatacaggtg gtgcatggtt      120
gtcgtcagct cgtgtcgtga gatgttgggt taagtcccgc aacgagcgca accccttatta     180 tcagttgcca gcattaagtt gggcactctg gtgagactgc cggtgacaaa ccggaggaag      240
gtggggatga cgtcaaatca tcatgcccct tatgacctgg gctacacacg tgctacaatg      300
gatggtacaa cgagttgcga actcgcgaga gtaagctaat ctcttaaagc cattctcagt      360
tcggattgta ggctgcaact cgcctacatg aagtcggaat cgctagtaat cgcggatcag      420
catgccgcgg tgaatacgtt cccgggcctt gtacacaccg cccgtcacac catgagagtt      480
tgtaacaccc aaagtcggtg ggtaaccttt taggaacca gccgcctaag gtgggacaga      540
tgattacggt gaagtcgtaa caaggtagcc cgta                                  574

<210> SEQ ID NO 73
<211> LENGTH: 679
<212> TYPE: DNA
<213> ORGANISM: Lactobacillus plantarum

<400> SEQUENCE: 73
gtactcccca ggcggaatgc ttaatgcgtt agctgcagca ctgaagggcg gaaaccctcc       60
aacacttagc attcatcgtt tacggtatgg actaccaggg tatctaatcc tgtttgctac      120
ccatactttc gagcctcagc gtcagttaca gaccagacag ccgccttcgc cactggtgtt      180
cttccatata tctacgcatt tcaccgctac acatggagtt ccactgtcct cttctgcact      240
caagtttccc agtttccgat gcacttcttc ggttgagccg aaggctttca catcagactt      300
aaaaaaccgc ctgcgctcgc tttacgccca ataaatccgg acaacgcttg ccacctacgt      360
attaccgcgc tgctggcac gtagttagcc gtggctttct ggttaaatac cgtcaatacc       420
tgaacagtta ctctcagata tgttcttctt taacaacaga gttttacgag ccgaaaccct      480
tcttcactca cgcggcgttg ctccatcaga ctttcgtcca ttgtggaaga ttccctactg      540
ctgcctcccg taggagtttg ggccgtgtct cagtcccaat gtggccgatt accctctcag      600
gtcggctacg tatcattgcc atggtgagcc gttacctcac catctagcta atacgccgcg      660
ggaccatcca aaagtgata                                                   679

<210> SEQ ID NO 74
<211> LENGTH: 521
<212> TYPE: DNA
<213> ORGANISM: Lactobacillus plantarum

<400> SEQUENCE: 74
tggctttctg gttaaatacc gtcaatacct gaacagttac tctcagatat gttcttcttt       60
```

-continued

```
aacaacagag ttttacgagc cgaaaccctt cttcactcac gcggcgttgc tccatcagac      120
tttcgtccat tgtggaagat tccctactgc tgcctcccgt aggagtttgg gccgtgtctc      180
agtcccaatg tggccgatta ccctctcagg tcggctacgt atcattgcca tggtgagccg      240
ttacctcacc atctagctaa tacgccgcgg gaccatctaa aagtgatagc cgaagccatc      300
tttcaaactc ggaccatgcg gtccaagttg ttatgcggta ttagcatctg tttccaggtg      360 ttatccccg cttctgggca ggtttcccac gtgttactca ccagttcgcc actcactcaa       420
atgtaaatca tgatgcaagc accaatcaat accagagttc gttcgacttg catgtattag      480
gcacgccgcc agcgttcgtc ctgagccatg atcaaactct a                          521

<210> SEQ ID NO 75
<211> LENGTH: 639
<212> TYPE: DNA
<213> ORGANISM: Lactobacillus plantarum

<400> SEQUENCE: 75
acttaggcgg ctggttccta aaaggttacc ccaccgactt tgggtgttac aaactctcat      60
ggtgtgacgg gcggtgtgta caaggcccgg gaacgtattc accgcggcat gctgatccgc      120
gattactagc gattccgact tcatgtaggc gagttgcagc ctacaatccg aactgagaat      180
ggctttaaga gattagctta ctctcgcgag ttcgcaactc gttgtaccat ccattgtagc      240
acgtgtgtag cccaggtcat aagggcatg atgatttgac gtcatcccca ccttcctccg      300
gtttgtcacc ggcagtctca ccagagtgcc caacttaatg ctggcaactg ataataaggg      360
ttgcgctcgt tgcgggactt aacccaacat ctcacgacac gagctgacga caaccatgca      420
ccacctgtat ccatgtcccc gaagggaacg tctaatctct tagatttgca tagtatgtca      480
agacctggta aggttcttcg cgtagcttcg aattaaacca catgctccac cgcttgtgcg      540 ggccccgtc aattcctttg agtttcagcc ttgcggccgt actccccagg cggaatgctt       600
aatgcgttag ctgcagcact gaagggcgga accctcca                              639

<210> SEQ ID NO 76
<211> LENGTH: 644
<212> TYPE: DNA
<213> ORGANISM: Lactobacillus reuteri

<400> SEQUENCE: 76
taatacatgc aagtcgtacg cactggccca actgattgat ggtgcttgca cctgattgac      60
gatggatcac cagtgagtgg cggacgggtg agtaacacgt aggtaacctg ccccggagcg      120
ggggataaca tttggaaaca gatgctaata ccgcataaca acaaaagcca catggctttt      180
gtttgaaaga tggctttggc tatcactctg ggatggacct gcggtgcatt agctagttgg      240
taaggtaacg gcttaccaag gcgatgatgc atagccgagt tgagagactg atcggccaca      300
atggaactga gacacggtcc atactcctac gggaggcagc agtagggaat cttccacaat      360
gggcgcaagc ctgatggagc aacaccgcgt gagtgaagaa gggtttcggc tcgtaaagct      420
ctgttgttgg agaagaacgt gcgtgagagt aactgttcac gcagtgacgg tatccaacca      480
gaaagtcacg gctaactacg tgccagcagc cgcggtaata cgtaggtggc aagcgtgatc      540
cggatttatt gggcgtaaag cgagcgcagg cggttgctta ggtctgatgt gaaagccttc      600
ggcttaaccg aagaagtgca tcggagacgg gcgacttgag tgca                      644

<210> SEQ ID NO 77
<211> LENGTH: 507
```

```
<212> TYPE: DNA
<213> ORGANISM: Lactobacillus reuteri
<220> FEATURE:
<221> NAME/KEY: modified_base
<222> LOCATION: (464)..(464)
<223> OTHER INFORMATION: a, c, t, g, unknown or other

<400> SEQUENCE: 77
ttatccggat ttattgggcg taaagcgagc gcaggcggtt gcttaggtct gatgtgaaag      60
ccttcggctt aaccgaagaa gtgcatcgga aaccgggcga cttgagtgca gaagaggaca     120
gtggaactcc atgtgtagcg gtggaatgcg tagatatatg gaagaacacc agtggcgaag     180
gcggctgtct ggtctgcaac tgacgctgag gctcgaaagc atgggtagcg aacaggatta     240
gataccctgg tagtccatgc cgtaaacgat gagtgctagg tgttggaggg tttccgccct     300
tcagtgccgg agctaacgca ttaagcactc cgcctgggga gtacgaccgc aaggttgaaa     360
cgcaaaggaa ttgacggggg cccgcacaag cggtggagca tgtggtttaa ttcgaagcta     420
cgcgaagaac cttaccaggt cttgacatct tgcgctaacc ttanaaggcg tccccttcgg     480
ggactcaatg acaggtggtg catggtt                                         507

<210> SEQ ID NO 78
<211> LENGTH: 568
<212> TYPE: DNA
<213> ORGANISM: Lactobacillus reuteri

<400> SEQUENCE: 78
ggtggagcat gtggtttaat tcgaagctac gcgaagaacc ttaccaggtc ttgacatctt      60
gcgctaacct tagagataag gcgttccctt cggggacgca atgacaggtg gtgcatggtc     120
gtcgtcagct cgtgtcgtga gatgttgggt taagtcccgc aacgagcgca acccttgtta     180
ctagttgcca gcattaagtt gggcactcta gtgagactgc cggtgacaaa ccggaggaag     240
gtggggacga cgtcagatca tcatgcccct tatgacctgg gctacacacg tgctacaatg     300
gacggtacaa cgagtcgcaa gctcgcgaga gtaagctaat ctcttaaagc cgttctcagt     360
tcggactgta ggctgcaact cgcctacacg aagtcggaat cgctagtaat cgcggatcag     420
catgccgcgg tgaatacgtt cccgggcctt gtacacaccg cccgtcacac catggagagtt     480
tgtaacgccc aaagtcggtg gcctaacctt tatggaggga ccgcctaag gcgggacaga     540
tgactggggt gaagtcgtaa caaggtag                                        568

<210> SEQ ID NO 79
<400> SEQUENCE: 79

000

<210> SEQ ID NO 80
<211> LENGTH: 518
<212> TYPE: DNA
<213> ORGANISM: Lactobacillus reuteri

<400> SEQUENCE: 80
gtgactttct ggttggatac cgtcactgcg tgaacagtta ctctcacgca cgttcttctc      60
caacaacaga gctttacgag ccgaaaccct tcttcactca cgcggtgttg ctccatcagg     120
cttgcgccca ttgtggaaga ttccctactg ctgcctcccg taggagtatg gaccgtgtct     180
cagttccatt gtggccgatc agtctctcaa ctcggctatg catcatcgcc ttggtaagcc     240
gttaccttac caactagcta atgcaccgca ggtccatccc agagtgatag ccaaagccat     300
```

```
ctttcaaaca aaagccatgt ggcttttgtt gttatgcggt attagcatct gtttccaaat    360
gttatccccc gctccggggc aggttaccta cgtgttactc acccgtccgc cactcactgg    420
taatccatcg tcaatcaggt gcaagcacca tcaatcagtt gggccagtgc gtacgacttg    480
catgtattag gcacaccgcc ggcgttcatc ctgagcca                            518
```

<210> SEQ ID NO 81
<211> LENGTH: 622
<212> TYPE: DNA
<213> ORGANISM: Lactobacillus reuteri

<400> SEQUENCE: 81

```
ctccctccat aaaggttagg ccaccgactt tgggcgttac aaactcccat ggtgtgacgg     60
gcggtgtgta caaggcccgg aacgtattc accgcggcat gctgatccgc gattactagc    120
gattccgact tcgtgtaggc gagttgcagc ctacagtccg aactgagaac ggctttaaga    180
gattagctta ctctcgcgag cttgcgactc gttgtaccgt ccattgtagc acgtgtgtag    240
cccaggtcat aaggggcatg atgatctgac gtcgtcccca ccttcctccg gtttgtcacc    300
ggcagtctca ctagagtgcc caacttaatg ctggcaacta gtaacaaggg ttgcgctcgt    360
tgcgggactt aacccaacat ctcacgacac gagctgacga cgaccatgca ccacctgtca    420
ttgcgtcccc gaagggaacg ccttatctct aaggttagcg caagatgtca agacctggta    480
aggttcttcg cgtagcttcg aattaaacca catgctccac cgcttgtgcg gccccccgtc    540
aattcctttg agtttcaacc ttggcggtcg tactccccag gcggagtgct taatgcgtta    600
gctccggcac tgaagggcgg aa                                             622
```

<210> SEQ ID NO 82
<211> LENGTH: 651
<212> TYPE: DNA
<213> ORGANISM: Lactobacillus reuteri

<400> SEQUENCE: 82

```
gtgtgcctaa tacatgcaag tcgtacgcac tggcccaact gattgatggt gcttgcacct     60
gattgacgat ggatcaccag tgagtggcgg acgggtgagt aacacgtagg taacctgccc    120
cggagcgggg gataacattt ggaaacagat gctaataccg cataacaaca aaagccacat    180
ggcttttgtt tgaaagatgg ctttggctat cactctggga tggacctgcg gtgcattagc    240
tagttggtaa ggtaacggct taccaaggcg atgatgcata gccgagttga gagactgatc    300
ggccacaatg gaactgagac acggtccata ctcctacggg aggcagcagt agggaatctt    360
ccacaatggg cgcaagcctg atggagcaac accgcgtgag tgaagaaggg tttcggctcg    420
taaagctctg ttgttggaga agaacgtgcg tgagagtaac tgttcacgca gtgacggtat    480
ccaaccagaa agtcacggct aactacgtgc cagcagccgc ggtaatacgt aggtggcaag    540
cgttatccgg attattgggg cgtaaagcga gcgcaggcgg ttgcttaggt ctgatgtgaa    600
agccttcggc ttaaccgaag aagtgcatcg gaaaccgggc gacttgagtg c             651
```

<210> SEQ ID NO 83
<211> LENGTH: 645
<212> TYPE: DNA
<213> ORGANISM: Lactobacillus reuteri

<400> SEQUENCE: 83

```
ttatccggat ttattgggcg taaagcgagc gcaggcggtt gcttaggtct gatgtgaaag     60
```

```
ccttcggctt aaccgaagaa gtgcatcgga aaccgggcaa cttgagtgca gaagaggaca    120
gtggaactcc atgtgtagcg gtggaatgcg tagatatatg gaagaacacc agtggcgaag    180
gcggctgtct ggtctgcaac tgacgctgag gctcgaaagc atgggtagcg aacaggatta    240
gatacccbgg tagtccatgc cgtaaacgat gagtgctagg tgttggaggg tttccgccct    300
tcagtgccgg agctaacgca ttaagcactc cgcctgggga gtacgaccgc aaggttgaaa    360
ctcaaaggaa ttgacggggg cccgcacaag cggtggagca tgtggtttaa ttcgaagcta    420
cgcgaagaac cttaccaggt cttgacatct gcgctaacct tagagataag gcgtcccttt    480
cggggacgca atgacaggtg gtgcatggtc gtcgtcagct cgtgtcgtga gatgttgggt    540
taagtcccgc aacgagcgca accctttgtta ctagttgcca gcattaagtt gggcactcta    600
gtgagactgc cggtgacaaa ccggaggaag gtggggacga cgtca                   645

<210> SEQ ID NO 84
<211> LENGTH: 573
<212> TYPE: DNA
<213> ORGANISM: Lactobacillus reuteri

<400> SEQUENCE: 84
ggtggagcat gtggtttaat tcgaagctac gcgaagaacc ttaccaggtc ttgacatctt    60
gcgctaacct tagagataag gcgttccctt cggggacgca atgacaggtg gtgcatggtc   120
gtcgtcagct cgtgtcgtga gatgttgggt taagtcccgc aacgagcgca accttttgtta  180
ctagttgcca gcattaagtt gggcactcta gtgagactgc cggtgacaaa ccggaggaag   240
gtggggacga cgtcagatca tcatgcccct tatgacctgg gctacacacg tgctacaatg   300
gacggtacaa cgagtcgcaa gctcgcgaga gtaagctaat ctcttaaagc cgttctcagt   360
tcggactgta ggctgcaact cgcctacacg aagtcggaat cgctagtaat cgcggatcag   420
catgccgcgg tgaatacgtt cccgggcctt gtacacaccg cccgtcacac catggagtt    480
tgtaacgccc aaagtcggtg gcctaaccat tatggaggga ccgcctaag gcgggacaga   540
tgactggggt gaagtcgtaa caaggtagcc gta                                 573

<210> SEQ ID NO 85
<211> LENGTH: 705
<212> TYPE: DNA
<213> ORGANISM: Lactobacillus reuteri

<400> SEQUENCE: 85
tactccccag gcggagtgct taatgcgtga gctccggcac tgaagggcgg aaaccctcca    60
acacctagca ctcatcgttt acggcatgga ctaccagggt atctaatcct gttcgctacc   120
catgctttcg agcctcagcg tcagttgcag accagacagc cgccttcgcc actggtgttc   180
ttccatatat ctacgcattc caccgctaca catggagttc cactgtcctc ttctgcactc   240
aagtcgcccg gtttccgatg cacttcttcg gttaagccga aggctttcac atcagaccta   300
agcaaccgcc tgcgctcgct ttacgcccaa taaatccgga taacgcttgc cacctacgta   360
ttaccgcggc tgctggcacg tagttagccg tgactttctg gttggatacc gtcactgcgt   420
gaacagttac tctcacgcac gttcttctcc aacaacagag ctttacgagc cgaaaccctt   480
cttcactcac gcggtgttgc tccatcaggc ttgcgcccat tgtggaagat tccctactgc   540
tgcctcccgt aggagtatgg accgtgtctc agttccattg tggccgatca gtctctcaac   600
tcggctatgc atcatcgcct tggtaagccg ttacttacc aactagctaa tgcaccgcag    660
gtccatccca gagtgatagc caaagccatc tttcaaacaa aagcc                   705
```

<210> SEQ ID NO 86
<211> LENGTH: 527
<212> TYPE: DNA
<213> ORGANISM: Lactobacillus reuteri

<400> SEQUENCE: 86

| | | | | | | |
|---|---|---|---|---|---|---|
| gtgactttct | ggttggatac | cgtcactgcg | tgaacagtta | ctctcacgca | cgtgcttctc | 60 |
| caacaacaga | gctttacgag | ccgaaaccct | tcttcactca | cgcggtgttg | ctccatcagg | 120 |
| cttgcgccca | ttgtggaaga | ttccctactg | ctgcctcccg | taggagtatg | gaccgtgtct | 180 |
| cagttccatt | gtggccgatc | agtctctcaa | ctcggctatg | catcatcgcc | ttggtaagcc | 240 |
| gttaccttac | caactagcta | atgcaccgca | ggtccatccc | agagtgatag | ccaaagccat | 300 |
| cttttcaaaca | aaagccatgt | ggcttttgtt | gttatgcggt | attagcatct | gtttccaaat | 360 |
| gttatccccc | gctccggggc | aggttaccta | cgtgttactc | acccgtccgc | cactcactgg | 420 |
| tgatccatcg | tcaatcaggt | gcaagcacca | tcaatcagtt | gggccagtgc | gtacgacttg | 480 |
| catgtattag | gcacaccgcc | ggcgttcatc | ctgagccatg | atcaaac | | 527 |

<210> SEQ ID NO 87
<211> LENGTH: 719
<212> TYPE: DNA
<213> ORGANISM: Lactobacillus reuteri

<400> SEQUENCE: 87

| | | | | | | |
|---|---|---|---|---|---|---|
| tcccgcactt | aggcggctcc | ctccataatg | gttaggccac | cgactttggg | cgttacaaac | 60 |
| tcccatggtg | tgacgggcgg | tgtgtacaag | gcccgggaac | gtattcaccg | cggcatgctg | 120 |
| atccgcgatt | actagcgatt | ccgacttcgt | gtaggcgagt | tgcagcctac | agtccgaact | 180 |
| gagaacggct | ttaagagatt | agcttactct | cgcgagcttg | cgactcgttg | taccgtccat | 240 |
| tgtagcacgt | gtgtagccca | ggtcataagg | ggcatgatga | tctgacgtcg | tccccacctt | 300 |
| cctccggttt | gtcaccggca | gtctcactag | agtgcccaac | ttaatgctgg | caactagtaa | 360 |
| caagggttgc | gctcgttgcg | ggacttaacc | caacatctca | cgacacgagc | tgacgacgac | 420 |
| catgcaccac | ctgtcattgc | gtccccgaag | ggaacgcctt | atctctaagg | ttagcgcaag | 480 |
| atgtcaagac | ctggtaaggt | tcttcgcgta | gcttcgaatt | aaaccacatg | ctccaccgct | 540 |
| tgtgcgggcc | cccgtcaatt | cctttgagtt | tcaaccttgc | ggtcgtactc | cccaggcgga | 600 |
| gtgcttaatg | cgttagctcc | ggcactgaag | ggcggaaacc | ctccaacacc | tagcactcat | 660 |
| cgtttacggc | atggactacc | agggtatcta | atcctgttcg | ctacccatgc | tttcgagcc | 719 |

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agagtttgat cctggctcag                                               20

<210> SEQ ID NO 89
<211> LENGTH: 21
<212> TYPE: DNA
<213> ORGANISM: Artificial Sequence
<220> FEATURE:
<223> OTHER INFORMATION: Description of Artificial Sequence: Synthetic

```
              primer

<400> SEQUENCE: 89
acggctacct tgttacgact t                                               21

<210> SEQ ID NO 90
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
attaccgcgg ctgctggcgc ccgccgcgcg cggcgggcgg ggcgggggca cgggggcct       60 acgggaggca gcag                                                       74

<210> SEQ ID NO 91
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
agcagtaggg aatcttccac gcccgccgcg cgcggcgggc ggggcggggg cacgggggga      60
ttycaccgct acacatg                                                    77

<210> SEQ ID NO 92
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
cgcccgccgc gcgcggcggg cggggcgggg gcacgggggg                           40
```

PORCINE LACTIC ACID BACTERIAL STRAINS

RELATED APPLICATIONS

This application is a national stage application of International Application No. PCT/GB2012/051686, filed Jul. 13, 2012, which claims the benefit of Great Britain Patent Application No. 1112091.2, filed on Jul. 14, 2011, the entire contents of which are incorporated herein by reference.

SEQUENCE LISTING

The instant application contains a Sequence Listing which has been submitted electronically in ASCII format and is hereby incorporated by reference in its entirety. Said ASCII copy, created on May 30, 2014, is named 553773(DYT-007US) SL.txt and is 82,954 bytes in size.

The present invention relates to bacterial strains isolated from pigs. More specifically, the invention relates to the isolation of lactic acid bacteria from organically-reared pigs. The claimed lactic acid bacteria have useful probiotic and therapeutic applications.

BACKGROUND TO THE INVENTION

The composition of the microbial flora of pigs, their gut innate immune function and possible susceptibility to infection is greatly influenced by the environment in which they were reared during early life (Mulder et al, 2009). Outdoor-reared pigs generally have a more developed gut immune system, perform better and are healthier than indoor-reared counterparts. The outdoor environment dramatically influences microbial diversity of the gut and is associated with high levels of Firmicutes, in particular Lactic Acid Bacteria [LAB].

LAB comprise a Glade of gram-positive, low-GC, acid-tolerant, generally non-sporulating, non-respiring bacteria that are associated with certain common metabolic and physiological characteristics. LAB are rod-shaped bacilli or coccus that are characterized by an increased tolerance to a lower pH range. LAB produce lactic acid as the major metabolic end-product of carbohydrate fermentation and are amongst the most important groups of microorganisms used in the food industry.

*Lactobacilli* are predominant in the gut flora of organically (outdoor) reared pigs. In contrast, the numbers of these bacteria are low in indoor-reared pigs and levels of potentially pathogenic phylotypes are high (Mulder et al, 2009). Furthermore, gut immune development and function of indoor-reared pigs is known to deviate from normal. In particular, expression of Type 1 interferon genes, Major Histocompatibility Complex class I and several chemokines are known to be increased (Mulder et al., 2009).

Lactic acid bacteria may modify the flora and gut structure and function in several ways (Cotter et al, 2005; Ohashi and Ushida, 2009). For example, they may compete with harmful bacteria for key nutrients or attachment sites on the gut, resulting in their exclusion. Alternatively, they can produce bioactive substances that aid or promote colonisation by beneficial bacteria or kill/interfere with the growth of potentially harmful or pathogenic bacteria. Alternatively, these bioactive factors can be immune-modulators that promote immune development and barrier integrity of the gut. Strains of LAB vary greatly in their biological activity. The present invention seeks to provide LAB strains that have therapeutically useful properties. More specifically, the invention seeks to provide LAB strains that are capable of promoting gut and immune development and health, thereby having considerable therapeutic potential as probiotics.

STATEMENT OF INVENTION

The present applicant has shown that the microbiota of out-door reared pigs contain LAB strains that produce potent and specific anti-microbial or cell-/immune-modulating bioactive factors.

Aspects of the invention, together with preferred embodiments, are set forth in the accompanying claims.

A first aspect of the invention relates to a porcine lactic acid bacterial strain, wherein said bacterial strain is characterised by one or more of the following characteristics:

(i) the ability to exhibit antimicrobial activity against *E. coli*;
(ii) the ability to exhibit antimicrobial activity against *S. enteritidis*;
(iii) the ability to suppress inflammation in IPEC cells induced by 12-O-tetradecaboylphorbol-13-acetate (PMA);
(iv) the ability to block the attachment or invasion of IPEC cells by *S. enteritidis*;
(v) the ability to block the attachment or invasion of IPEC cells by *E. coli*;
(vi) the absence of antibiotic resistance to one or more antibiotics selected from the following: ampicillin; cefotaxime; chloramphenicol; erythromycin; gentamicin; tetracycline; vancomycin; metronizadole; nalidixic acid; and kanamycin; and
(vii) the ability to exhibit heat stability when subjected to three cycles of heating, each cycle comprising heating at a temperature of 70° C. for a period of 15 minutes.

A second aspect relates to a composition comprising one or more lactic acid bacterial strains according to the invention and a pharmaceutically acceptable excipient, carrier or diluent.

A third aspect relates to a probiotic composition comprising one or more lactic acid bacterial strains according to the invention.

A fourth aspect relates to one or more lactic acid bacterial strains according to the invention for use in medicine.

A fifth aspect relates to one or more lactic acid bacterial strains according to the invention for use in treating an intestinal disorder in a subject.

A sixth aspect relates to the use of one or more lactic acid bacterial strains according to the invention in the preparation of a medicament for treating an intestinal disorder in a subject.

A seventh aspect relates to a method of treating an intestinal disorder in a subject, said method comprising administering to the subject a pharmaceutically effective amount of one or more lactic acid bacterial strains or composition according to the invention.

An eighth aspect of the invention relates to one or more lactic acid bacterial strains according to the invention for improving intestinal microbiota.

A ninth aspect of the invention relates to a method of improving intestinal microbiota in a subject, said method comprising administering to the subject one or more lactic acid bacterial strains or composition according to the invention.

A tenth aspect relates to a feedstuff comprising one or more lactic acid bacterial strains according to the invention.

An eleventh aspect relates to a food product comprising one or more lactic acid bacterial strains according to the invention.

A twelfth aspect relates to a dietary supplement comprising one or more lactic acid bacterial strains according to the invention.

A thirteenth aspect relates to a food additive comprising one or more lactic acid bacterial strains according to the invention.

A fourteenth aspect relates to a process for producing a probiotic, said process comprising culturing a lactic acid bacterial strain according to the invention.

A fifteenth aspect of the invention relates to a process for obtaining a porcine lactic acid bacterial strain, said process comprising obtaining faeces from an organically reared pig and extracting one or more porcine lactic acid bacterial strains from said faeces.

A sixteenth aspect of the invention relates to one or more porcine lactic acid bacterial strains obtained by, or obtainable by, the process described above.

DETAILED DESCRIPTION OF THE INVENTION

As mentioned above, the present invention relates to one or more porcine lactic acid bacterial strains. The lactic acid bacterial strain is characterised by one or more of the following characteristics:

(i) the ability to exhibit antimicrobial activity against *E. coli*;
(ii) the ability to exhibit antimicrobial activity against *S. enteritidis*;
(iii) the ability to suppress inflammation in IPEC cells induced by 12-O-tetradecaboylphorbol-13-acetate (PMA);
(iv) the ability to block the attachment or invasion of IPEC cells by *S. enteritidis*;
(v) the ability to block the attachment or invasion of IPEC cells by *E. coli*;
(vi) the absence of antibiotic resistance to one or more antibiotics selected from the following: ampicillin; cefotaxime; chloramphenicol; erythromycin; gentamicin; tetracycline; vancomycin; metronizadole; nalidixic acid; and kanamycin; and
(vii) the ability to exhibit heat stability when subjected to three cycles of heating, each cycle comprising heating at a temperature of 70° C. for a period of 15 minutes.

As used herein, the term "porcine" means "of or pertaining to swine", i.e. of or pertaining to any of several mammals of the family Suidae, especially the domesticated hog, *Sus scrofa* domesticus, or Sus domesticus when young or of comparatively small size.

Preferably, the pig is less than 3 months old, preferably, less than 2 months old.

Preferably, the porcine lactic acid bacterial strain is from an organically reared pig. In this regard, preferably, the pigs are reared free range, outside (with exposure to soil) and in the absence of antibiotics, growth promoters and/or growth enhancers.

Preferably, the porcine lactic acid bacterial strain is from an outdoor reared pig. Preferably, the pigs are reared outside for at least 60% of their lives. More preferably, the animals are reared outside for at least 80% of their lives, more preferably, at least 90% of their lives, even more preferably still, 100% of their lives.

In one preferred embodiment, the lactic acid bacterial strain is selected from *L. johnsonii, L. reuteri, L. plantarum, L. gasseri, L. pentosus, L. acidophilus, L. vaginalis* and *L. mucosae*.

In one preferred embodiment, the lactic acid bacterial strain is selected from *L. johnsonii, L. reuteri* and *L. plantarum*.

In another preferred embodiment, the lactic acid bacterial strain is in the form of a live bacterial population, a lyophilized bacterial population, a non-viable bacterial preparation, or the cellular components thereof. Preferably, where the bacterial strain is in the form of a non-viable bacterial preparation, it is selected from heat-killed bacteria, irradiated bacteria and lysed bacteria.

In one preferred embodiment, the lactic acid bacterial strain is in the form of a live bacterium, a dead bacterium, or the cellular components thereof.

In one preferred embodiment, the lactic acid bacterial strain is in isolated form. As used herein, the term "isolated" means isolated from its native environment.

In one preferred embodiment, the lactic acid bacterial strain is in biologically pure form. As used herein the term "biologically pure" refers to a bacterial strain in the form of a laboratory culture that is substantially free from other species of organism. Preferably, the lactic acid bacterial strain is in the form of a culture of a single species of organism.

As used herein, the term "lactic acid bacterial strain" also encompasses mutants of said lactic acid bacterial strain. As used herein, the term "mutant" includes derived bacterial strains having at least 93% homology, preferably at least 96% homology, more preferably 98% homology to the polynucleotide sequence of a referenced strain, but otherwise comprising mutations in other sequences in the bacterial genome. Mutants are obtainable by genetic engineering techniques inferring alteration of the genetic material of the strains of the invention or inferring a recombination of the genetic material of the strains of the invention with other molecules. Typically, in order to obtain such mutant strains, a person skilled in the art can use standard mutagenesis techniques such as UV radiation or exposure to mutagenic chemical products.

As used herein, the term "mutations" includes natural or induced mutations comprising at least single base alterations including deletions, insertions, transversions, and other modifications known to those skilled in the art, including genetic modification introduced into a parent nucleotide or amino acid sequence whilst maintaining at least 50% homology to the parent sequence. Preferably, the sequence comprising the mutation or mutations has at least 60%, more preferably at least 75%, more preferably still 85% homology with the parental sequence. As used herein, sequence "homology" can be determined using standard techniques known to those skilled in the art. For example, homology may be determined using the on-line homology algorithm "BLAST" program, publicly available at http)://www.ncbi.nlm.nih.gov/BLAST/.

As used herein, the term "lactic acid bacterial strain" also encompasses homologues of the lactic acid bacterial strains. As used herein the term "homologue" refers to a lactic acid bacterial strain having a nucleotide sequence having a degree of sequence identity or sequence homology with the nucleotide sequence of the parent lactic acid bacterial strain (hereinafter referred to as a "homologous sequence(s)"). Here, the term "homologous" means an entity having a certain homology with the subject nucleotide sequence. Here, the term "homology" can be equated with "identity".

In the present context, a homologous sequence is taken to include a nucleotide sequence which may be at least 50, 60, 70, 75, 80, 85 or 90% identical, preferably at least 95%, 97%, 98% or 99% identical to the nucleotide sequence of the parent lactic acid bacterial strain (the subject sequence).

Homology comparisons can be conducted by eye, or more usually, with the aid of readily available sequence comparison programs. These commercially available computer programs can calculate % homology between two or more sequences. % homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed.

Calculation of maximum % homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al 1999 Short Protocols in Molecular Biology, 4th Ed—Chapter 18), BLAST 2 (see FEMS Microbiol Lett 1999 174(2): 247-50; FEMS Microbiol Lett 1999 177(1): 187-8), FASTA (Altschul et al 1990 J. Mol. Biol. 403-410) and AlignX for example. At least BLAST, BLAST 2 and FASTA are available for offline and online searching (see Ausubel et al 1999, pages 7-58 to 7-60).

Preferably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides. Preferably, the degree of identity with regard to a nucleotide sequence may be determined over the whole sequence.

The traditional identification of bacteria on the basis of phenotypic characteristics is generally not as accurate as identification based on genotypic methods. Comparison of the bacterial 16S rRNA gene sequence has emerged as a preferred genetic technique and allows for new strains to be identified by comparison of sequences with known bacterial DNA sequences using BLAST (http://blast.ncbi.nlm.nih.gov/Blast.cgi). The 16S rRNA gene sequence is universal in bacteria, and so relationships can be measured across many different bacteria. In general, the comparison of the 16S rRNA sequence allows differentiation between organisms at the genus level across all major phyla of bacteria, in addition to classifying strains at multiple levels, including species and sub-species level. The 16S rRNA gene sequence has been determined for a large number of strains. GenBank, the largest databank of nucleotide sequences, has over 20 million deposited sequences, of which over 90,000 are of 16S rRNA genes. This means that there are many previously deposited sequences against which to compare the sequence of an unknown strain.

In one preferred embodiment, the lactic acid bacterial strain has a 16S rRNA gene sequence selected from SEQ ID NOS 1-87, or a homologue or variant thereof. Another embodiment of the invention relates to a lactic acid bacterial strain that comprises a 16S rRNA gene sequence selected from SEQ ID NOS 1-87, or a homologue or variant thereof. Preferred uses/methods apply to this aspect mutatis mutandis.

The term "homologue" is as defined hereinabove. As used herein, the term "variant" includes any variation wherein: (a) one or more nucleotides are substituted by another nucleotide or deleted, (b) the order of two or more nucleotides is reversed, (c) both (a) and (b) are present together. Preferably, the variants arise from one of (a), (b) or (c). More preferably, one or two nucleotides are substituted or deleted. Even more preferably, one nucleotide is substituted by another.

In one preferred embodiment of the invention, the lactic acid bacterial strain is characterised by the ability to exhibit antimicrobial activity against *E. coli*. The observed antimicrobial activity is most likely by virtue of anti-microbial substances produced by the lactic acid bacterial strains of the invention, although nature of these anti-microbial substances has not been determined.

In the context of the present invention, the ability to exhibit antimicrobial activity against *E. coil* can be determined by measuring inhibition of the growth of *E. coli* in an in vitro well diffusion assay. Further details of the well diffusion assay are set forth in the accompanying examples. The assay is carried out using *Escherichia coli* K88 on MacConkey No 3 agar, incubating the plates for 16 hours at 37° C. More specifically, *Escherichia coli* K88 is added to the agar (1 ml of a 1:1000 dilution of an overnight culture of *Escherichia coli* K88 in 200 ml agar to give the equivalent of 106 CFU/ml). The agar is poured into petri dishes and allowed to set. The plates are marked off into quadrants and an approximately 5 mm well cut out in each quadrant. An aliquot (60 µl) of conditioned media or MRS broth is added to the wells. The plates are covered and incubated for 16 hours at 37° C. They are photographed using a digital camera. Images are transferred to Photoshop, and the diameter of the well and zone of inhibition were determined using the measure tool.

In the context of killing *E. coli* in the above well diffusion assay, preferably the lactic acid bacterial strain of the invention exhibits <20000 units of inhibition, more preferably 20000-40000 units, even more preferably 40000-60000 units, more preferably 60000-80000 units, more preferably 80000-100000 units of inhibition, even more preferably still >100000 units of inhibition.

In one preferred embodiment of the invention, the lactic acid bacterial strain is characterised by the ability to exhibit antimicrobial activity against *S. enteritidis*. Again, the observed antimicrobial activity is most likely by virtue of anti-microbial substances produced by the lactic acid bacterial strains of the invention, although nature of these anti-microbial substances has not been determined.

In the context of the present invention, the ability to exhibit antimicrobial activity against *S. enteritidis* can be determined by measuring the ability to inhibit the growth of *S. enteritidis* in an in vitro well diffusion assay. Further details of the well diffusion assay are set forth in the accompanying examples. The assay is carried out using *Salmonella enteritidis* S1400 on XLD agar, incubating the plates for 16 hours at 37° C. XLD agar is prepared as per manufacturer's instructions and cooled to 45° C. *Salmonella enteritidis* S1400 is added to the XLD agar (1 ml of a 1:1000 dilution of an overnight culture of *Salmonella enteritidis* S1400 in 200 ml agar to give the equivalent of 106 CFU/ml). The XLD agar is poured into petri dishes and allowed to set. The plates are marked off into quadrants and an approximately 5 mm well cut out in each quadrant. An aliquot (60 µl) of conditioned media or MRS broth is added to the wells.

The plates are covered and incubated for 16 hours at 37° C. and the data analysed as described above for the *E. coli* assay.

In the context of killing *Salmonella enteritidis* in the above well diffusion assay, preferably the lactic acid bacterial strain of the invention exhibits <20000 units of inhibition, more preferably 20000-40000 units, even more preferably 40000-60000 units, more preferably 60000-80000 units, more preferably 80000-100000 units of inhibition, even more preferably still >100000 units of inhibition.

In an alternative embodiment, the ability to exhibit antimicrobial activity against *S. enteritidis* can be determined by measuring the ability to inhibit *S. enteritidis* in vivo in C3H/HeN or C57Bl/6 mice. Further details of appropriate in vivo assays are set forth in the accompanying examples.

Specifically, C3H/HeN and C57Bl/6 mice are treated with a lactic acid bacterial strain according to the invention prior to and post-challenge with *Salmonella enteritidis*. The mice are euthanased and dissected 6 (C57Bl/6) or 10 (C3H/HeN) days post-infection and viable *salmonella* are detected in systemic tissues (e.g. the mesenteric lymph node, liver and spleen), in the intestine (e.g. caecum, colon) and in the faeces as compared to appropriate controls. The in vivo activity of the lactic acid bacterial strain of the invention can also be measured by determining the level of myeloperoxidase [MPO], a marker for neutrophils, in the intestine of C3H/HeN mice treated with *salmonella* or *salmonella* plus LAB. MPO in the intestine is greatly increased by *salmonella* infection, due to recruitment of neutrophils to the intestine part of the host response to infection. Co-treatment with a lactic acid bacterial strain according to the invention reduces MPO activity in the intestine of *salmonella*-infected mice, indicating that the intestinal inflammatory responses to infection are lowered in these animals, relative to control experiments.

In one preferred embodiment of the invention, the lactic acid bacterial strain is characterised by the ability to suppress inflammation in IPEC cells induced by 12-O-tetradecaboylphorbol-13-acetate (PMA). In the context of the present invention, this refers to the ability of the lactic acid bacterial strain to block interleukin-8 (IL-8) gene expression triggered by PMA. More specifically, it can be determined by measuring the suppression of inflammation in IPEC-J2 cells induced by PMA when incubated for 2 hours at 37° C., 5% $CO_2$, 95% humidity. Following RNA and reverse transcription, real time PCR is carried out on a 7500 Fast Real-time PCR system operating with 7500 Fast System v 1.4.0 Sequence Detection Software version 1.4 (Applied Biosystem), using primers for porcine IL-8 and TNF-α (prepared by Sigma Aldrich). The reaction mix is: 10 µl Power Sybergreen Master mix, 2.5 µl of forward primer, 2.5 µl of reverse primer and 5 µl of cDNA, The Real Time PCR is then run according to the Standard 7500 protocol (95° C., 10 min, 1 cycle. 95° C., 15 sec, 40 cycles. 60° C., 1 min, 40 cycles. 95° C., 15 sec, 1 cycle. 60° C., 1 min, 1 cycle. 95° C., 15 sec, 1 cycle. 60° C., 15 sec, 1 cycle). Expression of IL-8 and TNF-α genes are analysed and compared to that of the 'house-keeping' gene β-actin. For comparison, values are given as the ratio of IL-8 and TNF-α per β-actin or fold-change. Further details of this assay are set forth in the accompanying examples.

In one preferred embodiment of the invention, the lactic acid bacterial strain is characterised by the ability to block the attachment or invasion of IPEC cells by *S. enteritidis*. This can be measured by the assay set forth in the accompanying examples. Specifically, monolayers of IPEC-J2 cells are grown to 3 days post-confluence in 24-well plates and synchronised by the addition of DTS media 24 hrs prior to use. Overnight cultures of pig LAB (10 ml) are centrifuged and the bacteria re-suspended in phosphate buffered saline [PBS]. An aliquot (50 µl) of LAB is added to the wells. The plates are incubated for 2 hours at 37° C., 5% $CO_2$, 95% humidity. An overnight culture of *Salmonella enterica* serovar *Enteritidis* S1400 [*S. enteritidis* S1400] is sub-cultured (0.5 ml in 10 ml) into Luria Bertani (LB) media and incubated aerobically for 2-3 hours at 37° C. until it reaches an optical density (560 nm) of 0.8 (a concentration equivalent to 1×108 CFU/ml). The culture is centrifuged and the bacteria re-suspended in PBS. An aliquot (50 µl) is added to the wells of IPEC-J2 cells. The plates are incubated for a further 2 hours at 37° C., 5% $CO_2$, 95% humidity. The IPEC-J2 cell monolayers are washed with HBSS. A solution (0.5 ml) of PBS containing Triton-X100 (10 ml/litre) is added to each well, the monolayer scraped off and dispersed. Viable *salmonella* are estimated on XLD agar plates (incubated for 24 hours at 37° C.) by the Miles and Misra method. Lactic acid bacteria are determined by the same procedure (incubated anaerobically for 48 hours at 37° C.).

Preferably, in the context of the adherence/invasion of IPEC cells by *S. enteritidis* the lactic acid bacterial strain of the invention exhibits 0-20% inhibition of adherence/invasion, more preferably 20-40%, even more preferably 40-60%, more preferably still, 60-80%, even more preferably still, 80-100% inhibition of adherence/invasion as measured by the above assay.

In one preferred embodiment of the invention, the lactic acid bacterial strain is characterised by the ability to block the attachment or invasion of IPEC cells by *E. coli*. This can be measured by a similar assay to that described above for *S. enteritidis*, and as set forth in the accompanying examples.

Preferably, in the context of the adherence/invasion of IPEC cells by *E. coli* K88 the lactic acid bacterial strain of the invention exhibits 0-20% inhibition of adherence/invasion, more preferably 20-40%, even more preferably 40-60%, more preferably still, 60-80%, even more preferably still, 80-100% inhibition of adherence/invasion as measured by the above assay.

In one preferred embodiment of the invention, the lactic acid bacterial strain is characterised by the absence of antibiotic resistance to one or more antibiotics selected from the following: ampicillin; cefotaxime; chloramphenicol; erythromycin; gentamicin; tetracycline; vancomycin; metronidazole; nalidixic acid; and kanamycin. In the context of the present invention, antibiotic resistance can be determined by measuring the effect of various antibiotic-containing discs on an MRS agar plate culture of the lactic acid bacterial strain, when placed in an anaerobic jar and incubated for 24 hours at 37° C. Further details of the assay are set forth in the accompanying examples. More specifically, pig LAB [0.5 ml of a 1:100 dilution of an overnight culture] is spread onto the surface of an MRS agar plate and dried off. The plates are marked off into 4 quadrants and in each quadrant is placed an antibiotic-containing disc [Ampicillin, 10 µg. Cefotaxime, 30 µg. Chloramphenicol, 10 µg. Erythromycin, 15 µg. Gentamicin, 10 µg. Kanamycin, 30 µg. Metronizadole, 50 µg. Nalidixic acid, 30 µg. Tetracycline, 30 µg. Vancomycin, 30 µg]. The plates are covered, placed in an anaerobic jar and incubated for 24 hours at 37° C. The plates are photographed using a digital camera. Images are transferred to Photoshop, and the diameter of the zone of inhibition is determined using the measure tool. For each antibiotic, the exclusion area for the test strain is taken and divided with the maximum area of exclusion obtained for that antibiotic.

Preferably, the LAB of the invention is characterised by the absence of resistance to the antibiotics ampicillin, cefotaxime, chloramphenicol, erythromycin, gentamicin, tetracycline, vancomycin, metronizadole, nalidixic acid and kanamycin. More preferably, the LAB of the invention is characterised by the absence of resistance to the antibiotics ampicillin, cefotaxime, chloramphenicol, erythromycin, gentamicin, tetracycline and vancomycin.

In one preferred embodiment of the invention, the lactic acid bacterial strain is characterised by the ability to exhibit heat stability when subjected to three cycles of heating, each cycle comprising heating at a temperature of 70° C. for a period of 15 minutes. Further details of heat stability studies are set forth in the accompanying examples. More specifically, in the context of the present invention, heat stability is measured by centrifuging an overnight culture (10 ml) of isolated pig LAB and resuspending the pellet in fresh MRS broth (10 ml). An aliquot (1 ml) is heated at 70° C. for 15 min and then plated out (0.5 ml) out on MRS agar and incubated in an anaerobic jar for 48 hours at 37° C. A small number of colonies are detected, picked off, seeded into Hungate tubes containing MRS broth and incubated for 48 hours at 37° C. This culture is centrifuged, re-suspended in MRS broth, heated again at 70° C. for 15 min, plated out on MRS agar, incubated in an anaerobic jar for 48 hours at 37° C., picked off, seeded into Hungate tubes containing MRS broth and incubated for 48 hours at 37° C. This culture is centrifuged, re-suspended in MRS broth, re-heated at 70° C. for 15 min, plated out (0.5 ml) out on MRS agar, incubated in an anaerobic jar for 48 hours at 37° C., picked off, seeded into Hungate tubes containing MRS broth and incubated for 48 hours at 37° C.

In one preferred embodiment, the lactic acid bacterial strain has any two of the characterising features selected from the group consisting of (i), (ii), (iii), (iv), (v), (vi) and (vii) set forth above.

In one preferred embodiment, the lactic acid bacterial strain has any three of the characterising features selected from the group consisting of (i), (ii), (iii), (iv), (v), (vi) and (vii) set forth above.

In one preferred embodiment, the lactic acid bacterial strain has any four of the characterising features selected from the group consisting of (i), (ii), (iii), (iv), (v), (vi) and (vii) set forth above.

In one preferred embodiment, the lactic acid bacterial strain has any five of the characterising features selected from the group consisting of (i), (ii), (iii), (iv), (v), (vi) and (vii) set forth above.

In one preferred embodiment, the lactic acid bacterial strain has any six of the characterising features selected from the group consisting of (i), (ii), (iii), (iv), (v), (vi) and (vii) set forth above.

In one preferred embodiment, the lactic acid bacterial strain has all seven of the characterising features (i), (ii), (iii), (iv), (v), (vi) and (vii) set forth above.

In one particularly preferred embodiment, (A), the lactic acid bacterial strain is characterised by features (i) and (ii) above.

In one particularly preferred embodiment, (B), the lactic acid bacterial strain is characterised by features (iv) and (v) above.

In one particularly preferred embodiment, (C), the lactic acid bacterial strain is characterised by features (iv) and (v) above.

In one particularly preferred embodiment, the lactic acid bacterial strain is characterised by features denoted (D) to (G) as follows:
(D) (i) and (iv); or
(E) (i) and (v); or
(F) (ii) and (iv); or
(G) (ii) and (v);

More preferably, the lactic acid bacterial strain is further characterised by feature (vi) in addition to those features recited in any one of embodiments (A) to (G) above.

Even more preferably, the lactic acid bacterial strain is further characterised by feature (iii) in addition to those features recited in any one of embodiments (A) to (G) above.

Even more preferably still, the lactic acid bacterial strain is further characterised by feature (vii) in addition to those features recited in any one of embodiments (A) to (G) above.

Biological Deposits

All microorganism deposits were made under the terms of the Budapest Treaty. Maintenance of a viable culture is assured for 30 years from the date of deposit. All restrictions on the availability to the public of the deposited microorganisms will be irrevocably removed upon the granting of a patent for this application. One embodiment of the invention relates to a lactic acid bacterial strain isolated from the faeces of organically reared pigs and selected from the group consisting of strains deposited on 27 Jun. 2011 under the terms of the Budapest Treaty at National Collections of Industrial, Food and Marine Bacteria (NCIMB) at NCIMB Ltd, Ferguson Building, Craibstone Estate, Bucksburn, Aberdeen, UK, AB21 9YA, under the following accession numbers: NCIMB 41846: *Lactobacillus reuteri* GGDK31; NCIMB 41847: *Lactobacillus plantarum/pentosus/paraplantarum* GGDK161; NCIMB 41848: *Lactobacillus johnsonii/taiwanensis/acidophilus/gasseri* GGDK255; NCIMB 41849: *Lactobacillus plantarum/pentosus/helveticus/paraplantarum* GGDK258; NCIMB 41850: *Lactobacillus johnsonii* GGDK266.

The above deposits NCIMB 41846, NCIMB 41847, NCIMB 41848, NCIMB 41849 and NCIMB 41850, were made by Dr George Grant of the Rowett Institute of Nutrition and Health, University of Aberdeen, Greenburn Road, Aberdeen, AB21 9SB on behalf of the Applicant, GT Biologics Limited.

Subsequent studies by the Applicant revealed that the strain deposited as NCIMB 41847 was a mixture of *Lactobacillus paraplantarum* and *Lactobacillus reuteri*.

Subsequent studies by the Applicant revealed that the strain deposited as NCIMB 41850 was a mixture of *Lactobacillus johnsonii* and *Lactobacillus reuteri*. Subsequent studies by the Applicant revealed that the strain deposited as NCIMB 41848 was *Lactobacillus reuteri*. Isolated strains for the respective components of strains NCIMB 41847 and NCIMB 41850 were subsequently deposited (see below).

Another embodiment of the invention relates to a lactic acid bacterial strain isolated from the faeces of organically reared pigs and selected from the group consisting of strains deposited on 12 Jul. 2012 under the terms of the Budapest Treaty at National Collections of Industrial, Food and Marine Bacteria (NCIMB) at NCIMB Ltd, Ferguson Building, Craibstone Estate, Bucksburn, Aberdeen, UK, AB21 9YA, under the following accession numbers:
NCIMB 42008 *Lactobacillus johnsonii;*
NCIMB 42009 *Lactobacillus reuteri;*
NCIMB 42010 *Lactobacillus plantarum;*
NCIMB 42011 *Lactobacillus reuteri;*
NCIMB 42012 *Lactobacillus reuteri*

The above deposits NCIMB 42008, NCIMB 42009, NCIMB 42010 and NCIMB 42011 and NCIMB 42012, were made by Professor Denise Kelly of GT Biologics Limited, do Institute of Medical Sciences, University of Aberdeen, Foresterhill, Aberdeen, Aberdeenshire, AB25 2ZD, UK, on behalf of the Applicant, GT Biologics Limited.

The invention also encompasses mutant strains, which can be obtained from said strains, and strains exhibiting a DNA-DNA homology of at least 70% and/or a 16S RNA identity of at least 99.5% with a strain selected from those deposited under the above accession numbers.

As used herein the term "16S rRNA identity" refers to the percentage identity with a known bacterial strain. In one preferred embodiment, the lactic acid bacterial strain has a 16S rRNA identity of at least 85% or at least 90%, or at least 95, 96, 97, 98 or 99% with a strain selected from those deposited under the above accession numbers. In one highly preferred embodiment, the lactic acid bacterial strain has a 16S rRNA identity of at least 99.5% with a strain selected from those deposited under the above accession numbers.

In the context of the present invention, the term "DNA-DNA homology" refers to how closely related two or more separate strands of DNA are to each other, based on their nucleotide sequence. Typically, this is measured in terms of their % identity. In one preferred embodiment, the lactic acid bacterial strain has a DNA-DNA homology of at least 70% with a strain selected from those deposited under the above accession numbers, more preferably, at least 80%, or at least 85%, more preferably still, at least 90, 95, 97, 98 or 99% homology with a strain selected from those deposited under the above accession numbers.

In one highly preferred embodiment, the lactic acid bacterial strain has a DNA-DNA homology of at least 70% and a 16S rRNA identity of at least 99.5% with a strain selected from those deposited under the above accession numbers.

Compositions

Another aspect of the invention relates to a composition comprising one or more lactic acid bacterial strains as described above and a pharmaceutically acceptable excipient, carrier or diluent. Suitable excipients, diluents, carriers are described below.

The composition may be any composition, but is preferably a composition to be administered orally, enterally or rectally. For example, the composition may be an edible composition. "Edible" means a material that is approved for human or animal consumption.

Another aspect of the invention relates to a probiotic composition comprising a lactic acid bacterial strain as described above.

Another aspect of the invention relates to combinations of two more lactic acid bacterial strains as described herein. In a particularly preferred embodiment, such combinations exhibit a synergistic functionality, for example, the combination is synergistic, i.e. the resultant effect is greater than the simple additive effects attributable to the individual lactic acid bacterial components in the combination.

One preferred embodiment of the invention relates to a combination of two, three, four or five different lactic acid bacteria, more preferably, two, three or four different lactic acid bacteria, more preferably, two or three different lactic acid bacteria. Where the invention relates to a combination of more than one lactic acid bacterial strain, the individual components of the combination may be present in any ratio.

More preferably still, the invention relates to a combination of two different lactic acid bacteria. Preferably, the two different lactic acid bacteria are present in a ratio of from 1/99.9 to 99.9/1 by weight, for example, 1/99 to 99/1 or 10/90 to 90/10, or 20/80 to 80/20, or 30/70 to 70/30 and the like.

In one highly preferred embodiment, the combination is a mixture of *Lactobacillus johnsonii* and *Lactobacillus reuteri*. Even more preferably, the combination is NCIMB 41850: *Lactobacillus johnsonii* and *Lactobacillus reuteri* GGDK266 as described above. Surprisingly, this particular combination of lactic acid bacteria unexpectedly gives rise to beneficial in vivo responses in early weaned pigs (see Examples).

In another highly preferred embodiment, the combination is a mixture of *Lactobacillus plantarum* and *Lactobacillus reuteri*. Even more preferably, the combination is NCIMB 41847: *Lactobacillus plantarum/pentosus/paraplantarum* and *Lactobacillus reuteri* GGDK161 as described above.

As used herein, the term "probiotic" means microbial cell preparations or components of microbial cells with a beneficial effect on the health or well-being of the host. (Salminen S, Ouwehand A. Benno Y. et al "Probiotics: how should they be defined" Trends Food Sci. Technol. 1999:10 107-10).

Preferably, the probiotic composition is an orally administrable composition of metabolically active, i.e., live and/or or lyophilized, or non-viable heat-killed, irradiated or lysed probiotic bacteria. The probiotic composition may contain other ingredients. The probiotic composition of the invention can be administered orally, i.e., in the form of a tablet, capsule or powder. Alternatively, the probiotic composition of the invention may be administered orally as a food or nutritional product, such as milk or whey based fermented dairy product, or as a pharmaceutical product.

A suitable daily dose of the probiotic bacteria is from about $1 \times 10^3$ to about $1 \times 10^{11}$ colony forming units (CFU), more preferably from about $1 \times 10^7$ to about $1 \times 10^{10}$ CFU, more preferably, about $1 \times 10^6$ to about $1 \times 10^{10}$ CFU.

In one preferred embodiment, the composition contains bacterial strains and/or their cellular components, as active ingredients, in an amount of from about $1 \times 10^6$ to about $1 \times 10^{12}$ CFU/g, respect to the weight of the composition, preferably from about $1 \times 10^8$ to about $1 \times 10^{10}$ CFU/g. The dose may be of 1 g, 3 g, 5 g, and 10 g, by way of example.

Typically, a probiotic is optionally combined with at least one suitable prebiotic compound. A prebiotic is usually a non-digestible carbohydrate such as an oligo- or polysaccharide, or a sugar alcohol which is not degraded or absorbed in the upper digestive tract. Known prebiotics include commercial products such as inulin and transgalacto-oligosaccharides.

Preferably, the composition of the present invention includes a prebiotic in an amount of from about 1 to about 30% by weight, respect to the total weight composition, preferably from 5 to 20% by weight. Preferred carbohydrates are selected from: fructo-oligosaccharides (or FOS), short-chain fructo-oligosaccharldes, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. Particularly preferred prebiotics are the short-chain fructo-oligosaccharides (for simplicity shown hereinbelow as FOSs-c.c); said FOSs-c.c. are not digestable glucides, generally obtained by the conversion of the beet sugar and including a saccharose molecule to which three glucose molecules are bonded.

Preparation of Lactic Acid Bacteria

A further aspect of the invention relates to a process for producing a probiotic, said process comprising culturing a lactic acid bacterial strain according to the invention. The skilled person in the art will be familiar with standard techniques and conditions suitable for culturing a bacterial strain according to the invention.

A further aspect of the invention relates to a method of preparing one or more bacterial strains according to the invention, said method comprising the steps of:
(i) obtaining faeces from an organically reared pig;
(ii) freezing the faeces and dispersing in a suitable diluent;
(iii) applying the dispersed faeces obtained in step (ii) to a suitable agar, optionally in the presence of supplemental pig colostrum carbohydrates, and incubating under an anaerobic conditions;
(v) selecting off distinct colonies of bacteria formed during step (iv) and seeding into a suitable broth, optionally in the presence of supplemental pig colostrum carbohydrates;
(vi) incubating the seeded colonies obtained in step (v).

Suitable agars include, for example, MRS or LAMVAB agar plates. However, other suitable agars can also be used, and would be familiar to the skilled person.

Suitable broths include, for example, MRS broth. However, other suitable broths can also be used, and would be familiar to the skilled person.

Preferably, step (iii) involves incubating the agar for at least 72 hours at a temperature of about 37° C.

Preferably, step (vi) involves incubating the seeded colonies for at least 48 hours at a temperature of about 37° C.

A further aspect of the invention relates to a process for obtaining a porcine lactic acid bacterial strain, said process comprising obtaining faeces from an organically reared pig and extracting one or more porcine lactic acid bacterial strains from said faeces.

Preferably, the process comprises the steps of:
(i) obtaining faeces from an organically reared pig;
(ii) freezing the faeces and dispersing in a suitable diluent;
(iii) applying the dispersed faeces obtained in step (ii) to a suitable agar, optionally in the presence of supplemental pig colostrum carbohydrates, and incubating under an anaerobic conditions;
(v) selecting off distinct colonies of bacteria formed during step (iv) and seeding into a suitable broth, optionally in the presence of supplemental pig colostrum carbohydrates;
(vi) incubating the seeded colonies obtained in step (v).

Another aspect of the invention relates to a porcine lactic acid bacterial strain obtained by, or obtainable by, the process described above.

Therapeutic Applications

Another aspect of the invention relates to one or more lactic acid bacterial strains as defined above for use in medicine.

Another aspect of the invention relates to one or more lactic acid bacterial strains as defined above for use in treating an intestinal disorder.

Another aspect of the invention relates to the use of one or more lactic acid bacterial strains or a composition as defined above in the preparation of a medicament for treating an intestinal disorder.

The term "medicament" as used herein encompasses medicaments for both human and animal usage in human and veterinary medicine. In addition, the term "medicament" as used herein means any substance which provides a therapeutic and/or beneficial effect. The term "medicament" as used herein is not necessarily limited to substances which need Marketing Approval, but may include substances which can be used in cosmetics, nutraceuticals, food (including feeds and beverages for example), probiotic cultures, and natural remedies. In addition, the term "medicament" as used herein encompasses a product designed for incorporation in animal feed, for example livestock feed and/or pet food.

Another aspect of the invention relates to a method of treating an intestinal disorder in a subject, said method comprising administering to the subject a pharmaceutically effective amount of one or more lactic acid bacterial strains or a pharmaceutical composition or a probiotic composition as described above.

Preferably, the intestinal disorder is selected from irritable bowel syndrome (IBS), inflammatory bowel disorder (IBD), functional dyspepsia, functional constipation, functional diarrhoea (including antibiotic associated diarrhoea, traveller's diarrhoea and pediatric diarrhoea), functional abdominal pain, functional bloating, Epigastric Pain Syndrome, Postprandial Distress Syndrome, Crohn's disease, ulcerative colitis, gastrointestinal reflux disease (GERD), allergies, atopic diseases e.g. atopic dermatitis, necrotising enterocolitis, other infections, and combinations thereof.

In one preferred embodiment, the intestinal disorder is IBS. The precise pathophysiology of IBS remains to be elucidated. Recent studies have described mucosal inflammation and alterations in intestinal microbiota in IBS patients and a disease correlation with intestinal infections.

In one highly preferred embodiment, the disorder is salmonellosis. Salmonellosis is a disease caused by various strains of *salmonella* that is characterized by fever and intestinal disorders.

Another aspect of the invention relates to one or more lactic acid bacterial strains as defined above for improving intestinal microbiota.

Another aspect of the invention relates to a method of improving intestinal microbiota in a subject, said method comprising administering to the subject a composition comprising one or more lactic acid bacterial strains or a pharmaceutical composition or a probiotic composition according to the invention.

The lactic acid bacterial strains according to the invention may also be used in prophylactic applications. In prophylactic applications, compositions according to the invention are administered to a patient susceptible to, or otherwise at risk of, a particular disease in an amount that is sufficient to at least partially reduce the risk of developing a disease. Such an amount is defined to be "a prophylactic effective dose". The precise amounts depend on a number of patient specific factors such as the patient's state of health and weight.

The lactic acid bacterial strains and probiotic compositions according to the invention may also be used in animal nutrition (e.g. in pig nutrition), particularly in the early-weaned period and growing fattening period. The probiotics are expected to enhance immune function reduce and prevent infectious diseases, beneficially alter the microbiota composition, and improve growth and performance of animals, for example, through increased feed conversion efficiency. The term "animal" includes all animals including humans. Examples of animals are non-ruminants and ruminants. Ruminant animals include for example, sheep, goat, and cattle eg. cow as beef cattle and dairy cows. In a particular embodiment, the animal is a non-ruminant animal. Non-ruminant animals include pet animals, eg horses, cats, and dogs; monogastric eg pigs or swine (including but not limited to, piglets growing pigs and sows); poultry such as turkeys, ducks, and chickens (including but not limited to broiler chicks, layers); fish (including but not limited to salmon, trout, tilapia, catfish and carp); and crustaceans (including but not limited to shrimp and prawn).

Feedstuffs/Products

A further aspect of the invention relates to food products, dietary supplements, nutraceuticals, nutritional formulae, drinks and medicaments containing one or more bacterial strains according to the invention.

In one preferred embodiment, the composition comprises additionally at least one other kind of other food grade bacterium, wherein the food grade bacterium is preferably selected from the group consisting of lactic acid bacteria, bifidobacteria, propionibacteria or mixtures thereof.

One aspect of the invention relates to a food product comprising one or more lactic acid bacterial strains according to the invention. The term "food product" is intended to cover all consumable products that can be solid, jellied or liquid. Suitable food products may include, for example, functional food products, food compositions, pet food, livestock feed, health foods, feedstuffs and the like. In one preferred embodiment, the food product is a health food.

As used herein, the term "functional food product" means food that is capable of providing not only a nutritional effect, but is also capable of delivering a further beneficial effect to the consumer. Accordingly, functional foods are ordinary foods that have components or ingredients (such as those described herein) incorporated into them that impart to the food a specific functional—e.g. medical or physiological benefit—other than a purely nutritional effect.

Examples of specific food products that are applicable to the present invention include milk-based products, ready to eat desserts, powders for re-constitution with, e.g., milk or water, chocolate milk drinks, malt drinks, ready-to-eat dishes, instant dishes or drinks for humans or food compositions representing a complete or a partial diet intended for pets or livestock.

In one preferred embodiment the composition according to the present invention is a food product intended for humans, pets or livestock. The composition may be intended for animals selected from the group consisting of dogs, cats, pigs, cattle, horses, goats, sheep or poultry. In a preferred embodiment, the composition is a food product intended for adult species, in particular human adults.

In the present invention, "milk-based product" means any liquid or semi-solid milk or whey based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

One aspect of the invention relates to a feedstuff or animal feed comprising one or more bacterial strains according to the invention.

Feedstuff can be a food additive, a feed premixor an animal feed. Particular examples of feedstuffs according to the invention include the following: animal feed additive comprising (a) porcine lactic acid bacteria according to the present invention (b) at least one fat soluble vitamin (c) at least one water soluble vitamin (d) at least one trace mineral and/or at least one macro mineral; an animal feed composition comprising a porcine lactic acid bacteria according to the present invention and a crude protein content of 50-88 g/kg feed. The so-called premixes are examples of animal feed additives of the invention. A premix designates a preferably uniform mixture of one or more micro-ingredients with diluent and/or carrier. Premixes are used to facilitate uniform dispersion of micro-ingredients in a larger mix.

Further, optional, feed-additive ingredients are coloring agents, e.g. carotenoids such as beta-carotene, astaxanthin, and lutein; aroma compounds; stabilisers; antimicrobial peptides; polyunsaturated fatty acids; reactive oxygen generating species; and/or at least one enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.), phospholipase A1 (EC 3.1.1.32); phospholipase A2 (EC 3.1.1.4); lysophospholipase (EC 3.1.1.5); phospholipase C (EC 3.1.4.3); phospholipase D (EC 3.1.4.4); amylase such as, for example, alpha-amylase (EC 3.2.1.1); and/or beta-glucanase (EC 3.2.1.4 or EC 3.2.1.6).

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthetase.

Usually fat- and water-soluble vitamins, as well as trace minerals form part of a so-called premix intended for addition to the feed, whereas macro minerals are usually separately added to the feed. Either of these composition types, when enriched with a porcine lactic acid bacteria according to the present invention, is an animal feed additive within the scope of the invention.

The following are non-exclusive lists of examples of these components: Examples of fat-soluble vitamins are vitamin A, vitamin D3, vitamin E, and vitamin K, e.g. vitamin K3. Examples of water-soluble vitamins are vitamin B12, biotin and choline, vitamin B1, vitamin B2, vitamin B6, niacin, folic acid and panthothenate, e.g. Ca-D-panthothenate. Examples of trace minerals are manganese, zinc, iron, copper, iodine, selenium, and cobalt. Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated. In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A of WO 01/58275.

Animal feed compositions or diets typically have a relatively high content of protein. Poultry and pig diets can be characterized as indicated in Table B of WO 01/58275, columns 2-3. Fish diets can be characterized as indicated in column 4 of this Table B. Furthermore such fish diets usually have a crude fat content of 200-310 g/kg. WO 01/58275 corresponds to U.S. Ser. No. 09/779,334 which is hereby incorporated by reference.

An animal feed composition according to the invention typically has a crude protein content of 50-800 g/kg, and furthermore comprises a porcine lactic acid bacteria according to the present invention thereof as described and/or claimed herein.

Furthermore, or in the alternative (to the crude protein content indicated above), the animal feed composition of the invention may have a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In certain preferred embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5). Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.). Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In one preferred embodiment, the animal feed composition of the invention contains at least one vegetable protein or protein source. It may also contain animal protein, such as Meat and Bone Meal, and/or Fish Meal, typically in an amount of 0-25%. The term vegetable proteins as used herein refers to any compound, composition, preparation or mixture that includes at least one protein derived from or originating from a vegetable, including modified proteins and protein-derivatives. In certain particularly preferred embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal. In a particular embodiment, the vegetable protein source is material from one or more plants of the family Fabaceae, e.g. soybean, lupine, pea, or bean. Other examples of vegetable protein sources are rapeseed, sunflower seed, cotton seed, and cabbage. Other examples of vegetable protein sources are cereals such as barley, wheat, rye, oat, maize (corn), rice, triticale, and sorghum.

Animal diets can e.g. be manufactured as mash feed (non pelleted) or pelleted feed. Typically, the milled feed-stuffs are mixed and sufficient amounts of essential vitamins and minerals are added according to the specifications for the species in question. A porcine lactic acid bacteria according to the present invention thereof can be added as solid or liquid formulations.

The compositions of the present invention may be—or may be added to—food supplements, also referred to herein as dietary supplements or food additives. Thus, another aspect of the invention relates to a dietary supplement or food additive comprising one or more bacterial strains according to the invention.

Another embodiment of the invention relates to the use of a feedstuff as described above for improving animal growth performance as measured by daily weight gain and/or feed conversion ratio.

In a preferred embodiment, the invention relates to methods for using a feedstuff comprising one or more porcine lactic acid bacteria according to the present invention in animal feed for improving daily weight gain, improving the Feed Conversion Ratio (FCR) and/or for modulation of the gut microflora.

In alternative preferred embodiments, the feedstuff comprising one or more porcine lactic acid bacteria according to the present invention improves animal feed digestibility, and/or maintains animal health by aiding in proper digestion and/or supporting immune system function.

The FCR may be determined on the basis of a piglet growth trial comprising a first treatment in which the feedstuff comprising a porcine lactic acid bacteria according to the present invention is added to the animal feed in a suitable concentration per kg feed, and a second treatment (control) with no addition of a porcine lactic acid bacteria according to the present invention to the animal feed. In the present context, the term Feed Conversion Ratio, or FCR, is used synonymously with the term feed conversion. The FCR is calculated as the feed intake in g/animal relative to the weight gain in g/animal. As it is generally known, an improved FCR is lower than the control FCR. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%.

The term "gut" as used herein designates the gastrointestinal or digestive tract (also referred to as the alimentary canal) and it refers to the system of organs within multicellular animals which takes in food, digests it to extract energy and nutrients, and expels the remaining waste.

The term gut "microflora" as used herein refers to the natural microbial cultures residing in the gut and maintaining health by aiding in proper digestion and/or supporting immune system function.

The term "modulate" as used herein in connection with the gut microflora generally means to change, manipulate, alter, or adjust the function or status thereof in a healthy and normally functioning animal, i.e. a non-therapeutic use.

Diluents, Excipients and Carriers

As mentioned above, the invention also relates to compositions, more preferably pharmaceutical compositions, comprising a lactic acid bacterial strain according to the invention. The lactic acid bacterial strains of the present invention are generally administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Administration

The compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration. Preferably, the compositions of the present invention are adapted for oral, rectal, vaginal, parenteral, nasal, buccal or sublingual routes of administration.

For oral administration, particular use is made of compressed tablets, pills, tablets, gellules, drops, and capsules.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The lactic acid bacterial strain can also be incorporated into an ointment consisting of a white wax or white soft paraffin base together with such stabilisers and preservatives as may be required.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific bacterial strain employed, the metabolic stability and length of action of that strain, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

The usual effective daily dose in humans or in animals is from about $1 \times 10^3$ to about $1 \times 10^{11}$, more preferably, from about $1 \times 10^7$ to about $1 \times 10^{11}$, even more preferably, from about $1 \times 10^6$ to about $1 \times 10^{10}$ CFU.

Combinations

In one preferred embodiment, the compositions of the invention are administered in any combination, for example, two or more of the lactic acid bacteria may be administered in any combination or ratio.

In another particularly preferred embodiment, the compositions of the invention are administered in combination with one or more other active agents. In such cases, the compositions of the invention may be administered consecutively, simultaneously or sequentially with the one or more other active agents.

Isolation and Characterisation of Bacterial Strains

The LAB strains isolated (total of 436 individual colony picks) from faeces of organically-reared pigs were predominantly L. reuteri, L. johnsonii, L. gassed, L. pentosus, strains with a small number of L. plantarum, L. acidophilus, L. vaginalis, a single L. mucosae and several uncultured strains.

Most of the LAB produced substances that could inhibit the growth of S. enteritidis and/or E. coli K88 in vitro. The potency of these anti-pathogen effects varied greatly between the individual bacterial strains.

Certain strains were selected on the basis of anti-microbial potency as determined in vitro. These bacteria were further screened for their ability to block adherence/invasion of intestinal pig epithelial cells (IPEC) by pathogens in vitro and their susceptibility to antibiotics.

Certain strains were assayed for substrate range and specificity and their capacity to suppress inflammation in IPEC cells in vitro. From these, fourteen LAB (5 L. johnsonii, 6 L. reuteri and 3 L. Plantarum) with favourable properties were identified. Two of these strains [GGDK266 and GGDK31] were prepared in bulk for in vivo evaluation in newly-weaned piglets. Other potentially important candidates were present amongst this set of 14 LAB.

Small losses in viability were evident on freeze drying and storage of LAB dried in skimmed milk powder. A combination of skimmed milk powder and simple sugars was slightly more effective, but difficult to maintain. Bulk preparations of GGDK266 and GGDK31 were freeze-dried and stored in this medium.

Five heat-conditioned cultures of LAB were obtained. However, the biological properties in vitro and probiotic potential of three strains were adversely affected by heat-treatment. Nonetheless, two of the bacteria retained the biological properties of the native non-heat-treated forms.

Oral treatment of mice with pig LAB (L. reuteri or L. mucosae) greatly reduced the pathogenicity of S. enteritidis in acute (C57Bl/6 mouse) and chronic (C3H/HeN mouse) forms of salmonellosis.

The data indicate that LAB from organically-reared pigs have considerable potential as a source of novel and potent probiotics.

Studies carried out by the applicant involved isolating large numbers of LAB from organically-reared pigs and screening for potent probiotic LAB strains by assessing their biological potency and mode of action both in vitro and in vivo.

More specifically, experiments were undertaken to establish cultures of LAB derived from faeces of organically-reared pigs. The LAB strains were screened for anti-microbial activity against a number of pathogens in vitro. Experiments were undertaken to determine whether the LAB strains could block the attachment of pathogens to pig epithelial cells in vitro. Studies were also undertaken to evaluate the capacity of LAB to block inflammatory responses in pig epithelial cells in vitro. Strains demonstrating a good bioactive profile in vitro were selected and cultured in bulk for a large-scale study in vivo.

Further details on the experimental techniques are described in the accompanying examples section. In brief, LAB strains were isolated and cultured from pig faeces using selective microbiological media. Individual bacterial colonies were isolated and 16S rRNA gene sequences were analysed to enable genotypic identification of bacterial strains. Phenotypic characteristic of potential probiotics was further determined following measurement of adherence, anti-bacterial and anti-inflammatory activities, antibiotic susceptibility and finally heat stability. Anti-bacterial activity of conditioned media derived from LAB was evaluated using well-diffusion assays to determine killing activity against the enteric pathogens *Salmonella enteritidis* and *E. coli* K88. The ability of LAB strains to block or interfere with *S. enteritidis* and *E. coli* K88 adherence/invasion of pig epithelial (IPEC) was also evaluated, as was their capacity to suppress inflammation in IPEC cells induced by 12-O-Tetradecaboylphorbol-13-acetate [PMA]. In addition, the metabolic properties of LAB strains (API CH 50 kit) and their susceptibility to antibiotics was further determined. A ranking system, based on scoring the biological properties of LAB was established and used for the selection of candidate LAB strains for probiotic evaluation in vivo.

Further details on the results of the above experiments are described in the accompanying examples.

The LAB (436 individual colony picks) isolated from faeces of organically-reared pigs were predominantly *L. johnsonii* or *L. johnsonii*-related and *L. reuteri* or *L. reuteri*-related with small numbers of *L. plantarum*-related and uncultured strains. This represented a much narrower range of porcine-associated LAB than reported by others (Martin et al, 2009; Yun et al, 2009; Lahteinen et al, 2010; Yao et al, 2011). However, in comparison to conventionally/intensively-reared pigs, out-door organically-reared pigs had high levels of LAB and more developed intestinal immune function (Mulder et al., 2009). The present bacterial data indicate that *L. johnsonii* and *L. reuteri* strains are of particular importance in proper development of the gut and immune system in young pigs. In addition, the inclusion of other lactic acid bacteria derived from the gut or faeces of organically-reared pigs, in particular, *Lactobacillus delbrueckii* and *Lactobacillus amylovorous* may enhance the immune homeostatic properties of *Lactobacillus reuteri, Lactobacillus plantarum* and *Lactobacillus johnsonii*.

All of the isolated pig LAB produced substances that could kill or interfere with the growth of *S. enteritidis* in a well-diffusion assay and the majority killed or suppressed growth of *E. coli* K88. The potency of the anti-microbial activities varied greatly between individual colonies, irrespective of whether they were *L. reuteri, L. johnsonii* or *L. plantarum*. There was no general correlation between the anti-salmonella and anti-*E. coli* K88 potency of each of the LAB. LAB are known to produce a range of active factors, including organic acids, small anti-microbial compounds and anti-bacterial peptides (Cintas et al, 2001). The nature of these anti-microbial substances produced by LAB from organically-reared pigs has not been established.

Thirty three pig LAB strains, selected on the basis of anti-pathogen activity, were tested for the ability to block attachment/invasion of IPEC cells by *S. enteritidis* and *E. coli* K88. They were all able to dramatically reduce attachment/invasion of IPEC cells by *salmonella*. The majority could also block *E. coli* K88. As with pathogen killing, there was no general correlation between the abilities of the LAB to block *salmonella* and *E. coli* K88. Without wishing to be bound by theory, it is believe that the LAB may limit the access of pathogens to the epithelial layer by occupying binding-sites on the cell monolayer or by production of factors that interfere with attachment of the pathogen to the epithelial cells, such as blocking binding sites of surface adhesins (Ljungh and Wadstrom, 2006; Blandino et al, 2008; Williams, 2010).

Pig LAB may also block or suppress inflammatory gene (Interleukin-8, IL-8)-expression triggered in IPEC cells by PMA. Individual cultures varied greatly in their ability to affect inflammation, but five strains (RINH vial 29, 30, 31 86 and 266) had potent anti-inflammatory properties. Certain LAB strains are known to have immuno-modulatory or anti-inflammatory properties (Cotter et al, 2005; Blandino et al, 2008; Ohashi and Ushida, 2009; Elmadfa et al, 2010; Liu et al, 2010). The mechanisms involved remain unclear, but are likely to involve modulation of molecular signalling systems by bioactive factors produced by the LAB.

Antibiotic resistance is an increasing problem and can spread between bacteria by gene transfer (Korhonen et al, 2007; Gousia et al, 2011; Nicolau, 2011). Ideally, candidate probiotics should have little or no resistance to antibiotics to minimise the risk of transfer of resistance genes to the host flora. Pig LAB (33 strains) were screened for resistance to 10 individual antibiotics. One strain (RINH vial 266) was susceptible to all the tested antibiotics. Most were susceptible to ampicillin, cefotaxime, chloramphenicol, erythromycin, gentamicin, tetracycline and vancomycin. However, most exhibited resistance to metronizadole, nalidixic acid and to a lesser extent kanamycin. This relatively low incidence of antibiotic resistance amongst these LAB isolates may be linked to the environment in which the source piglets were reared [organic out-door reared] (Mulder et al, 2009).

*L. johnsonii, L. reuteri* and *L. plantarum*, as expected, exhibited strain-specific general substrate reaction profiles, when assayed using an API CH 50 kit. However, most genotype strains exhibited fine differences in their substrate reactivity. This indicated that they were unique individual strains of the genotype.

On the basis of their biological activities in vitro, fourteen LAB [4 *L. plantarum-related,* 3 *L. johnsonii*-related and 1 *L. reuteri*] were identified as having potential for testing in vivo. Two of these LAB strains [GGDK266 and GGDK31] were prepared in bulk. Interestingly, 7 of the fourteen LAB (RINH vials 85, 86, 131, 230, 255, 266) had been isolated from LAB-selective agars supplemented with carbohydrate fractions from pig colostrum. The growth and bioactivity profile of LAB is, in part, dependent on the carbohydrate substrate in which it is grown (Gopal et al, 2001; Tzortzis et al, 2004), The present data may indicate that some of the LAB are host-adapted and require certain pig-associated carbohydrates for optimal growth or bioactivity.

It is advantageous if the LAB can withstand being freeze dried to allow them to be handled and processed as probiotics. However, their viability can be greatly reduced during freezing and drying (Tomas et al, 2009; Strasser et al, 2009; Reddy et al, 2009). Skimmed milk powder, alone or in combination with simple sugars, is often used as a cryoprotectant to preserve the viability of the bacteria (Tomas et al, 2009; Strasser et al, 2009). In the present study, small losses in viability were evident on drying and storage of pig LAB in skimmed milk powder alone. Sucrose or lactose in combination with skimmed milk powder was slightly more protective. However, the product was hygroscopic and difficult to store or handle. It was therefore decided to dry and store pig LAB in skimmed milk powder.

Supplemental feeds for animal are often given as pellets, production of which involves high temperatures (De Angelis et al, 2006). LAB to be added to animal feeds should therefore have a significant degree of heat-stability to minimise loss of viability during processing. In the present study, five LAB were subject to heating three times for 15 minutes at 70° C. All of the bacteria that were recovered after the third heat-treatment were viable and in most cases grew at rates similar to the native forms of the bacteria. Two of the bacteria retained the biological properties of the native non-heat-treated forms. However, one of the heat-treated strains had lost the ability to block attachment of pathogen to epithelial cells in vitro and another had greatly reduced blocking activity. A further strain was unable to block PMA-induced inflammation in epithelial cells in vitro, although the native form was a potent suppressor of inflammation. Heat-treatment can thus differentially affect the biological properties of individual LAB. This needs to be taken into account when considering inclusion of LAB in pelleted animal feeds.

Experiments demonstrated that the pathogenicity of *S. enteritidis* was attenuated if mice were co-treated with LAB derived from organically-reared pigs. RINH vial 323 (*L. mucosae*) greatly reduced the ability of *S. enteritidis* to invade, spread to and proliferate in systemic tissues in acute (C57Bl/6 mouse) and chronic (C3H/Hen mouse) salmonellosis. Furthermore, RINH vial 31 [GGDK31], RINH vial 32, RINH vial 46 or RINH vial 47 (all *L. reuten*) reduced colonisation of the large intestine, invasion and systemic spread and proliferation in C3H/HeN mice by *S. enteritidis*. Overall, RINH vial 31 [GGDK31] and RINH vial 32 were the most effective in this chronic model of salmonellosis. These LAB have potential as novel probiotics to promote gut health or increase resistance to infection in vivo.

Infection by *salmonella* is a multi-factorial process (Naughton and Grant, 2005). *S. enteritidis* colonises the whole gastro-intestinal tract, moves through the mucus layer and attaches to the mucosa. The large intestine acts as a reservoir for the pathogen but invasion is primarily via M cells, present on the Peyer's patches of the ileum. Most invaded *salmonella* spread to the mesenteric lymph nodes and then out to the liver and spleen (Naughton and Grant, 2005). Without wishing to be bound by theory, it is believed that LAB could be blocking *salmonella* at various stages of the infection (Cintas et al, 2001; Cotter et al, 2005; Ohashi and Ushida, 2009). By competing for nutrients, killing of pathogen or blocking of attachment sites, LAB could limit the numbers of *salmonella* in the large intestine reservoir. LAB may also prevent attachment to ileal mucosal cells, in a manner similar to that observed here with IPEC-J2 cells and with Caco-2 cells (Neeser et al, 2000) and thereby limit invasion. Alternatively, LAB may directly modulate host responses to the infection, in particular suppression of inflammation. By limiting gut damage and preserving barrier integrity (Smith et al, 2008; Schreiber et al, 2009), the ability of *salmonella* to invade and spread would be greatly reduced.

The present invention is further described by way of non-limiting example, and with reference to the following non-limiting figures, wherein:

FIG. 1 shows an assay of antibacterial activity of conditioned media from Lactic Acid Bacteria.

FIGS. 2a & b show inhibitory activity against *S. enteritidis* S1400 (expressed as area of inhibition in a well diffusion assay) of conditioned media of all individual LAB cultured from faeces of organically-reared pigs.

FIGS. 3a & b show inhibitory activity against *E. coli* K88 (expressed as area of inhibition in a well diffusion assay) of conditioned media of all individual LAB cultured from faeces of organically-reared pigs.

FIGS. 3c & d show inhibitory activity (expressed as area of inhibition in a well diffusion assay) of conditioned media of all individual LAB cultured from faeces of organically-reared pigs.

FIGS. 4a, b, c shown inhibition of adherence by (a) *S. enteritidis* S1400; and (b) *E. coli* K88 to IPEC cells in culture by LAB cultured from faeces of organically-reared pigs; (c) comparison between inhibition of *S. enteritidis* S1400 and (b) *E. coli* K88.

FIG. 5 shows an assay of the antibiotic susceptibility of Lactic Acid Bacteria using discs impregnated with a defined amount of antibiotic.

FIG. 10 shows a protocol for the C3H/HeN mouse study to evaluate efficacy of vial 323 (*L. mucosae*) to counteract *salmonella* infection in vivo.

FIGS. 11a-c show the distribution of *S. enteritidis* S1400 in tissues at 10 days post-infection in C3H/HeN mice that had or had not been co-treated with 323 (*L. mucosae*, LM).

Figure 12A:
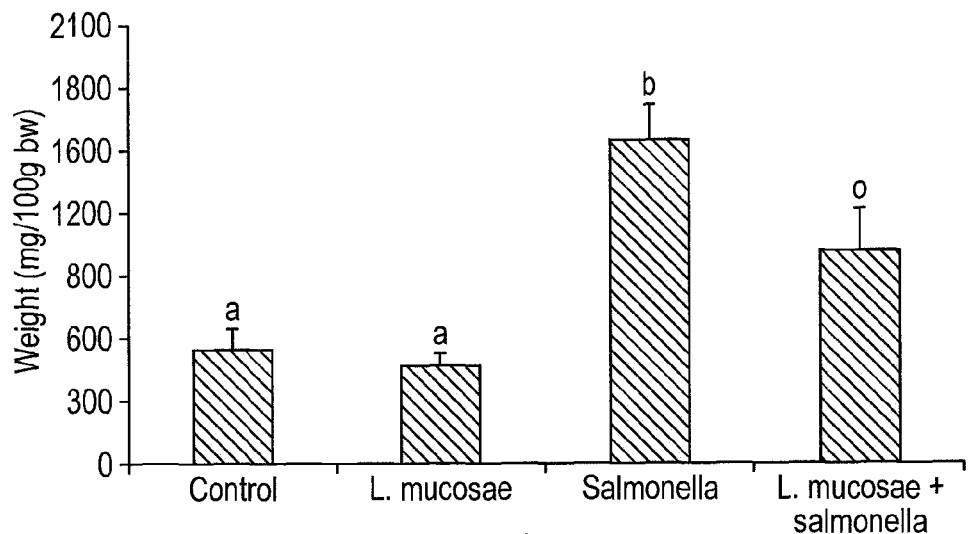
Figure 12B:
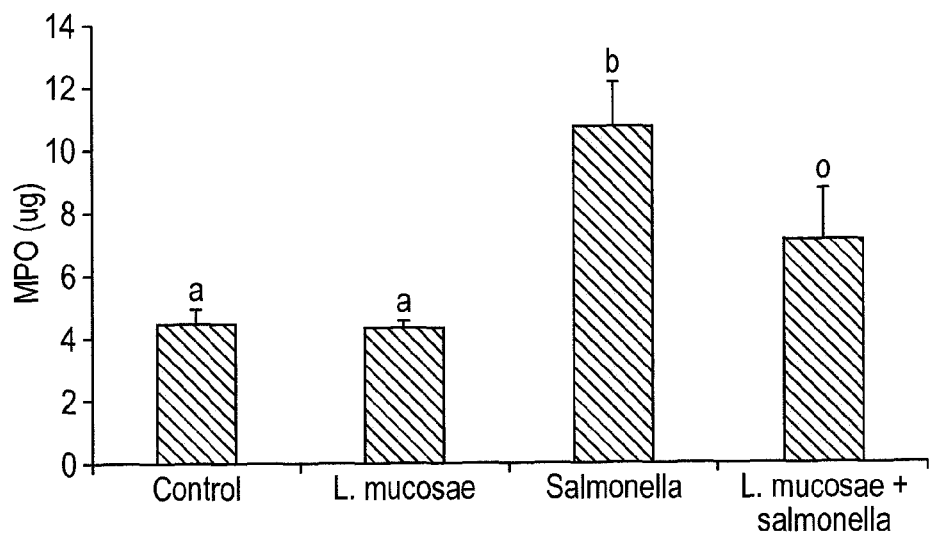

FIGS. 12a-b show spleen weight (mg/100 g BW) and intestinal (ileal) myeloperoxidase (μg) at 10 days post-infection in C3H/HeN mice that had or had not been co-treated with vial 323 (*L. mucosae*).

FIG. 13 shows a protocol for the C57 Bl/6 mouse study to evaluate efficacy of vial 323 (*L. mucosae*) to counteract acute *salmonella* infection in viva FIGS. 14a-c shows the distribution of *S. enteritidis* S1400 in tissues at 6 days post-infection in C57Bl/6 mice that had or had not been co-treated with RINH vial 323.

FIG. 15 shows spleen weight (mg/100 g BW) at 6 days post-infection in C57Bl/6 mice that had or had not been co-treated with vial 323 (*L. mucosae*).

FIG. 16 shows a protocol for the C3H/HeN mouse study to evaluate efficacy of selected LAB from faeces of organically reared pigs to counteract *salmonella* infection in vivo.

Figure 17:
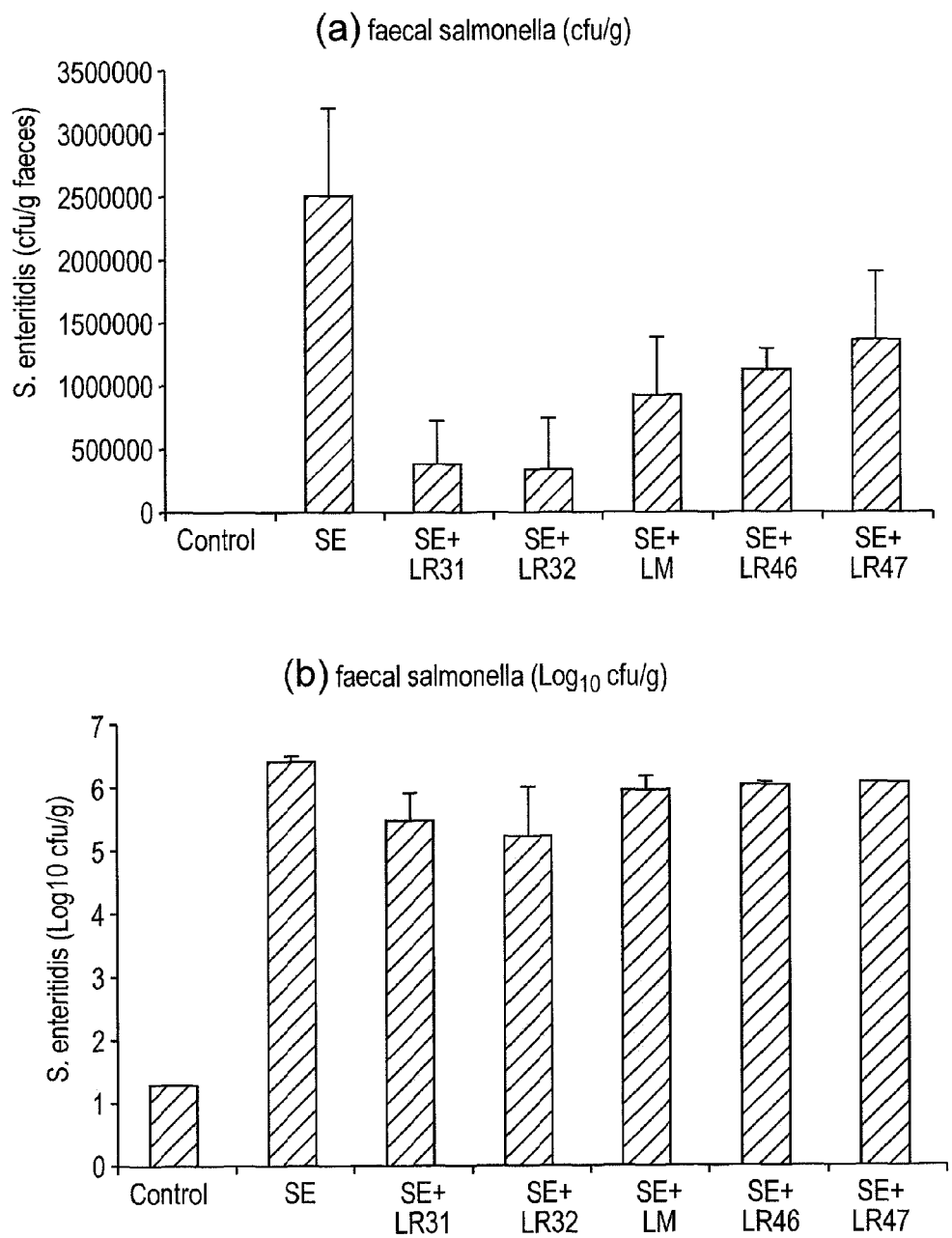

FIGS. 17a & b show excretion of *S. enteritidis* in faeces at 7-8 days post-infection by C3H/HeN mice that had or had not been co-treated with selected LAB.

FIGS. 18a-b show the distribution of *S. enteritidis* (Log 10 CFU/g) in ileum (a), caecum (b) and colon (c) at 10 days post-infection of C3H/HeN mice that had or had not been co-treated with selected LAB.

Figure 19:
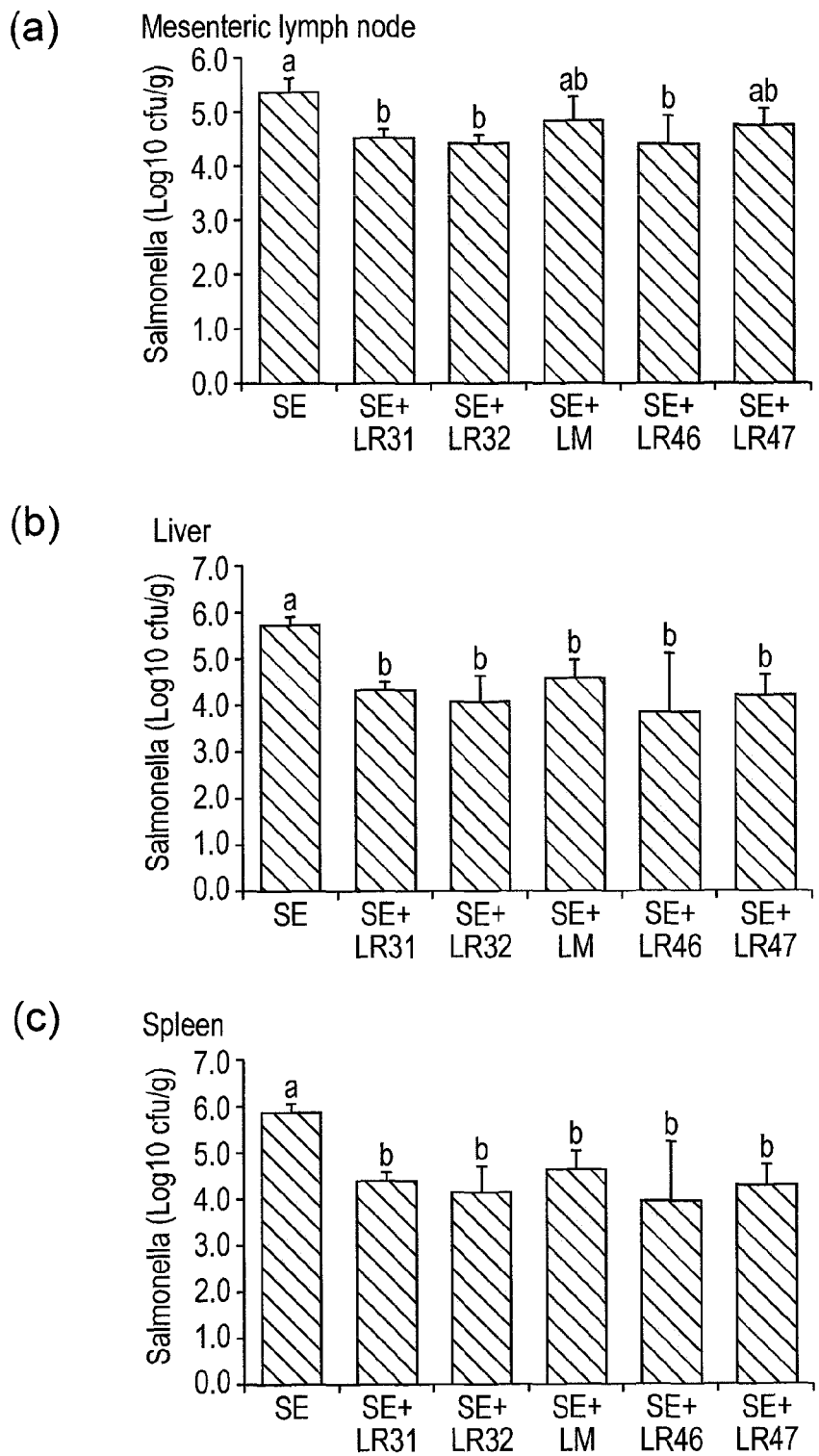

FIGS. 19a-c show the distribution of *S. enteritidis* (Log 10 CFU/g) in mesenteric lymph node (a), liver (b) and spleen (c) at 10 days post-infection of C3H/HeN mice that had or had not been co-treated with selected LAB.

Figure 20:
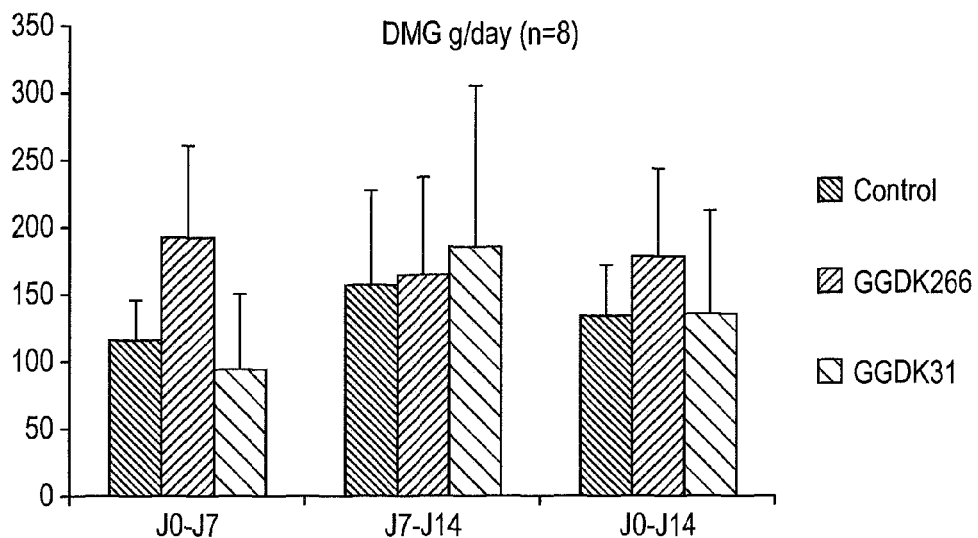

FIG. 20 shows the performance of pigs fed GGDK266 and GGDK31 versus a control (daily weight gain, DWG, in g/day) for days 0-7, 7-14 and 0-14.

Figure 21:
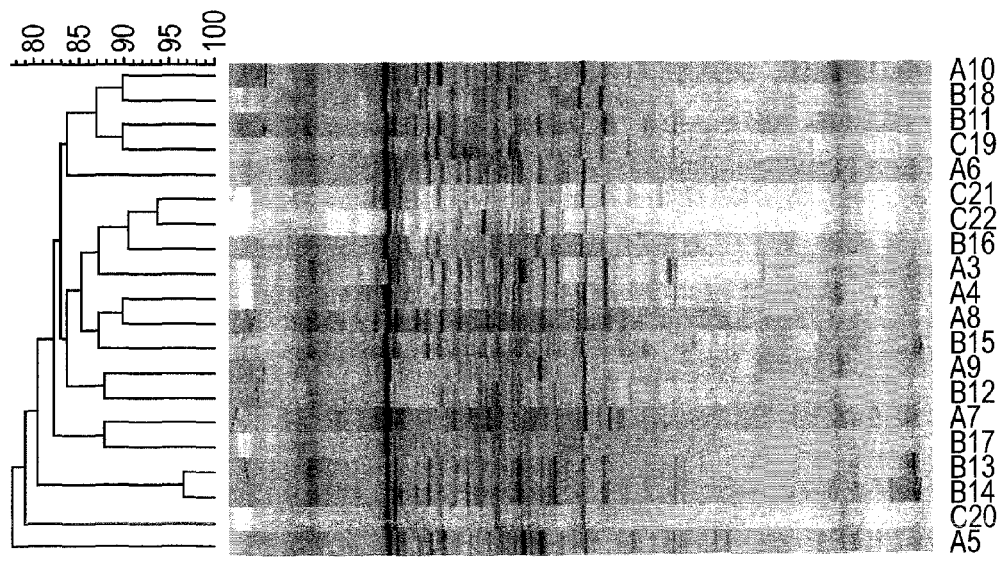

FIG. 21 shows microbial diversity analysis using denaturing gel gradient electrophoresis (DGGE; Trial 1). DGGE using universal primers revealed no differences in overall microbial diversity between the treatments and placebo. Bands on the gel are visualised by silver staining.

Figure 22:
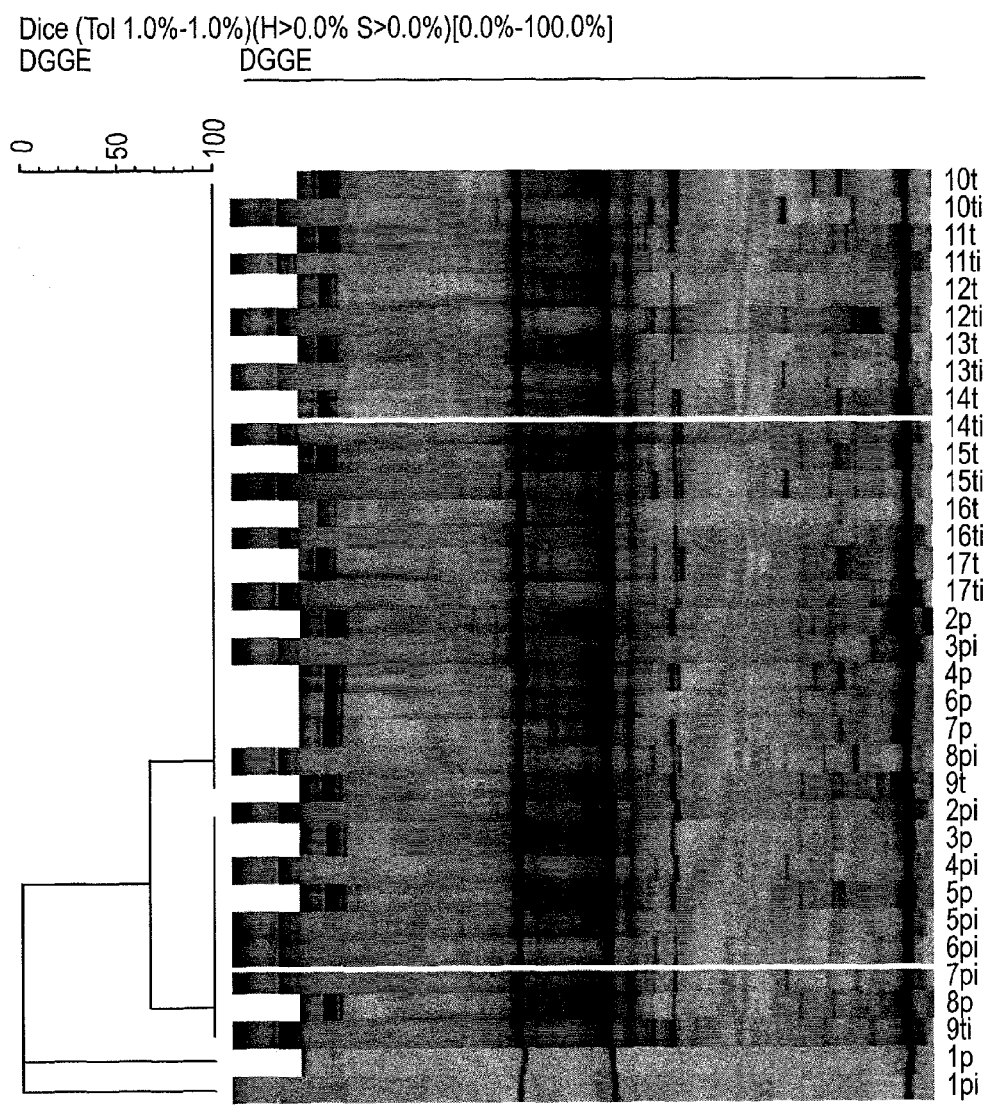

FIG. 22 shows microbial diversity analysis using DGGE. DGGE using lactic acid bacteria (LAB) specific primers revealed significant differences in LAB diversity between treatment with GGDK266 and placebo in both caecal and ileal samples. Bands on the gel are visualised by silver staining.

Figure 23:
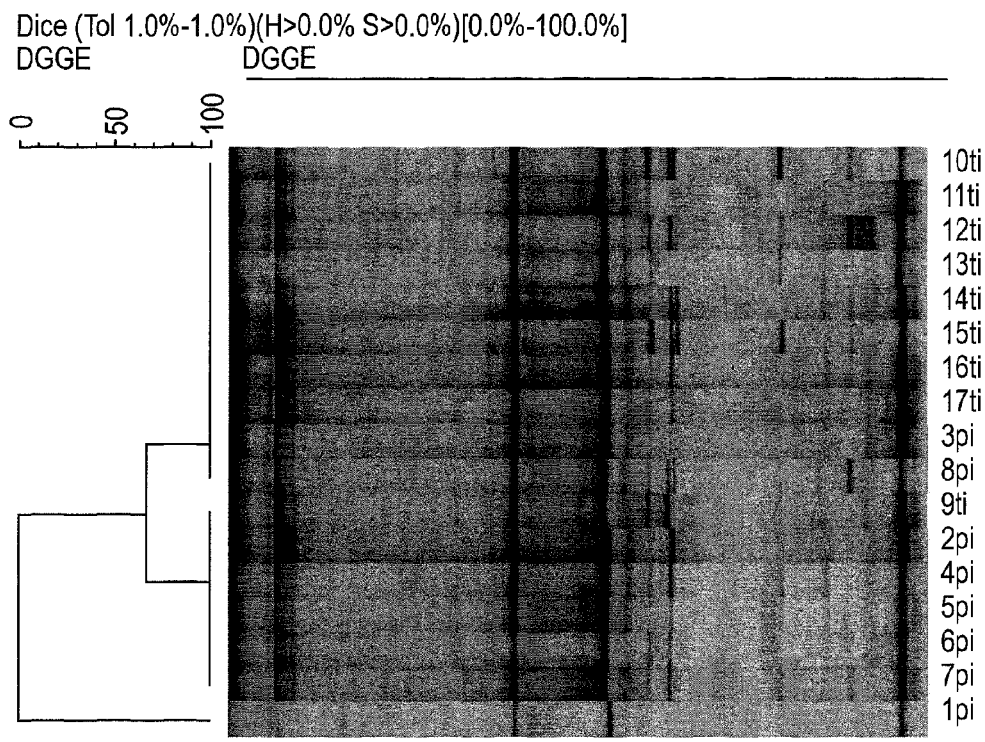

FIG. 23 shows microbial diversity analysis using DGGE. DGGE using lactic acid bacteria (LAB) specific primers revealed significant differences in LAB diversity between treatment with GGDK266 and placebo in ileal samples. Bands on the gel are visualised by silver staining.

Figure 24:
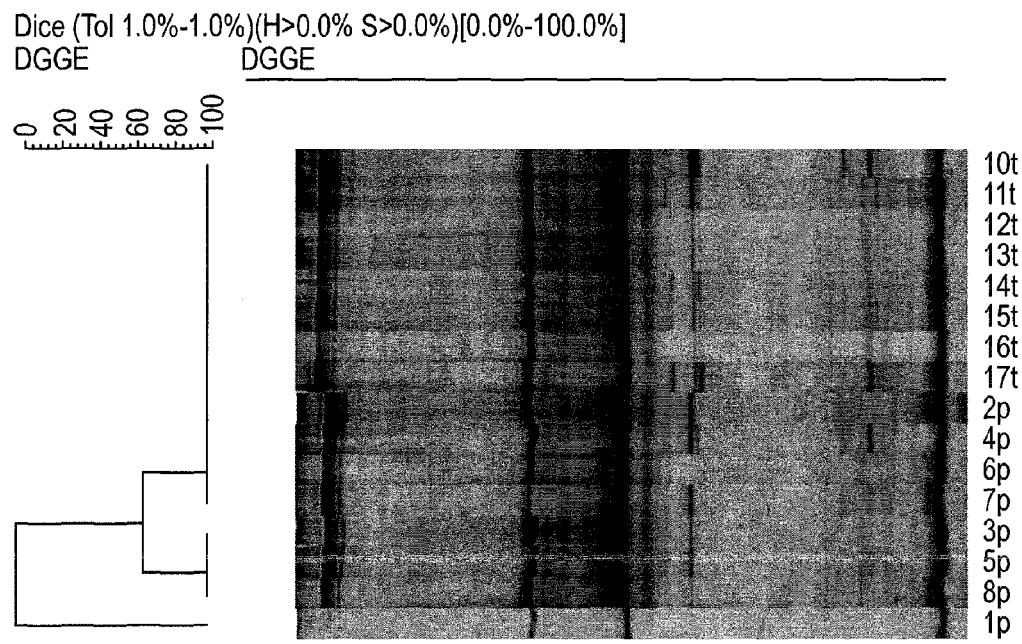

FIG. 24 shows microbial diversity analysis using DGGE. DGGE using lactic acid bacteria (LAB) specific primers revealed significant differences in LAB diversity between treatment with GGDK266 and placebo in caecal samples. Bands on the gel are visualised by silver staining.

Figure 25:
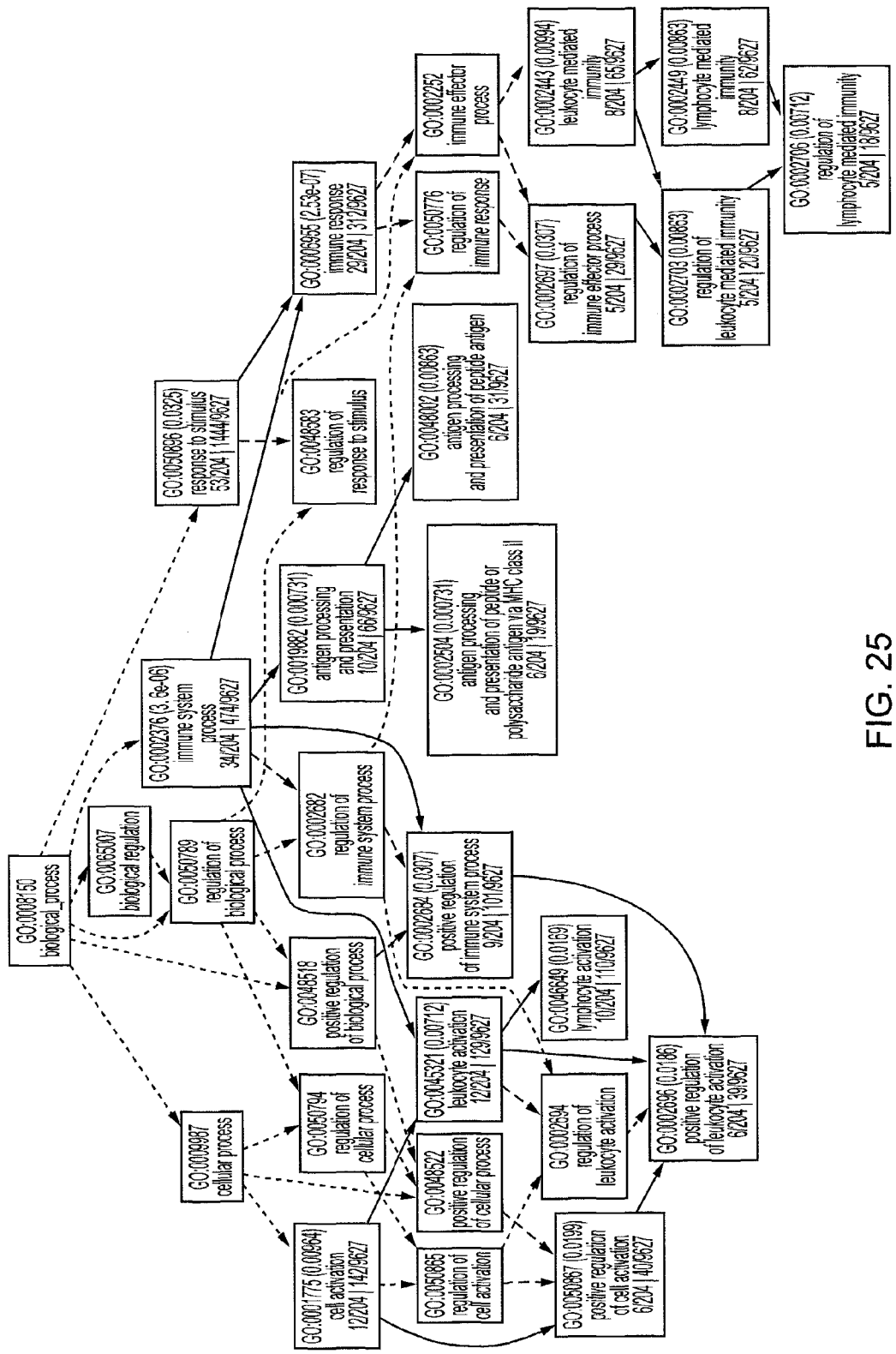

FIG. 25 shows the gene ontology biological processes significantly down-regulated by oral administration of GGDK266.

Figure 26:
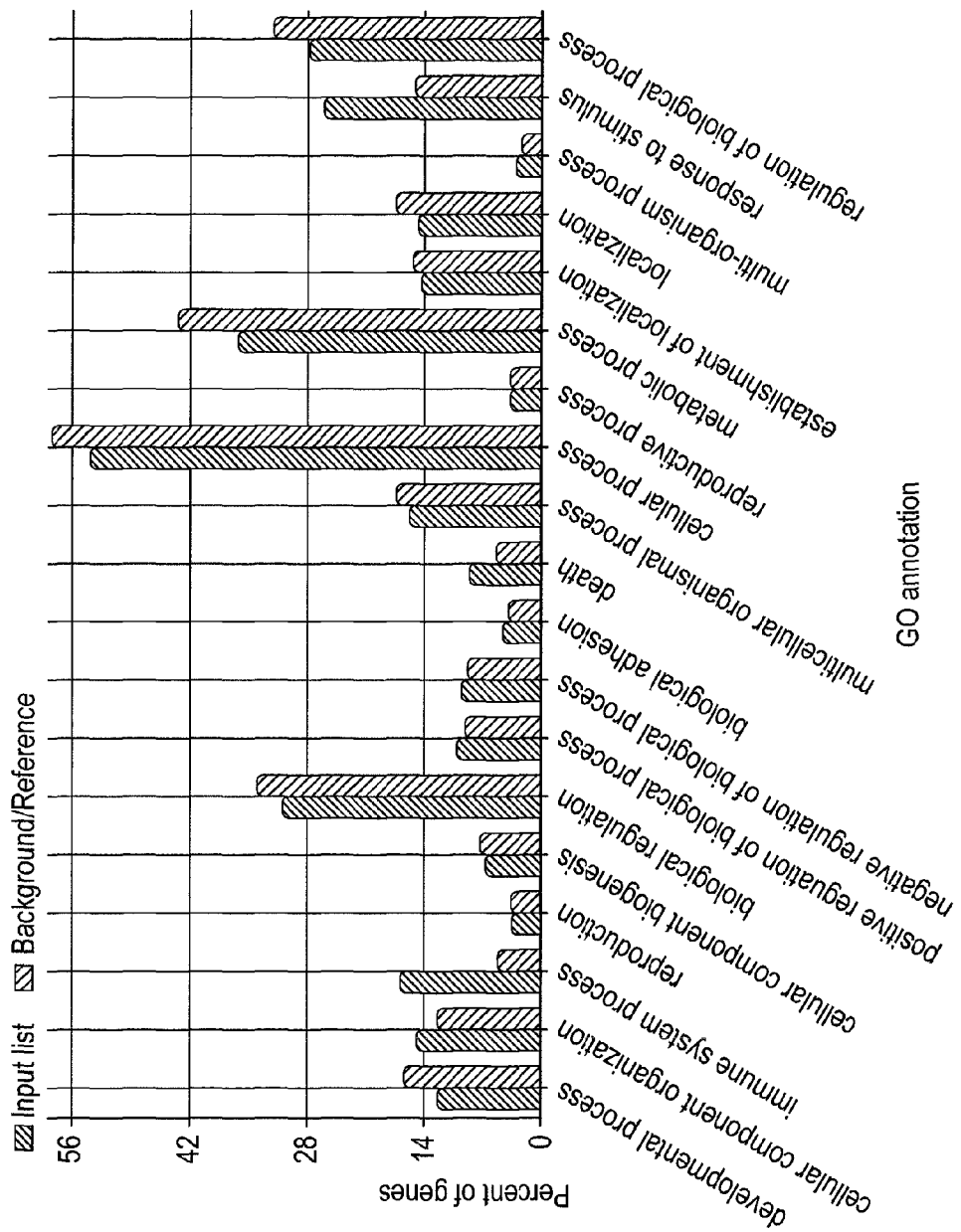

FIG. 26 shows changes in immune response and response to stimuli in animals treated with GGDK266 versus animals treated with placebo (percent of genes versus a range of different GO annotations).

Figure 27:
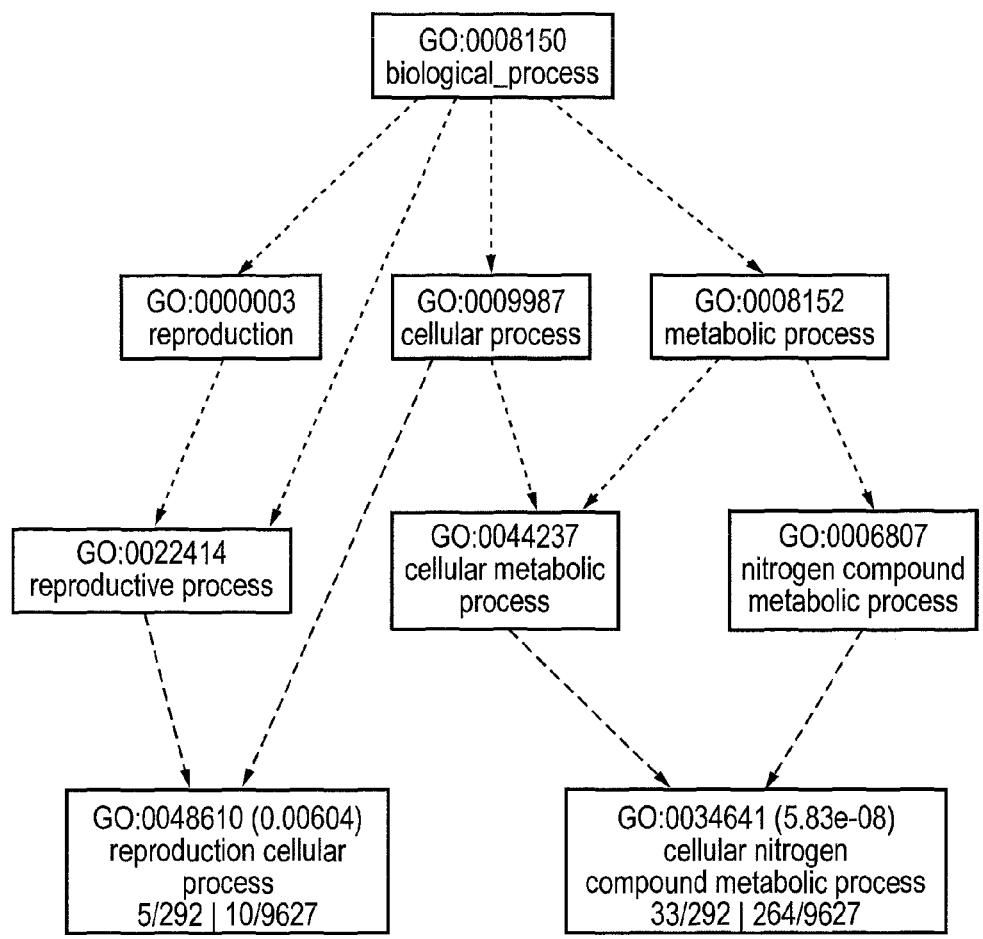

FIG. 27 shows the gene ontology biological processes significantly enriched by oral administration of GGDK266.

EXAMPLES

Materials and Methods

Materials: Pig faeces samples collected during the course of the study of outdoor- and indoor-reared pigs (Mulder et al, 2009) were used in these studies. The culture collection was based primarily on LAB collected from frozen samples 411, 412 and 416, which were from outdoor-reared pigs with particularly high levels of LAB in their faeces. MRS broth premix, agar and vancomycin, anaerobe gas packs and indicator and antibiotic discs were purchased from Oxoid, anaerobe catalyst from Fisher Scientific and cysteine-HCL, bromocresol green and skimmed milk powder from Sigma-Aldrich. Pig colostrum carbohydrate fractions were prepared as part of the SMART 163 programme of D. Kelly. DNA extraction kits were purchased from MP Biomedicals and PCR reagents and clean-up kits from Promega. API CH 50 kits were purchased from Biomerieux UK Ltd.

Standard Media: MRS broth and MRS agar were prepared according to the manufacturer's instructions. LAMVAB agar was prepared according to the method of Jackson et al. (2002). Agar plates were prepared immediately before use. MRS broth was decanted (10 ml per tube) into sterile Hungate tubes under anaerobic conditions and stored at room temperature.

Carbohydrate-Supplemented Media: SMART 163 ammonium sulphate precipitate of pig colostrum: precipitated at 0, 20, 25, 30, 35, 45, 50, 55 or 65% saturation or soluble at 65% saturation were weighed out in proportion to the amounts recovered from 15 ml or 50 ml of colostrum. Carbohydrate fractions were each dispersed in 15 ml of MRS or LAMVAB agar, held at 45° C., and then individual plates were poured for each fraction. They were also dispersed in MRS broth (50 ml) and the supplemented broth decanted to eight (6 ml/tube) sterile Hungate tubes under anaerobic conditions.

Animals: Female C3H/HeN and C57Bl/6 mice (5-6 weeks old) were purchased from Harlan UK. They were housed as groups or pairs in standard caging within HEPA-filtered flexifilm isolators situated in a class 2 containment facility. They had free access to a high quality rodent chow and sterile deionised water at all times and were allowed to acclimatise for 7 to 10 days prior to commencement of experiments. The Rowett Institute of Nutrition and Health (RINH) is licensed under the UK Animals (Scientific Procedures) Act 1986. Studies herein were carried out under the auspices of an approved Home Office Project Licence by staff holding the requisite Home Office Personal Licence (as defined and set out in the UK Animals (Scientific Procedures) Act 1986), and were reviewed and approved by the RINH Ethical Review Committee.

Methods

Culture of LAB: In initial studies, a small amount of frozen faeces (100 mg) was dispersed in 1 ml of maximum recovery diluent (MRD). Two further sequential ten-fold dilutions were made. All three suspensions were streaked out on MRS or LAMVAB agar plates. In later studies, the faeces sample was dispersed in 5 ml of MRD, further diluted (1:40) in MRD and 0.5 ml of this dilution spread over the surface of MRS or LAMVAB agar plates with or without supplemental pig colostrum carbohydrates. In all cases, the plates were incubated in an anaerobic jar for 72 hours at 37° C. Distinct colonies (at least 8 per plate) were picked off the agar plates and seeded into Hungate tubes containing MRS broth or where appropriate MRS broth containing pig colostral carbohydrates. The tubes were incubated for 48 hours at 37° C.

Frozen Stock: An aliquot (0.7 ml) of each culture was drawn off with a sterile syringe and needle and dispensed into a plastic tube that was flushed with $CO_2$ and contained 0.3 ml glycerol and 2 mg L-cysteine. The tube was sealed with a plastic stopper, labelled, the contents mixed, frozen and stored at −80° C.

Conditioned Medium: The remaining culture was transferred to a Corning 15 ml centrifuge tube, centrifuged at 1000 g×5 min at room temperature, the supernatant decanted, aliquoted and frozen. The pellets were either extracted immediately for 16S rRNA gene analysis or frozen.

16S rRNA gene analysis (Clarridge, 2004): Bacterial DNA was extracted using a FastDNA® Spin kit for Soil in conjunction with a Fastprep 120 bead beater system, according to the protocol supplied with the kit. PCR was carried out (reaction mix: buffer, 10 μl. dNTPs (2mM), 5 μl. 27F Primer (20pmol/ μl), 2 μl. 1492R Primer (20pmol/ μl). 2 μl Go Taq Flexi Polymerase, 0.5 μl. MgCl2, 5 μl. H2O, 23.5 μl and 2 μl of extracted DNA) using MJ Research PTC-200 Peltier Thermal Cycler run through 35 cycles of 95° C. for 3 minutes, 95° C. for 30 seconds, 57° C. for 30 seconds and 72° C. for two minutes. Primer: 27F (F01) AGAGTTT-GATCCTGGCTCAG (SEQ ID NO: 88); 1492R (RP2) ACGGCTACCTTGTTACGACTT (SEQ ID NO: 89). PCR product cleanup was done with a Wizard® SV Gel and PCR Clean-up kit (Promega), used according to the manufacturer's instructions. 16S PCR products were sequenced using fully automated genetic analysers based on capillary electrophoresis technology (Genomics Section, RINH, UoA) using the reverse and forward primers 519R and 926F. Bacterial strains were identified by comparison of sequences with known bacterial DNA sequences using BLAST (http://blast.ncbi.nlm.nih.gov/Blast.cgi).

Antibacterial Activity: XLD agar was prepared as per manufacturer's instructions and cooled to 45° C. *Salmonella enteritidis* S1400 was added to the XLD agar [1 ml of a 1:1000 dilution of an overnight culture of *salmonella* in 200 ml XLD agar to give the equivalent of 106 CFU/ml]. The agar was poured into petri dishes and allowed to set. The plates were marked off into 4 quadrants and an approximately 5 mm well cut out in each quadrant. An aliquot (60 µl) of conditioned media or MRS broth was added to the wells. The plates were covered and incubated for 16 hours at 37° C. They were photographed using a digital camera. Images transferred to Photoshop, and the diameter of the well and zone of inhibition were determined using the measure tool. Values were calculated and stored on an Excel spreadsheet. The same procedure was used with *Escherichia coli* K88, except that MacConkey No 3 agar was used.

Antibiotic Susceptibility: Pig LAB [0.5 ml of a 1:100 dilution of an overnight culture] was spread onto the surface of an MRS agar [90 mm] plate and dried off. The plates were marked off into 4 quadrants and in each quadrant was placed an antibiotic-containing disc [Ampicillin, 10 µg. Cefotaxime, 30 µg. Chloramphenicol, 10 µg. Erythromycin, 15 µg. Gentamicin, 10 µg. Kanamycin, 30 µg. Metronizadole, 50 µg. Nalidixic acid, 30 µg. Tetracycline, 30 µg. Vancomycin, 30 µg]. The plates were covered, placed in an anaerobic jar and incubated for 24 hours at 37° C. They were photographed using a digital camera. Images transferred to Photoshop, and the diameter of the zone of inhibition was determined using the measure tool. Values were calculated and stored on an Excel spreadsheet.

Prevention of Adherence/Invasion by *salmonella* In Vitro: Monolayers of IPEC-J2 cells were grown to 3 days post-confluence in 24-well plates and synchronised by the addition of DTS media 24 hrs prior to use. Overnight cultures of pig LAB (10 ml) were centrifuged [1000 g×5 min at room temperature] and the bacteria re-suspended in 1 ml of phosphate buffered saline [PBS]. An aliquot (50 µl) of LAB was added to the wells. The plates were incubated for 2 hours at 37° C., 5% $CO_2$, 95% humidity. An overnight culture of *Salmonella enterica* serovar Enteritidis S1400 [*S. enteritidis* S1400] was sub-cultured (0.5 ml in 10 ml) into Luria Bertani (LB) media and incubated aerobically for 2-3 hours at 37° C. until it reached an optical density (560 nm) of 0.8. This gave a concentration equivalent to $1\times10^8$ CFU/ml. The culture was centrifuged [1000 g×5 min at room temperature], the bacteria re-suspended in 10 ml of PBS. An aliquot (50 µl) was added to the wells of IPEC-J2 cells. Wells treated with PBS were used as controls. The plates were incubated for a further 2 hours at 37° C., 5% $CO_2$, 95% humidity. The IPEC-J2 cell monolayers were washed 5 times with HBSS. A solution (0.5 ml) of PBS containing Triton-X100 (10 ml/litre) was added to each well, the monolayer scraped off and dispersed. Viable *salmonella* were estimated on XLD agar plates [incubated for 24 hours at 37° C.] by the Miles and Misra method [Robertson et al, 2003]. LAB were determined by the same procedure [incubated anaerobically for 48 hours at 37° C.].

Inhibition of Inflammatory Responses: Monolayers of IPEC-J2 cells were grown to 3 days post-confluence in 24-well plates and synchronised by the addition of DTS media 24 hrs prior to use. Overnight cultures of pig LAB (10 ml) were centrifuged [1000 g×5 min at room temperature] and the bacteria re-suspended in 1 ml of PBS. An aliquot (50 µl) of LAB was added to each well [3 wells for each sample] along with 220 ng 12-O-Tetradecaboylphorbol-13-acetate [PMA] per well. PMA or PBS alone served as controls. The plates were incubated for 2 hours at 37° C., 5% $CO_2$, 95% humidity. Culture media was removed from the dishes and the cells washed twice with PBS. RLT buffer (0.5 ml) containing mercaptoethanol was added to each well, the cells scraped off and transferred to an eppendorf tube [for each sample scrapings from 3 wells were combined]. RNA extraction was done using RNeasy® Mini kit in accordance with the manufacturer's protocols and reverse transcription with a high capacity cDNA Reverse Transcription Kit (Applied Biosystems). Real Time PCR was done on a 7500 Fast Real-time PCR system operating with 7500 Fast System v 1.4.0 Sequence Detection Software version 1.4 (Applied Biosystem). Primers for porcine IL-8 and TNF-α [IPEC-J2, SY100604186-096 IL-8-2 Reverse, SY100604186-090 TNF1a Reverse, SY100604186-095 IL-8 2 Forward, SY100604186-089 TNFa1 Forward, and SY100604186-093] were prepared by Sigma Aldrich. The reaction mix was: 10 µl Power Sybergreen Master mix, 2.5 µl of forward primer, 2.5 µl of reverse primer and 5 µl of cDNA, The Real Time PCR was then run according to the Standard 7500 protocol [95° C., 10 min, 1 cycle. 95° C., 15 sec, 40 cycles. 60° C., 1 min, 40 cycles. 95° C., 15 sec, 1 cycle. 60° C., 1 min, 1 cycle. 95° C., 15 sec, 1 cycle. 60° C., 15 sec, 1 cycle]. Expression of IL-8 and TNF-α genes were analysed and compared to that of the 'house-keeping' gene β-actin. For comparison, values were given as the ratio of IL-8 and TNF-α per β-actin or fold-change.

For example:
a. Calculate ΔCt (2 h) for IL-8 [Ct IL-8 minus Ct β-actin]
b. Calculate ΔCt (2 h) for PMA [Ct PMA minus Ct β-actin]
c. Divide ΔCt (IL-8) with ΔCt (PMA)
d. Round up value to whole number Substrate Reactivity: The carbohydrate reactivity of individual LAB was determined using an API CH 50 kit (Biomerieux UK Ltd). Assays were done according to the manufacturer's instructions and reactions were recorded after incubation for 24 and 48 hours at 37° C. There are 50 capules on an API CH 50 plate. These contain various potential substrates and negative controls. The range of substrates is as follows: Monosaccharides 16, Monosaccharides/alcohols 4, Disaccharides 8, Trisaccharides 2, Polysaccharides 3, Alcohols 6, Others 7. For each substrate group the number of positive reactions is counted. This is divided by the maximum possible to give the rank for that substrate group. The sum of all the substrate scores gives the overall ranking for the bacterium. High Ranking indicates broad spectrum of substrate reactivity Heat-Treatment of LAB: A small amount of frozen faeces (100 mg) was dispersed in 5 ml of maximum recovery diluent (MRD). Sediment was allowed to settle out and the upper layer was decanted into eppendorf tubes (1 ml/tube). The tubes were heated at 50° C., 60° C. or 70° C. for 10 min. An aliquot (0.4 ml) of each was plated out on MRS agar and incubated in an anaerobic jar for 72 hours at 37° C. A small number of colonies were detected after heating at 70° C. Distinct colonies were picked off, seeded into Hungate tubes containing MRS broth and incubated for 48 hours at 37° C.

In a second study, a small amount of frozen faeces (100 mg) was dispersed in 5 ml of maximum recovery diluent (MRD). Sediment was allowed to settle out and the upper layer was decanted into eppendorf tubes (1 ml/tube). The tubes were heated at 50° C. for 20 min, 50° C. for 20 min plus 60° C. for 20 min or 50° C. for 20 min plus 60° C. for 20 min plus 70° C. for 20 min. An aliquot (0.5 ml) of each was plated out on MRS agar and incubated in an anaerobic jar for 48 hours at 37° C. A small number of colonies were detected, picked off, seeded into Hungate tubes containing MRS broth and incubated for 48 hours at 37° C.

In the third study, an overnight culture (10 ml) of isolated pig LAB was centrifuged (1000 g×5 min at room temperature), the pellet re-suspended in fresh MRS broth (10 ml). An aliquot (1 ml) was heated at 70° C. for 15 min and then plated out (0.5 ml) out on MRS agar and incubated in an anaerobic jar for 48 hours at 37° C. A small number of colonies were detected, picked off, seeded into Hungate tubes containing MRS broth and incubated for 48 hours at 37° C. This culture was centrifuged, re-suspended in MRS broth, heated again at 70° C. for 15 min, plated out on MRS agar, incubated in an anaerobic jar for 48 hours at 37° C., picked off, seeded into Hungate tubes containing MRS broth and incubated for 48 hours at 37° C. As before, this culture was centrifuged, re-suspended in MRS broth, re-heated at 70° C. for 15 min, plated out (0.5 ml) out on MRS agar, incubated in an anaerobic jar for 48 hours at 37° C., picked off, seeded into Hungate tubes containing MRS broth and incubated for 48 hours at 37° C.

Stability of Freeze Dried Bacteria: Overnight cultures of LAB were centrifuged (1000 g×5 min at room temperature. Pellets were re-suspended in 2 ml sterile PBS and re-centrifuged. The subsequent pellets were then re-suspended in 5 ml of freezing solution [defatted skimmed milk powder (SKP), 100 g/l; SKP+lactose, both 100 g/l; SKP+sucrose, both 100 g/l; or SKP, 200 g/l]. The samples were frozen at −20° C. (2-3 hours) and then stored at −80° C. overnight. They were freeze-dried for 48 hours and dried material stored at room temperature. Viable bacteria in the samples were determined at 0 and approximately 40 and 80 days after completion of freeze drying. They were plated out on MRS agar and incubated anaerobically for 48 hours at 37° C.

Bulk Preparation of GGDK31 and GGDK266: Two 500 ml batches of MRS broth were prepared in 500 ml glass screw-top bottles, autclaved and allowed to cool to room temperature (in proximity to gas flame) whilst being flushed with $CO_2$. Four ml of a 24 hour culture of GGDK31 or GGDK266 was added to each bottles of MRS and the lids lightly closed. The bottles were placed in an anaerobic jar and incubated at 37° C. for 24 hours. The culture was centrifuged [1000 g×5 min at room temperature] in 6 sterile 50 ml centrifuge tubes. The supernatant was discarded, tubes refilled with culture and re-centrifuged until all the bacteria had been recovered. Each of the 6 tubes contained almost equal amounts of bacteria. The bacteria in each tube were re-suspended in 40 ml of sterile PBS, re-centrifuged and the supernatant discarded. The bacteria in each tube was re-suspended in 20 ml of SKM (100 g/l), frozen at −20° C. (2-3 hours) and then overnight at −80° C., freeze-dried for 48-72 hours and stored at 4° C. To evaluate viable bacteria in the sample, one tube of freeze dried material was re-suspended in 20 ml of MRS broth, incubated at room temperature for 2 hours, diluted, plated out on MRS agar and incubated anaerobically for 48 hours at 37° C.

*L. mucosae* In Vivo Study 1: Sixteen (6 week) old female C3H/HeN mice were dosed with an overnight culture of vial 323 (*L. mucosae*; 50 µl; >109 CFU) at day −7, −4, −2 and 0 and daily thereafter up to day +9. A further 16 mice (control) were given media. On day 0, eight mice (*L. mucosae*-treated) and eight control mice were given, by gavage, a single dose of *Salmonella enteritidis* S1400 (50 µl; ≥108 CFU). In addition, eight mice (*L. mucosae*-treated) and eight control mice were given a single dose of culture medium. Body weight and health score were monitored twice daily post-*salmonella* infection. The mice were euthanased (isoflurane overdose and exsanguination) and dissected at 10 days post-salmonella infection. Stomach, representative portions of jejunum and ileum, caecum plus contents, colon plus contents, spleen and liver and one kidney and the mesenteric lymph node were collected under near aseptic conditions for microbiology. Representative portions of upper jejunum, mid jejunum, ileum, caecum and ascending and descending colon were placed in neutral buffered formalin or RNA-later and stored for future analysis.

*L. mucosae* In Vivo Study 2: Five (6 week) old female C57Bl/6 mice were dosed with an overnight culture of vial 323 (*L. mucosae*; 50 µl; >109 CFU) at day −7, −4, −2 and 0 and daily thereafter up to day +5. A further 5 mice were given media. On day 0, all ten mice were given, by gavage, a single dose of *Salmonella enteritidis* S1400 (50 µl; ≥107CFU). The mice were euthanased and dissected on day 6, according to the procedure for study 1.

Novel Pig LAB In Vivo: Four (6 week) old female C3H/HeN mice were dosed with an overnight culture of RINH vial 31 (*L. reuteri*; 50 µl; >109 CFU), four with RINH vial 32 (*L. reuteri*). Four with vial 323 (*L. mucosae*), four with RINH vial 46 (*L. reuteri*), four with RINH vial 47 (*L. reuteri*) and eight with MRS. This was done at day −6, −4, −2 and 0 and daily thereafter up to day +9. On day 0, all *lactobacilli*-treated mice and four control mice were given, by gavage, a single dose of *Salmonella enteritidis* S1400 (50 µl; ≥108 CFU). In addition, the remaining four control mice were given a single dose of culture medium. The mice were euthanased and dissected on day 10, according to the procedure for study 1.

Microbiology: Tissues were homogenised [1:100 w/v] in MRD using a Janke-Kunkel Ultra-Turrax T25 tissue homogeniser at 20,000 rpm for 30 seconds, as were jejunal and ileal contents. Up to eight sequential dilutions (1:10 v/v) of the primary homogenates were made, plated out onto XLD agar and MacConkey No. 3 agar and incubated overnight at 37° C. Viable counts were estimated as before [Robertson et al, 2003].

Statistical Analysis: Where appropriate data were initially assessed by one-way analysis of variance (ANOVA) regarding treatment outcome. If ANOVA indicated that there were significant differences (p<0.05) amongst all groups, the data was then analysed by the Tukey-Kramer Multiple Comparisons Test or the Kruskal-Wallis Multiple Comparisons Test as appropriate. This was done using the Instat Statistical Package (GraphPad Software Inc., San Diego, USA).

Based on the outputs from the multiple comparison tests, means in tables or graphs were marked with superscript letters. Means that differed significantly from each other (p<0.05) were allocated distinct superscript letters. Means that did not differ significantly from each other were allocated common superscript letters.

Results

1. Isolation of LAB

Faeces from organically-reared piglets were plated out on selective agars and were incubated under anaerobic conditions. From all studies, a total of 436 individual colonies of Lactic Acid Bacteria [LAB] were picked off, seeded into MRS broth and incubated under anaerobic conditions. Each culture was given a unique RINH vial number and an aliquot was frozen down in MRS media containing 30% glycerol and L-cysteine (~2 mg/ml) and stored at −80° C. 16S rRNA gene analysis was done and bacterial strains were identified by comparison of sequences with known bacterial DNA sequences (Table 1).

The majority of the cultured LAB colonies were *L. johnsonii* and *L. johnsonii*-related strains [*L. johnsonii, L. johnsonii/gasseri, L. johnsonii/taiwanensis*] (240/436) and *L. reuteri* or *L. reuteri*-related [*L. reuteri, L. reuteri/pontis, L. reuteri/vaginalis, L. reuteri/acidophilus* (169/436)]. There were 7 *L. plantarum/pentosus* colonies, 19 other species and 5 uncultured strains.

2. Anti-Salmonella Activity In Vitro

Conditioned media from isolated LAB were screened for anti-bacterial activity against *Salmonella enteritidis* S1400 using a well-diffusion assay (FIG. 1).

Figure 2A:
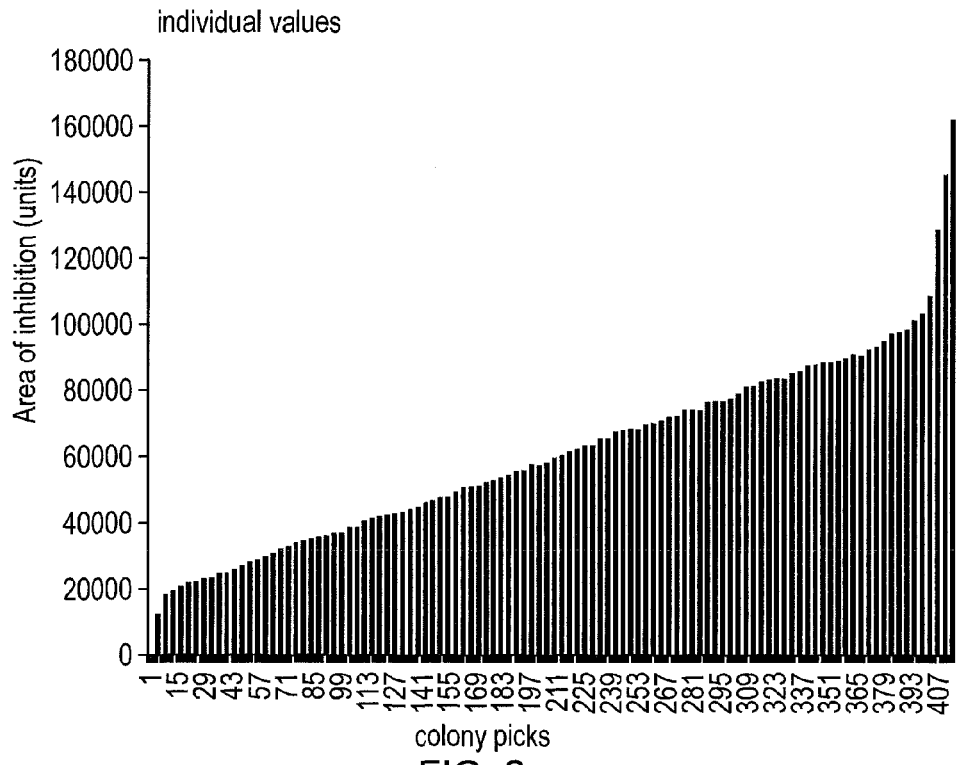
Figure 2B:
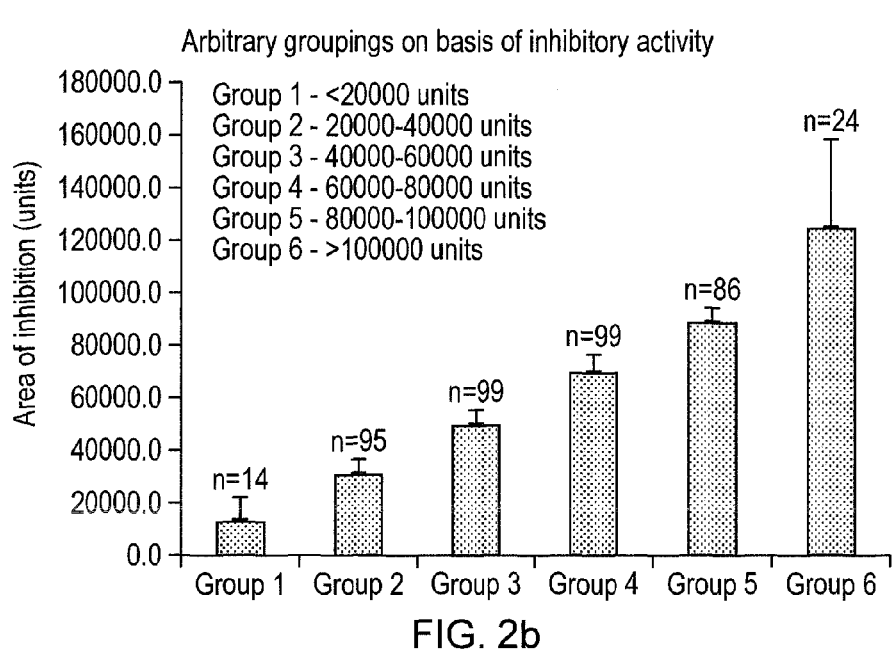

Conditioned media from individual colonies of LAB varied greatly in their activity against *S. enteritidis* (FIG. 2a). This was not strain dependent. The range of anti-*salmonella* activities amongst *L. johnsonii* was similar to that amongst *L. reuteri*. On an arbitrary basis, the cultures were separated into groupings on the basis of their capacity to inhibit *salmonella* in vitro (FIG. 2b). Group 1 had <20000 units of inhibition, Group 2 20000-40000 units of inhibition, Group 3 40000-60000 units of inhibition, Group 4 60000-80000 units of inhibition, Group 5 80000-100000 units of inhibition and Group 6 >>100000 units of inhibition (FIG. 2b). Group 1 comprised of 14 strains (3.4% of total), Group 2 of 95 strains (22.8%), Group 3 of 99 strains (23.7%), Group 4 of 99 strains (23.7%), Group 5 of 86 strains (20.6%) and Group 6 of 24 strains (5.8%). The latter group comprised of seventeen *L. johnsonii* and *L. johnsonii*-related, six *L. reuteri* or *L. reuteri*-related strains and one uncultured strain.

3. Anti-*E. coli* K88 Activity In Vitro

Figure 3A:
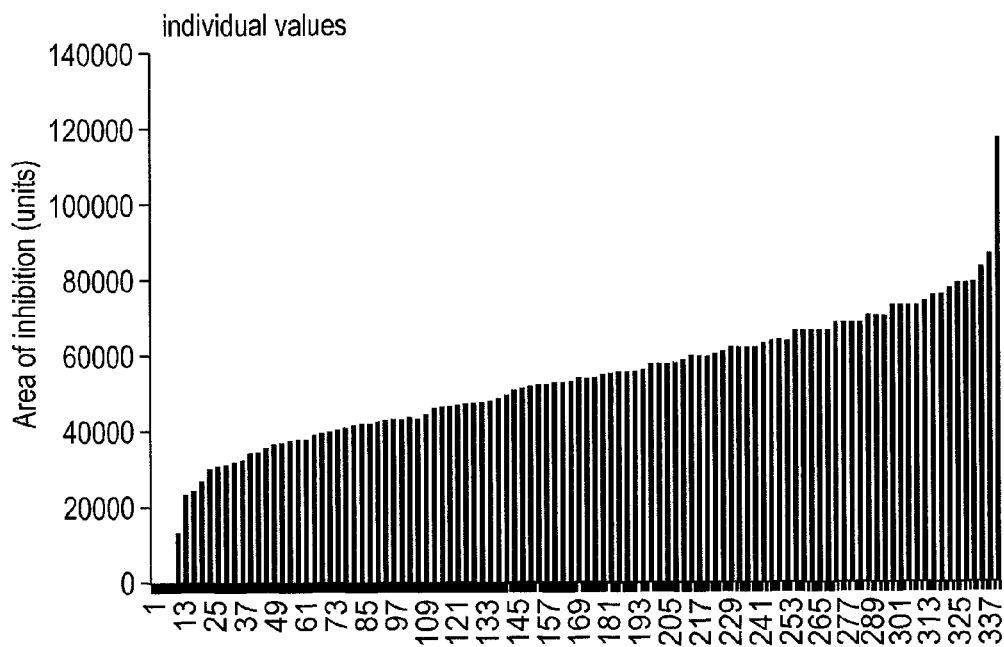
Figure 3B:
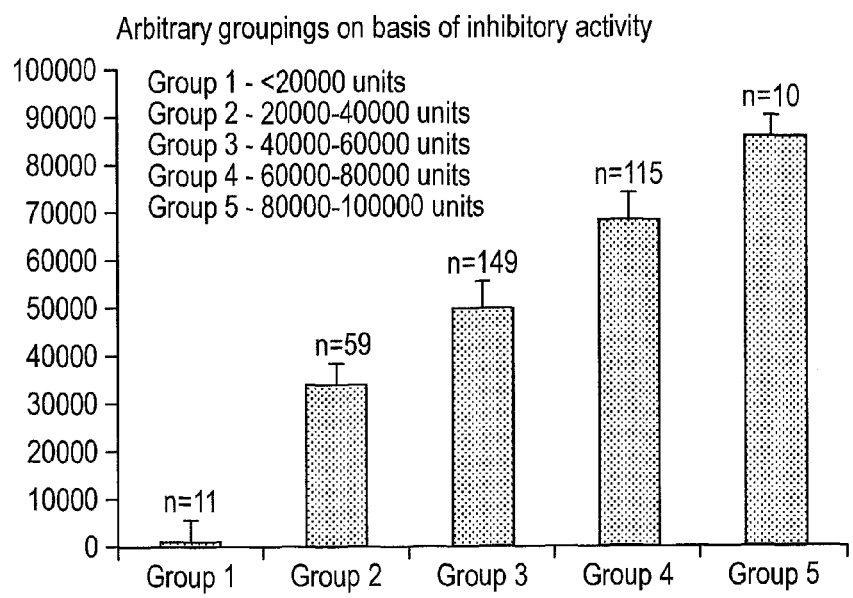
Figure 3C:
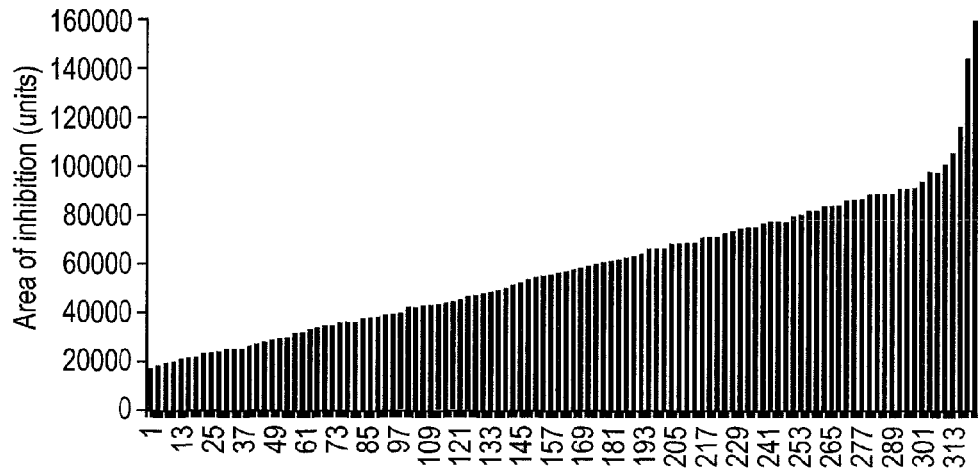
Figure 3D:
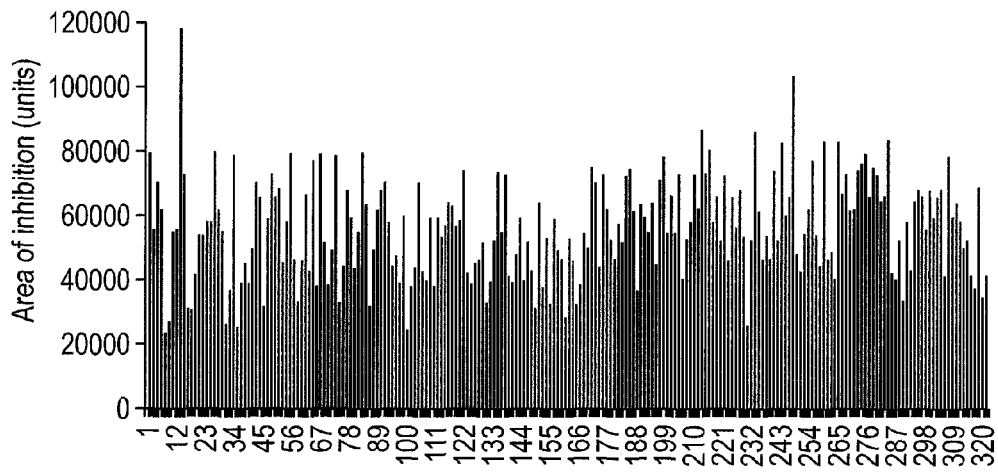

Conditioned media from LAB were also screened for anti-*Escherichia coli* K88 activity by the well diffusion assay. Activity against *E. coli* K88, as with *salmonella*, varied greatly between individual colonies of LAB (FIG. 3a). The range and variation in the activity was similar amongst the *L. johnsonii* and *L. reuteri* strains. In general, there was no direct correlation between the anti-salmonella and anti *E. coli* K88 activities for any individual LAB (FIG. 3c, 3d). However of the ten strains in *E. coli* K88 group 5 (FIG. 3b), seven had relatively high activities against both pathogens, two had high activity against *E. coli* K88 but moderate activity against *salmonella* and one was active primarily against *E. coli* K88.

4. Initial Selection of Candidate LAB

Thirty-three strains were identified for further testing in vitro (Table 2). These comprised 18 *L. johnsonii* and *L. johnsonii*-related strains, 11 *L. reuteri* or *L. reuteri*-related and 4 *L. plantarum* and *L. plantarum*-related strains (Table 2a).

5. Attachment/Invasion of Pig Intestinal Epithelial [IPEC-J2] Cells

Figure 4A:
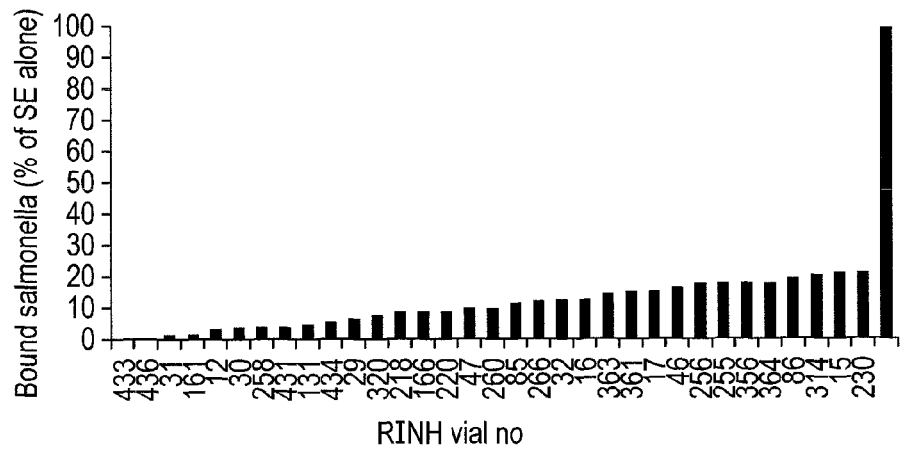
Figure 4B:
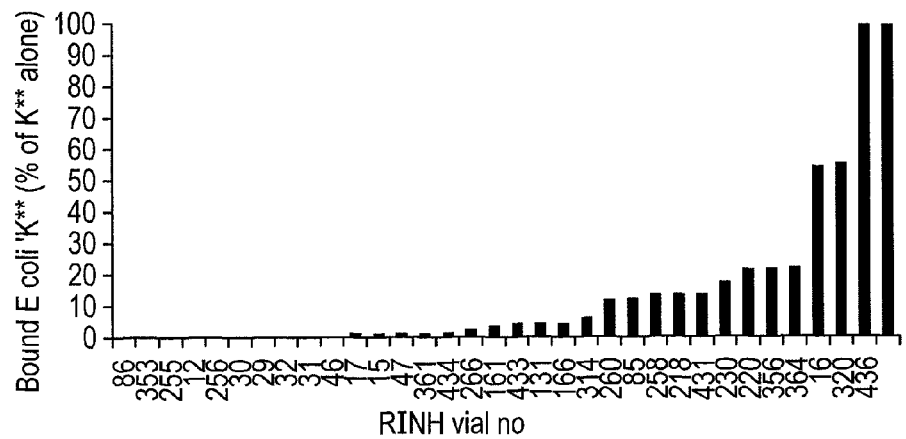
Figure 4C:
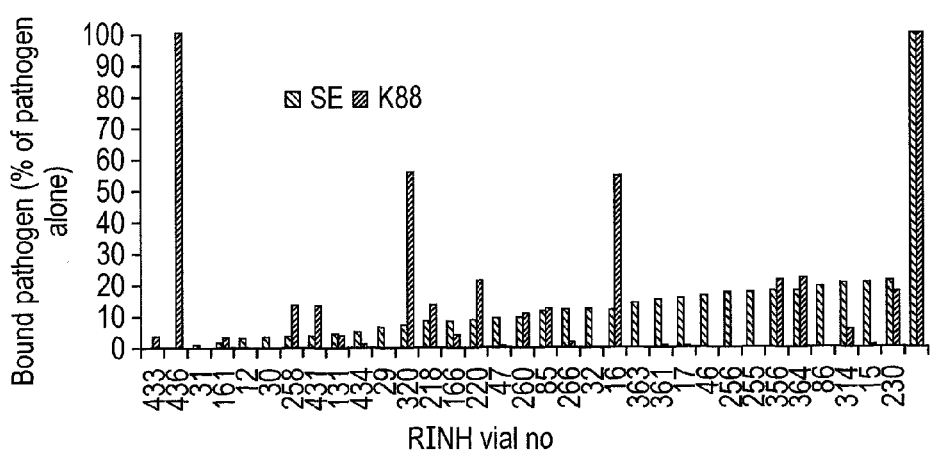

The capacity of LAB to block adhesion/invasion of IPEC cells by *S. enteritidis* and *E. coli* K88 was evaluated (FIG. 4a, 4b, 4c). The candidate LAB all greatly reduced attachment and invasion of IPEC cells by *salmonella*. Most of them were also very effective against *E. coli* K88. However, 3 of the strains had only limited effects on adhesion/invasion of IPEC cells by *E. coli* K88.

6. Susceptibility of LAB to Antibiotics.

The susceptibility of the candidate LAB to a range of antibiotics was evaluated (Table 4, FIG. 5). All but one strain (RINH vial 266) exhibited some degree of resistance to individual antibiotics. All were susceptible to ampicillin (10 µg), cefotaxime (30 µg) and chloramphenicol (10 µg). The majority were susceptible to erythromycin (15 µg), gentamicin (10 µg), tetracycline (30 µg) and vancomycin (30 µg). Most strains were resistant to metronizadole (50 µg) and nalidixic acid (30 µg) and to a lesser extent kanamycin (30 µg). 23

7. Refined Selection of Candidate LAB

Twenty-three high ranking strains were identified for further testing in vitro.

8. Substrate Specificity of LAB

Figure 6:
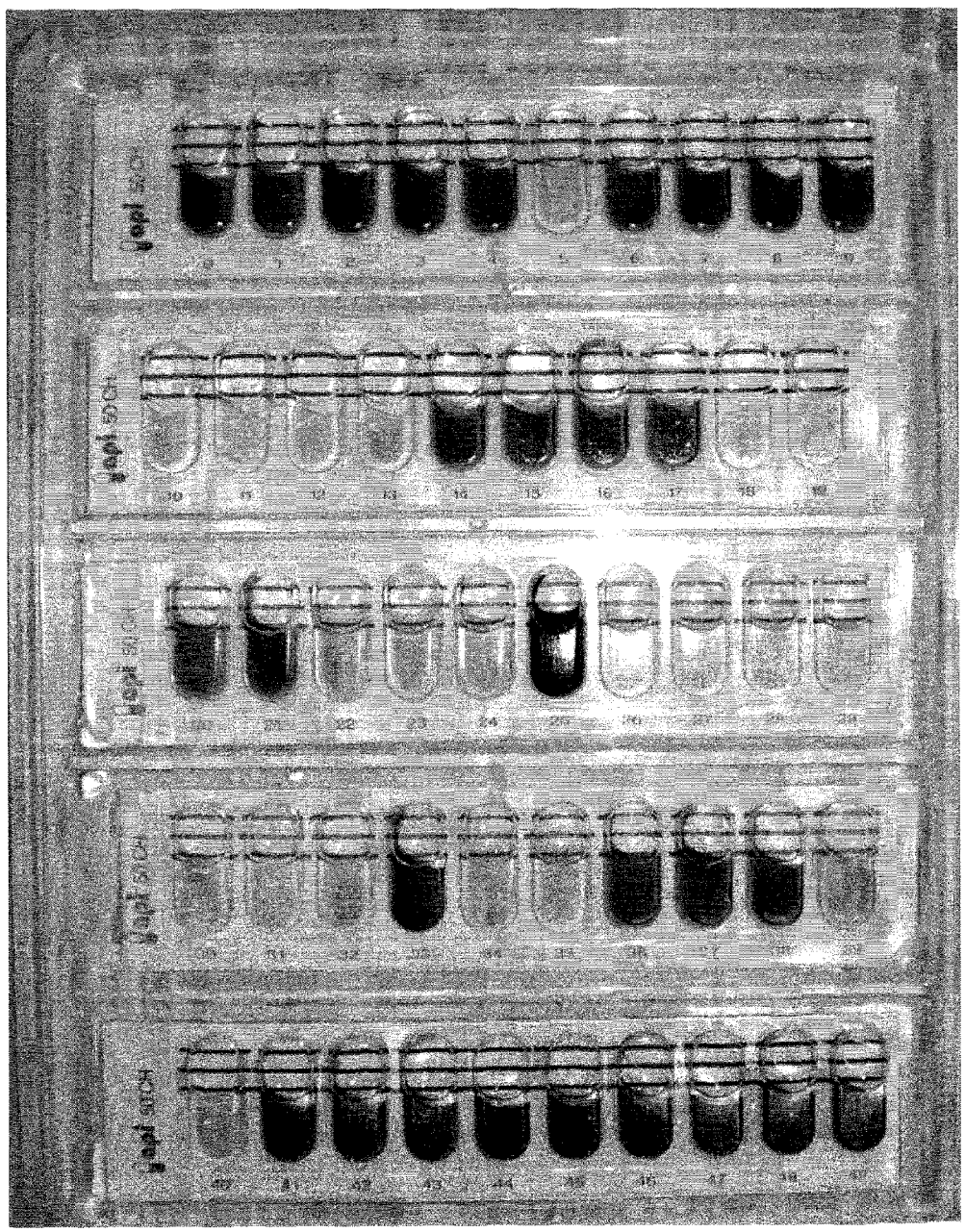
FIG. 6 shows an evaluation of substrate profile of LAB using an API CH 50 kit [49 substrates, pale colour indicated positive reaction, except 25 where positive reaction is black, dark colour indicates no reaction].

The candidate LAB were screened for substrate reactivity using an API CH 50 kit (Table 5, 6, FIG. 6). *L. johnsonii, L, reuteri* and *L. plantarum* each exhibited strain-specific general substrate reaction profiles. In addition, most strains of each genotype exhibited fine differences in their substrate reactivity, indicative that they were unique individual strains.

9. Suppression of Inflammation in Pig Intestinal Epithelial [IPEC-J2] Cells

Figure 7A:
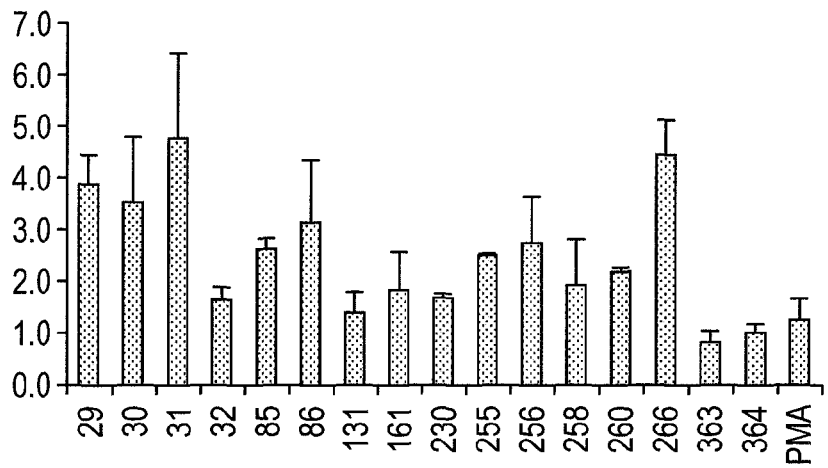
FIG. 7 shows the ΔCt (a), ratio (b) and fold-change (c) for IL-8 gene expression in IPEC cells treated with PMA and pig LAB.
Figure 7B:
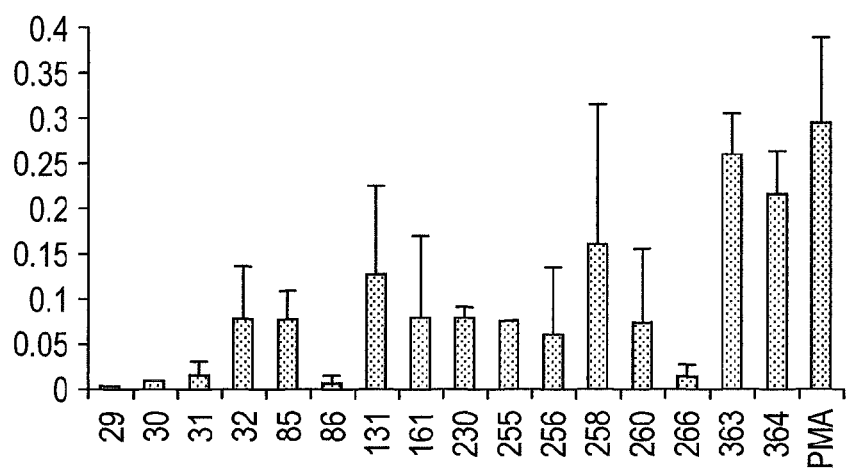
Figure 7C:
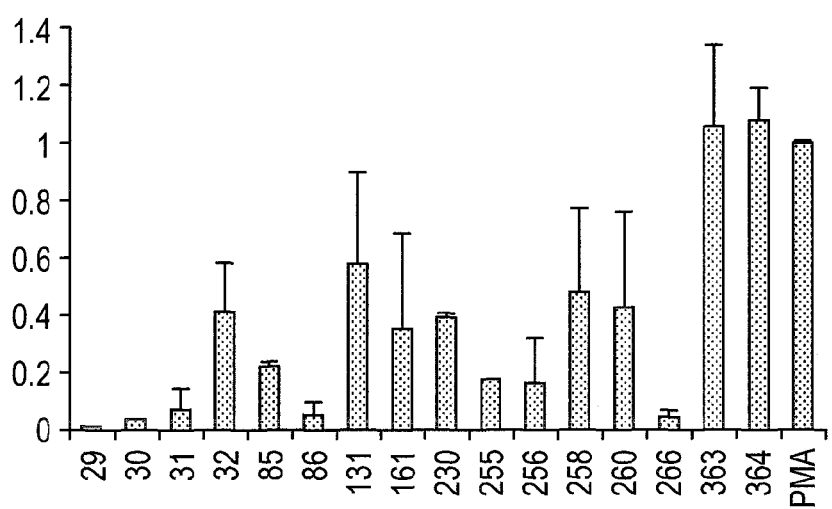

The ability of candidate LAB to block or suppress inflammatory responses triggered in IPEC cells by 12-O-Tetradecaboylphorbol-13-acetate [PMA] was tested (FIG. 7; Table 7). The candidate strains varied greatly in their capacity to block interleukin-8 (IL-8) gene-expression triggered by PMA. Five strains (RINH vial 29, 30, 31 86 and 266) had potent anti-inflammatory effects.

10. Final Selection of Candidate LAB

Fourteen strains were identified having killing and blocking activities against *salmonella* and *E. coli* K88, susceptibility to antibiotics carbohydrate reactivity and capacity to suppress inflammation in vitro. Seven of these were particularly preferred. The latter set comprised 4 *L. plantarum*-related, 3 *L. johnsonii*-related and one *L. reuteri*. Two of these LAB strains [GGDK266 and GGDK31] were prepared in bulk for evaluation in a trial with newly-weaned piglets (Table 8).

11. Freeze Drying and Storage of LAB

Figure 8A:
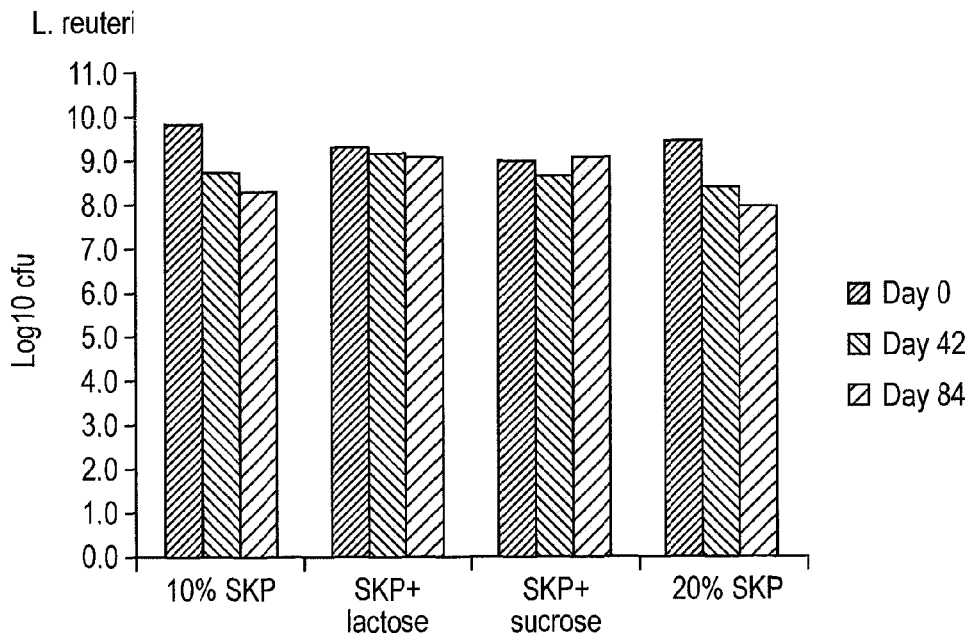
FIG. 8 shows the stability of pig LAB after freeze-drying in skimmed milk powder (SKP, (100 g/l), SKP+lactose (both 100 g/l), SKP+sucrose (both 100 g/l) or SKP (200 g/l).
Figure 8B:
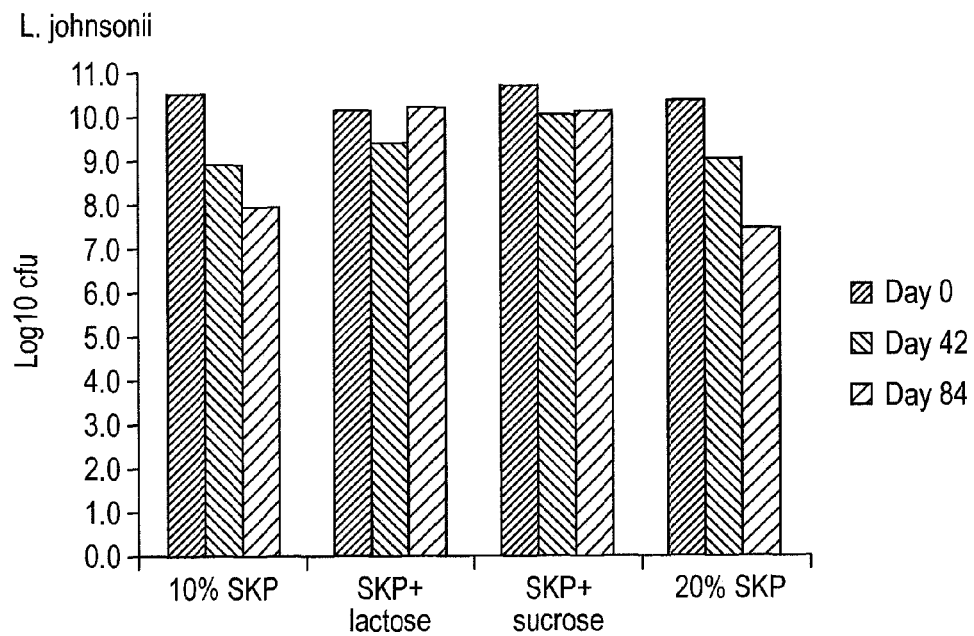
Figure 9A:
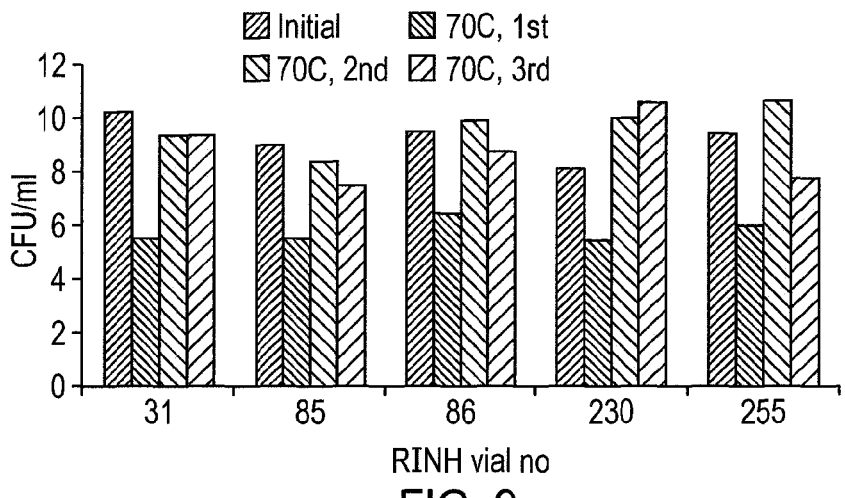
FIG. 9 shows the stability of isolated LAB to heat-treatment (a), the ratio (b) and fold-change (c) for IL-8 gene expression in IPEC cells treated with PMA and naive or heat-treated pig LAB; (d) Antibiotic susceptibility of native and heat-treated RINH vial 31.
Figure 9B:
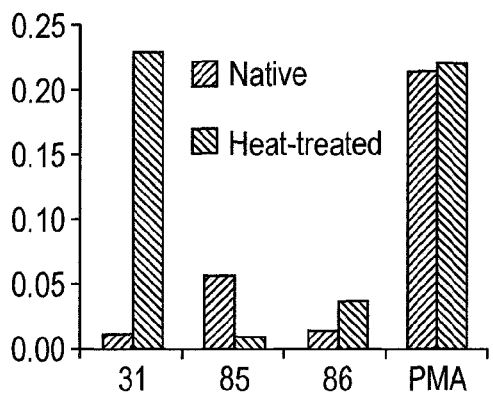
Figure 9C:
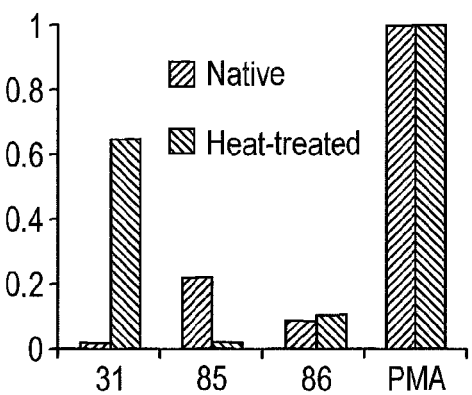
Figure 9D:
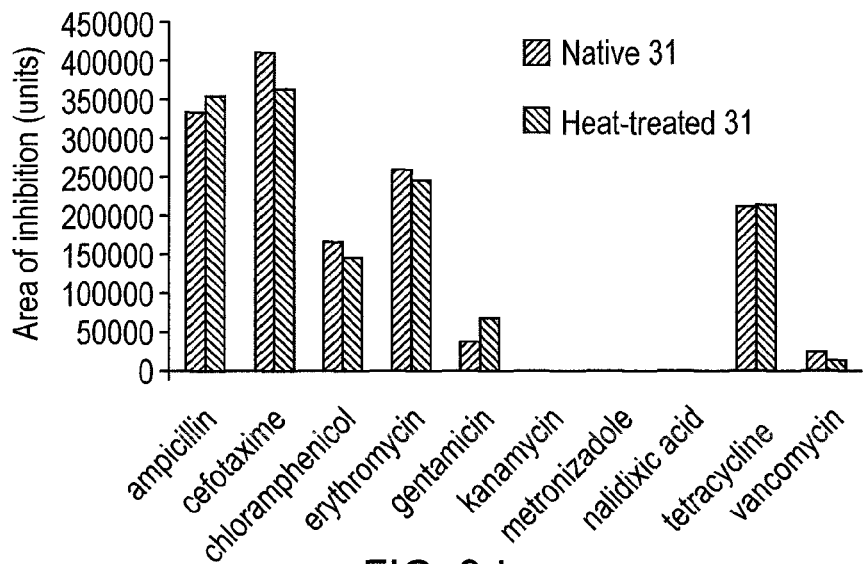

The survival and viability of LAB after freeze drying in skimmed milk powder [SKP], SKP plus lactose or SKP plus sucrose was evaluated (FIG. 8). Small losses in viability were evident on storage for 42 and 84 days at room temperature of samples dried in SKP. This was less marked when skimmed milk powder and sugars were used in combination. However, the 24 latter preparations tended to be hygroscopic and difficult to maintain. Bulk preparations of GGDK266 and GGDK31 were therefore prepared by drying the bacteria in skimmed milk powder [100 g/1] (Table 8).

12. Heat-treatment Studies

Suspensions of faeces from organically reared pigs were heat treated for varying periods of time at 50-70° C., plated out on MRS agar, colonies picked off and cultured in MRS broth [RINH vial 417-506]. The strain types recovered were variable and *clostridium* species formed a high proportion, the isolated strains remained sensitive to heat.

Isolated cultures of LAB were subject to heating three times for 15 minutes at 70° C. FIG. 9). Viable bacteria decreased by 3-4 log orders after heat-treatment for the first time. However, the surviving bacteria had a degree of heat-resistance. With one exception, losses of viable bacteria were low when the bacteria were re-cultured and re-heated a further two times.

Heat-treatment three times at 70° C. altered the biological activities of the strains FIG. 9. RINH vial 521 (vial 255 heat-treated) was not able to block attachment of pathogens to IPEC cells and the capacity of RINH vial 520 (vial 230 heat-treated) to prevent attachment was reduced. The ability of RINH vial 517 (vial 31 heat-treated) to abolish inflammatory responses triggered in IPEC cells was abolished. In contrast, the biological properties of RINH vial 518 (vial 85 heat-treated) and RINH vial 519 (vial 86 heat-treated) were similar to those of the native strains.

13. Mouse Infection Studies

13.1 *L. mucosae* (RINH Vial 323)

C3H/HeN mice develop a persistent but non-lethal, intestinal and systemic infection, which has many characteristics of the major form of human salmonellosis, when challenged with high levels of *Salmonella enteritidis* S1400. In contrast, C57Bl/6 mice develop a severe primarily systemic, infection, reminiscent of acute infection in humans, when challenged with the same pathogen. To evaluate the capacity of *L. mucosae* (vial 323) to ameliorate salmonellosis, C3H/HeN and C57Bl/6 mice were treated with *L. mucosae* prior to and post-challenge with *Salmonella enteritidis* (FIGS. 10, 13). The mice were euthanased and dissected 6 (C57Bl/6) or 10 (C3H/HeN) days post-infection.

Systemic Tissues: Oral treatment with *L. mucosae* limited the capacity of *S. enteritidis* to cause systemic infection both in C3H/HeN and C57Bl/6 mice (FIG. 11*a-c*; 14*a-c*). High numbers of viable *salmonella* were detected in the mesenteric lymph node, liver and spleen of mice. In contrast, the numbers present in these tissues were greatly reduced if the mice had been co-treated with RINH vial 323 (*L. mucosae*). *Salmonella* infection caused enlargement of the spleen (FIG. 12*a*; 15). This tissue response was significantly reduced in mice treated with both RINH vial 323 (*L. mucosae*) and *salmonella*.

Intestine: Intestinal myeloperoxidase [MPO], a marker for neutrophils, was determined in C3H/HeN mice treated with *salmonella* or *salmonella* plus RINH vial 323 (*L. mucosae*). MPO in the intestine was greatly increased by *salmonella* infection, due to recruitment of neutrophils to the intestine part of the host response to infection (FIG. 12*b*), Co-treatment with RINH vial 323 (*L. mucosae*) reduced MPO activity in the intestine of *salmonella*-infected mice, indicating that the intestinal inflammatory responses to infection were lowered in these animals.

13.2 Novel Pig LAB

Four LAB were selected: RINH vial 31, RINH vial 32, RINH vial 46 and RINH vial 47 (All *L. reuteri*; LR31, LR 32, LR 36 and LR47 respectively). To assess their efficacy to ameliorate a pathogen infection, C3H/HeN mice were treated with these LAB or RINH vial 323 (*L. mucosae*, LM] prior to and post-challenge with *Salmonella enteritidis* (FIG. 16). The mice were euthanased and dissected 10 days post-infection. Faecal excretion of *S. enteritidis* was reduced, if the mice had been co-treated with LAB (FIG. 17*a*, *b*). LR31 and LR32 tended to have the greatest effects on faecal *salmonella* outputs.

Intestine: Treatment with LR31, LR32, LM, LR46 or LR47 significantly reduced the numbers of *salmonella* in the caecum (FIG. 18*a*). Furthermore, LR31, LR32, LR46 and LR47 but not LM lowered *salmonella* numbers in the colon (FIG. 18 *b*). The reductions tended to be greater with LR31 and LR32. In contrast to the large intestine, the LAB had no significant effects on numbers of *salmonella* in the small intestine.

Systemic Tissues: Treatment with LR31, LR32, LM, LR46 or LR47 greatly reduced the numbers of *salmonella* detected in the spleen and liver (FIGS. 19*a-c*). The reductions were more marked with LR31 and LR32 than with LM, LR46, or LR47. *Salmonella* numbers in the mesenteric lymph node were lowered following treatment with LR31, LR32 and LR46 but not with LM or LR47.

Discussion

The LAB strains isolated (total of 436 individual colony picks) from faeces of organically-reared pigs were predominantly *L. reuteri*, *L. johnsonii*, *L. gasseri*, *L. pentosus*, strains with a small number of *L. plantarum*, *L. acidophilus*, *L. vaginalis*, a single *L. mucosae* and several uncultured strains. Most of the LAB produced substances that could inhibit the growth of *S. enteritidis* and/or *E. coli* K88 in vitro. The potency of these anti-pathogen effects varied greatly between the individual bacterial strains. A proportion of LAB had high activity against *S. enteritidis* but low activity against *E. coli* K88 and vice-versa, but the majority had similar activities against both pathogens.

Thirty-three strains were selected on the basis of anti-microbial potency as determined in vitro. These bacteria were further screened for their ability to block adherence/invasion of intestinal pig epithelial cells (IPEC) by pathogens in vitro and their susceptibility to antibiotics.

Twenty-three strains were assayed for substrate range and specificity and their capacity to suppress inflammation in IPEC cells in vitro. From these, fourteen LAB (5 *L. johnsonii*, 6 *L. reuteri* and 3 *L. Plantarum*) with particularly favourable properties were identified.

Two LAB strains [GGDK266 and GGDK31] were prepared in bulk for in vivo evaluation in newly-weaned piglets. Other potentially important candidate strains were present in this set of 14 LAB.

The survival and viability of LAB after freeze drying in various solutions was also evaluated. Small losses in viability were evident on prolonged storage of samples dried with skimmed milk powder. This was less marked when skimmed milk powder and sugars were used. However, the latter preparations were hygroscopic and were difficult to maintain. It was therefore decided to use a skimmed milk powder suspension for freeze drying and storage of LAB. The bulk preparations of GGDK266 and GGDK31 were freeze-dried in this medium.

Heat stability is a useful feature for LAB to be used in pelleted animal foods. Five heat-conditioned viable strains of isolated pig LAB were obtained. However, the biological properties in vitro and probiotic potential of three of the strains were adversely affected by heat-treatment. Nonetheless, two of the bacteria retained the biological properties of their native non-heat-treated forms.

Five pig LAB (*L. reuteri* [4] or *L. mucosae* [1]) were tested for ability to ameliorate salmonellosis in vivo. Treatment of mice with these LAB greatly reduced the pathogenicity of *S. enteritidis*.

14. Evaluation of Oral Administration of Organic *Lactobacilli* Probiotic Strains on the Modulation of the Gut Microbiota and Performance of Early Weaned Pigs In vivo trials were carried out on early weaned piglets to test the effect of two probiotic strains according to the invention, *Lactobacilli* strains GGDK266 and GGDK31.

Trial Design

Animals:
 24 Large—White×Redon piglets
 Early weaned (21 days old, ≈7-8 kg), born in a local farm
 Weighted then distributed equally between the different group
 3 experimental treatments (n=8):
  A—Basal diet+Placebo
  B—Basal diet+probiotic GDDK 266–dose $10 \times 10^{12}$
  C—Basal diet+probiotic GDDK 31–dose $10 \times 10^{12}$
 Observation period: 14 days Diet:
 Diets based on barley, wheat & soybean meal
 Feed composition (%):

| | |
|---|---|
| Barley | 36.5 |
| Wheat | 21 |
| SBM 48 | 19 |
| Corn | 10 |
| Soy oil | 4 |
| Sugar | 4 |
| Potato protein | 2 |
| Premix | 3.5 | feed ad libitum in pelleted form

Tissue Sampling and Measurements

Sampling: Day 0 Slaughter of 6 "naïve" piglets for collection of the caecum Individual collection of faeces (if possible)

Day 7 Individual collection of faeces during weight measurement

Day 14 Slaughter of 24 piglets for collection of:

| Content (5 g): | Tissus (10 cm): |
|---|---|
| Gastric | Jejunum |
| Jejunum | Ileum |
| Ileum | Caecum |
| Caecum | Lymphatic nodes (distal ileum level) |

Storage: All samples were weighed, frozen in liquid nitrogen and stored at −80° C.

Performance: ($1^{st}$ Step)

Daily Weight gain (DWG), Feed Intake (FI) and Feed Conversion Ratio (FCR)

Analysis: ($2^{nd}$ Step)

Determination of the microbiota profile in the different gut content samples by the molecular microbiology technique Denaturing gradient gel electrophoresis (DGGE).

Molecular analysis of gene expression data using pig affymetrix gene expression arrays to determine gene modulation patterns.

Determination of immunity markers in intestinal tissues

Microbial Analysis Using Denaturing Gel Gradient Electrophoresis DGGE (Trial 1)

DGGE Methodology

DNA is extracted from faecal or tissue samples utilizing the MP Bio FastDNA™ spin kit for soil sample—116560000. The DNA is then amplified using Muyzer primers, as it is essential to use primers with a GC Clamp to be run on the gel. For samples of *lactobacillus*, specialised *lactobacillus* primers with a GC clamp were used.

| Target Group | Primer | Primer Sequence (5'-3') | Amplicon Size (bp) | Annealing temperature (° C.) | DGGE gradient (%) |
|---|---|---|---|---|---|
| All Bacteria | MF<br>MR-GC$^a$ | ATTACCGCGGCTGCTGG<br>GC-clamp-CCTACGGGAGGCAGCAG<br>(SEQ ID NO: 90) | 233 | 55 | 35-70 |
| LABs | Lac1<br>Lac2-GC$^a$ | AGCAGTAGGGAATCTTCCA<br>GC-Clamp-ATTYCACCGCTACACATG$^c$<br>(SEQ ID NO: 91) | 327 | 55 | 30-50 |

Annotations:
$^a$The GCclamp is as follows: CGCCCGCCGCGCGCGGCGGGCGGGGCGGGGGCACGGGGGG (SEQ ID NO: 92)
$^c$Y = C or T PCR Program:

| Time | Temperature | Cycles |
|---|---|---|
| 5 minutes | 94° C. | 1 |
| 30 seconds | 94° C. | 35 |
| 30 seconds | 55° C. | 72° C. |
| 2 minutes | | |
| 10 minutes | 72° C. | 1 |

DGGE is a genetic analysis technique in which amplified PCR products are separated by the denaturants formamide and urea within the gel, based on the genetic sequence by as little as a single base difference. DGGE can be utilised to visualise the differences in microbial diversity between samples. DNA obtained from a range of samples can be used in DGGE e.g. tissue and faecal samples. Bands on the gel were visualised using silver staining.

Molecular Analysis and Gene Expression Profiles of Pig Tissues RNA Extraction and Affymetrix Microarray Analysis RNA was isolated from both animal tissue and cultured cells for use on Affymetrix GeneChips. For animal tissue, approximately 200 mg tissue sample was removed from RNAlater (Ambion) and lyzed in Trizol (Invitrogen) using a polytron homogenizer. The tissue was further homogenized by passing the lysate through a syringe fitted with a 19G needle 3-5 times. The samples were incubated for 5 min at RT to permit the complete dissociation of nucleoprotein complexes. Then, chloroform, isopropanol and ethanol steps were performed according to the manufacturer's instructions. Briefly, 0.2 mL of chloroform was added per 1 mL of Trizol, vortexed and incubated at RT for 5 min. The samples were centrifuged at 12,000×g for 15 min at 4° C. The resultant aqueous phase was transferred to a fresh tube, and the RNA was precipitated by the addition of 0.5 mL of isopropanol per 1 mL of Trizol. The tubes were shaken vigorously by hand for 10s, incubated at 4° C. for 10 min and centrifuged at 12,000×g for 10 min at 4° C. The RNA precipitate was washed with ice-cold 75% ethanol, adding at least 1 mL of 75% ethanol per 1 mL of Trizol. The samples were vortexed and centrifuged at 7,400×g for 5 min at 4° C. After air-drying the resultant RNA pellet, the RNA was re-suspended in up to 100 μL RNase-free water. Total RNA was further extracted with the RNeasy kit (Qiagen) according to the manufacturer's instructions, including an RNase-free DNase I (Qiagen) digestion step.

Cultured cells were homogenized by adding 350 μL Buffer RLT+1% β-mercaptoethanol. The cells were scraped off culture dishes with a filter tip and further homogenized by passing the lysate through a syringe fitted with a 19G needle 3-5 times. The cell lysate was then further processed using the RNeasy kit (Qiagen) according to the manufacturer's instructions, including an RNase-free DNase I (Qiagen) digestion step.

RNA concentration and integrity was ascertained using a Nanodrop instrument and/or Agilent Bioanalyzer, and purified RNA was stored at −70° C.

250 ng RNA was processed for Affymetrix GeneChips using the GeneChip 3' IVT Express Kit (Affymetrix) according to the manufacturer's instructions. aRNA quality was determined by Agilent 2100 Bioanalyzer. Hybridization to the GeneChip Mouse Genome 430 2.0 and GeneChip Human Genome 0133 Plus 2.0 (Affymetrix) on a GeneChip Fluidics Station 450 (Affymetrix) was performed at the Institute of Medical Sciences Microarray Core Facility (University of Aberdeen, UK). Chips were scanned with an Affymetrix GeneChip Scanner 3000 (Affymetrix). Image quality analysis was performed using Gene Chip Operating Software (GCOS) (Affymetrix). Further quality analysis, normalization (gcRMA), statistical analysis and heatmap generation was performed with the freely available software packages R (http://www.r-project.org) and Bioconductor (http://www.bioconductor.org). Microarray data were submitted to the National Center for Biotechnology Information (NCBI) Gene Expression Omnibus (http://www.ncbi.nlm.nih.gov/geo).

Results

Performance of Pigs Fed Probiotics GGDK266 and GGDK31

The results for pigs fed probiotics GGDK266 and GGDK31 are shown in FIG. 20.

DWG (Daily weight gain), FI (food intake) and FCR (feed conversion ratio) are shown below:

| GGDK266 | DWG | FI | FCR |
|---|---|---|---|
| d0-d7 | +++ (*) | + | + |
| d7-d14 | = | + | + |
| d0-d14 | + | + | + |

Piglets fed GGDK266 exhibited significantly improved daily weight gain (DWG) during the first week post-weaning relative to GGDK31 and placebo fed piglets.

Microbial Diversity Analysis Using DGGE (Trial 1)

DGGE using universal primers revealed no differences in overall microbial diversity between the treatments and placebo (see FIG. 21).

DGGE using lactic acid bacteria (LAB) specific primers revealed significant differences in LAB diversity between treatment with GGDK 266 and placebo in both caecal and ileal samples (see FIG. 22).

DGGE using LAB specific primers revealed significant differences in LAB diversity between the treatment with GGDK266 and placebo in ileal samples (see FIG. 23).

DGGE using LAB specific primers revealed significant differences in LAB diversity between the treatment with 266 and placebo in caecal samples (see FIG. 24).

Overall the microbial diversity analysis revealed significant clustering of the LAB population in piglets fed GGDK266 indicating that the populations in individual animals on this treatment has a similar and stable microbiota.

Molecular Analysis of Ileal Tissue Samples: Affymetrix Pig Arrays

Downregulated in GDK266 Versus Placebo

Gene ontology analysis of differentially expressed gene revealed that a significant reduction in immune system processes and pro-inflammatory activation in response to feeding young piglets probiotic GGDK266 relative to placebo (see FIG. 25).

Results reveal that GGDK266 had a very specific and targeted effect on the immune system and the functional groups associated with response to stimuli (see FIG. 26).

Upregulated in GGDK266 Versus Placebo

In contrast to the effects on the immune system, GGDK266 promoted metabolic processes particularly in relation to nitrogen (see FIG. 27). Without wishing to be bound by theory, it is believed that these effects may explain the improved DWG in animals fed GGDK266.

Top Differentially Expressed Genes Between GGDK266 and Placebo

| affy.id | Gene Name | Product | FC | p-value |
|---|---|---|---|---|
| Ssc.545.1.S1_at | CSTA | Cystatin A | 44.06 | 0.00000 |
| Ssc.11608.1.A1_at | TIP_HUMAN | T-cell immunomodulatory protein precursor | 28.92 | 0.00030 |
| Ssc.10837.1.A1_at | ROBO1 | Roundabout homolog 1 precursor | 13.35 | 0.00178 |
| Ssc.8960.1.A1_at | BPI | Bactericidal permeability-increasing protein precursor | 11.65 | 0.00476 |
| Ssc.16234.1.S1_at | TCN1 | Transcobalamin I precursor | 11.48 | 0.00023 |
| Ssc.1411.1.S1_at | THBS4 | Thrombospondin 4 precursor | 8.92 | 0.00198 |
| Ssc.837.1.A1_at | BPI | Bactericidal permeability-increasing protein precursor | 4.55 | 0.00573 |
| Ssc.30008.1.A1_at | ESR1 | Estrogen receptor | 4.48 | 0.00053 |
| Ssc.13539.1.A1_at | PLAGL1 | Zinc finger protein PLAGL1 | 4.42 | 0.00881 |
| Ssc.26324.1.S1_at | NP_981932 | Iodotyrosine dehalogenase 1 protein | 4.26 | 0.00200 |
| Ssc.29413.1.A1_at | B3GALT2 | UDP-Gal:betaGlcNAc beta 1,3-galactosyltransferase 2 | 4.00 | 0.00046 |
| Ssc.27410.1.S1_at | MYCN | N-myc proto-oncogene protein | 3.80 | 0.00261 |
| Ssc.25176.1.A1_at | GOLPH4 | Golgi phosphoprotein 4 | 3.80 | 0.00009 |
| Ssc.15890.1.S1_at | VNN1 | Pantetheinase precursor | 3.61 | 0.00271 |
| Ssc.23427.1.A1_at | CYB561 | Cytochrome b561 | 3.29 | 0.01512 |
| Ssc.16186.1.S1_at | CD3E | T-cell Surface glycoprotein CD3 epsilon chain precursor | −2.62 | 0.00764 |
| Ssc.22676.1.S1_at | CXCR6 | C—X—C chemokine receptor type 6 | −2.63 | 0.01652 |
| Ssc.15565.1.S1_at | LCP2 | Lymphocyte cytosolic protein 2 | −2.76 | 0.00024 |
| Ssc.18652.1.S1_at | IL16 | Interleukin-16 precursor | −2.97 | 0.01132 |
| Ssc.181.1.S1_at | TRGV9 | T-cell receptor gamma chain V region PT-gamma-1/2 precursor | −3.04 | 0.01615 |
| Ssc.23489.1.S1_at | CD8A | T-cell surface glycoprotein CD8 alpha chain precursor | −3.08 | 0.00071 |
| Ssc.428.6.S1_a_at | TCA_HUMAN | T-cell receptor alpha chain C region | −3.15 | 0.00027 |
| Ssc.10357.1.A1_at | FMN2 | Formin 2 | −3.46 | 0.00308 |
| Ssc.27354.1.S1_at | STXBP5 | Tomosyn | −3.88 | 0.02438 |
| Ssc.28909.3.A1_at | TPH2 | Tryptophan 5-hydroxylase 2 | −4.36 | 0.00717 |

-continued

| affy.id | Gene Name | Product | FC | p-value |
|---|---|---|---|---|
| Ssc.25976.1.S1_at | GZMH | Granzyme H precursor | −5.46 | 0.00179 |
| Ssc.11070.1.S1_at | IGHM | Ig alpha-1 chain C region | −9.07 | 0.00115 |
| Ssc.16566.1.S1_at | LCT | Lactase-phlorizin hydrolase precursor | −11.31 | 0.00828 |
| Ssc.13273.1.A1_at | GCNT3 | glucosaminyl (N-acetyl) transferase 3, mucin type | −19.75 | 0.00016 |
| Ssc.11098.1.S1_at | IFITM3 | Interferon-induced transmembrane protein 3 | −51.36 | 0.00044 |

Gene expression data revealed that a number of genes were significantly increased including antimicrobial peptides (eg. CSTA, BP1) and immune-regulatory genes (TIP). In contrast GGDK266 reduced the expression of a diverse panel of genes involved in pro-inflammatory immunity (IFITM3, IL-16).

CONCLUSIONS

Cellular and metabolic processes, particularly in relation to nitrogen, are increased in animals treated with GGDK266 relative to placebo.

Immune system processes are downregulated in animals treated with GGDK266 relative to placebo. Examples include T-cell markers CD3 and CD8, T cell receptor chains, chemokines/cytokines and IFN-related genes.

Animals administered with GGDK266 exhibited a stable population of lactic acid bacteria revealed by clustering of the bacterial profile of the individual induced by the adminiatration of probiotic GGDK266.

FCR and performance were significantly improved during the first weeks of post-weaning life.

This improvement in growth performance correlated with the reduction in inflammatory immune responses and the increase in specific metabolic processing.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

TABLE 1

Summary of bacteria colonies selected from cultures of faeces from organically-reared pigs.

| Total number of cultured colony picks | 443 |
|---|---|
| Media: | |
| LAMVAB agar | 55 |
| LAMVAB agar + pig colostral carbohydrate | 88 |
| MRS agar | 29 |
| MRS agar + pig colostrum carbohydrate | 176 |
| Glucose-free MRS agar + carbohydrate | 57 |
| MRS agar after heat-treatment at up to 70° C. | 38 |
| Main strains identified: | |
| *Lactobacillus reuteri* | |
| *Lactobacillus johnsonii* | |
| *Lactobacillus plantarum* | |

Five isolated LAB were heated once, twice or three times at 70° C. for 15 min. Surviving bacteria were re-grown.

TABLE 1-continued

Summary of bacteria colonies selected from cultures of faeces from organically-reared pigs.

| In stock | |
|---|---|
| 5 LAB heated once at 70° C. | |
| 5 LAB heated twice at 70° C. | |
| 5 LAB heated three times at 70° C. | |

TABLE 2

Candidate LAB strains for further study selected on the basis of killing activity in well diffusion assays (note 266 and 161 contain LR)

| RINH Vial no. | | Pathogen killing (units) Well diffusion assay | |
|---|---|---|---|
| | | anti-SE | anti-KSS |
| 85 | LR | 129886 | 60168 |
| 255 | LJ | 101477 | 64390 |
| 266 | LJ | 101335 | 60168 |
| 436 | LJ | 81656 | 85010 |
| 161 | LP | 77894 | 103346 |
| 12 | LJ | 162709 | 42977 |
| 16 | LJ | 117621 | 41365 |
| 29 | LR | 174471 | 45720 |
| 31 | LR | 116867 | 46907 |
| 86 | LR | 98520 | 75147 |
| 230 | LJ | 95705 | 64340 |
| 256 | LJ | 94012 | 77459 |
| 314 | LJ | 103497 | 48936 |
| 361 | LJ | 100770 | 40254 |
| 17 | LJ | 144765 | 23072 |
| 30 | LR | 125463 | 36050 |
| 32 | LR | 168892 | 32572 |
| 258 | LP | 70724 | 68612 |
| 260 | LP | 78197 | 68562 |
| 320 | LJ | 66350 | 78044 |
| 364 | LJ | 99137 | 55123 |
| 433 | LJ | 95083 | 51461 |
| 15 | LP | 77459 | 58669 |
| 218 | LJ | 62329 | 50416 |
| 220 | LJ | 68612 | 53834 |
| 356 | LJ | 72986 | 55302 |
| 363 | LJ | 79125 | 45555 |
| 131 | LR | 42223 | 44108 |
| 434 | LR | 10000 | 81656 |
| 166 | LJ | 17064 | 79621 |
| 431 | LR | 48657 | 31674 |
| 47 | LR | 20722 | 34633 |
| 46 | LR | 19867 | 34633 |

LJ. *L. johnsonii.*
LR. *L. reuteri.*
LP. *L. Plantarum*

TABLE 2a

Identification of candidate LAB strains (by 16S rRNA gene sequence) selected
on the basis of killing activity in well diffusion assays (note 266 and 161 contain LR)

| RINH Vial no. | forward sequence | reverse sequence |
|---|---|---|
| 85 | *Lactobacillus reuteri* | *Lactobacillus reuteri* |
| 255 | *Lactobacillus johnsonii, taiwanensis, acidophilus* | *Lactobacillus johnsonii, gasseri* |
| 266 | *Lactobacillus johnsonii* | *Lactobacillus johnsonii* |
| 436 | *lactobacillus johnsonii* str. 466 | *lactobacillus johnsonii* F19785 |
| 161 | *Lactobacillus plantarum, pentosus, paraplantarum* | *Lactobacillus plantarum, pentosus* |
| 12 | *Lactobacillus johnsonii, gasseri, taiwanensis* | *Lactobacillus johnsonii, gasseri* |
| 16 | *Lactobacillus johnsonii, gasseri, taiwanensis* | *Lactobacillus johnsonii* |
| 29 | *Lactobacillus reuteri, pontis, vaginalis, frumenti* | *Lactobacillus reuteri* |
| 31 | *Lactobacillus reuteri* | *Lactobacillus reuteri* |
| 86 | *Lactobacillus reuteri* | *Lactobacillus reuteri* |
| 230 | *Lactobacillus johnsonii, taiwanensis, acidophilus* | *Lactobacillus johnsonii* |
| 256 | *Lactobacillus johnsonii, taiwanensis, acidophilus* | *Lactobacillus johnsonii* |
| 314 | *lactobacillus johnsonii* BR0315 | uncultured bacterium |
| 361 | *lactobacillus johnsonii* str. NCC2822 | *lactobacillus johnsonii* F19785 |
| 17 | *Lactobacillus johnsonii, gasseri, taiwanensis* | *Lactobacillus johnsonii* |
| 30 | *Lactobacillus reuteri, pontis* | *Lactobacillus reuteri* |
| 32 | *Lactobacillus reuteri* | *Lactobacillus reuteri* |
| 258 | *Lactobacillus plantarum, pentosus, helveticus* | *Lactobacillus plantarum, pentosus, paraplantarum* |
| 260 | *Lactobacillus plantarum, pentosus, paraplantarum* | *Lactobacillus pentosus, plantarum, paraplantarum* |
| 320 | *lactobacillus johnsonii* NCC2822 | *Lactobacillus johnsonii* F19785 |
| 364 | *lactobacillus johnsonii* 466 | *lactobacillus johnsonii* F10785 |
| 433 | *lactobacillus johnsonii* str. CECT 289 | *lactobacillus johnsonii* F19785 |
| 15 | *Lactobacillus plantarum, pentosus* | *Lactobacillus plantarum, pentosus* |
| 218 | *Lactobacillus johnsonii, taiwanensis* | uncultured Firmicutes, *Lactobacillus johnsonii* |
| 220 | *Lactobacillus johnsonii, taiwanensis* | uncultured Firmicutes, *Lactobacillus johnsonii* |
| 356 | *lactobacillus johnsonii* NCC2822 | *lactobacillus johnsonii* F19785 |
| 363 | *lactobacillus johnsonii* 466 | *lactobacillus johnsonii* F10785 |
| 131 | *Lactobacillus reuteri* | *Lactobacillus reuteri* |
| 434 | *Lactobacillus reuteri* NM99-1 | *lactobacillus reuteri* |
| 166 | *Lactobacillus johnsonii, taiwanensis, acidophilus* | *Lactobacillus johnsonii* |
| 431 | *lactobacillus reuteri* str. Probio-16 | *lactobacillus reuteri* JCM 1112 |
| 47 | *Lactobacillus reuteri* | *Lactobacillus reuteri* |
| 46 | *Lactobacillus reuteri* | *Lactobacillus reuteri* |

TABLE 3

Candidate LAB strains for further study selected on the basis of killing activity in well diffusion assays and capacity to block adherence of pathogen to IPEC cells

| RINH Vial no. | Inhibition of adherence (%) | |
|---|---|---|
| | SE | KSS |
| 85 | 88.31 | 87.93 |
| 255 | 82.37 | 99.93 |
| 266 | 88.03 | 98.09 |
| 161 | 98.32 | 96.94 |
| 12 | 96.89 | 99.92 |
| 29 | 93.7 | 99.91 |
| 31 | 98.64 | 99.75 |
| 86 | 81 | 99.98 |
| 256 | 82.47 | 99.92 |
| 361 | 85.07 | 99.44 |
| 17 | 84.56 | 99.66 |
| 30 | 96.44 | 99.91 |
| 32 | 87.74 | 99.86 |
| 230 | 78.89 | 82.45 |
| 258 | 96.37 | 86.5 |
| 260 | 90.22 | 88.79 |
| 314 | 79.68 | 94.2 |
| 433 | 99.99 | 96.23 |
| 16 | 87.68 | 45.38 |
| 218 | 91.53 | 86.49 |
| 363 | 85.61 | 99.93 |
| 364 | 82.13 | 78.12 |
| 15 | 79.19 | 99.52 |
| 131 | 95.5 | 96.03 |
| 220 | 91.04 | 78.6 |
| 320 | 92.7 | 44.17 |
| 356 | 82.15 | 78.4 |
| 434 | 94.78 | 98.85 |
| 436 | 99.97 | 1 |
| 166 | 91.45 | 95.97 |
| 431 | 96.35 | 86.47 |
| 47 | 90.47 | 99.47 |
| 46 | 83.51 | 99.7 |

TABLE 4

Area of inhibition of LAB by defined amounts of antibiotic (arbitrary units)

| | ampicillin | cefotaxime | chloramphenicol | erythromycin | gentamicin | kanamycin | metronizadole | nal. acid | tetracycline | vancomycin |
|---|---|---|---|---|---|---|---|---|---|---|
| 12 | 244011 | 340402 | 186699 | 13151 | 0 | 0 | 0 | 0 | 37668 | 22581 |
| 15 | 277117 | 311725 | 204282 | 214008 | 0 | 0 | 0 | 0 | 0 | 0 |
| 16 | 266033 | 294166 | 187805 | 64681 | 17000 | 7157 | 0 | 0 | 0 | 105209 |
| 17 | 387224 | 400570 | 235450 | 277145 | 9193 | 0 | 0 | 0 | 50328 | 117741 |
| 29 | 410335 | 444193 | 190293 | 114511 | 0 | 0 | 0 | 0 | 252497 | 11483 |
| 30 | 292728 | 335927 | 77133 | 208117 | 31261 | 0 | 0 | 0 | 187805 | 31402 |
| 31 | 334789 | 410966 | 165904 | 262226 | 38221 | 0 | 0 | 0 | 214037 | 24901 |
| 32 | 404496 | 402291 | 247436 | 350238 | 71608 | 23786 | 0 | 0 | 261979 | 10691 |
| 46 | 359232 | 402588 | 210421 | 251461 | 29550 | 0 | 0 | 0 | 21382 | 25069 |
| 47 | 328283 | 410579 | 185515 | 270105 | 30342 | 0 | 0 | 0 | 211556 | 22231 |
| 85 | 356114 | 369916 | 204992 | 309439 | 0 | 0 | 0 | 0 | 276800 | 3971 |
| 86 | 250812 | 381270 | 183399 | 250805 | 41858 | 0 | 31264 | 0 | 16643 | 13355 |
| 131 | 349955 | 473065 | 248521 | 123562 | 82466 | 14932 | 0 | 0 | 19354 | 7479 |
| 161 | 338497 | 412977 | 258724 | 261133 | 51991 | 4536 | 29126 | 0 | 20435 | 5542 |
| 166 | 268783 | 417393 | 185508 | 251607 | 61136 | 17671 | 0 | 0 | 24606 | 0 |
| 218 | 209117 | 271547 | 148617 | 0 | 0 | 0 | 0 | 0 | 88668 | 122870 |
| 220 | 209371 | 319970 | 165815 | 34230 | 58814 | 32572 | 0 | 0 | 34636 | 111666 |
| 230 | 254614 | 335143 | 164405 | 51078 | 65717 | 45705 | 0 | 0 | 36644 | 41991 |
| 255 | 330364 | 392169 | 217758 | 59224 | 56563 | 8486 | 0 | 0 | 29872 | 0 |
| 256 | 456892 | 502325 | 228531 | 71258 | 93058 | 0 | 0 | 0 | 20955 | 42203 |
| 258 | 401257 | 271932 | 195909 | 233326 | 28608 | 0 | 0 | 0 | 223143 | 0 |
| 260 | 286400 | 364573 | 203796 | 33393 | 78821 | 78364 | 0 | 0 | 21757 | 62792 |
| 266 | 287070 | 322869 | 198614 | 247085 | 54008 | 3079 | 6437 | 2737 | 48286 | 107882 |
| 314 | 297057 | 332853 | 154830 | 44115 | 0 | 0 | 0 | 0 | 0 | 90259 |
| 356 | 291920 | 339895 | 203692 | 62656 | 10472 | 5890 | 0 | 0 | 24194 | 8202 |
| 361 | 320695 | 323713 | 201886 | 234140 | 0 | 0 | 0 | 0 | 0 | 91863 |
| 363 | 275304 | 308159 | 193271 | 44491 | 86683 | 0 | 0 | 0 | 28212 | 18146 |
| 364 | 288514 | 341651 | 194320 | 143978 | 45880 | 0 | 0 | 0 | 18322 | 103995 |
| 431 | 339016 | 380459 | 226484 | 311725 | 74991 | 0 | 0 | 0 | 0 | 26302 |
| 433 | 241710 | 203588 | 174124 | 63381 | 19139 | 0 | 0 | 0 | 19965 | 79034 |
| 434 | 198112 | 261065 | 172223 | 68052 | 6049 | 0 | 0 | 0 | 60344 | 45863 |
| 436 | 290458 | 287331 | 185812 | 142842 | 0 | 0 | 0 | 0 | 52279 | 61810 |

Nal. Acid, naladixie acid.

TABLE 5

Substrates in capsules of API CH 50 Kit

Substrates in capules of API CH 50 kit

| 1 | glycerol | polyol |
| 2 | erythritol | polyol |
| 3 | D-arabinose | monosaccharide |
| 4 | L-arabinose | monosaccharide |
| 5 | D-ribose | monosaccharide |
| 6 | D-xylose | monosaccharide |
| 7 | L-xylose | monosaccharide |
| 8 | D-adonotol | alcohol |
| 9 | Methyl-βD-Xylopyranoside | cyclic |
| 10 | D-galactose | monosaccharide |
| 11 | D-glucose | monosaccharide |
| 12 | D-fructose | monosaccharide |
| 13 | D-mamose | monosaccharide |
| 14 | L-sorbose | monosaccharide |
| 15 | L-rhamose | monosaccharide |
| 16 | dulcitol | monosaccharide/alcohol |
| 17 | inositol | polyol |
| 18 | D-mamitol | polyol |
| 19 | D-sorbitol | sugar/alcohol |
| 20 | Methyl-αD-Mannopyranoside | cyclic |
| 21 | Methyl-αD-Glucopyranoside | cyclic |
| 22 | N-acetylglucosamine | monosaccharide |
| 23 | amygdalin | glycoside |
| 24 | arbutin | glycoside |
| 25 | esculin ferric citrate | |
| 26 | salicin | glycoside |
| 27 | D-cellobiose | disaccharide |
| 28 | D-maltose | disaccharide |
| 29 | D-lactose (bovine) | disaccharide |
| 30 | D-Melibiose | disaccharide |
| 31 | D-saccharose | disaccharide |
| 32 | D-trehalose | disaccharide |
| 33 | inulin | polysaccharide |
| 34 | D-melezitose | trisaccharide |
| 35 | D-rafinose | trisaccharide |
| 36 | amidon (starch) | polysaccharide |
| 37 | glycogen | polysaccharide |
| 38 | xylitol | monosaccharide/alcohol |
| 39 | gentiobiose | disaccharide |
| 40 | D-turanose | disaccharide |
| 41 | D-lyxose | monosaccharide |
| 42 | D-tagatose | monosaccharide |
| 43 | D-fucose | monosaccharide |
| 44 | L-fucose | monosaccharide |
| 45 | D-arabitol | monosaccharide/alcohol |
| 46 | L-arabitol | monosaccharide/alcohol |
| 47 | potassium gluconate | sequestrant |
| 48 | potassium 2-ketogluconate | sequestrant |
| 49 | potassium 5-ketogluconate | sequestrant |

TABLE 6

Substrate profile of LAB using an API CH 50 kit

| | mono-saccharides | alcohol/mono-saccharides | di-saccharides | tri-saccharides | poly-saccharides | alcohols | others |
|---|---|---|---|---|---|---|---|
| 17 | 0.4 | 0.0 | 0.8 | 0.5 | 0.3 | 0.0 | 0.4 |
| 30 | 0.2 | 0.0 | 0.0 | 0.0 | 0.0 | 0.0 | 0.3 |
| 31 | 0.3 | 0.0 | 0.6 | 0.5 | 0.0 | 0.0 | 0.6 |
| 32 | 0.3 | 0.0 | 0.5 | 0.5 | 0.0 | 0.0 | 0.3 |
| 46 | 0.2 | 0.0 | 0.5 | 0.5 | 0.0 | 0.0 | 0.4 |

TABLE 6-continued

Substrate profile of LAB using an API CH 50 kit

| | mono-sac-charides | alcohol/mono-sac-charides | di-sac-charides | tri-sac-charides | poly-sac-charides | alcohols | others |
|---|---|---|---|---|---|---|---|
| 47 | 0.2 | 0.3 | 0.5 | 0.5 | 0.0 | 0.0 | 0.4 |
| 85 | 0.1 | 0.0 | 0.3 | 0.0 | 0.0 | 0.0 | 0.4 |
| 86 | 0.3 | 0.0 | 0.5 | 0.5 | 0.0 | 0.0 | 0.4 |
| 131 | 0.4 | 0.0 | 1.0 | 1.0 | 0.3 | 0.3 | 0.9 |
| 161 | 0.7 | 0.3 | 0.9 | 1.0 | 0.0 | 0.3 | 0.9 |
| 166 | 0.4 | 0.0 | 0.6 | 0.0 | 0.7 | 0.0 | 0.3 |
| 220 | 0.1 | 0.0 | 0.5 | 0.5 | 0.0 | 0.0 | 0.4 |
| 230 | 0.3 | 0.0 | 0.8 | 0.5 | 0.0 | 0.0 | 0.4 |
| 255 | 0.1 | 0.0 | 0.6 | 1.0 | 0.3 | 0.0 | 0.4 |
| 256 | 0.2 | 0.0 | 0.5 | 1.0 | 0.0 | 0.2 | 0.6 |
| 258 | 0.6 | 0.3 | 1.0 | 1.0 | 0.7 | 0.7 | 0.9 |
| 260 | 0.4 | 0.3 | 0.9 | 1.0 | 1.0 | 0.0 | 0.6 |
| 266 | 0.3 | 0.0 | 0.9 | 0.5 | 0.3 | 0.0 | 0.4 |
| 320 | 0.3 | 0.0 | 0.5 | 0.5 | 0.3 | 0.0 | 0.3 |
| 363 | 0.4 | 0.0 | 0.8 | 1.0 | 0.3 | 0.0 | 0.4 |
| 364 | 0.4 | 0.0 | 0.8 | 0.5 | 0.3 | 0.0 | 0.4 |
| 433 | 0.2 | 0.0 | 0.5 | 0.0 | 0.0 | 0.2 | 0.3 |

TABLE 7

Candidate LAB strains selected on the basis of killing activity, capacity to block adherence of pathogen to IPEC cells, antibiotic susceptibility, substrate reactivity and ability to suppress inflammation (note 266 and 161 contain LR)

| RINH Vial no. | forward sequence | reverse sequence |
|---|---|---|
| 266 | Lactobacillus johnsonii | Lactobacillus johnsonii |
| 31 | Lactobacillus reuteri | Lactobacillus reuteri |
| 258 | Lactobacillus plantarum, pentosus, helveticus | Lactobacillus plantarum, pentosus, paraplantarum |
| 260 | Lactobacillus plantarum, pentosus, paraplantarum | Lactobacillus pentosus, plantarum, paraplantarum |
| 255 | Lactobacillus johnsonii, taiwanensis, acidophilus | Lactobacillus johnsonii, gasseri |
| 161 | Lactobacillus plantarum, pentosus, paraplantarum | Lactobacillus plantarum, pentosus |
| 256 | Lactobacillus johnsonii, taiwanensis, acidophilus | Lactobacillus johnsonii |
| 86 | Lactobacillus reuteri | Lactobacillus reuteri |
| 85 | Lactobacillus reuteri | Lactobacillus reuteri |
| 32 | Lactobacillus reuteri | Lactobacillus reuteri |
| 230 | Lactobacillus johnsonii, taiwanensis, acidophilus | Lactobacillus johnsonii |
| 131 | Lactobacillus reuteri | Lactobacillus reuteri |
| 30 | Lactobacillus reuteri, pontis | Lactobacillus reuteri |
| 364 | lactobacillus johnsonii 466 | lactobacillus johnsonii F10785 |

TABLE 8

Identity for pig LAB strains selected for bulk preparation (note 266 and 161 contain LR)

| RINH vial no | Seq code primer 926F | Bacteria identified by BLAST | Seq code primer 519R | Bacteria identified by BLAST |
|---|---|---|---|---|
| | | GGDK266 | | |
| 266 | S10CM218 | Lactobacillus johnsonii | S10CM171 | Lactobacillus johnsonii |
| | | GGDK31 | | |
| 31 | S10BL123 | Lactobacillus reuteri | S10BL141 | Lactobacillus reuteri |

SEQ ID NO: 1

31 S10BL123 with 926F
GGTGGAGCATGTGGTTTAATTCGAAGCTACGCGAAGAACCTTACCAGGTCTTGACATCTTGCGCTAACCTTAGAGATAAG

GCGTTCCCTTCGGGGACGCAATGACAGGTGGTGCATGGTCGTCGTCAGCTCGTGTCGTGAGATGTTGGGTTAAGTCCCGC

AACGAGCGCAACCCTTGTTACTAGTTGCCAGCATTAAGTTGGGCACTCTAGTGAGACTGCCGGTGACAAACCGGAGGAAG

GTGGGGACGACGTCAGATCATCATGCCCCTTATGACCTGGGCTACACACGTGCTACAATGGACGGTACAACGAGTCGCAA

GCTCGCGAGAGTAAGCTAATCTCTTAAAGCCGTTCTCAGTTCGGACTGTAGGCTGCAACTCGCCTACACGAAGTCGGAAT

CGCTAGTAATCGCGGATCAGCATGCCGCGGTGAATACGTTCCCGGGCCTTGTACACACCGCCCGTCACACCATGGGAGTT

TGTAACGCCCAAAGTCGGTGGCCTAACCATTATGGAGGGAGCCGCCTAAGTGCGGGACAGATGACTGGGGTGAAGTCGTA

ACAAGGTAGCCTGTATTTTCTTGCGGTTGTTCCCCCCCCNGGCGGGACTGCCTTACTCCTTTCACCNCCCGCGCCCCTGG

AGGGGGCCGGAACCCCCCTCCCAACCCCCCTAACCCACCTCCTTCCTTTTAACCNGCT

SEQ ID NO: 2

31 S10BL141 with 519R
GACTTTCTAGGTTGGATACCGTCACTGCGTGAACAGTTACTCTCACGCACGTTCTTCTCCAACAACAGAGCTTTACGAGC

CGAAACCCTTCTTCACTCACGCGGTGTTGCTCCATCAGGCTTGCGCCCATTGCGAAGATTCCCTACTGCTGCCTCCCGT

AGGAGTATGGACCGTGTCTCAGTTCCATTGTGGCCGATCAGTCTCTCAACTCGGCTATGCATCATCGCCTTGGTAAGCCG

TTACCTTACCAACTAGCTAATGCACCGCAGGTCCATCCCAGAGTGATAGCCAAAGCCATCTTTCAAACAAAAGCCATGTG

GACTTTCTTGTTATGCGGTATTAGCATCTGTTTCCAAATGTTATCCCCGCTCCGGGGCAGGTTACCTACGTGTTACTCA

CCCGTCCGCCACTCACTGGTGATCCATCGTCAATCAGGTGCAAGCACCATCAATCAGTTGGGCCAGTGCGTACGACTTGC

ATGTATTAGGCACACCGCCGGCGTTCATCCTGAGCCATGATCAAACTCTANGCGTCAGTTTTACGGTCTCGGCTCGTTTC

TCTGTTNTCTGACATCAACGTGCGTTACATTTGCGGTTTACGCATTGATTGTACTCCCTCCACATAGGTGGCGGCATACC

CTTCGTGCTCCTCTACTCATCTCGTTCATTACAACTCGCTTTGTTACCTTCCCGGTGGGGTTCTCTACCTCCTTCGTTTT

CTCTCACCTCATTCTCTCTCCCATCCTCTCNCTTTCCTCTTGCTC

SEQ ID NO: 3

161 S10BL282 with 926F
GGTGGAGCATGTGGTTTAATTCGAAGCTACGCGAAGAACCTTACCAGGTCTTGACATACTATGCAAATCTAAGAGATTAG

ACGTTCCCTTCGGGGACATGGATACAGGTGGTGCATGGTTGTAGTCAGCTCGTGTCGTGAGATGTTGGGTTAAGTCCCGC

AACGAGCGCAACCCTTGTTATCAGTTGCCAGCATTAAGTTGGGCACTCTGGTGAGACTGCCGGTGACAAACCGGAGGAAG

GTGGGGATGACGTCAAATCATCATGCCCCTTGATGACCTGGGCTAGACACGTGCTACAATGGATGGTACAACGAGTTGCG

AACTCGCGAGAGTAAGCTAATCTCTTAAAGCCATTCTCAGTTACGGATGTGTAGGCTGCAACTCGCCATACATGAAGTCG

GAATCGCTAGTAATCGCGGATACAGCATGCCGCGGTGAATACTGTTCCCGGGCCTATGTGACACACCGCCCGTCACACCA

TGAGCAGTTTGTAATCACCCACACAGTCGGTGGGGTAACCTTTATAGGAACCAGCCGCCTACAGTGCGGGACCGATGATT

ATGGGTGCACTCGTATCACTGTAACTTAAACCCTTGCGGCCGTACTCCCCAGGCGGAATGCTTAATACGTTACCTGCAAC

CCTGAAGGGCGGAATCCCTCCAACGATTATCAAT

SEQ ID NO: 4

161 S10BL300 with 519R
GTGGCTTTCTGGTTAAATACCGTCAATACCTGAACAGTTACTCTCAGATATGTTCTTCTTTAACAACAGAGTTTTACGAG

CCGAAACCCTTCTTCACTCACGCGGCGTTGCTCCATCAGACTTTCGTCCATTGTGGAAGATTCCCTACTGCTGCCTCCCG

TAGGAGTTTGGGCCGTGTCTCAGTCCCAATGTGGCCGATTACCCTCTCAGGTCGGCTACGTATCATTGCCATGGTGAGCC

GTTACCCCACCATCTAGCTAATACGCCGCGGGACCATCCAAAAGTGATAGCCGAAGCCATCTTTCAAGCTCGGACCATGC

GGTCCAAGTTGTTATGCGGTATTAGCATCTGTTTCCAGGTGTTATCCCCGCTTCTGGGCAGGTTTCCCACGTGTTACTC

ACCAGTTCGCCACTCACTCAAATGTAAATCATGATGAAGCACCAATCAATACCAAGTTCGTTCGACTTGCATGTATTA

GGCACGCCGCCAGCGTTCGTCGCTGAGCCATGATCAAACTACTAAAGGCCCCNATGCCTCCCACCCGCTTTGTTGCCGG

GGCCCCCCGTTCCCATACCCCTTTTGGACGTTTTCCAGCCCCTTGGCGGGCCCTGTACCTCCCCCCAGGGCGGGAATGC

CTTAATTGCGTTNACCTTGCACCCCCTGAAGGGGCGGAATCCCTCCAACGATTACCT

-continued

SEQ ID NO: 5
255 S10BL504 with 926F
GGTGGAGGATGTGGTTTAATTGGAAGCAACGCGAAGAACCTTACCAGGTCTTGACATCCAGTCGCATAACCTAAGAGATT
AGGTGTTCCCTTCGGGGACGCTGAGACAGGTGGTGCATGGCTGTCGTCAGCTCGTGTCGTCACATGTTGGGTTAAGTCCC
GCAACGAGCGCAACCCTTGTCATTAGTTGCCATCATTAAGTTGGGCACTCTAATGAGACTGCCGGTGACAAACCGGAGGA
AGGTGGGGATGACGTCAAGATCATCATGCCCCTTATGACCTGGGCTACACACGTGCTAGAATGGACGGTAGAACGAGATA
GCGAACCTGCGAAGAGCTAAGCGGATCTCTTAAAGCCGTTCTCAGTTCGGACTGTAGGCTGGAACTCGCGTACACGAAGC
TTGGAATCGCTAGTAATCGCGGATCAGCACTGCCGCGGTGAATACGTTCCCGGGCCTTGTACACACGGCCCGTCACACCA
TGAGAGTCTGTAACTCCCAAAGTCGGTGGGATAACCTTCTATAGCGAGTGAGTCCGTTCGATGGGTAGGGACAAGATGAA
TGAGCGGTGAAAGGTGGTTAAACCAAGGGTAGCAAGTAAGGATCCTTTTGGGGGTTTTATCTCCACGGGGGGGTGTTTC
TTTTCTGTCTTTA SEQ ID NO: 6
255 S10BL530 with 519R
ACTTTCTAGAGTTAGATGATACCGTTGAACATGACAGATGGCCACGTTTACTTACTCTCACTGACTACTGTTCTTTCATC
TCACACAACAGAGCTTTACGAGCCGAAACCCTTCTTCACTCACGCGGCGTTGCTCCATCAGAGCTTTGCGTCCCATTGTG
GAACATTCCCTACTGCTGCCTCCCGTAGGAGTATGGGCCGTGTCTCAGTCCCATTGTGGCCGATCAGTCTCTCAACTCGG
CTATGGATCATGGCCTTGGTAAGCCGTTACCTTACCAACTAGCTAATGCACCGCAGGTCCATCCAAGAGTGATAGCCGAA
CCATCTTTCACAACTCTAAACATGCTTGTAGTGTTGTTATTCCGGTATTAACATTCTGTTTCCAGGTTGTTATTCCCAGC
TGATCTCGGGGCAGGGTTTACCCCAACGTTGGTTTACCTTCACCCCCGGTTNCGGGCCGGCTTCGNCCTTGGGTTAGTAC
TNACGATTCTGCTATTATATACGATGGGCTAGACGACCAGCCTAACACAATTTCAATTTCGTNAAGTGTCGAGAGGNCCT
ACGGTCGTCCCGTTAACGTGTAGNCNATTTGGCTTATTTGTTAAGTTGTCCANCGGGCCACCGACCCCCAGGGCCCGGTT
GGTCCGGGTTTCCCCCATTGCAACGTCGCCAAAGTGCGGAAATTTCGAAAATACCCTTAACCAATGAAAAAAACATA SEQ ID NO: 7
258 S10BL414 with 926F
GGTGGAGCATGTGGTTTAATTCGAAGCTACGCGAAGAACCTTACCAGGTCTTGACATACTATGCAAATCTAAGAGATTAG
ACGTTCCCTTCGGGGACATGGATACAGGTGGTGCATGGTTGTCGTCAGCTCGTGTCGTGAGATGTTGGGGTTAAGTCCCT
CAACGAGCGCAACCCTTATTATCAGTTGCCAGCATTAAGTTGGGCACTCTGGTGAGACTGCCGGTGACAAACCGGAGGAA
GGTGGGGATGACGTCAAATCATCATGCCCCTTATGACCTGGGCTACACACGTGCTACAATGGATGGTACAACGAGTTGCG
AACTCGCGAGAGTAAGCTAATCTCTTAAAGCCATTCTCAGTTCGGATTGTAGGCTGCAACTCGCCTACATGAAGTCGGAA
TCGCTAGTAATCGCGGATCAGCATGCCGCGGTGAATACGTTCCCGGGCCTTGTACACACCGCCCGTCACACCATGAGAGT
TTGTAACACCCAAAGTCGGTGGGGTAACCTTTTTAGGAAACCAGCCCGCCCTAAAGGGTGGGGAACAAGAATGAATTAA
GGGGGTTGAAAAGTTCCGTTAAACCAAAAGGGGTTAGCCCCNGNTNNGANNNNNNNNNNGAC SEQ ID NO: 8
258 S10BL438 with 519R
GCTTTCTGGTTAAATACCGTCAATACCTGAACAGTTACTCTCAGATATGTGTCTTCTTTAACAACAGAGTTTTACGAGCC
GAAACCCTTCTTCACTCACGCGGCGTTGCTCCATCAGACTTTCGTCCATTGTGGAAGATTCCCTACTGCTGCCTCCCGTA
GGAGTTTGGGCCGTGTCTCAGTCCCAATGTGGCCGATTACCCTCTCAGGTCGGCTACGTATCATTGCCATGGTGAGCCGT
TACCCCACCATCTAGCTAATACGCCGCGGGACCATCCAAAAGTGATAGCCGAAGCCATCTTTCAAGCTCGGACCATGCGG
TCCAAGTTGTTATGCGGTATTAGCATCTGTTTCCAGGGTGTTATTCCCCCGCTTCGTGGGCAGGGTTTCCCACGTGTTAC
TCACCAGTTCGCCACTCACTCAAATGTAAATCATGATGCAAGCACCAATCAATACCAGAGTTCGTTCGACTTGCATGTAT
TAGGCACGCCGCCAGCGTTCGTCCTGAGCCATGATCAAACTCNGA NCIMB 41846 GGDK31 - *Lactobacillus reuteri*

SEQ ID NO: 10
S12KG200 GGDK 31-1 27F
TGCCTAATACATGCAAGTCGTACGCACTGGCCCAACTGATTGATGGTGCTTGCACCTGATTGACGATGGATCACCAGTGA
GTGGCGGACGGGTGAGTAACACGTAGGTAACCTGCCCCGGAGCGGGGGATAACATTTGGAAACAGATGCTAATACCGCAT

-continued

AACAACAAAAGCCACATGGCTTTTGTTTGAAAGATGGCTTTGGCTATCACTCTGGGATGGACCTGCGGTGCATTAGCTAG

TTGGTAAGGTAACGGCTTACCAAGGCGATGATGCATAGCCGAGTTGAGAGACTGATCGGCCACAATGGAACTGAGACACG

GTCCATACTCCTACGGGAGGCAGCAGTAGGGAATCTTCCACAATGGGCGCAAGCCTGATGGAGCAACACCGCGTGAGTGA

AGAAGGGTTTCGGCTCGTAAAGCTCTGTTGTTGGAGAAGAACGTGCGTGAGAGTAACTGTTCACGCAGTGACGGTATCCA

ACCAGAAAGTCACGGCTAACTACGTGCCAGCAGCCGCGGTAATACGTAGGTGGCAAGCGTTATCCGGATTTATTGGGCGT

AAAGCGAGCGCAGGCGGTTGCTTAGGTCTGATGTGAAAGCCTTCGGCTTAACCGAAGAAGTGCATCGGAAACCGGGCGAC

TTGAGTGCAGAAGAGGACAGTGGAACTC

SEQ ID NO: 11

S12KG201 GGDK 31-1 519F
TCGGATTTATTGGGCGTAAAGCGAGCGCAGGCGGTTGCTTAGGTCTGATGTGAAAGCCTTCGGCTTAACCGAAGAAGTGC

ATCGGAAACCGGGCGACTTGAGTGCAGAAGAGGACAGTGGAACTCCATGTGTAGCGGTGGAATGCGTAGATATATGGAAG

AACACCAGTGGCGAAGGCGGCTGTCTGGTCTGCAACTGACGCTGAGGCTCGAAAGCATGGGTAGCGAACAGGATTAGATA

CCCTGGTAGTCCATGCCGTAAACGATGAGTGCTAGGTGTTGGAGGGTTTCCGCCCTTCAGTGCCGGAGCTAACGCATTAA

GCACTCCGCCTGGGGAGTACGACCGCAAGGTTGAAACTCAAAGGAATTGACGGGGGCCCGCACAAGCGGTGGAGCATGTG

GTTTAATTCGAAGCTACGCGAAGAACCTTACCAGGTCTTGACATCTTGCGCTAACCTTAGAGATAAGGCGTTCCCTTCG

GGGACGCAATGACAGGTGGTGCATGGTCGTCGTCAGCTCGTGTCGTGAGATGTTGGGTTAAGTCCCGCAACGAGCGCAAC

CCTTGTTACTAGTTGCCAGCATTAAGTTGGGCACTCTAGTGAGACTGCCGGTGACAAACCGGAGGAAGGTGGGGACGACG

TCAGATCATCATGCCCCTTATGACCTGGGCTA

SEQ ID NO: 12

S12KG202 GGDK 31-1 926F
GAGCATGTGGTTTAATTCGAAGCTACGCGAAGAACCTTACCAGGTCTTGACATCTTGCGCTAACCTTAGAGATAAGGCGT

TCCCTTCGGGGACGCAATGACAGGTGGTGCATGGTCGTCGTCAGCTCGTGTCGTGAGATGTTGGGTTAAGTCCCGCAACG

AGCGCAACCCTTGTTACTAGTTGCCAGCATTAAGTTGGGCACTCTAGTGAGACTGCCGGTGACAAACCGGAGGAAGGTGG

GGACGACGTCAGATCATCATGCCCCTTATGACCTGGGCTACACACGTGCTACAATGGACGGTACAACGAGTCGCAAGCTC

GCGAGAGTAAGCTAATCACTTAAAGCCGTTCTCAGTTCGGACTGTAGGCTGCAACTCGCCTACACGAAGTCGGAATCGCT

AGTAATCGCGGATCAGCATGCCGCGGTGAATACGTTCCCGGGCCTTGTACACACCGCCCGTCACACCATGGGAGTTTGTA

ACGCCCAAAGTCGGTGGCCTAACCATTATGGAGGGAGCCGCCTAAGGCGGGACAGATGACTGGGGTGAAGTCGTAACAAG

GTAGCCGTA

SEQ ID NO: 13

S12KG203 GGDK 31-1 926R
CTCCCCAGGCGGAGTGCTTAATGCGTTAGCTCCGGCACTGAAGGGCGGAAACCCTCCAACACCTAGCACTCATCGTTTAC

GGCATGGACTACCAGGGTATCTAATCCTGTTCGCTACCCATGCTTTCGAGCCTCAGCGTCAGTTGCAGACCAGACAGCCG

CCTTCGCCACTGGTGTTCTTCCATATATCTACGCATTCCACCGCTACACATGGAGTTCCACTGTCCTCTTCTGCACTCAA

GTCGCCCGGTTTCCGATGCACTTCTTCGGTTAAGCCGAAGGCTTTCACATCAGACCTAAGCAACCGCCTGCGCTCGCTTT

ACGCCCAATAAATCCGGATAACGCTTGCCACCTACGTATTACCGCGGCTGCTGGCACGTAGTTAGCCGTGACTTTCTGGT

TGGATACCGTCACTGCGTGAACAGTTACTCTCACGCACGTTCTTCTCCAACAACAGAGCTTTACGAGCCGAAACCCTTCT

TCACTCACGCGGTGTTGCTCCATCAGGCTTGCGCCCATTGTGGAAGATTCCCTACTGCTGCCTCCCGTAGGAGTATGGAC

CGTGTCTCAGTTCCATTGTGGCCGATCAGTCTCTCAACTCGGCTATGCATCATCGCCTTGGTAAGCCGTTACCTTACCAA

CTAGCTAATGCACCGCAGGTCCATCCCAGAGTGATAGCCAAAGCCATCTTTCAAACAAAAGCCATGTGGCTTTTGTTGT

TATGC

SEQ ID NO: 14

S12KG204 GGDK 31-1 519R
TTTCTGGTTGGATACCGTCACTGCGTGAACAGTTACTCTCACGCACGTTCTTCTCCAACAACAGAGCTTTACGAGCCGAA

ACCCTTCTTCACTCACGCGGTGTTGCTCCATCAGGCTTGCGCCCATTGTGGAAGATTCCCTACTGCTGCCTCCCGTAGGA

-continued

GTATGGACCGTGTCTCAGTTCCATTGTGGCCGATCAGTCTCTCAACTCGGCTATGCATCATCGCCTTGGTAAGCCGTTAC

CTTACCAACTAGCTAATGCACCGCAGGTCCATCCCAGAGTGATAGCCAAAGCCATCTTTCAAACAAAAGCCATGTGGCTT

TTGTTGTTATGCGGTATTAGCATCTGTTTCCAAATGTTATCCCCCGCTCCGGGGCAGGTTACCTACGTGTTACTCACCCG

TCCGCCACTCACTGGTGATCCATCGTCAATCAGGTGCAAGCACCATCAATCAGTTGGGCCAGTGCGTACGACTTGCATGT

ATTAGGCACACCGCCGGCGTTCATCCTGAGCCATGATCAAAC

SEQ ID NO: 15

S12KG205 GGDK 31-1 RP2
CCGCCTTAGGCGGCTCCCTCCATAATGGTTAGGCCACCGACTTTGGGCGTTACAAACTCCCATGGTGTGACGGGCGGTGT

GTACAAGGCCCGGGAACGTATTCACCGCGGCATGCTGATCCGCGATTACTAGCGATTCCGACTTCGTGTAGGCGAGTTGC

AGCCTACAGTCCGAACTGAGAACGGCTTTAAGAGATTAGCTTACTCTCGCGAGCTTGCGACTCGTTGTACCGTCCATTGT

AGCACGTGTGTAGCCCAGGTCATAAGGGGCATGATGATCTGACGTCGTCCCCACCTTCCTCCGGTTTGTCACCGGCAGTC

TCACTAGAGTGCCCAACTTAATGCTGGCAACTAGTAACAAGGGTTGCGCTCGTTGCGGGACTTAACCCAACATCTCACGA

CACGAGCTGACGACGACCATGCACCACCTGTCATTGCGTCCCCGAAGGGAACGCCTTATCTCTAAGGTTAGCGCAAGATG

TCAAGACCTGGTAAGGTTCTTCGCGTAGCTTCGAATTAAACCACATGCTCCACCGCTTGTGCGGGCCCCCGTCAATTCCTTT

GAGTTTCCACCTTGCGGTCGTACTCCCCAGGCGGAGTGCTTAATGCGTTAGCTCCGGCACTGAAGGGCGGAAACCCT

CCAACACCTAGCACTCATCGTTTACGGCATGGACTACCAGGG

NCIMB 41847 GGDK161 - contains both Lactobacillus plantarum and Lactobacillus reuteri
Lactobacillus plantarum

SEQ ID NO: 16

S12KG218 GGDK 161-1 27F
GTGCCTAATACATGCAAGTCGAACGAACTCTGGTATTGATTGGTGCTTGCATCATGATTTACATTTGAGTGAGTGGCGAA

CTGGTGAGTAACACGTGGGAAACCTGCCCAGAAGCGGGGGATAACACCTGGAAACAGATGCTAATACCGCATAACAACTT

GGACCGCATGGTCCGAGTTTGAAAGATGGCTTCGGCTATCACTTTTGGATGGTCCCGCGGCGTATTAGCTAGATGGTGAG

GTAACGGCTCACCATGGCAATGATACGTAGCCGACCTGAGAGGGTAATCGGCCACATTGGGACTGAGACACGGCCCAAAC

TCCTACGGGAGGCAGCAGTAGGGAATCTTCCACAATGGACGAAAGTCTGATGGAGCAACGCCGCGTGAGTGAAGAAGGGT

TTCGGCTCGTAAAACTCTGTTGTTAAAGAAGAACATATCTGAGAGTAACTGTTCAGGTATTGACGGTATTTAACCAGAA

AGCCACGGCTAACTACGTGCCAGCAGCCGCGGTAATACGTAGGTGGCAAGCGTTGTCCGGATTTATTGGGCGTAAAGCGA

GCGCAGGCGGTTTTTTAAGTCTGATGTGAAAGCCTTCGGCTCAACCGAAGAAGTGCATCGGAAACTGGGAAGCTTGAGTG

CAGAAGAGGACAGTGGAACTCCATGTGTAGCGGTGAAATGCGT

SEQ ID NO: 17

S12KG219 GGDK 161-1 519F
CGGATTTATTGGGCGTAAAGCGAGCGCAGGCGGTTTTTTAAGTCTGATGTGAAAGCCTTCGGCTCAACCGAAGAAGTGC

ATCGGAAACTGGGAAACTTGAGTGCAGAAGAGGACAGTGGAACTCCATGTGTAGCGGTGAAATGCGTAGATATATGGAAG

AACACCAGTGGCGAAGGCGGCTGTCTGGTCTGTAACTGACGCTGAGGCTCGAAAGTATGGGTAGCAAACAGGATTAGATA

CCCTGGTAGTCCATACCGTAAACGATGAATGCTAAGTGTTGGAGGGTTTCCGCCCTTCAGTGCTGCAGCTAACGCATTAA

GCATTCCGCCTGGGGAGTACGGCCGCAAGGCTGAAACTCAAAGGAATTGACGGGGGCCCGCACAAGCGGTGGAGCATGTG

GTTTAATTCGAAGCTACGCGAAGAACCTTACCAGGTCTTGACATACTATGCAAATCTAAGAGATTAGACGTTCCCTTCGG

GGACATGGATACAGGTGGTGCATGGTTGTCGTCAGCTCGTGTCGTGAGATGTTGGGTTAAGTCCCGCAACGAGCGCAACC

CTTATTATCAGTTGCCAGCATTAAGTTGGGCACTCTGGTGAGACTGCCGGTGACAAACCGGA

SEQ ID NO: 18

S12K5220 GGDK 161-1 926F
TGGAGCATGTGGTTTAATTCGAAGCTACGCGAAGAACCTTACCAGGTCTTGACATACTATGCAAATCTAAGAGATTAGAC

GTTCCCTTCGGGACATGGATACAGGTGGTGCATGGTTGTCGTCAGCTCGTGTCGTGAGATGTTGGGTTAAGTCCCGCAA

CGAGCGCAACCCTTATTATCAGTTGCCAGCATTAAGTTGGGCACTCTGGTGAGACTGCCGGTGACAAACCGGAGGAAGGT

GGGGATGACGTCAAATCATCATGCCCCTTATGACCTGGGCTACACACGTGCTACAATGGATGGTACAACGAGTTGCGAAC

TCGCGAGAGTAAGCTAATCTCTTAAAGCCATTCTCAGTTCGGATTGTAGGCTGCAACTCGCCTACATGAAGTCGGAATCG

-continued

CTAGTAATCGCGGATCAGCATGCCGCGGTGAATACGTTCCCGGGCCTTGTACACACCGCCCGTCACACCATGAGAGTTTG

TAACACCCAAAGTCGGTGGGGTAACCTTTTAGGAACCAGCCGCCTAAGGTGGGACAGATGATTAGGGTGAAGTCGTAAC

AAGGTAGCCCGTA

SEQ ID NO: 19

S12KG221 GGDK 161-1 926R
ACTCCCCAGGCGGAATGCTTAATGCGTTAGCTGCAGCACTGAAGGGCGGAAACCCTCCAACACTTAGCATTCATCGTTTA

CGGTATGGACTACCAGGGTATCTAATCCTGTTTGCTACCCATACTTTCGAGCCTCAGCGTCAGTTACAGACCAGACAGCC

GCCTTCGCCACTGGTGTTCTTCCATATATCTACGCATTTCACCGCTACACATGGAGTTCCACTGTCCTCTTCTGCACTCA

AGTTTCCCAGTTTCCGATGCACTTCTTCGGTTGAGCCGAAGGCTTTCACATCAGACTTAAAAAACCGCCTGCGCTCGCTT

TACGCCCAATAAATCCGGACAACGCTTGCCACCTACGTATTACCGCGGCTGCTGGCACGTAGTTAGCCGTGGCTTTCTGG

TTAAATACCGTCAATACCTGAACAGTTACTCTCAGATATGTTCTTCTTTAACAACAGAGTTTTACGAGCCGAAACCCTTC

TTCACTCACGCGGCGTTGCTCCATCAGACTTTCGTCCATTGTGGAAGATTCCCTACTGCTGCCTCCCGTAGGAGTTTGGG

CCGTGTCTCAGTCCCAATGTGGCCGATTACCCTCTCAGGTCGGCTACGTATCATTGCCATGGTGAGCCGTTACCCCACCA

TCTAGCTAATACGCCGCGGGACCATCCAAAAGTGATAGCCGAAGCCATCTTTCAAACTCGGACCATGCGGTCCAAGTTG

T

SEQ ID NO: 20

S12KG222 GGDK 161-1 519R
GCTTTCTGGTTAAATACCGTCAATACCTGAACAGTTACTCTCAGATATGTTCTTCTTTAACAACAGAGTTTTACGAGCCG

AAACCCTTCTTCACTCACGCGGCGTTGCTCCATCAGACTTTCGTCCATTGTGGAAGATTCCCTACTGCTGCCTCCCGTAG

GAGTTTGGGCCGTGTCTCAGTCCCAATGTGGCCGATTACCCTCTCAGGTCGGCTACGTATCATTGCCATGGTGAGCCGTT

ACCCCACCATCTAGCTAATACGCCGCGGGACCATCCAAAAGTGATAGCCGAAGCCATCTTTCAAACTCGGACCATGCGGT

CCAAGTTGTTATGCGGTATTAGCATCTGTTTCCAGGTGTTATCCCCCGCTTCTGGGCAGGTTTCCCACGTGTTACTCAC

CAGTTCGCCACTCACTCAAATGTAAATCATGATGCAAGCACCAATCAATACCAAAGTTCGTTCGACTTGCATGTATTAG

GCACGCCGCCAGCGTTCGTCCTGAGCCAGATCAAACTCTAA

SEQ ID NO: 21

S12KG223 GGDK 161-1 RP2
CCACCTTAGGCGGCTGGTTCCTAAAAGGTTACCCCACCGACTTTGGGTGTTACAAACTCTCATGGTGTGACGGGCGGTGT

GTACAAGGCCCGGGAACGTATTCACCGCGGCATGCTGATCCGCGATTACTAGCGATTCCGACTTCATGTAGGCGAGTTGC

AGCCTACAATCCGAACTGAGAATGGCTTTAAGAGATTAGCTTACTCTCGCGAGTTCGCAACTCGTTGTACCATCCATTGT

AGCACGTGTGTAGCCCAGGTCATAAGGGGCATGATGATTTGACGTCATCCCCACCTTCCTCCGGTTTGTCACCGGCAGTC

TCACCAGAGTGCCCAACTTAATGCTGGCAACTGATAATAAGGGTTGCGCTCGTTGCGGGACTTAACCCAACATCTCACGA

CACGAGCTGACGACAACCATGCACCACCTGTATCCATGTCCCCGAAGGGAACGTCTAATCTCTTAGATTTGCATAGTATG

TCAAGACCTGGTAAGGTTCTTCGCGTAGCTTCGAATTAAACCACATGCTCCACCGCTTGTGCGGGCCCCCGTCAATTCCT

TTGAGTTTCAGCCTTGCGGCCGTACTCCCCAGGCGGAATGCTTAATGCGTTAGCTGCAGCACTGAAGGGCGGAAACCCTC

CAACACTTAGCATTCATCGTTTACGGTATGGACTACCAGGGTATCTA

NCIMB 41847 GGDK161 - contains both *Lactobacillus plantarum* and *Lactobacillus reuteri*
*Lactobacillus reuteri*

SEQ ID NO: 22

S12KG309 cGGDK 161-1 27F
ATGCTAGTCGTACGCACTGGCCCAACTGATTGATGGTGCTTGCACCTGATTGACGAT

GGATCACCAGTGAGTGGCGGACGGGTGAGTAACACGTAGGTAACCTGCCCCGGAGCGGGGGATAACATTTGGAAACAGAT

GCTAATACCGCATAACAACAAAAGCCACATGGCTTTTGTTTGAAAGATGGCTTTGGCTATCACTCTGGGATGGACCTGCG

GTGCATTAGCTAGTTGGTAAGGTAACGGCTTACCAAGGCGATGATGCATAGCCGAGTTGAGAGACTGATCGGCCACAATG

GAACTGAGACACGGTCCATACTCCTACGGGAGGCAGCAGTAGGGAATCTTCCACAATGGGCGCAAGCCTGATGGAGCAAC

ACCGCGTGAGTGAAGAAGGGTTTCGGCTCGTAAAGCTCTGTTGTTGGAGAAGAACGTGCGTGAGAGTAACTGTTCACGCA

```
                                                              -continued
GTGACGGTATCCAACCAGAAAGTCACGGCTAACTACGTGCCAGCAGCCGCGGTAATACGTAGGTGGCAAGCGTTATCCGG

ATTTATTGGGCGTAAAGCGAGCGCAGGCGGTTGCTTAGGTCTGATGTGAAAGCCTTCGGCTTAACCGAAGAAGTGCATCG

GAAACCGGGCGACTTGAGTGCAGAAGAGGACAGTGGAAC

SEQ ID NO: 23
S12KG310 cGGDK 161-1 519F
TCCGGATTTATTGGGCGTAAAGCGAGCGCAGGCGGTTGCTTAGGTCTGATGTGAAAGCCTTCGGCTTAACCGAAGAAGTG

CATCGGAAACCGGGCGACTTGAGTGCAGAAGAGGACAGTGGAACTCCATGTGTAGCGGTGGAATGCGTAGATATATGGAA

GAACACCAGTGGCGAAGGCGGCTGTCTGGTCTGCAACTGACGCTGAGGCTCGAAAGCATGGGTAGCGAACAGGATTAGAT

ACCCTGGTAGTCCATGCCGTAAACGATGAGTGCTAGGTGTTGGAGGGTTTCCGCCCTTCAGTGCCGGAGCTAACGCATTA

AGCACTCCGCCTGGGGAGTACGACCGCAAGGTTGAAACTCAAAGGAATTGACGGGGGCCCGCACAAGCGGTGGAGCATGT

GGTTTAATTCGAAGCTACGCGAAGAACCTTACCAGGTCTTGACATCTTGCGCTAACCTTAGAGATAAGGCGTTCCCTTCG

GGGACGCAATGACAGGTGGTGCATGGTCGTCGTCAGCTCGTGTCGTGAGATGTTGGGTTAAGTCCCGCAACGAGCGCAAC

CCTTGTTACTAGTTGCCAGCATTAAGTTGGGCACTCTAGTGAGACTGCCGGTGACAAACCGGAGGAAGGTGGGGACGACG

TCAGATCATCATGCCCCTTATGACCTGGGCTACACACGTGCTACAATGGACGGTACAACGAGTCGCAAGCTCGCGAGAG

SEQ ID NO: 24
S12KG311 cGGDK 161-1 926F
GGAGCATGTGGTTTAATTCGAAGCTACGCGAAGAACCTTACCAGGTCTTGACATCTTGCGCTAACCTTAGAGATAAGGCG

TTCCCTTCGGGGACGCAATGACAGGTGGTGCATGGTCGTCGTCAGCTCGTGTCGTGAGATGTTGGGTTAAGTCCCGCAAC

GAGCGCAACCCTTGTTACTAGTTGCCAGCATTAAGTTGGGCACTCTAGTGAGACTGCCGGTGACAAACCGGAGGAAGGTG

GGGACGACGTCAGATCATCATGCCCCTTATGACCTGGGCTACACACGTGCTACAATGGACGGTACAACGAGTCGCAAGCT

CGCGAGAGTAAGCTAATCTCTTAAAGCCGTTCTCAGTTCGGACTGTAGGCTGCAACTCGCCTACACGAAGTCGGAATCGC

TAGTAATCGCGGATCAGCATGCCGCGGTGAATACGTTCCCGGGCCTTGTACACACCGCCCGTCACACCATGGGAGTTTGT

AACGCCCAAAGTCGGTGGCCTAACCTTTATGGAGGGAGCCGCCTAAGGCGGGACAGATGACTGGGGTGAAGTCGTAACAA

GGTAGCCGTA

SEQ ID NO: 25
S12KG312 cGGDK 161-1 926R
TCCCCAGGCGGAGTGCTTAATGCGTTAGCTCCGGCACTGAAGGGCGGAAACCCTCCAACACCTAGCACTCATCGTTTACG

GCATGGACTACCAGGGTATCTAATCCTGTTCGCTACCCATGCTTTCGAGCCTCAGCGTCAGTTGCAGACCAGACAGCCGC

CTTCGCCACTGGTGTTCTTCCATATATCTACGCATTCCACCGCTACACATGGAGTTCCACTGTCCTCTTCTGCACTCAAG

TCGCCCGGTTTCCGATGCACTTCTTCGGTTAAGCCGAAGGCTTTCACATCAGACCTAAGCAACCGCCTGCGCTCGCTTTA

CGCCCAATAAATCCGGATAACGCTTGCCACCTACGTATTACCGCGGCTGCTGGCACGTAGTTAGCCGTGACTTTCTGGTT

GGATACCGTCACTGCGTGAACAGTTACTCTCACGCACGTTCTTCTCCAACAACAGAGCTTTACGAGCCGAAACCCTTCTT

CACTCACGCGGTGTTGCTCCATCAGGCTTGCGCCCATTGTGGAAGATTCCCTACTGCTGCCTCCCGTAGGAGTATGGACC

GTGTCTCAGTTCCATTGTGGCCGATCAGTCTCTCAACTCGGCTATGCATCATCGCCTTGGTAAGCCGTTACCTTACCAAC

TAGCTAATGCACCGCAGGTCCATCCCAGAGTGATAGCCAAAGCCATCTTTCAAACAAAAGCCATGTGGCTTTT

SEQ ID NO: 26
S12KG313 cGGDK 161-1 519R
TTTCTGGTTGGATACCGTCACTGCGTGAACAGTTACTCTCACGCACGTTCTTCTCCAACAACAGAGCTTTACGAGCCGAA

ACCCTTCTTCACTCACGCGGTGTTGCTCCATCAGGCTTGCGCCCATTGTGGAAGATTCCCTACTGCTGCCTCCCGTAGGA

GTATGGACCGTGTCTCAGTTCCATTGTGGCCGATCAGTCTCTCAACTCGGCTATGCATCATCGCCTTGGTAAGCCGTTAC

CTTACCAACTAGCTAATGCACCGCAGGTCCATCCCAGAGTGATAGCCAAAGCCATCTTTCAAACAAAAGCCATGTGGCTT

TTGTTGTTATGCGGTATTAGCATCTGTTTCCAAATGTTATCCCCCGCTCCGGGGCAGGTTACCTACGTGTTACTCACCCG

TCCGCCACTCACTGGTAATCCATCGTCAATCAGGTGCAAGCACCATCAATCAGTTGGGCCAGTGCGTACGACTTGCATG

TATTAGGCACACCGCCGGCGTTCATCCTGAGCCATGATCAAAC
```

SEQ ID NO: 27

S12KG314 cGGDK 161-1 RP2
GCGGCTCCCTCCATAAAGGTTAGCGCCACCGACTTTGGGCGTTACAAACTCCCATGGTGTGACGGGCG
GTGTGTACAAGGCCCGGGAACGTATTCACCGCGGCATGCTGATCCGCGATTACTAGCGATTCCGACTTCGTGTAGGCGAG
TTGCAGCCTACAGTCCGAACTGAGAACGGCTTTAAGAGATTAGCTTACTCTCGCGAGCTTGCGACTCGTTGTACCGTCCA
TTGTAGCACGTGTGTAGCCCAGGTCATAAGGGGCATGATGATCTGACGTCGTCCCCACCTTCCTCCGGTTTGTCACCGGC
AGTCTCACTAGAGTGCCCAACTTAATGCTGGCAACTAGTAACAAGGGTTGCGCTCGTTGCGGGACTTAACCCAACATCTC
ACGACACGAGCTGACGACGACCATGCACCACCTGTCATTGCGTCCCCGAAGGGAACGCCTTATCTCTAAGGTTAGCGCAA
GATGTCAAGACCTGGTAAGGTTCTTCGCGTAGCTTCGAATTAAACCACATGCTCCACCGCTTGTGCGGGCCCCCGTCA
ATTCCTTTGAGTTTCAACCTTGCGGTCGTACTCCCCAGGCGGAGTGCTTAATGCGTTAGCTCCGGCACTGAAGGGCGGAA
ACCCTCCAACACCTAGCACTCATCGTTTACGGCAT

NCIMB 41848 GGDK255 - *Lactobacillus reuteri*

SEQ ID NO: 28

S12KG237 GGDK 255-1 27F
GTGTGCCTAATACATGCAAGTCGTACGCACTGGCCCAACTGATTGATGGTGCTTGCACCTGATTGACGATGGATCACCAG
TGAGTGGCGGACGGGTGAGTAACACGTAGGTAACCTGCCCCGGAGCGGGGGATAACATTTGGAAACAGATGCTAATACCG
CATAACAACAAAAGCCACATGCTTTTGTTTGAAAGATGGCTTTGGCTATCACTCTGGGATGGACCTGCGGTGCATTAGC
TAGTTGGTAAGGTAACGGCTTACCAAGGCGATGATGCATAGCCGAGTTGAGAGACTGATCGGCCACAATGGAACTGAGAC
ACGGTCCATACTCCTACGGGAGGCAGCAGTAGGGAATCTTCCACAATGGGCGCAAGCCTGATGGAGCAACACCGCGTGAG
TGAAGAAGGGTTTCGGCTCGTAAAGCTCTGTTGTTGGAGAAGAACGTGCGTGAGAGTAACTGTTCACGCAGTGACGGTAT
CCAACCAGAAAGTCACGGCTAACTACGTGCCAGCAGCCGCGGTAATACGTAGGTGGCAAGCGTTATCCGGATTTATTGGG
CGTAAAGCGAGCGCAGGCGGTTGCTTAGGTCTGATGTGAAAGCCTTCGGCTTAACCGAAGAAGTGCATCGGAAACCGGGC
GACTTGAGTGCAGAAGAGGACAGTGGAACTCCATGTGTAGCGGTGGAATGCGTAGATATATGGAAGAACACCAGTG

SEQ ID NO: 29

S12KG238 GGDK 255-1 519F
TCGGATTTATTGGGCGTAAAGCGAGCGCAGGCGGTTGCTAGGTCTGATGTGAAAGCCTTCGGCTTAACCGAAGAAGTGC
ATCGGAAACCGGGCGACTTGAGTGCAGAAGAGGACAGTGGAACTCCATGTGTAGCGGTGGAATGCGTAGATATATGGAAG
AACACCAGTGGCGAAGGCGGCTGTCTGGTCTGCAACTGACGCTGAGGCTCGAAAGCATGGGTAGCGAACAGGATTAGATA
CCCTGGTAGTCCATGCCGTAAACGATGAGTGCTAGGTGTTGGAGGGTTTCCGCCCTTCAGTGCCGGAGCTAACGCATTAA
GCACTCCGCCTGGGGAGTACGACCGCAAGGTTGAAACTCAAAGGAATTGACGGGGGCCCGCACAAGCGGTGGAGCATGTG
GTTTAATTCGAAGCTACGCGAAGAACCTTACCAGGTCTTGACATCTTGCGCTAACCTTAGAGATAAGGCGTTCCCTTCGG
GGACGCAATGACAGGTGGTGCATGGTCGTCGTCAGCTCGTGTCGTGAGATGTTGGGTTAAGTCCCGCAACGAGCGCAACC
CTTGTTACTAGTTGCCAGCATTAAGTTGGGCACTCTAGTGAGACTGCCGGTGACAAACCGGAGGAAGGTGGGGACGACG
TCAGATCATCATGCCCCTTATGACCTGGGCTACACACGTGCTAC

SEQ ID NO: 30

S12KG239 GGDK 255-1 926F
TGGAGCATGTGGTTTAATTCGAAGCTACGCGAAGAACCTTACCAGGTCTTGACATCTTGCGCTAACCTTAGAGATAAGGC
GTTCCCTTCGGGGACGCAATGACAGGTGGTGCATGGTCGTCGTCAGCTCGTGTCGTGAGATGTTGGGTTAAGTCCCGCAA
CGAGCGCAACCCTTGTTACTAGTTGCCAGCATTAAGTTGGGCACTCTAGTGAGACTGCCGGTGACAAACCGGAGGAAGGT
GGGGACGACGTCAGATCATCATGCCCCTTATGACCTGGGCTACACACGTGCTACAATGGACGGTACAACGAGTCGCAAGC
TCGCGAGAGTAAGCTAATCTCTTAAAGCCGTTCTCAGTTCGGACTGTAGGCTGCAACTCGCCTACACGAAGTCGGAATCG
CTAGTAATCGCGGATCAGCATGCCGCGGTGAATACGTTCCCGGGCCTTGTACACACCGCCCGTCACACCATGGGAGTTTG
TAACGCCCAAAGTCGGTGGCCTAACCTTTATGGAGGGAGCCGCCTAAGGCGGGACAGATGACTGGGGTGAAGTCGTAACA
AGGTAGCCGTA

SEQ ID NO: 31

S12KG240 GGDK 255-1 926R
TACTCCCCAGGCGGAGTGCTTAATGCGTTAGCTCCGGCACTGAAGGGCGGAAACCCTCCAACACCTAGCACTCATCGTTT

ACGGCATGGACTACCAGGGTATCTAATCCTGTTCGCTACCCATGCTTTCGAGCCTCAGCGTCAGTTGCAGACCAGACAGC

CGCCTTCGCCACTGGTGTTCTTCCATATATCTACGCATTCCACCGCTACACATGGAGTTCCACTGTCCTCTTCTGCACTC

AAGTCGCCCGGTTTCCGATGCACTTCTTCGGTTAAGCCGAAGGCTTTCACATCAGACCTAAGCAACCGCCTGCGCTCGCT

TTACGCCCAATAAATCCGGATAACGCTTGCCACCTACGTATTACCGCGGCTGCTGGCACGTAGTTAGCCGTGACTTTCTG

GTTGGATACCGTCACTGCGTGAACAGTTACTCTCACGCACGTTCTTCTCCAACAACAGAGCTTTACGAGCCGAAACCCTT

CTTCACTCACGCGGTGTTGCTCCATCAGGCTTGCGCCCATTGTGGAAGATTCCCTACTGCTGCCTCCCGTAGGAGTATGG

ACCGTGTCTCAGTTCCATTGTGGCCGATCAGTCTCTCAACTCGGCTATGCATCATCGCCTTGGTAAGCCGTTACCTTACC

AACTAGCTAATGCACCGCAGGTCCATCCCAGAGTGATAGCCAAAGCCATCTTTCAAACAAAAGCCATGTGGCTTTTG

SEQ ID NO: 32

S12KG241 GGDK 255-1 519R
TTTCTGGTTGGATACCGTCACTGCGTGAACAGTTACTCTCACGCACGTTCTTCTCCAACAACAGAGCTTTACGAGCCGAA

ACCCTTCTTCACTCACGCGGTGTTGCTCCATCAGGCTTGCGCCCATTGTGGAAGATTCCCTACTGCTGCCTCCCGTAGGA

GTATGGACCGTGTCTCAGTTCCATTGTGGCCGATCAGTCTCTCAACTCGGCTATGCATCATCGCCTTGGTAAGCCGTTAC

CTTACCAACTAGCTAATGCACCGCAGGTCCATCCCAGAGTGATAGCCAAAGCCATCTTTCAAACAAAAGCCATGTGGCT

TTTGTTGTTATGCGGTATTAGCATCTGTTTCCAAATGTTATCCCCGCTCCGGGCAGGTTACCTACGTGTTACTCACC

CGTCCGCCACTCACTGGTGATCCATCGTCAATCAGGTGCAAGCACCATCAATCAGTTGGGCCAGTGCGTACGACTTGCAT

GTATTAGGCACACCGCCGGCGTCCATCCTGAGCCATGATCAAAC

SEQ ID NO: 33

S12KG242 GGDK 255-1 RP2
CCGCCTTAGGCGGCTCCCTCCATAAAGGTTAGGCCACCGACTTTGGGCGTTACAAACTCCCATGGTGTGACGGGCGGTGT

GTACAAGGCCCGGGAACGTATTCACCGCGGCATGCTGATCCGCGATTACTAGCGATTCCGACTTCGTGTAGGCGAGTTGC

AGCCTACAGTCCGAACTGAGAACGGLTTTAAGAGATTAGCTTACTCTCGCGAGCTTGCGACTCGTTGTACCGTCCATTGT

AGCACGTGTGTAGCCCAGGTCATAAGGGGCATGATGATCTGACGTCGTCCCCACCTTCCTCCGGTTTGTCACCGGCAGTC

TCACTAGAGTGCCCAACTTAATGCTGGCAACTAGTAACAAGGGTTGCGCTCGTTGCGGGACTTAACCCAACATCTCACGA

CACGAGCTGACGACGACCATGCACCACCTGTCATTGCGTCCCCGAAGGGAACGCCTTATCTCTAAGGTTAGCGCAAGATG

TCAAGACCTGGTAAGGTTCTTCGCGTAGCTTCGAATTAAACCACATGCTCCACCGCTTGTGCGGGCCCCCGTCAATTCCT

TTGAGTTTCAACCTTGCGGTCGTACTCCCCAGGCGGAGTGCTTAATGCGTTAGCTCCGGCACTGAAGGGCGGAAACCCTCCAA

CACCTAGCACTCATCGTT

NCIMB 41849 GGDK 258 - *Lactobacillus plantarum*

SEQ ID NO: 34

S12KG267 GGDK 258-3 27F
GTGCCTAATACATGCAAGTCGAACGAACTCTGGTATTGATTGGTGCTTGCATCATGATTTACATTTGAGTGAGTGGCGAA

CTGGTGAGTAACACGTGGGAAACCTGCCCAGAAGCGGGGGATAACACCTGGAAACAGATGCTAATACCGCATAACAACTT

GGACCGCATGGTCCGAGTTTGAAAGATGGCTTCGGCTATCACTTTTGGATGGTCCCGCGGCGTATTAGCTAGATGGTGAG

GTAACGGCTCACCATGGCAATGATACGTAGCCGACCTGAGAGGGTAATCGGCCACATTGGGACTGAGACACGGCCCAAAC

TCCTACGGGAGGCAGCAGTAGGGAATCTTCCACAATGGACGAAAGTCTGATGGAGCAACGCCGCGTGAGTGAAGAAGGGT

TTCGGCTCGTAAAACTCTGTTGTTAAAGAAGAACATATCTGAGAGTAACTGTTCAGGTATTGACGGTATTTAACCAGAAA

GCCACGGCTAACTACGTGCCAGCAGCCGCGGTAATACGTAGGTGGCAAGCGTTGTCCGGATTTATTGGGCGTAAAGCGAG

CGCAGGCGGTTTTTTAAGTCTGATGTGAAAGCCTTCGGCTCAACCGAAGAAGTGCATCGGAAACTGGGAAACTTGAGTGC

AGAAGAGGACAGTGGAACTC

SEQ ID NO: 35

S12KG268 GGDK 258-3 519F
GGATTTATTGGGCGTAAAGCGAGCGCAGGCGGTTTTTTAAGTCTGATGTGAAAGCCTTCGGCTCAACCGAAGAAGTGCAT

CGGAAACTGGGAAACTTGAGTGCAGAAGAGGACAGTGGAACTCCATGTGTAGCGGTGAAATGCGTAGATATATGGAAGAA

CACCAGTGGCGAAGGCGGCTGTCTGGTCTGTAACTGACGCTGAGGCTCGAAAGTATGGGTAGCAAACAGGATTAGATACC

CTGGTAGTCCATACCGTAAACGATGAATGCTAAGTGTTGGAGGGTTTCCGCCCTTCAGTGCTGCAGCTAACGCATTAAGC

ATTCCGCCTGGGGAGTACGGCCGCAAGGCTGAAACTCAAAGGAATTGACGGGGGCCCGCACAAGCGGTGGAGCATGTGGT

TTAATTCGAAGCTACGCGAAGAACCTTACCAGGTCTTGACATACTATGCAAATCTAAGAGATTAGACGTTCCCTTCGGGG

ACATGGATACAGGTGGTGCATGGTTGTCGTCAGCTCGTGTCGTGAGATGTTGGGTTAAGTCCCGCAACGAGCGCAACCCT

TATTATCAGTTGCCAGCATTAAGTTGGGCACTCTGGTGAGACTGCCGGTGACAAACCGGAGGAAGGTGGGGATGACGTCA

AATCATCATGCCCCTTATGACCTGGGCTAC

SEQ ID NO: 36

S12KG269 GGDK 258-3 926F
GTGGAGCATGTGGTTTAATTCGAAGCTACGCGAAGAACCTTACCAGGTCTTGACATACTATGCAAATCTAAGAGATTAGA

CGTTCCCTTCGGGGACATGGATACAGGTGGTGCATGGTTGTCGTCAGCTCGTGTCGTGAGATGTTGGGTTAAGTCCCGCA

ACGAGCGCAACCCTTATTATCAGTTGCCAGCATTAAGTTGGGCACTCTGGTGAGACTGCCGGTGACAAACCGGAGGAAGG

TGGGGATGACGTCAAATCATCATGCCCCTTATGACCTGGGCTACACACGTGCTACAATGGATGGTACAACGAGTTGCGAA

CTCGCGAGAGTAAGCTAATCTCTTAAAGCCATTCTCAGTTCGGATTGTAGGCTGCAACTCGCCTACATGAAGTCGGAATC

GCTAGTAATCGCGGATCAGCATGCCGCGGTGAATACGTTCCCGGGCCTTGTACACACCGCCCGTCACACCATGAGAGTTT

GTAACACCCAAAGTCGGTGGGGTAACCTTTTAGGAACCAGCCGCCTAAGGTGGGACAGATGATTAGGGTGAAGTCGTAA

CAAGGTAGCCCGTA

SEQ ID NO: 37

S12KG270 GGDK 258-3 926R
ACTCCCCAGGCGGAATGCTTAATGCGTTAGCTGCAGCACTGAAGGGCGGAAACCCTCCAACACTTAGCATTCATCGTTTA

CGGTATGGACTACCAGGGTATCTAATCCTGTTTGCTACCCATACTTTCGAGCCTCAGCGTCAGTTACAGACCAGACAGCC

GCCTTCGCCACTGGTGTTCTTCCATATATCTACGCATTTCACCGCTACACATGGAGTTCCACTGTCCTCTTCTGCACTCA

AGTTTCCCAGTTTCCGATGCACTTCTTCGGTTGAGCCGAAGGCTTTCACATCAGACTTAAAAAACCGCCTGCGCTCGCTT

TACGCCCAATAAATCCGGACAACGCTTGCCACCTACGTATTACCGCGGCTGCTGGCACGTAGTTAGCCGTGGCTTTCTGG

TTAAATACCGTCAATACCTGAACAGTTACTCTCAGATATGTTCTTCTTTAACAACAGAGTTTTACGAGCCGAAACCCTTC

TTCACTCACGCGGCGTTGCTCCATCAGACTTTCGTCCATTGTGGAAGATTCCCTACTGCTGCCTCCCGTAGGAGTTTGGG

CCGTGTCTCAGTCCCAATGTGGCCGATTACCCTCTCAGGTCGGCTACGTATCATTGCCATGGTGAGCCGTTACCTCACCA

TCTAGCTAATACGCCGCGGGACCATCCAAAAGTGATAGCCGAAGCCATCTTTCAAACTCGGACCATGCGGTCCAAGTTG

TTATGCGGTATTAGCATCTGTTTC

SEQ ID NO: 38

S12KG271 GGDK 258-3 519R
TTTCTGGTTAAATACCGTCAATACCTGAACAGTTACTCTCAGATATGTTCTTCTTTAACAACAGAGTTTTACGAGCCGAA

ACCCTTCTTCACTCACGCGGCGTTGCTCCATCAGACTT1CGTCCATTGTGGAAGATTCCCTACTGCTGCCTCCCGTAGGA

GTTTGGGCCGTGTCTCAGTCCCAATGTGGCCGATTACCCTCTCAGGTCGGCTACGTATCATTGCCATGGTGAGCCGTTAC

CTCACCATCTAGCTAATACGCCGCGGGACCATCCAAAAGTGATAGCCGAAGCCATCTTTCAAACTCGGACCATGCGGTCC

AAGTTGTTATGCGGTATTAGCATCTGTTTCCAGGTGTTATCCCCGCTTCTGGGCAGGTTTCCCACGTGTTACTCACCAG

TTCGCCACTCACTCAAATGTAAATCATGATGCAAGCACCAATCAATACCAGAGTTCGTTCGACTTGCATGTATTAGGCAC

GCCGCCAGCGTTCGTCCTGAGCCATGATCAAAC

SEQ ID NO: 39

S12KG272 GGDK 258-3 RP2
CCACCTTAGGCGGCTGGTTCCTAAAAGGTTACCCCACCGACTTTGGGTGTTACAAACTCTCATGGTGTGACGGGCGGTGT

GTACAAGGCCCGGGAACGTATTCACCGCGGCATGCTGATCCGCGATTACTAGCGATTCCGACTTCATGTAGGCGAGTTGC

AGCCTACAATCCGAACTGAGAATGGCTTTAAGAGATTAGCTTACTCTCGCGAGTTCGCAACTCGTTGTACCATCCATTGT

AGCACGTGTGTAGCCCAGGTCATAAGGGGCATGATGATTTGACGTCATCCCCACCTTCCTCCGGTTTGTCACCGGCAGTC

TCACCAGAGTGCCCAACTTAATGCTGGCAACTGATAATAAGGGTTGCGCTCGTTGCGGGACTTAACCCAACATCTCACGA

CACGAGCTGACGACAACCATGCACCACCTGTATCCATGTCCCCGAAGGGAACGTCTAATCTCTTAGATTTGCATAGTATG

TCAAGACCTGGTAAGG1TCTTCGCGTAGCTTCGAATTAAACCACATGCTCCACCGCTTGTGCGGGCCCCCGTCAATTCCT

TTGAGTTTCAGCCTTGCGGCCGTACTCCCCAGGCGGAATGCTTAATGCGTTAGCTGCAGCACTGAAGGGCGGAAACCCTC

CAACACTTAGCATTCATCGTTTACGGTATGGACTACCAGGGTATCTAATCCTGTTTGCTACCCATACTTTCGAGCCTCAGC

GTCAGTTACAGACCAGACAGCCGCCT

NCIMB 41850 GGDK 266 - contains both *Lactobacillus johnsonii* and *Lactobacillus reuteri*
*Lactobacillus johnsonii*

SEQ ID NO: 40

512KG273 GGDK 266-1 27F - repeat
GTGCCTAATACATGCAAGTCGAGCGAGCTTGCCTAGATGATTTTAGTGCTTGCACTAAATGAAACTAGATACAAGCGAGC

GGCGGACGGGTGAGTAACACGTGGGTAACCTGCCCAAGAGACTGGGATAACACCTGGAAACAGATGCTAATACCGGATAA

CAACACTAGACGCATGTCTAGAGTTTGAAAGATGGTTCTGCTATCACTCTTGGATGGACCTGCGGTGCATTAGCTAGTTG

GTAAGGTAACGGCTTACCAAGGCAATGATGCATAGCCGAGTTGAGAGACTGATCGGCCACATTGGGACTGAGACACGGCC

CAAACTCCTACGGGAGGCAGCAGTAGGGAATCTTCCACAATGGACGAAAGTCTGATGGAGCAACGCCGCGTGAGTGAAGA

AGGGTTTCGGCTCGTAAAGCTCTGTTGGTAGTGAAGAAAGATAGAGGTAGTAACTGGCCTTTATTTGACGGTAATTACTT

AGAAAGTCACGGCTAACTACGTGCCAGCAGCCGCGGTAATACGTAGGTGGCAAGCGTTGTCCGGATTTATTGGGCGTAA

AGCGAGTGCAGGCGGTTCAATAAGTCTGATGTGAAAGCCTTCGGCTCAACCGGAGAAT

SEQ ID NO: 41

S12KG274 GGDK 266-1 519F
TCCGGATTTATTGGGCGTAAAGCGAGTGCAGGCGGTTCAATAAGTCTGATGTGAAAGCCTTCGGCTCAACCGGAGAATTG

CATCAGAAACTGTTGAACTTGAGTGCAGAAGAGGAGAGTGGAACTCCATGTGTAGCGGTGGAATGCGTAGATATATGGAA

GAACACCAGTGGCGAAGGCGGCTCTCTGGTCTGCAACTGACGCTGAGGCTCGAAAGCATGGGTAGCGAACAGGATTAGAT

ACCCTGGTAGTCCATGCCGTAAACGATGAGTGCTAAGTGTTGGGAGGTTTCCGCCTCTCAGTGCTGCAGCTAACGCATTA

AGCACTCCGCCTGGGGAGTACGACCGCAAGGTTGAAACTCAAAGGAATTGACGGGGGCCCGCACAAGCGGTGGAGCATGT

GGTTTAATTCGAAGCAACGCGAAGAACCTTACCAGGTCTTGACATCCAGTGCAAACCTAAGAGATTAGGTGTTCCCTTC

GGGGACGCTGAGACAGGTGGTGCATGGCTGTCGTCAGCTCGTGT

SEQ ID NO: 42

S12KG275 GGDK 266-1 926F - repeat
GGAGCATGTGGTTTAATTCGAAGCAACGCGAAGAACCTTACCAGGTCTTGACATCCAGTGCAAACCTAAGAGATTAGGTG

TGTCCCTTCGGGGACGCTGAGACAGGTGGTGCATGGCTGTCGTCAGCTCGTGTCGTGAGATGTTGGGTTAAGTCCCGCAA

CGAGCGCAACCCTTGTCATTAGTTGCCATCATTAAGTTGGGCACTCTAATGAGACTGCCGGTGACAAACCGGAGGAAGGT

GGGGATGACGTCAAGTCATCATGCCCCTTATGACCTGGGCTACACACGTGCTACAATGGACGGTACAACGAGAAGCGAAC

CTGCGAAGGCAAGCGGATCTCTTAAAGCCGTTCTCAGTTCGGACTGTAGGCTGCAACTCGCCTACACGAAGCTGGAATCG

CTAGTAATCGCGGATCAGCACGCCGCGGTGAATACGTTCCCGGGCCTTGTACACACCGCCCGTCACACCATGAGAG

TCTGTA

SEQ ID NO: 43

S12KG276 GGDK 266-1 926R
ACTCCCCAGGCGGAGTGCTTAATGCGTTAGCTGCAGCACTGAGAGGCGGAAACCTCCCAACACTTAGCACTCATCGTTTA

CGGCATGGACTACCAGGGTATCTAATCCTGTTCGCTACCCATGCTTTCGAGCCTCAGCGTCAGTTGCAGACCAGAGAGCC

GCCTTCGCCACTGGTGTTCTTCCATATATCTACGCATTCCACCGCTACACATGGAGTTCCACTCTCCTCTTCTGCACTCA

AGTTCAACAGTTTCTGATGCAATTCTCCGGTTGAGCCGAAGGCTTTCACATCAGACTTATTGAACCGCCTGCACTCGCTT

TACGCCCAATAAATCCGGACAACGCTTGCCACCTACGTATTACCGCGGCTGCTGGCACGTAGTTAGCCGTGACTTTCTAA

GTAATTACCGTCAAATAAAGGCCAGTTACTACCTCTATCT1TCTTCACTACCAACAGAGCTTTACGAGCCGAAACCCTTC

TTCACTCACGCGGCGTTGCTCCATCAGACTTTCGTCCATTGTGGAAGATTCCCTACTGCTGCCTCCCGTAGGAGTTTGGG

```
CCGTGTCTCAGTCCCAATGTGGCCGATCAGTCTCTCAACTCGGCTATGCATCATTGCCTTGGTAAGCCGTTACCTTACCA

ACTAGCTAATGCACCGCAGGTCCATCCAAGAGTGATAGCAGAACCATCTTTCAAACTCTAGACATGCGTCTAGTGTTGT
```

SEQ ID NO: 44

S12KG277 GGDK 266-1 519R
```
ACTTTCTAAGTAATTACCGTCAAATAAAGGCCAGTTACTACCTCTATCTTTCTTCACTACCAACAGAGCT1TACGAGCCG

AAACCCTTCTTCACTCACGCGGCGTTGCTCCATCAGACTTTCGTCCATTGTGGAAGATTCCCTACTGCTGCCTCCCGTAG

GAGTTTGGGCCGTGTCTCAGTCCCAATGTGGCCGATCAGTCTCTCAACTCGGCTATGCATCATTGCCTTGGTAAGCCGTT

ACCTTACCAACTAGCTAATGCACCGCAGGTCCATCCAAGAGTGATAGCAGAACCATTTTTCAAACTCTAGACATGCGTCT

AGTGTTGTTATCCGGTATTAGCATCTGTTTCCAGGTGTTATCCCAGTCTCTTGGGCAGGTTACCCACGTGTTACTCACCC

GTCCGCCGCTCGCTTGTATCTAGTTTCATTTAGTGCAAGCACTAAAATCATCTAGGCAAGCTCGCTCGACTTGCATGTAT

TAGGCACGCCGCCAGCGTTCGTCCTGAGCCATGATCAAACT
```

SEQ ID NO: 45

S12KG278 GGDK 266-1 RP2
```
CTACCTTAGACGGCTGACTCCTATAAAGGTTATCCCACCGGCTTTGGGTGTTACAGACTCTCATGGTGTGACGGGCGGTG

TGTACAAGGCCCGGGAACGTATTCACCGCGGCGTGCTGATCCGCGATTACTAGCGATTCCAGCTTCGTGTAGGCGAGTTG

CAGCCTACAGTCCGAACTGAGAACGGCTTTAAGAGATCCGCTTGCCTTCGCAGGTTCGCTTCTCGTTGTACCGTCCATTG

TAGCACGTGTGTAGCCCAGGTCATAAGGGGCATGATGACTTGACGTCATCCCCACCTTCCTCCGGTTTGTCACCGGCAGT

CTCATTAGAGTGCCCAACTTAATGATGGCAACTAATGACAAGGGTTGCGCTCGTTGCGGGACTTAACCCAACATCTCACG

ACACGAGCTGACGACAGCCATGCACCACCTGTCTCAGCGTCCCCGAAGGGAACACCTAATCTLTTAGGTTTGCACTGGAT

GTCAAGACCTGGTAAGGTTCTTCGCGTTGCTTCGAATTAAACCACATGCTCCACCGCTTGTGCGGGCCCCCGTCAATTCC

TTTGAGTTTCAACCTTGCGGTCGTACTCCCCAGGCGGAGTGCTTAATGCGTTAGCTGCAGCACTGAGAGGCGGAAACCTC

CCAACACTTAGCACTCATCGTTTACGGCATGGACTACCAGGGTATCTAATCCTGTTCGCTACCCATGCTTTCGAGCCTCA

GCGTCAGTTGCAGACCAGAGAGCCGCCT
```

NCIMB 41850 GGDK 266 - contains both *Lactobacillus johnsonii* and *Lactobacillus reuteri*
*Lactobacillus reuteri*

SEQ ID NO: 46

S12KG279 GGDK-266-2 27F
```
GTGTGCCTAATACATGCAAGTCGTACGCACTGGCCCAACTGATTGATGGTGCTTGCACCTGATTGACGATGGATCACCAG

TGAGTGGCGGACGGGTGAGTAACACGTAGGTAACCTGCCCCGGAGCGGGGGATAACATTTGGAAACAGATGCTAATACCG

CATAACAACAAAAGCCACATGGCTTTTGTTTGAAAGATGGCTTCGGCTATCACTCTGGGATGGACCTGCGGTGCATTAGC

TAGTTGGTAAGGTAACGGCTTACCAAGGCGATGATGCATAGCCGAGTTGAGAGACTGATCGGCCACAATGGAACTGAGAC

ACGGTCCATACTCCTACGGGAGGCAGCAGTAGGGAATCTTCCACAATGGGCGCAAGCCTGATGGAGCAACACCGCGTGAG

TGAAGAAGGGTTTCGGCTCGTAAAGCTCTGTTGTTGGAGAAGAACGTGCGTGAGAGTAACTGTTCACGCAGTGACGGTAT

CCAACCAGAAAGTCACGGCTAACTACGTGCCAGCAGCCGCGGTAATACGTAGGTGGCAAGCGTTATCCGGATTTATTGGG

CGTAAAGCGAGCGCAGGCGGTTGCTTAGGTCTGATGTGAAAGCCTTCGGCTTAACCGAAGAAGTGCATCGGAAACCGGGC

GACTTGAGTGCAGAAGAGGACAGTGGAACTCCATGTGTAGCGGTGGAATGCGTA
```

SEQ ID NO: 47

S12KG280 GGDK-266-2 519F - repeat
```
CGGATTTATTGGGCGTAAAGCGAGCGCAGGCGGTTGCTTAGGTCTGATGTGAAAGCCTTCGGCTTAACCGAAGAAGTGCA

TCGGAAACCGGGCGACTTGAGTGCAGAAGAGGACAGTGGAACTCCATGTGTAGCGGTGGAATGCGTAGATATATGGAAGA

ACACCAGTGGCGAAGGCGGCTGTCTGGTCTGCAACTGACGCTGAGGCTCGAAAGCATGGGTAGCGAACAGGATTAGATAC

CCTGGTAGTCCATGCCGTAAACGATGAGTGCTAGGTGTTGGAGGGTTTCCGCCCTTCAGTGCCGGAGCTAACGCATTAAG

CACTCCGCCTGGGGAGTACGACCGCAAGGTTGAAACTCAAAGGAATTGACGGGGCCCGCACAAGCGGTGGAGCATGTG

GTTTAATTCG
```

SEQ ID NO: 48

S12KG281 GGDK-266-2 926F - repeat
GAGCATGTGGTTTAATTCGAAGCTACGCGAAGAACCTTACCAGGTCTTGACATCTTGCGCTAACCTTAGAGATAAGGCGT

TCCCTTCGGGGACGCAATGACAGGTGGTGCATGGTCGTCGTCAGCTCGTGTCGTGAGATGTTGGGTTAAGTCCCGCAACG

AGCGCAACCCTTGTTACTAGTTGCCAGCATTAAGTTGGGCACTCTAGTGAGACTGCCGGTGACAAACCGGAGGAAGGTGG

GGACGACGTCAGATCATCATGCCCCTTATGACCTGGGCTACACACGTGCTACAATGGACGGTACAACGAGTCGCAAGCT

CGCGAGAGTAAGCTAATCTCTTAAAGCCGTTCTCAGTTCGGACTGTAGGCTGCAACTCGCCTACACGAAGTCGGAATCGC

TAGTAATCGCGGATCAGCATGCCGCGGTGAATACGTTCCCGGGCCTTGTACACACCGCCCGTCACACC

SEQ ID NO: 49

S12KG282 GGDK-266-2 926R - repeat
ACTCCCCAGGCGGAGTGCTTAATGCGTTAGCTCCGGCACTGAAGGGCGGAAACCCTCCAACACCTAGCACTCATCGTTTA

CGGCATGGACTACCAGGGTATCTAATCCTGTTCGCTACCCATGCTTTCGAGCCTCAGCGTCAGTTGCAGACCAGACAGCC

GCCTTCGCCACTGGTGTTCTTCCATATATCTACGCATTCCACCGCTACACATGGAGTTCCACTGTCCTCTTCTGCACTCA

AGTCGCCCGGTTTCCGATGCACTTCTTCGGTTAAGCCGAAGGCTTTCACATCAGACCTAAGCAACCGCCTGCGCTCGCTT

TACGCCCAATAAATCCGGATAACGCTTGCCACCTACGTATTACCGCGGCTGCTGGCACGTAGTTAGCCGTGACTTTCTGG

TTGGATACCGTCACTGCGTGAACAGTTACTCTCACGCACGTTCTTCTCCAACAACAGAGCTTTACGAGCCGAAACCCTTC

TTCACTCACGCGGTGTTGCTCCATCAGGCTTGCGCCCATTGTGGAAGATTCCCTACTGCTGCCTCCCGTAGGAGTATGGA

CCGTGTCTCAGTTCCATTGTGGCCGATCAGTCTCTCAACTCGGCTATGCATCATCGCCTTGGTAAGCCGTTACCTTACCA

ACTAGCTAATGCACCGCAGGT

SEQ ID NO: 50

S12KG283 GGDK-266-2 519R
TTTCTGGTTGGATACCGTCACTGCGTGAACAGTTACTCTCACGCACGTTCTTCTCCAACAACAGAGCTTTACGAGCCGAA

ACCCTTCTTCACTCACGCGGTGTTGCTCCATCAGGCTTGCGCCCATTGTGGAAGATTCCCTACTGCTGCCTCCCGTAGGA

GTATGGACCGTGTCTCAGTTCCATTGTGGCCGATCAGTCTCTCAACTCGGCTATGCATCATCGCCTTGGTAAGCCGTTAC

CTTACCAACTAGCTAATGCACCGCAGGTCCATCCCAGAGTGATAGCCAAAGCCATCTTTCAAACAAAAGCCATGTGGCTT

TTGTTGTTATGCGGTATTAGCATCTGTTTCCAAATGTTATCCCCCGCTCCGGGGCAGGTTACCTACGTGTTACTCACCCG

TCCGCCACTCACTGGTGATCCATCGTCAATCAGGTGCAAGCACCATCAATCAGTTGGGCCAGTGCGTACGACTTGCATGT

ATTAGGCACACCGCCGGCGTTCATCCTGAGCCATGATCAAACTCT

SEQ ID NO: 51

S12KG284 GGDK-266-2 RP2
TCCCGCCTTAGGCGGCTCCCTCCATAATGGTTAGGCCACCGACTTTGGGCGTTACAAACTCCCATGGTGTGACGGGCGGT

GTGTACAAGGCCCGGGAACGTATTCACCGCGGCATGCTGATCCGCGATTACTAGCGATTCCGACTTCGTGTAGGCGAGTT

GCAGCCTACAGTCCGAACTGAGAACGGCTTTAAGAGATTAGCTTACTCTCGCGAGCTTGCGACTCGTTGTACCGTCCATT

GTAGCACGTGTGTAGCCCAGGTCATAAGGGGCATGATGATCTGACGTCGTCCCCACCTTCCTCCGGTTTGTCACCGGCAG

TCTCACTAGAGTGCCCAACTTAATGCTGGCAACTAGTAACAAGGGTTGCGCTCGTTGCGGGACTTAACCCAACATCTCAC

GACACGAGCTGACGACGACCATGCACCACCTGTCATTGCGTCCCCGAAGGGAACGCCTTATCTCTAAGGTTAGCGCAAGA

TGTCAAGACCTGGTAAGGTTCTTCGCGTAGCTTCGAATTAAACCACATGCTCCACCGCTTGTGCGGGCCCCCGTCAATTC

CTTTGAGTTTCAACCTTGCGGTCGTACTCCCCAGGCGGAGTGCTTAATGCGTTAGCTCCGGCACTGAAGGGCGGAAACCC

TCCAACACCTAGCACTCATCGTTTACGGCATGGACTACCAGGGTATCTAATCCTGTTCGCTACCCATGCTTTCGAGCCTC

AGCGTCAGTTGCAGACCAGACAGCCGCCTTCGCCACTGGTG

NCIMB 41850 GGDK 266 - contains both *Lactobacillus johnsonii* and *Lactobacillus reuteri*
*Lactobacillus reuteri*

SEQ ID NO: 52

S12KG381 27F
GTGTGCCTAATACATGCAAGTCGTACGCACTGGCCCAACTGATTGATGGTGCTTGCACCTGATTGACGATGGATCACCAGTGAGTGGCGGACG

GGTGAGTAACACGTAGGTAACCTGCCCCGGAGCGGGGGATAACATTTGGAAACAGATGCTAATACCGCATAACAACAAAAGCCACATGGCTTT

-continued

```
TGTTTGAAAGATGGCTTTGGCTATCACTCTGGGATGGACCTGCGGTGCATTAGCTAGTTGGTAAGGTAACGGCTTACCAAGGCGATGATGCAT

AGCCGAGTTGAGAGACTGATCGGCCACAATGGAACTGAGACACGGTCCATACTCCTACGGGAGGCAGCAGTAGGGAATCTTCCACAATGGGC

GCAAGCCTGATGGAGCAACACCGCGTGAGTGAAGAAGGGTTTCGGCTCGTAAAGCTCTGTTGTTGGAGAAGAACGTGCGTGAGAGTAACTGT

TCACGCAGTGACGGTATCCAACCAGAAAGTCACGGCTAACTACGTGCCAGCAGCCGCGGTAATACGTAGGTGGCAAGCGTTATCCGGATTTAT

TGGGCGTAAAGCGAGCGCAGGCGGTTGCTTAGGTCTGATGTGAAAGCCTTCGGCTTAACCGAAGAAGTGCATCGGAAACCGGGCGACTTGAG

TGC
```

SEQ ID NO: 53
S12KG382 519E
```
TTATCCGGATTTATTGGGCGTAAAGCGAGCGCAGGCGGTTGCTTAGGTCTGATGTGAAAGCCTTCGGCTTAACCGAAGAAGTGCATCGGAAAC

CGGGCAACTTGAGTGCAGAAGAGGACAGTGGAACTCCATGTGTAGCGGTGGAATGCGTAGATATATGGAAGAACACCAGTGGCGAAGGCGG

CTGTCTGGTCTGCAACTGACGCTGAGGCTCGAAAGCATGGGTAGCGAACAGGATTAGATACCCTGGTAGTCCATGCCGTAAACGATGAGTGCT

AGGTGTTGGAGGGTTTCCGCCCTTCAGTGCCGGAGCTAACGCATTAAGCACTCCGCCTGGGGAGTACGACCGCAAGGTTGAAACTCAAGGA

ATTGACGGGGGCCCGCACAAGCGGTGGAGCATGTGGTTTAATTCGAAGCTACGCGAAGAACCTTACCAGGTCTTGACATCTTGCGCTAACCTT

AGAGATAAGGCGTCCCTTCGGGGACGCAATGACAGGTGGTGCATGGTCGTCGTCAGCTCGTGTCGTGAGATGTTGGGTTAAGTCCCGCAACG

AGCGCAACCCTTGTTACTAGTTGCCAGCATTAAGTTGGGCACTCTAGTGAGACTGCCGGTGACAAACCGGAGGAAGGTGGGGACGACGTCA
```

SEQ ID NO: 54
S12KG383 926F
```
GGTGGAGCATGTGGTTTAATTCGAAGCTACGCGAAGAACCTTACCAGGTCTTGACATCTTGCGCTAACCTTAGAGATAAGGCGTTCCCTTCGGG

GACGCAATGACAGGTGGTGCATGGTCGTCGTCAGCTCGTGTCGTGAGATGTTGGGTTAAGTCCCGCAACGAGCGCAACCCTTGTTACTAGTTG

CCAGCATTAAGTTGGGCACTCTAGTGAGACTGCCGGTGACAAACCGGAGGAAGGTGGGGACGACGTCAGATCATCATGCCCCTTATGACCTG

GGCTACACACGTGCTACAATGGACGGTACAACGAGTCGCAAGCTCGCGAGAGTAAGCTAATCTCTTAAAGCCGTTCTCAGTTCGGACTGTAGG

CTGCAACTCGCCTACACGAAGTCGGAATCGCTAGTAATCGCGGATCAGCATGCCGCGGTGAATACGTTCCCGGGCCTTGTACACACCGCCCGTC

ACACCATGGGAGTTTGTAACGCCCAAAGTCGGTGGCCTAACCATTATGGAGGGAGCCGCCTAAGGCGGGACAGATGACTGGGGTGAAGTCGT

AACAAGGTAGCCGTA
```

SEQ ID NO: 55
S12KG384 926R
```
TACTCCCCAGGCGGAGTGCTTAATGCGTGAGCTCCGGCACTGAAGGGCGGAAACCCTCCAACACCTAGCACTCATCGTTTACGGCATGGACTA

CCAGGGTATCTAATCCTGTTCGCTACCCATGCTTTCGAGCCTCAGCGTCAGTTGCAGACCAGACAGCCGCCTTCGCCACTGGTGTTCTTCCATAT

ATCTACGCATTCCACCGCTACACATGGAGTTCCACTGTCCTCTTCTGCACTCAAGTCGCCCGGTTTCCGATGCACTTCTTCGGTTAAGCCGAAGG

CTTTCACATCAGACCTAAGCAACCGCCTGCGCTCGCTTTACGCCCAATAAATCCGGATAACGCTTGCCACCTACGTATTACCGCGGCTGCTGGCA

CGTAGTTAGCCGTGACTTTCTGGTTGGATACCGTCACTGCGTGAACAGTTACTCTCACGCACGTTCTTCTCCAACAACAGAGCTTTACGAGCCGA

AACCCTTCTTCACTCACGCGGTGTTGCTCCATCAGGCTTGCGCCCATTGTGGAAGATTCCCTACTGCTGCCTCCCGTAGGAGTATGGACCGTGTC

TCAGTTCCATTGTGGCCGATCAGTCTCTCAACTCGGCTATGCATCATCGCCTTGGTAAGCCGTTACCTTACCAACTAGCTAATGCACCGCAGGTC

CATCCCAGAGTGATAGCCAAAGCCATCTTTCAAACAAAAGCC
```

SEQ ID NO: 56
S12KG385 519R
```
GTGACTTTCTGGTTGGATACCGTCACTGCGTGAACAGTTACTCTCACGCACGTGCTTCTCCAACAACAGAGCTTTACGAGCCGAAACCCTTCTTC

ACTCACGCGGTGTTGCTCCATCAGGCTTGCGCCCATTGTGGAAGATTCCCTACTGCTGCCTCCCGTAGGAGTATGGACCGTGTCTCAGTTCCATT

GTGGCCGATCAGTCTCTCAACTCGGCTATGCATCATCGCCTTGGTAAGCCGTTACCTTACCAACTAGCTAATGCACCGCAGGTCCATCCCAGAGT

GATAGCCAAAGCCATCTTTCAAACAAAAGCCATGTGGCTTTTGTTGTTATGCGGTATTAGCATCTGTTTCCAAATGTTATCCCCGCTCCGGGGC

AGGTTACCTACGTGTTACTCACCCGTCCGCCACTCACTGGTGATCCATCGTCAATCAGGTGCAAGCACCATCAATCAGTTGGGCCAGTGCGTAC

GACTTGCATGTATTAGGCACACCGCCGGCGTTCATCCTGAGCCATGATCAAAC
```

SEQ ID NO: 57
S12KG386 RP2
```
TCCCGCACTTAGGCGGCTCCCTCCATAATGGTTAGGCCACCGATTTTGGGCGTTACAAACTCCCATGGTGTGACGGGCGGTGTGTACAAGGCC

CGGGAACGTATTCACCGCGGCATGCTGATCCGCGATTACTAGCGATTCCGACTTCGTGTAGGCGAGTTGCAGCCTACAGTCCGAACTGAGAAC
```

-continued

GGCTTTAAGAGATTAGCTTACTCTCGCGAGCTTGCGACTCGTTGTACCGTCCATTGTAGCACGTGTGTAGCCCAGGTCATAAGGGGCATGATGA

TCTGACGTCGTCCCCACCTTCCTCCGGTTTGTCACCGGCAGTCTCACTAGAGTGCCCAACTTAATGCTGGCAACTAGTAACAAGGGTTGCGCTCG

TTGCGGGACTTAACCCAACATCTCACGACACGAGCTGACGACGACCATGCACCACCTGTCATTGCGTCCCCGAAGGGAACGCCTTATCTCTAAG

GTTAGCGCAAGATGTCAAGACCTGGTAAGGTTCTTCGCGTAGCTTCGAATTAAACCACATGCTCCACCGCTTGTGCGGGCCCCCGTCAATTCCT

TTGAGTTTCAACCTTGCGGTCGTACTCCCCAGGCGGAGTGCTTAATGCGTTAGCTCCGGCACTGAAGGGCGGAAACCCTCCAACACCTAGCACT

CATCGTTTACGGCATGGACTACCAGGGTATCTAATCCTGTTCGCTACCCATGCTTTCGAGCC

NCIMB 42008 GGDK266a - *L. johnsonii* (sample 4a)

SEQ ID NO: 58

S12KG399 27F

GCGTGCCTAATACATGCAAGTCGAGCGAGCTTGCCTAGATGATTTTAGTGCTTGCACTAAATGAAACTAGATACAAGCGAGCGGCGGACGGGT

GAGTAACACGTGGGTAACCTGCCCAAGAGACTGGGATAACACCTGGAAACAGATGCTAATACCGGATAACAACACTAGACGCATGTCTAGAG

TTTGAAAGATGGTTCTGCTATCACTCTTGGATGGACCTGCGGTGCATTAGCTAGTTGGTAAGGTAACGGCTTACCAAGGCAATGATGCATAGCC

GAGTTGAGAGACTGATCGGCCACATTGGGACTGAGACACGGCCCAAACTCCTACGGGAGGCAGCAGTAGGGAATCTTCCACAATGGACGAAA

GTCTGATGGAGCAACGCCGCGTGAGTGAAGAAGGGTTTCGGCTCGTAAAGCTCTGTTGGTAGTGAAGAAAGATAGAGGTAGTAACTGGCCTT

TATTTGACGGTAATTACTTAGAAAGTCACGGCTAACTACGTGCCAGCAGCCGCGGTAATACGTAGGTGGCAAGCGTTGTCCGGATTTATTGGG

CGTAAAGCGAGTGCAGGCGGTTCAATAAGTCTGATGTGAAAGCCTTCGGCTCAACCGGAGAATTGCATCAGAAACTGTTGAACTTGAGTGCAG

AAGAGGAGAGTGGAACTCCATGTGTAGCGGTGGAATGCGTA

SEQ ID NO: 59

S12KG400 519F

TGTCCGGATTTATTGGGCGTAAAGCGAGTGCAGGCGGTTCAATAAGTCTGATGTGAAAGCCTTCGGCTCAACCGGAGAATTGCATCAGAAACT

GTTGAACTTGAGTGCAGAAGAGGAGAGTGGAACTCCATGTGTAGCGGTGGAATGCGTAGATATATGGAAGAACACCAGTGGCGAAGGCGGC

TCTCTGGTCTGCAACTGACGCTGAGGCTCGAAAGCATGGGTAGCGAACAGGATTAGATACCCTGGTAGTCCATGCCGTAAACGATGAGTGCTA

AGTGTTGGGAGGTTTCCGCCTCTCAGTGCTGCAGCTAACGCATTAAGCACTCCGCCTGGGGAGTACGACCGCAAGGTTGAAACTCAAAGGAAT

TGACGGGGGCCCGCACAAGCGGTGGAGCATGTGGTTTAATTCGAAGCAACGCGAAGAACCTTACCAGGTCTTGACATCCAGTGCAAACCTAA

GAGATTAGGTGTTCCCTTCGGGGACGCTGAGACAGGTGGTGCATGGCTGTCGTCAGCTCGTGTCGTGAGATGTTGGGTTAAGTCCCGCAACGA

GCGCAACCCTTGTCATTAGTTGCCATCATTAAGTTGGGCACTCTAATGAGACTGCCGGTGACAAACCGGAGGAAGGTGGGGAT

SEQ ID NO: 60

S12KG401 926F

GGTGGAGCATGTGGTTTAATTCGAAGCAACGCGAAGAACCTTACCAGGTCTTGACATCCAGTGCAAACCTAAGAGATTAGGTGTTCCCTTCGG

GGACGCTGAGACAGGTGGTGCATGGCTGTCGTCAGCTCGTGTCGTGAGATGTTGGGTTAAGTCCCGCAACGAGCGCAACCCTTGTCATTAGTT

GCCATCATTAAGTTGGGCACTCTAATGAGACTGCCGGTGACAAACCGGAGGAAGGTGGGGATGACGTCAAGTCATCATGCCCCTTATGACCTG

GGCTACACACGTGCTACAATGGACGGTACAACGAGAAGCGAACCTGCGAAGGCAAGCGGATCTCTTAAAGCCGTTCTCAGTTCGGACTGTAG

GCTGCAACTCGCCTACACGAAGCTGGAATCGCTAGTAATCGCGGATCAGCACGCCGCGGTGAATACGTTCCCGGGCCTTGTACACACCGCCCG

TCACACCATGAGAGTCTGTAACACCCAAAGCCGGTGGGATAACCTTTATAGGAGTCAGCCGTCTAAGGTAGGACAGATGATTAGGGTGAAGTC

GTAACAAGGTAG

SEQ ID NO: 61

S12KG402 926R

TACTCCCCAGGCGGAGTGCTTAATGCGTTAGCTGCAGCACTGAGAGGCGGAAACCTCCCAACACTTAGCACTCATCGTTTACGGCATGGACTAC

CAGGGTATCTAATCCTGTTCGCTACCCATGCTTTCGAGCCTCAGCGTCAGTTGCAGACCAGAGAGCCGCCTTCGCCACTGGTGTTCTTCCATATA

TCTACGCATTCCACCGCTACACATGGAGTTCCACTCTCCTCTTCTGCACTCAAGTTCAACAGTTTCTGATGCAATTCTCCGGTTGAGCCGAAGGCT

TTCACATCAGACTTATTGAACCGCCTGCACTCGCTTTACGCCCAATAAATCGGACAACGCTTGCCACCTACGTATTACCGCGGCTGCTGGCACG

TAGTTAGCCGTGACTTTCTAAGTAATTACCGTCAAATAAAGGCCAGTTACTACCTCTATCTTTCTTCACTACCAACAGAGCTTFACGAGCCGAAA

CCCTTCTTCACTCACGCGGCGTTGCTCCATCAGACTTTCGTCCATTGTGGAAGATTCCCTACTGCTGCCTCCCGTAGGAGTTTGGGCCGTGTCTC

AGTCCCAATGTGGCCGATCAGTCTCTCAACTCGGCTATGCATCATTGCCTTGGTAAGCCGTTACCTTACCAACTAGCTAATGCACCGCAGGTCCA

TCCAAGAGTGATAGCAGANCCATCTTTCAAACTCTAGACATGCGTCTAGTG

SEQ ID NO: 62
S12KG403 519R
GTGACTTTCTAAGTAATTACCGTCAAATAAAGGCCAGTTACTACCTCTATCTTTCTTCACTACCAACAGAGCTTTACGAGCCGAAACCCTTCTTCA
CTCACGCGGCGTTGCTCCATCAGACTTTCGTCCATTGTGGAAGATTCCCTACTGCTGCCTCCCGTAGGAGTTTGGGCCGTGTCTCAGTCCCAATG
TGGCCGATCAGTCTCTCAACTCGGCTATGCATCATTGCCTTGGTAAGCCGTTACCTTACCAACTAGCTAATGCACCGCAGGTCCATCCAAGAGTG
ATAGCAGAACCATCTTTCAAACTCTAGACATGCGTCTAGTGTTGTTATCCGGTATTAGCATCTGTTTCCAGGTGTTATCCCAGTCTCTTGGGCAG
GTTACCCACGTGTTACTCACCCGTCCGCCGCTCGCTTGTATCTAGTTTCATTTAGTGCAAGCACTAAAATCATCTAGGCAAGCTCGCTCGACTTG
CATGTATTAGGCACGCCGCCAGCGTTCGTCCTGAGCCA

SEQ ID NO: 63
S12KG404 RP2
TCCTACACTTAGACGGCTGACTCCTATAAAGGTTATCCCACCGGCTTTGGGTGTTACAGACTCTCATGGTGTGACGGGCGGTGTGTACAAGGCC
CGGGAACGTATTCACCGCGGCGTGCTGATCCGCGATTACTAGCGATTCCAGCTTCGTGTAGGCGAGTTGCAGCCTACAGTCCGAACTGAGAAC
GGCTTTAAGAGATCCGCTTGCCTTCGCAGGTTCGCTTCTCGTTGTACCGTCCATTGTAGCACGTGTGTAGCCCAGGTCATAAGGGGCATGATGA
CTTGACGTCATCCCCACCTTCCTCCGGTTTGTCACCGGCAGTCTCATTAGAGTGCCCAACTTAATGATGGCAACTAATGACAAGGGTTGCGCTCG
TTGCGGGACTTAACCCAACATCTCACGACACGAGCTGACGACAGCCATGCACCACCTGTCTCAGCGTCCCCGAAGGGAACACCTAATCTCTTAG
GTTTGCACTGGATGTCAAGACCTGGTAAGGTTCTTCGCGTTGCTTCGAATTAAACCACATGCTCCACCGCTTGTGCGGGCCCCCGTCAATTCCTT
TGAGTTTCAACCTTGCGGTCGTACTCCCCAGGCGGAGTGCTTAATGCGTTAGCTGCAGCACTGAGAGGCGGAAACCTCCCAACACTTAGCACTC
ATCGTTTACGGCATGGACTACCAGGGTATCTAATCCTGTTCGCTACCCATGC

SEQ ID NO: 64
NCIMB 42009 GGDK266b - *L. reuteri* (sample 6a)
S12KG411 27F
GTGTGCCTAATACATGCAAGTCGTACGCACTGGCCCAACTGATTGATGGTGCTTGCACCTGATTGACGATGGATCACCAGTGAGTGGCGGACG
GGTGAGTAACACGTAGGTAACCTGCCCCGGAGCGGGGGATAACATTTGGAAACAGATGCTAATACCGCATAACAACAAAAGCCACATGGCTTT
TGTTTGAAAGATGGCTTTGGCTATCACTCTGGGATGGACCTGCGGTGCATTAGCTAGTTGGTAAGGTAACGGCTTACCAAGGCGATGATGCAT
AGCCGAGTTGAGAGACTGATCGGCCACAATGGAACTGAGACACGGTCCATACTCCTACGGGAGGCAGCAGTAGGGAATCTTCCACAATGGGC
GCAAGCCTGATGGAGCAACACCGCGTGAGTGAAGAAGGGTTTCGGCTCGTAAAGCTCTGTTGTTGGAGAAGAACGTGCGTGAGAGTAACTGT
TCACGCAGTGACGGTATCCAACCAGAAAGTCACGGCTAACTACGTGCCAGCAGCCGCGGTAATACGTAGGTGGCAAGCGT SEQ ID NO: 65
S12KG412 519F
TATCCGGATTTATTGGGCGTAAAGCGAGCGCAGGCGGTTGCTTAGGTCTGATGTGAAAGCCTTCGGCTTAACCGAAGAAGTGCATCGGAAACC
GGGCGACTTGAGTGCAGAAGAGGACAGTGAACTCCATGTGTAGCGGTGAAATGCGTAGATATATGGAAGAACACCAGTGGCGAAGGCGGC
TGTCTGGTCTGCAACTGACGCTGAGGCTCGAAAGCATGGGTAGCGAACAGGATTAGATACCCTGGTAGTCCATGCCGTAAACGATGAGTGCTA
GGTGTTGGAGGGTTTCCGCCCTTCAGTGCCGGAGCTAACGCATTAAGCACTCCGCCTGGGGAGTACGACCGCAAGGTTGAAACTCAAAGGAAT
TGACGGGGGCCCGCACAAGCGGTGGAGCATGTGGTTTAATTCGAAGCTACGCGAAGAACCTTACCAGGTCTTGACATCTTGCGCTAACCTTAG
AGATAAGGCGTTCCCTTCGGGGACGCAATGACAGGTGGTGCATGGTCGTCGTCAGCTCGTGTCGTGAGATGTTGGGTTAAGTCCCGCAACGA
GCGCAACCCTTGTTACTAGTTGCCAGCATTAAGTTGGGCACTCTAGTGAGACTGCCGGTGACAAACCGGAGGA SEQ ID NO: 66
S12KG413 926F
GTGGAGCATGTGGTTTAATTCGAAGCTACGCGAAGAACCTTACCAGGTCTTGACATCTTGCGCTAACCTTAGAGATAAGGCGTTCCCTTCGGGG
ACGCAATGACAGGTGGTGCATGGTCGTCGTCAGCTCGTGTCGTGAGATGTTGGGTTAAGTCCCGCAACGAGCGCAACCCTTGTTACTAGTTGC
CAGCATTAAGTTGGGCACTCTAGTGAGACTGCCGGTGACAAACCGGAGGAAGGTGGGGACGACGTCAGATCATCATGCCCCTTATGACCTGG
GCTACACACGTGCTACAATGGACGGTACAACGAGTCGCAAGCTCGCGAGAGTAAGCTAATCTCTTAAAGCCGTTCTCAGTTCGGACTGTAGGC
TGCAACTCGCCTACACGAAGTCGGAATCGCTAGTAATCGCGGATCAGCATGCCGCGGTGAATACGTTCCCGGGCCTTGTACACACCGCCCGTC
ACACCATGGGAGTTTGTAACGCCCAAAGTCGGTGGCCTAACCATTATGGAGGGAGCCGCCTAAGGCGGGACAGATGACTGGGGTGAAGTCGT SEQ ID NO: 67
S12KG414 926R
TACTCCCCAGGCGGAGTGCTTAATGCGTTAGCTCCGGCACTGAAGGGCGGAAACCCTCCAACACCTAGCACTCATCGTTTACGGCATGGACTAC -continued CAGGGTATCTAATCCTGTTCGCTACCCATGCTTTCGAGCCTCAGCGTCAGTTGCAGACCAGACAGCCGCCTTCGCCACTGGTGTTCTTCCATATA TCTACGCATTCCACCGCTACACATGGAGTTCCACTGTCCTCTTCTGCACTCAAGTCGCCCGGTTTCCGATGCACTTCTTCGGTTAAGCCGAAGGC TTTCACATCAGACCTAAGCAACCGCCTGCGCTCGCTTTACGCCCAATAAATCCGGATAACGCTTGCCACCTACGTATTACCGCGGCTGCTGGCAC GTAGTTAGCCGTGACTTTCTGGTTGGATACCGTCACTGCGTGAACAGTTACTCTCACGCACGTTCTTCTCCAACAACAGAGCTTTACGAGCCGAA ACCCTTCTTCACTCACGCGGTGTTGCTCCATCAGGCTTGCGCCCATTGTGGAAGATTCCCTACTGCTGCCTCCCGTAGGAGTATGGACCGTGTCT

CAGTTCCATTGTGGCCGATCAGTCTCTCAACTCGGCTATGCATCATCGCC

SEQ ID NO: 68

S12KG415 519R
GTGACTTTCTGGTTGGATACCGTCACTGCGTGAACAGTTACTCTCACGCACGTTCTTCTCCAACAACAGAGCTTTACGAGCCGAAACCCTTCTTC

ACTCACGCGGTGTTGCTCCATCAGGCTTGCGCCCATTGTGGAAGATTCCCTACTGCTGCCTCCCGTAGGAGTATGGACCGTGTCTCAGTTCCATT

GTGGCCGATCAGTCTCTCAACTCGGCTATGCATCATCGCCTTGGTAAGCCGTTACCTTACCAACTAGCTAATGCACCGCAGGTCCATCCCAGAGT

GATAGCCAAAGCCATCTTTCAAACAAAAGCCATGTGGCTTTTGTTGTTATGCGGTATTAGCATCTGTTTCCAAATGTTATCCCCCGCTCCGGGGC

AGGTTACCTACGTGTTACTCACCCGTCCGCCACTCACTGGTGATCCATCGTCAATCAGGTGCAAGCACCATCAATCAGTTGGGCCAGTGCGTAC

GACTTGCATGTATTAGGCACACCGCCGGCGTTCAT

SEQ ID NO: 69

S12KG416 RP2
TCCCGCCTTAGGCGGCTCCCTCCATAATGGTTAGGCCACCGACTTTGGGCGTTACAAACTCCCATGGTGTGACGGGCGGTGTGTACAAGGCCC

GGGAACGTATTCACCGCGGCATGCTGATCCGCGATTACTAGCGATTCCGACTTCGTGTAGGCGAGTTGCAGCCTACAGTCCGAACTGAGAACG

GCTTTAAGAGATTAGCTTACTCTCGCGAGCTTGCGACTCGTTGTACCGTCCATTGTAGCACGTGTGTAGCCCAGGTCATAAGGGGCATGATGAT

CTGACGTCGTCCCCACCTTCCTCCGGTTTGTCACCGGCAGTCTCACTAGAGTGCCCAACTTAATGCTGGCAACTAGTAACAAGGGTTGCGCTCGT

TGCGGGACTTAACCCAACATCTCACGACACGAGCTGACGACGACCATGCACCACCTGTCATTGCGTCCCCGAAGGGAACGCCTTATCTCTAAGG

TTAGCGCAAGATGTCAAGACCTGGTAAGGTTCTTCGCGTAGCTTCGAATTAAACCACATGCTCCACCGCTTGTGCGGGCCCCCGTCAATTCCTTT

GAGTTTCAACCTTGCGGTCGTACTCC

SEQ ID NO: 70

NCIMB 42010 GGDK161a - *L. plantarum* (sample 7a)
S12KG417 27F
GTGCCTAATACATGCAAGTCGAACGAACTCTGGTATTGATTGGTGCTTGCATCATGATTTACATTTGAGTGAGTGGCGAACTGGTGAGTAACAC GTGGGAAACCTGCCCAGAAGCGGGGGATAACACCTGGAAACAGATGCTAATACCGCATAACAACTTGGACCGCATGGTCCGAGTTTGAAAGA TGGCTTCGGCTATCACTTTTGGATGGTCCCGCGGCGTATTAGCTAGATGGTGAGGTAACGGCTCACCATGGCAATGATACGTAGCCGACCTGA GAGGGTAATCGGCCACATTGGGACTGAGACACGGCCCAAACTCCTACGGGAGGCAGCAGTAGGGAATCTTCCACAATGGACGAAAGTCTGAT GGAGCAACGCCGCGTGAGTGAAGAAGGGTTTCGGCTCGTAAAACTCTGTTGTTAAAGAAGAACATATCTGAGAGTAACTGTTCAGGTATTGAC GGTATTTAACCAGAAAGCCACGGCTAACTACGTGCCAGCAGCCGCGGTAATACGTAGGTGGCAAGCGTTGTCCGGATTTATTGGGCGTAAAGC GAGCGCAGGCGGTTTTTTAAGTCTGATGTGAAAGCCTTCGGCTCAACCGAAGAAGTGCATCGGAAACTGGGAAACTTGAGTGCAGAAGAGGA

CAGTGGAACTCATGTGT

SEQ ID NO: 71

S12KG418 519F
TCCGGATTTATTGGGCGTAAAGCGAGCGCAGGCGGTTTTTTAAGTCTGATGTGAAAGCCTTCGGCTCAACCGAAGAAGTGCATCGGAAACTGG

GAAACTTGAGTGCAGAAGAGGACAGTGGAACTCCATGTGTAGCGGTGAAATGCGTAGATATATGGAAGAACACCAGTGGCGAAGGCGGCTG

TCTGGTCTGTAACTGACGCTGAGGCTCGAAAGTATGGGTAGCAAACAGGATTAGATACCCTGGTAGTCCATACCGTAAACGATGAATGCTAAG

TGTTGGAGGGTTTCCGCCCTTCAGTGCTGCAGCTAACGCATTAAGCATTCCGCCTGGGGAGTACGGCCGCAAGGCTGAAACTCAAAGGAATTG

ACGGGGGCCCGCACAAGCGGTGGAGCATGTGGTTTAATTCGAAGCTACGCGAAGAACCTTACCAGGTCTTGACATACTATGCAAATCTAAGAG

ATTAGACGTTCCCTTCGGGGACATGGATACAGGTGGTGCATGGTTGTCGTCAGCTCGTGTCGTGAGATGTTGGGTTAAGTCCCGCAACGAGCG

CAACCCTTATTATCAGTTGCCAGCATTAAGTTGGGCACTCTGGTGAGACTGCCGGTGACAAACCGGAGGAAGGTGGGGATGACGTCAAATCAT

CATGCCCCTTATGACCTGGGCTACACAC

SEQ ID NO: 72
S12KG419 926F
GGTGGAGCATGTGGTTTAATTCGAAGCTACGCGAAGAACCTTACCAGGTCTTGACATACTATGCAAATCTAAGAGATTAGACGTTCCCTTCGGG

GACATGGATACAGGTGGTGCATGGTTGTCGTCAGCTCGTGTCGTGAGATGTTGGGTTAAGTCCCGCAACGAGCGCAACCCTTATTATCAGTTG

CCAGCATTAAGTTGGGCACTCTGGTGAGACTGCCGGTGACAAACCGGAGGAAGGTGGGGATGACGTCAAATCATCATGCCCCTTATGACCTG

GGCTACACACGTGCTACAATGGATGGTACAACGAGTTGCGAACTCGCGAGAGTAAGCTAATCTCTTAAAGCCATTCTCAGTTCGGATTGTAGG

CTGCAACTCGCCTACATGAAGTCGGAATCGCTAGTAATCGCGGATCAGCATGCCGCGGTGAATACGTTCCCGGGCCTTGTACACACCGCCCGTC

ACACCATGAGAGTTTGTAACACCCAAAGTCGGTGGGGTAACCTTTTAGGAACCAGCCGCCTAAGGTGGGACAGATGATTACGGTGAAGTCGTA

ACAAGGTAGCCCGTA

SEQ ID NO: 73
S12KG420 926R
GTACTCCCCAGGCGGAATGCTTAATGCGTTAGCTGCAGCACTGAAGGGCGGAAACCCTCCAACACTTAGCATTCATCGTTTACGGTATGGACTA

CCAGGGTATCTAATCCTGTTTGCTACCCATACTTTCGAGCCTCAGCGTCAGTTACAGACCAGACAGCCGCCTTCGCCACTGGTGTTCTTCCATAT

ATCTACGCATTTCACCGCTACACATGGAGTTCCACTGTCCTCTTCTGCACTCAAGTTTCCCAGTTTCCGATGCACTTCTTCGGTTGAGCCGAAGGC

TTTCACATCAGACTTAAAAAACCGCCTGCGCTCGCTTTACGCCCAATAAATCCGGACAACGCTTGCCACCTACGTATTACCGCGGCTGCTGGCAC

GTAGTTAGCCGTGGCTTTCTGGTTAAATACCGTCAATACCTGAACAGTTACTCTCAGATATGTTCTTCTTTAACAACAGAGTTTTACGAGCCGAA

ACCCTTCTTCACTCACGCGGCGTTGCTCCATCAGACTTTCGTCCATTGTGGAAGATTCCCTACTGCTGCCTCCCGTAGGAGTTTGGGCCGTGTCT

CAGTCCCAATGTGGCCGATTACCCTCTCAGGTCGGCTACGTATCATTGCCATGGTGAGCCGTTACCTCACCATCTAGCTAATACGCCGCGGGAC

CATCCAAAAGTGATA

SEQ ID NO: 74
S12KG421 519R
TGGCTTTCTGGTTAAATACCGTCAATACCTGAACAGTTACTCTCAGATATGTTCTTCTTTAACAACAGAGTTTTACGAGCCGAAACCCTTCTTCAC

TCACGCGGCGTTGCTCCATCAGACTTTCGTCCATTGTGGAAGATTCCCTACTGCTGCCTCCCGTAGGAGTTTGGGCCGTGTCTCAGTCCCAATGT

GGCCGATTACCCTCTCAGGTCGGCTACGTATCATTGCCATGGTGAGCCGTTACCTCACCATCTAGCTAATACGCCGCGGGACCATCTAAAAGTG

ATAGCCGAAGCCATCTTTCAAACTCGGACCATGCGGTCCAAGTTGTTATGCGGTATTAGCATCTGTTTCCAGGTGTTATCCCCCGCTTCTGGGCA

GGTTTCCCACGTGTTACTCACCAGTTCGCCACTCACTCAAATGTAAATCATGATGCAAGCACCAATCAATACCAGAGTTCGTTCGACTTGCATGT

ATTAGGCACGCCGCCAGCGTTCGTCCTGAGCCATGATCAAACTCTA

SEQ ID NO: 75
S12KG422 RP2
ACTTAGGCGGCTGGTTCCTAAAAGGTTACCCCACCGACTTTGGGTGTTACAAACTCTCATGGTGTGACGGGCGGTGTGTACAAGGCCCGGGAA

CGTATTCACCGCGGCATGCTGATCCGCGATTACTAGCGATTCCGACTTCATGTAGGCGAGTTGCAGCCTACAATCCGAACTGAGAATGGCTTTA

AGAGATTAGCTTACTCTCGCGAGTTCGCAACTCGTTGTACCATCCATTGTAGCACGTGTGTAGCCCAGGTCATAAGGGGCATGATGATTTGACG

TCATCCCCACCT1CCTCCGGTTTGTCACCGGCAGTCTCACCAGAGTGCCCAACTTAATGCTGGCAACTGATAATAAGGGTTGCGCTCGTTGCGG

GACTTAACCCAACATCTCACGACACGAGCTGACGACAACCATGCACCACCTGTATCCATGTCCCCGAAGGGAACGTCTAATCTCTTAGATTTGC

ATAGTATGTCAAGACCTGGTAAGGTTCTTCGCGTAGCTTCGAATTAAACCACATGCTCCACCGCTTGTGCGGGCCCCGTCAATTCCTTTGAGTT

TCAGCCTTGCGGCCGTACTCCCCAGGCGGAATGCTTAATGCGTTAGCTGCAGCACTGAAGGGCGGAAACCCTCCA

NCIMB 42011 GGDK161b - *L. reuteri* (sample 11a)

SEQ ID NO: 76
S12KG441 27F
TAATACATGCAAGTCGTACGCACTGGCCCAACTGATTGATGGTGCTTGCACCTGATTGACGATGGATCACCAGTGAGTGGCGGACGGGTGAGT

AACACGTAGGTAACCTGCCCCGGAGCGGGGATAACATTTGGAAACAGATGCTAATACCGCATAACAACAAAAGCCACATGGCTTTTGTTTGA

AAGATGGCTTTGGCTATCACTCTGGGATGGACCTGCGGTGCATTAGCTAGTTGGTAAGGTAACGGCTTACCAAGGCGATGATGCATAGCCGAG

TTGAGAGACTGATCGGCCACAATGGAACTGAGACACGGTCCATACTCCTACGGGAGGCAGCAGTAGGGAATCTTCCACAATGGGCGCAAGCC

TGATGGAGCAACACCGCGTGAGTGAAGAAGGGTTTCGGCTCGTAAAGCTCTGTTGTTGGAGAAGAACGTGCGTGAGAGTAACTGTTCACGCA

GTGACGGTATCCAACCAGAAAGTCACGGCTAACTACGTGCCAGCAGCCGCGGTAATACGTAGGTGGCAAGCGTGATCCGGATTTATTGGGCG

TAAAGCGAGCGCAGGCGGTTGCTTAGGTCTGATGTGAAAGCCTTCGGCTTAACCGAAGAAGTGCATCGGAGACGGGCGACTTGAGTGCA

SEQ ID NO: 77

S12KG442 519F
TTATCCGGATTTATTGGGCGTAAAGCGAGCGCAGGCGGTTGCTTAGGTCTGATGTGAAAGCCTTCGGCTTAACCGAAGAAGTGCATCGGAAAC

CGGGCGACTTGAGTGCAGAAGAGGACAGTGGAACTCCATGTGTAGCGGTGGAATGCGTAGATATATGGAAGAACACCAGTGGCGAAGGCGG

CTGTCTGGTCTGCAACTGACGCTGAGGCTCGAAAGCATGGGTAGCGAACAGGATTAGATACCCTGGTAGTCCATGCCGTAAACGATGAGTGCT

AGGTGTTGGAGGGTTTCCGCCCTTCAGTGCCGGAGCTAACGCATTAAGCACTCCGCCTGGGGAGTACGACCGCAAGGTTGAAACGCAAGGA

ATTGACGGGGGCCCGCACAAGCGGTGGAGCATGTGGTTTAATTCGAAGCTACGCGAAGAACCTTACCAGGTCTTGACATCTTGCGCTAACCTT

ANAAGGCGTCCCCTTCGGGGACTCAATGACAGGTGGTGCATGGTT

SEQ ID NO: 78

S12KG443 926F
GGTGGAGCATGTGGTTTAATTCGAAGCTACGCGAAGAACCTTACCAGGTCTTGACATCTTGCGCTAACCTTAGAGATAAGGCGTTCCCTTCGGG

GACGCAATGACAGGTGGTGCATGGTCGTCGTCAGCTCGTGTCGTGAGATGTTGGGTTAAGTCCCGCAACGAGCGCAACCCTTGTTACTAGTTG

CCAGCATTAAGTTGGGCACTCTAGTGAGACTGCCGGTGACAAACCGGAGGAAGGTGGGGACGACGTCAGATCATCATGCCCCTTATGACCTG

GGCTACACACGTGCTACAATGGACGGTACAACGAGTCGCAAGCTCGCGAGAGTAAGCTAATCTCTTAAAGCCGTTCTCAGTTCGGACTGTAGG

CTGCAACTCGCCTACACGAAGTCGGAATCGCTAGTAATCGCGGATCAGCATGCCGCGGTGAATACGTTCCCGGGCCTTGTACACACCGCCCGTC

ACACCATGGGAGTTTGTAACGCCCAAAGTCGGTGGCCTAACCTTTATGGAGGGAGCCGCCTAAGGCGGGACAGATGACTGGGGTGAAGTCGT

AACAAGGTAG

SEQ ID NO: 79

S12KG444 926R
No results

SEQ ID NO: 80

S12KG445 519R
GTGACTTTCTGGTTGGATACCGTCACTGCGTGAACAGTTACTCTCACGCACGTTCTTCTCCAACAACAGAGCTTTACGAGCCGAAACCCTTCTTC

ACTCACGCGGTGTTGCTCCATCAGGCTTGCGCCCATTGTGGAAGATTCCCTACTGCTGCCTCCCGTAGGAGTATGGACCGTGTCTCAGTTCCATT

GTGGCCGATCAGTCTCTCAACTCGGCTATGCATCATCGCCTTGGTAAGCCGTTACCTTACCAACTAGCTAATGCACCGCAGGTCCATCCCAGAGT

GATAGCCAAAGCCATCTTTCAAACAAAAGCCATGTGGCTTTTGTTGTTATGCGGTATTAGCATCTGTTTCCAAATGTTATCCCCGCTCCGGGGC

AGGTTACCTACGTGTTACTCACCCGTCCGCCACTCACTGGTAATCCATCGTCAATCAGGTGCAAGCACCATCAATCAGTTGGGCCAGTGCGTAC

GACTTGCATGTATTAGGCACACCGCCGGCGTTCATCCTGAGCCA

SEQ ID NO: 81

S12KG446 RP2
CTCCCTCCATAAAGGTTAGGCCACCGACTTTGGGCGTTACAAACTCCCATGGTGTGACGGGCGGTGTGTACAAGGCCCGGGAACGTATTCACC

GCGGCATGCTGATCCGCGATTACTAGCGATTCCGACTTCGTGTAGGCGAGTTGCAGCCTACAGTCCGAACTGAGAACGGCTTTAAGAGATTAG

CTTACTCTCGCGAGCTTGCGACTCGTTGTACCGTCCATTGTAGCACGTGTGTAGCCCAGGTCATAAGGGGCATGATGATCTGACGTCGTCCCCA

CCTTCCTCCGGTTTGTCACCGGCAGTCTCACTAGAGTGCCCAACTTAATGCTGGCAACTAGTAACAAGGGTTGCGCTCGTTGCGGGACTTAACC

CAACATCTCACGACACGAGCTGACGACGACCATGCACCACCTGTCATTGCGTCCCCGAAGGGAACGCCTTATCTCTAAGGTTAGCGCAAGATGT

CAAGACCTGGTAAGGTTCTTCGCGTAGCTTCGAATTAAACCACATGCTCCACCGCTTGTGCGGGCCCCCGTCAATTCCTTTGAGTTTCAACCTTG

GCGGTCGTACTCCCCAGGCGGAGTGCTTAATGCGTTAGCTCCGGCACTGAAGGGCGGAA

NCIMB 42012 GGDK266c - *L. reuteri* (sample 1a)

SEQ ID NO: 82

S12KG381 27F
GTGTGCCTAATACATGCAAGTCGTACGCACTGGCCCAACTGATTGATGGTGCTTGCACCTGATTGACGATGGATCACCAGTGAGTGGCGGACG

GGTGAGTAACACGTAGGTAACCTGCCCCGGAGCGGGGGATAACATTTGGAAACAGATGCTAATACCGCATAACAACAAAAGCCACATGGCTTT

TGTTTGAAAGATGGCTTTGGCTATCACTCTGGGATGGACCTGCGGTGCATTAGCTAGTTGGTAAGGTAACGGCTTACCAAGGCGATGATGCAT

AGCCGAGTTGAGAGACTGATCGGCCACAATGGAACTGAGACACGGTCCATACTCCTACGGGAGGCAGCAGTAGGGAATCTTCCACAATGGGC

GCAAGCCTGATGGAGCAACACCGCGTGAGTGAAGAAGGGTTTCGGCTCGTAAAGCTCTGTTGTTGGAGAAGAACGTGCGTGAGAGTAACTGT

TCACGCAGTGACGGTATCCAACCAGAAAGTCACGGCTAACTACGTGCCAGCAGCCGCGGTAATACGTAGGTGGCAAGCGTTATCCGGATTTAT

TGGGCGTAAAGCGAGCGCAGGCGGTTGCTTAGGTCTGATGTGAAAGCCTTCGGCTTAACCGAAGAAGTGCATCGGAAACCGGGCGACTTGAG

TGC

SEQ ID NO: 83

S12KG382 519F
TTATCCGGATTTATTGGGCGTAAAGCGAGCGCAGGCGGTTGCTTAGGTCTGATGTGAAAGCCTTCGGCTTAACCGAAGAAGTGCATCGGAAAC

CGGGCAACTTGAGTGCAGAAGAGGACAGTGGAACTCCATGTGTAGCGGTGGAATGCGTAGATATATGGAAGAACACCAGTGGCGAAGGCGG

CTGTCTGGTCTGCAACTGACGCTGAGGCTCGAAAGCATGGGTAGCGAACAGGATTAGATACCCTGGTAGTCCATGCCGTAAACGATGAGTGCT

AGGTGTTGGAGGGTTTCCGCCCTTCAGTGCCGGAGCTAACGCATTAAGCACTCCGCCTGGGGAGTACGACCGCAAGGTTGAAACTCAAAGGA

ATTGACGGGGGCCCGCACAAGCGGTGGAGCATGTGGTTTAATTCGAAGCTACGCGAAGAACCTTACCAGGTCTTGACATCTTGCGCTAACCTT

AGAGATAAGGCGTCCCTTCGGGGACGCAATGACAGGTGGTGCATGGTCGTCGTCAGCTCGTGTCGTGAGATGTTGGGTTAAGTCCCGCAACG

AGCGCAACCCTTGTTACTAGTTGCCAGCATTAAGTTGGGCACTCTAGTGAGACTGCCGGTGACAAACCGGAGGAAGGTGGGGACGACGTCA

SEQ ID NO: 84

S12KG383 926F
GGTGGAGCATGTGGTTTAATTCGAAGCTACGCGAAGAACCTTACCAGGTCTTGACATCTTGCGCTAACCTTAGAGATAAGGCGTTCCCTTCGGG

GACGCAATGACAGGTGGTGCATGGTCGTCGTCAGCTCGTGTCGTGAGATGTTGGGTTAAGTCCCGCAACGAGCGCAACCCTTGTTACTAGTTG

CCAGCATTAAGTTGGGCACTCTAGTGAGACTGCCGGTGACAAACCGGAGGAAGGTGGGGACGACGTCAGATCATCATGCCCCTTATGACCTG

GGCTACACACGTGCTACAATGGACGGTACAACGAGTCGCAAGCTCGCGAGAGTAAGCTAATCTCTTAAAGCCGTTCTCAGTTCGGACTGTAGG

CTGCAACTCGCCTACACGAAGTCGGAATCGCTAGTAATCGCGGATCAGCATGCCGCGGTGAATACGTTCCCGGGCCTTGTACACACCGCCCGTC

ACACCATGGGAGTTTGTAACGCCCAAAGTCGGTGGCCTAACCATTATGGAGGGAGCCGCCTAAGGCGGGACAGATGACTGGGGTGAAGTCGT

AACAAGGTAGCCGTA

SEQ ID NO: 85

S12KG384 926R
TACTCCCCAGGCGGAGTGCTTAATGCGTGAGCTCCGGCACTGAAGGGCGGAAACCCTCCAACACCTAGCACTCATCGTTTACGGCATGGACTA

CCAGGGTATCTAATCCTGTTCGCTACCCATGCTTTCGAGCCTCAGCGTCAGTTGCAGACCAGACAGCCGCCTTCGCCACTGGTGTTCTTCCATAT

ATCTACGCATTCCACCGCTACACATGGAGTTCCACTGTCCTCTTCTGCACTCAAGTCGCCCGGTTTCCGATGCACTTCTTCGGTTAAGCCGAAGG

CTTTCACATCAGACCTAAGCAACCGCCTGCGCTCGCTTTACGCCCAATAAATCCGGATAACGCTTGCCACCTACGTATTACCGCGGCTGCTGGCA

CGTAGTTAGCCGTGACTTTCTGGTTGGATACCGTCACTGCGTGAACAGTTACTCTCACGCACGTTCTTCTCCAACAACAGAGCTTTACGAGCCGA

AACCCTTTTTCACTCACGCGGTGTTGCTCCATCAGGCTTGCGCCCATTGTGGAAGATTCCCTACTGCTGCCTCCCGTAGGAGTATGGACCGTGTC

TCAGTTCCATTGTGGCCGATCAGTCTCTCAACTCGGCTATGCATCATCGCCTTGGTAAGCCGTTACCTTACCAACTAGCTAATGCACCGCAGGTC

CATCCCAGAGTGATAGCCAAAGCCATCTTTCAAACAAAAGCC

SEQ ID NO: 86

S12KG385 519R
GTGACTTTCTGGTTGGATACCGTCACTGCGTGAACAGTTACTCTCACGCACGTGCTTCTCCAACAACAGAGCTTTACGAGCCGAAACCCTTCTTC

ACTCACGCGGTGTTGCTCCATCAGGCTTGCGCCCATTGTGGAAGATTCCCTACTGCTGCCTCCCGTAGGAGTATGGACCGTGTCTCAGTTCCATT

GTGGCCGATCAGTCTCTCAACTCGGCTATGCATCATCGCCTTGGTAAGCCGTTACCTTACCAACTAGCTAATGCACCGCAGGTCCATCCCAGAGT

GATAGCCAAAGCCATCTTTCAAACAAAAGCCATGTGGCTTTTGTTGTTATGCGGTATTAGCATCTGTTTCCAAATGTTATCCCCCGCTCCGGGGC

AGGTTACCTACGTGTTACTCACCCGTCCGCCACTCACTGGTGATCCATCGTCAATCAGGTGCAAGCACCATCAATCAGTTGGGCCAGTGCGTAC

GACTTGCATGTATTAGGCACACCGCCGGCGTTCATCCTGAGCCATGATCAAAC

SEQ ID NO: 87

S12KG386 RP2
TCCCGCACTTAGGCGGCTCCCTCCATAATGGTTAGGCCACCGACTTTGGGCGTTACAAACTCCCATGGTGTGACGGGCGGTGTGTACAAGGCC

CGGGAACGTATTCACCGCGGCATGCTGATCCGCGATTACTAGCGATTCCGACTTCGTGTAGGCGAGTTGCAGCCTACAGTCCGAACTGAGAAC

GGCTTTAAGAGATTAGCTTACTCTCGCGAGCTTGCGACTCGTTGTACCGTCCATTGTAGCACGTGTGTAGCCCAGGTCATAAGGGGCATGATGA

TCTGACGTCGTCCCCACCTTCCTCCGGTTTGTCACCGGCAGTCTCACTAGAGTGCCCAACTTAATGCTGGCAACTAGTAACAAGGGTTGCGCTCG

TTGCGGGACTTAACCCAACATCTCACGACACGAGCTGACGACGACCATGCACCACCTGTCATTGCGTCCCCGAAGGGAACGCCTTATCTCTAAG

```
-continued
GTTAGCGCAAGATGTCAAGACCTGGTAAGGTTCTTCGCGTAGCTTCGAATTAAACCACATGCTCCACCGCTTGTGCGGGCCCCGTCAATTCCT TTGAGTTTCAACCTTGCGGTCGTACTCCCCAGGCGGAGTGCTTAATGCGTTAGCTCCGGCACTGAAGGGCGGAAACCCTCCAACACCTAGCACT

CATCGTTTACGGCATGGACTACCAGGGTATCTAATCCTGTTCGCTACCCATGCTTTCGAGCC
```

REFERENCES

Blandino, G., Fazio, D., Di Marco, R. Probiotics: Overview of microbiological and immunological characteristics (2008). *Expert Review of Anti-Infective Therapy*, 6 (4), pp. 497-508.

Cintas L M, Casaus M P, Herranz C, Nes I F, Hernandez P E. Review: bacteriocins of lactic acid bacteria (2001). Food Sci Technol Int. 7(4):281-305.

Clarridge III, J. E. Impact of 16S rRNA gene sequence analysis for identification of bacteria on clinical microbiology and infectious diseases (2004). Clinical Microbiology Reviews, 17 (4), pp. 840-862.

Cotter, P. D., Hill, C., Ross, R. P. Food microbiology: Bacteriocins: Developing innate immunity for food (2005). Nature Reviews Microbiology, 3 (10), pp. 777-788.

De Angelis, M., Siragusa, S., Berloco, M., Caputo, L., Settanni, L., Alfonsi, G., Amerio, M., Grandi, A., Ragni, A., Gobbetti, M. Selection of potential probiotic *lactobacilli* from pig feces to be used as additives in pelleted feeding (2006). Research in Microbiology, 157 (8), pp. 792-801

Elmadfa, I., Klein, P., Meyer, A. L. Immune-stimulating effects of lactic acid bacteria in vivo and in vitro (2010). *Proceedings of the Nutrition Society*, 69 (3), pp. 416-420.

Gopal, P. K., Sullivan, P. A., Smart, J. B. Utilisation of galacto-oligosaccharides as selective substrates for growth by lactic acid bacteria including *Bifidobacterium lactis* DR10 and *Lactobacillus rhamnosus* DR20 (2001). International Dairy Journal, 11 (1-2), pp. 19-25.

Gousia, P., Economou, V., Sakkas, H., Leveidiotou, S., Papadopoulou, C. Antimicrobial resistance of major foodborne pathogens from major meat products (2011). *Foodborne Pathogens and Disease*, 8 (1), pp. 27-38.

Jackson M S, Bird A R, McOrist A L. Comparison of two selective media for the detection and enumeration of *Lactobacilli* in human faeces (2002). J Microbiol Methods. 51(3):313-21.

Korhonen, J. M., Sclivagnotis, Y., Wright, A. V. Characterization of dominant cultivable *lactobacilli* and their antibiotic resistance profiles from faecal samples of weaning piglets (2007). *Journal of Applied Microbiology*, 103 (6), pp. 2496-2503.

Lähteinen, T., Malinen, E., Koort, J. M. K., Mertaniemi-Hannus, U., Hankimo, T., Karikoski, N., Pakkanen, S., Laine, H., Sillanpää, H., Söderholm, H., Palva, A. Probiotic properties of *Lactobacillus* isolates originating from porcine intestine and feces (2010). Anaerobe, 16 (3), pp. 293-300

Liu, Y., Fatheree, N.Y., Mangalat, N., Rhoads, J. M. Human-derived probiotic *Lactobacillus reuteri* strains differentially reduce intestinal inflammation (2010). *American Journal of Physiology—Gastrointestinal and Liver Physiology*, 299 (5), pp. G1087-G1096.

Ljungh, A., Wadström, T. Lactic acid bacteria as probiotics (2006). *Current Issues in Intestinal Microbiology*, 7 (2), pp. 73-90.

Martin, R, Delgado, S, Maldonado, A, Jiménez, E, Olivares, M, Fernández, L, Sobrino, O J, Rodriguez, J M. Isolation of *lactobacilli* from sow milk and evaluation of their probiotic potential (2009). Journal of Dairy Research, 76 (4), pp. 418-425. Mulder I E, Schmidt B, Stokes C R, Lewis M, Bailey M, Aminov R I, Prosser J I, Gill B P, Pluske J R, Mayer C D, Musk C C, Kelly D. Environmentally-acquired bacteria influence microbial diversity and natural innate immune responses at gut surfaces (2009). BMC Biol. 7:79.

Naughton P J; Grant G. (2005) Modelling of salmonellosis In: Microbial Ecology of the Growing Animal Holzapfel W H, Naughton P J. (Eds). London, Elsevier. pp. 235-257

Neeser, J.-R., Granato, D., Rouvet, M., Servin, A., Teneberg, S., Karlsson, K.-A. *Lactobacillus johnsonii* La1 shares carbohydrate-binding specificities with several enteropathogenic bacteria (2000). Glycobiology, 10 (11), pp. 1193-1199.

Nicolau, D. P. Current challenges in the management of the infected patient (2011). *Current Opinion in Infectious Diseases*, 24 (Suppl 1), pp. S1-S10.

Ohashi, Y., Ushida, K. Health-beneficial effects of probiotics: Its mode of action (2009). Animal Science Journal, 80 (4), pp. 361-371.

Reddy, K. B. P. K., Awasthi, S. P., Madhu, A. N., Prapulla, S. G. Role of cryoprotectants on the viability and functional properties of probiotic lactic acid bacteria during freeze drying (2009). *Food Biotechnology*, 23 (3), pp. 243-265.

Robertson, J. M. C., McKenzie, N. H., Duncan, M., Allen-Vercoe, E., Woodward, M. J., Flint, H. J., Grant, G. Lack of flagella disadvantages *Salmonella enterica* serovar Enteritidis during the early stages of infection in the rat (2003). Journal of Medical Microbiology, 52 (1), pp. 91-99.

Schreiber, O., Petersson, J., Phillipson, M., Perry, M., Roos, S., Holm, L. *Lactobacillus reuteri* prevents colitis by reducing P-selectin-associated leukocyte- and platelet-endothelial cell interactions (2009). American Journal of Physiology—Gastrointestinal and Liver Physiology, 296 (3), pp. G534-G542.

Smith, C. L., Geier, M. S., Yazbeck, R., Torres, D. M., Butler, R. N., Howarth, G. S. *Lactobacillus fermentum* BR11 and fructo-oligosaccharide partially reduce jejunal inflammation in a model of intestinal mucositis in rats (2008). Nutrition and Cancer, 60 (6), pp. 757-767.

Strasser, S., Neureiter, M., Geppl, M., Braun, R., Danner, H. Influence of lyophilization, fluidized bed drying, addition of protectants, and storage on the viability of lactic acid bacteria (2009). *Journal of Applied Microbiology*, 107 (1), pp. 167-177.

Tomás, M. S. J., Bru, E., Martos, G., Nader-Macías, M. E. Stability of freeze-dried vaginal *Lactobacillus* strains in the presence of different lyoprotectors (2009). *Canadian Journal of Microbiology*, 55 (5), pp. 544-552.

Tzortzis, G., Baillon, M.-L. A., Gibson, G. R., Rastall, R. A. Modulation of anti-pathogenic activity in canine-derived *Lactobacillus* species by carbohydrate growth substrate (2004). Journal of Applied Microbiology, 96 (3), pp. 552-559.

Williams, N. T. Probiotics (2010). *American Journal of Health-System Pharmacy*, 67 (6), pp. 449-458.

Yao, W., Zhu Wei-yun, W.-Y., Smidt, H., Verstegen, M. W. A. Cultivation-Independent Analysis of the Development of the *Lactobacillus* spp. Community in the Intestinal Tract of Newborn Piglets (2011) *Agricultural Sciences in China*, 10 (3), pp. 438-447.

Yun, J. H., Lee, K. B., Sung, Y. K., Kim, E. B., Lee, H.-G., Choi, Y. J. Isolation and characterization of potential probiotic *lactobacilli* from pig feces (2009). Journal of Basic Microbiology, 49 (2), pp. 220-226.

The invention claimed is:

1. A composition comprising at least one porcine lactic acid bacterial strain wherein said at least one porcine lactic acid bacterial strain is selected from the group consisting of:
   NCIMB 41846;
   NCIMB 41847;
   NCIMB 41848;
   NCIMB 41849;
   NCIMB 41850;
   NCIMB 42008;
   NCIMB 42009;
   NCIMB 42010;
   NCIMB 42011;
   NCIMB 42012; and any combination of two or more thereof;
   and an excipient, diluent or carrier;
   wherein said at least one porcine lactic acid bacterial strain is in an amount sufficient to treat or prevent an intestinal disorder in a subject.

2. The composition of claim 1, wherein the excipient, diluent or carrier is a pharmaceutically acceptable excipient, diluent or carrier.

3. The composition of claim 1, wherein the composition is a probiotic composition comprising one or more porcine lactic acid bacterial strains.

4. A method of treating an intestinal disorder in a subject, said method comprising administering to the subject the composition of claim 1.

5. A method of improving intestinal microbiota in a subject, said method comprising administering to the subject the composition of claim 1.

6. A feedstuff comprising the composition of claim 1.

7. A food product comprising the composition of claim 1.

8. A dietary supplement comprising the composition of claim 1.

9. A food additive comprising the composition of claim 1.

10. A process for producing the composition of claim 1, said process comprising culturing at least one porcine lactic acid bacterial strain in a culture medium and recovering said at least one porcine lactic acid bacterial strain from the culture medium; wherein said at least one porcine lactic acid bacterial strain is selected from the group consisting of:
   NCIMB 41846; NCIMB 41847; NCIMB 41848; NCIMB 41849; NCIMB 41850; NCIMB 42008; NCIMB 42009; NCIMB 42010; NCIMB 42011; NCIMB 42012; and any combination of two or more thereof; and
   mixing said porcine lactic acid bacterial strain with an excipient, diluent or carrier.

11. A method of preparing one or more porcine lactic acid bacterial strains, said method comprising the steps of:
  (i) obtaining faeces from an organically reared pig;
  (ii) freezing the faeces and dispersing in a suitable diluent;
  (iii) applying the dispersed faeces obtained in step (ii) to a suitable agar, optionally in the presence of supplemental pig colostrum carbohydrates, and incubating under an anaerobic conditions;
  (iv) selecting off distinct colonies of bacteria formed during step (iii) and seeding into a suitable broth, optionally in the presence of supplemental pig colostrum carbohydrates;
  (v) incubating the seeded colonies obtained in step (iv) and
  (vi) obtaining an aliquot of the incubated broth, said aliquot comprising one or more porcine lactic acid bacterial strains selected from the group consisting of: NCIMB 41846; NCIMB 41847; NCIMB 41848; NCIMB 41849; NCIMB 41850; NCIMB 42008; NCIMB 42009; NCIMB 42010; NCIMB 42011; NCIMB 42012; and any combination of two or more thereof.

12. A lactic acid bacterial strain comprising a 16S rRNA gene sequence selected from SEQ ID NOs 1-87, or a variant or homologue thereof of said sequence.

13. The method of claim 4, wherein the intestinal disorder is selected from the group consisting of: salmonellosis, irritable bowel syndrome (IBS), inflammatory bowel disorder (IBD), functional dyspepsia, functional constipation, functional diarrhea, functional abdominal pain, functional bloating, Epigastric Pain Syndrome, Postprandial Distress Syndrome, Crohn's disease, ulcerative colitis, gastroesophageal reflux disease (GERD), necrotizing enterocolitis, and combinations thereof.

14. The method of claim 13, wherein the intestinal disorder is functional diarrhea, and wherein the functional diarrhea is selected from the group consisting of antibiotic associated diarrhea, traveler's diarrhea and pediatric diarrhea.

* * * * *